US012667604B2

(12) United States Patent
Holten-Andersen et al.

(10) Patent No.: US 12,667,604 B2
(45) Date of Patent: Jun. 30, 2026

(54) COMBINATION THERAPY WITH CONTROLLED-RELEASE CNP AGONISTS

(71) Applicant: ASCENDIS PHARMA GROWTH DISORDERS A/S, Hellerup (DK)

(72) Inventors: Lars Holten-Andersen, Vanløse (DK); Vibeke Miller Breinholt, Frederiksberg (DK); Kennett Sprogøe, Holte (DK)

(73) Assignee: ASCENDIS PHARMA GROWTH DISORDERS A/S, Hellerup (DK)

( * ) Notice: Subject to any disclaimer, the term of this patent is extended or adjusted under 35 U.S.C. 154(b) by 0 days.

(21) Appl. No.: 18/145,676

(22) Filed: Dec. 22, 2022

(65) Prior Publication Data

US 2023/0302091 A1 Sep. 28, 2023

Related U.S. Application Data

(62) Division of application No. 16/338,185, filed as application No. PCT/EP2017/074596 on Sep. 28, 2017, now Pat. No. 11,564,974.

(30) Foreign Application Priority Data

Sep. 29, 2016 (EP) .................................... 16191456

(51) Int. Cl.

| | |
|---|---|
| ***A61K 38/22*** | (2006.01) |
| ***A61K 31/505*** | (2006.01) |
| ***A61K 38/27*** | (2006.01) |
| ***A61K 45/06*** | (2006.01) |
| ***A61P 19/08*** | (2006.01) |

(52) U.S. Cl.

CPC ............ *A61K 38/22* (2013.01); *A61K 31/505* (2013.01); *A61K 38/2242* (2013.01); *A61K 38/27* (2013.01); *A61K 45/06* (2013.01); *A61P 19/08* (2018.01)

(58) Field of Classification Search

None

See application file for complete search history.

(56) References Cited

U.S. PATENT DOCUMENTS

| | | | |
|---|---|---|---|
| 5,252,714 | A | 10/1993 | Harris et al. |
| 5,340,920 | A | 8/1994 | Matsuo et al. |
| 5,824,784 | A | 10/1998 | Kinstler et al. |
| 6,743,425 | B2 | 6/2004 | Nakao |
| 6,833,358 | B1 | 12/2004 | Nakata et al. |
| 7,585,837 | B2 | 9/2009 | Shechter et al. |
| 8,198,242 | B2 | 6/2012 | Wendt et al. |
| 8,377,884 | B2 | 2/2013 | Wendt et al. |
| 8,551,937 | B2 | 10/2013 | Wakabayshi et al. |
| 8,618,124 | B2 | 12/2013 | Greenwald et al. |
| 8,703,893 | B2 | 4/2014 | Hernandez et al. |
| 8,754,190 | B2 | 6/2014 | Ashley et al. |
| 8,946,405 | B2 | 2/2015 | Ashley et al. |
| 10,052,366 | B2 | 8/2018 | Crine et al. |
| 10,835,578 | B2 * | 11/2020 | Rau ........................ C07K 14/58 |
| 11,154,593 | B2 * | 10/2021 | Rau .................... A61K 31/4015 |
| 11,224,661 | B2 | 1/2022 | Sprogøe et al. |
| 11,311,604 | B2 | 4/2022 | Rau et al. |
| 11,389,510 | B2 | 7/2022 | Sprogøe et al. |
| 11,389,511 | B2 | 7/2022 | Sprogøe et al. |
| 11,413,351 | B2 | 8/2022 | Rau et al. |
| 11,564,974 | B2 | 1/2023 | Holton-Anderson et al. |
| 12,083,182 | B2 | 9/2024 | Sprogøe et al. |
| 12,156,917 | B2 | 12/2024 | Rau et al. |
| 12,239,689 | B2 * | 3/2025 | Sprogøe ................. A61P 19/00 |
| 12,377,133 | B2 | 8/2025 | Skands et al. |
| 2003/0068313 | A1 | 4/2003 | Nakao |
| 2004/0137557 | A1 | 7/2004 | DeFrees et al. |
| 2007/0197434 | A1 | 8/2007 | Nakao et al. |
| 2008/0113027 | A1 | 5/2008 | Asgharian et al. |
| 2008/0312142 | A1 | 12/2008 | Nakao et al. |
| 2009/0258017 | A1 | 10/2009 | Callahan et al. |
| 2010/0316625 | A1 | 12/2010 | Mankarious et al. |
| 2012/0035101 | A1 | 2/2012 | Fares et al. |
| 2012/0276190 | A1 | 11/2012 | Fitzgerald et al. |
| 2012/0316114 | A1 | 12/2012 | Wendt et al. |
| 2012/0322721 | A1 | 12/2012 | Rasmussen et al. |
| 2013/0315966 | A1 | 11/2013 | Randolph et al. |

(Continued)

FOREIGN PATENT DOCUMENTS

| | | | |
|---|---|---|---|
| CA | 2763817 | A1 | 10/2004 |
| EP | 0 447 971 | A2 | 4/1992 |

(Continued)

OTHER PUBLICATIONS

Grigorian et al., Prot. Sci. 14:902-913 (2005) (Year: 2005).*
Bruno et al., "Basics and recent advances in peptide and protein drug delivery," Ther Deliv. 4(11): 1443-1467, (Nov. 2013).
Chen et al., "Fusion Protein Linkers: Property, Design and Functionality," Adv Drug Deliv Rev., 65(10): 1357-1369, (Oct. 2013).
Cohen, "Short-limb skeletal dysplasias and raniosynostosis: what do they have in common?" Pediatr Radiol, 27, 442-446, (1997).
He et al., " Peptide Conjugates with Small Molecules Designed to Enhance Efficacy and Safety," Molecules, 24, 1855, (2019).
Lu et al., "Linkers Having a Crucial Role in Antibody-Drug Conjugates," Int. J. Mol. Sci, 17, 561, (2016).
U.S. Appl. No. 17/526,481, Non-Final Office Action mailed Aug. 7, 2023.

(Continued)

*Primary Examiner* — Thea D'Ambrosio
(74) *Attorney, Agent, or Firm* — Alston & Bird LLP

(57) ABSTRACT

The present invention relates to a combination of a CNP agonist and at least one further biologically active moiety or drug for use in a method for the treatment or prevention of disorders that benefit from stimulating growth, pharmaceutical compositions comprising at least one CNP agonist, preferably controlled-release CNP agonist, wherein the pharmaceutical composition comprises at least one further biologically active moiety or drug, to using these pharmaceutical compositions as a medicament, to their use in the treatment of disorders that benefit from stimulating growth and to methods of preventing or treating a patient having a disorder that benefits from stimulating growth.

17 Claims, 2 Drawing Sheets

Specification includes a Sequence Listing.

(56) References Cited

U.S. PATENT DOCUMENTS

| | | | |
|---|---|---|---|
| 2017/0080049 | A1 | 3/2017 | Morozumi |
| 2017/0189487 | A1 | 7/2017 | Ohori et al. |
| 2017/0368189 | A1 | 12/2017 | Sprogoe et al. |
| 2019/0000926 | A1 | 1/2019 | Rau et al. |
| 2019/0008977 | A1 | 1/2019 | Rau et al. |
| 2019/0015481 | A1 | 1/2019 | Rau et al. |
| 2019/0022237 | A1 | 1/2019 | Sprogøe et al. |
| 2019/0255183 | A1 | 8/2019 | Sprogøe et al. |
| 2019/0328840 | A1 | 10/2019 | Sprogøe et al. |
| 2019/0328841 | A1 | 10/2019 | Sprogøe et al. |
| 2020/0276270 | A1 | 9/2020 | Holton-Anderson et al. |
| 2021/0069339 | A1 | 3/2021 | Sprogøe et al. |
| 2021/0077584 | A1 | 3/2021 | Rau et al. |
| 2021/0177952 | A1 | 6/2021 | Rau et al. |
| 2022/0088206 | A1 | 3/2022 | Sprogøe et al. |
| 2022/0118053 | A1 | 4/2022 | Rau et al. |
| 2022/0211817 | A1 | 7/2022 | Rau et al. |
| 2022/0296682 | A1 | 9/2022 | Rau et al. |
| 2022/0331438 | A1 | 10/2022 | Rau et al. |
| 2022/0409700 | A1 | 12/2022 | Sprogøe et al. |
| 2023/0103820 | A1 | 4/2023 | Sprogøe et al. |
| 2023/0116746 | A1 | 4/2023 | Sprogøe et al. |

FOREIGN PATENT DOCUMENTS

| | | | |
|---|---|---|---|
| EP | 1 333 036 | A1 | 8/2003 |
| EP | 0 769 554 | B1 | 3/2008 |
| EP | 2275119 | A1 | 1/2011 |
| EP | 1534334 | B1 | 6/2014 |
| EP | 2853273 | A1 | 4/2015 |
| EP | 3078387 | A1 | 10/2016 |
| EP | 3135296 | A1 | 3/2017 |
| RU | 2573911 | C2 | 1/2016 |
| WO | WO 2000/0072870 | A1 | 12/2000 |
| WO | WO 02/089789 | A1 | 11/2002 |
| WO | WO 02/098446 | A1 | 12/2002 |
| WO | WO 2004/043396 | A2 | 5/2004 |
| WO | WO 2004/047871 | A2 | 6/2004 |
| WO | WO 2005/099768 | A2 | 10/2005 |
| WO | WO 2006/005140 | A2 | 1/2006 |
| WO | WO 2006/136586 | A2 | 12/2006 |
| WO | WO 2008/031045 | A2 | 3/2008 |
| WO | WO 2008/034122 | A2 | 3/2008 |
| WO | WO 2008/136611 | A1 | 11/2008 |
| WO | WO 2008/155134 | A1 | 12/2008 |
| WO | WO 2009/009712 | A1 | 1/2009 |
| WO | WO 2009/067639 | A2 | 5/2009 |
| WO | WO 2009/086166 | A1 | 7/2009 |
| WO | WO 2009/095479 | A2 | 8/2009 |
| WO | WO 2009/143412 | A2 | 11/2009 |
| WO | WO 2009/156481 | A1 | 12/2009 |
| WO | WO 2010/033217 | A1 | 3/2010 |
| WO | WO 2010/091122 | A1 | 8/2010 |
| WO | WO 2010/135541 | A2 | 11/2010 |
| WO | WO 2011/012722 | A1 | 2/2011 |
| WO | WO 2011/075471 | A2 | 6/2011 |
| WO | WO 2011/082368 | A2 | 7/2011 |
| WO | WO 2011/089214 | A1 | 7/2011 |
| WO | WO 2011/089215 | A1 | 7/2011 |
| WO | WO 2011/089216 | A1 | 7/2011 |
| WO | WO 2011/123813 | A2 | 10/2011 |
| WO | WO 2011/144756 | A1 | 11/2011 |
| WO | WO 2013/024047 | A1 | 2/2013 |
| WO | WO 2013/024048 | A1 | 2/2013 |
| WO | WO 2013/024049 | A1 | 2/2013 |
| WO | WO 2013/024052 | A1 | 2/2013 |
| WO | WO 2013/024053 | A1 | 2/2013 |
| WO | WO 2013/036857 | A1 | 3/2013 |
| WO | WO 2013/160340 | A1 | 10/2013 |
| WO | WO 2015/083582 | A1 | 6/2015 |
| WO | WO 2015/129812 | A1 | 9/2015 |
| WO | WO 2016/020373 | A1 | 2/2016 |
| WO | WO 2016/110577 | A1 | 7/2016 |
| WO | WO 2017/020034 | A1 | 2/2017 |
| WO | WO 2017/100400 | A2 | 6/2017 |
| WO | WO 2017/118693 | A1 | 7/2017 |
| WO | WO 2017/118698 | A1 | 7/2017 |
| WO | WO 2017/118700 | A1 | 7/2017 |
| WO | WO 2017/118703 | A1 | 7/2017 |
| WO | WO 2017/118704 | A1 | 7/2017 |
| WO | WO 2017/118707 | A1 | 7/2017 |
| WO | WO 2018/060314 | A1 | 4/2018 |
| WO | WO 2020/165081 | A1 | 8/2020 |

OTHER PUBLICATIONS

U.S. Appl. No. 17/538,971, Non-Final Office Action mailed May 25, 2023.

U.S. Appl. No. 17/538,971, Notice of Allowance mailed Oct. 10, 2023.

U.S. Appl. No. 17/752,664, Final Office Action mailed Aug. 28, 2023.

U.S. Appl. No. 17/839,390, Non-Final Office Action mailed11-Jun. 2023.

U.S. Appl. No. 17/842,436, Non-Final Office Action mailed Aug. 17, 2023.

U.S. Appl. No. 17/842,436, Notice of Allowance mailed Jun. 26, 2023.

U.S. Appl. No. 17/839,390, Requirement for Restriction/Election mailed Jul. 6, 2023.

U.S. Appl. No. 17/848,180, Requirement for Restriction/Election mailed Sep. 13, 2023.

"BioMarin Announces Decision to Start Phase 3 Program for PEG-PAL in 2Q 2013," BioMarin, Press Release, 3 pages, (2012). [Author Unknown].

"PEG Products," JenKem Technology USA, 7 pages, (2015). [Retrieved from the Internet: <URL: http://www.jenkemusa.com/products>]. [Author Unknown].

Ansel, et al., "Drug Dosage and Terminology," Pharmaceutical Dosage Forms and Drug Delivery, Seventh Edition, pp. 48-53, (1999).

Bowie et al., "Deciphering the Message in Protein Sequences: Tolerance to Amino Acid Substitutions," Science, 247:1306-1310, (1990). [Retrieved from the Internet May 18, 2011: <URL: http://www.sciencemag.org >].

Delgado et al., "The Uses and Properties of PEG-Linked Proteins," Critical Re-views in Therapeutic Drug Carrier Systems, , 9(3,4):249-304, (1992).

Einav, et al., "The hepatitis C virus (HCV) NS4B RNA binding inhibitor clemizole is highly synergistic with HCV protease inhibitors," Journal of Infectious Diseases, 202(1):65-74, (2010).

Farnum et al., "In vivo Delivery of Fluoresceinated Dextrans to the Murine Growth Plate: Imaging of Three Vascular Routes by Multiphoton Microscopy," Anat Rec A Discov Mol Cell Evol Biol, 288(1):91-103, doi:10.1002/ar.a.20272, (2006).

Furuya et al., "Structural requirements of C-type natriuretic peptide for elevation of cyclic GMP in cultured vascular smooth muscle cells," Biochemical and Biophysical Research Communications, 183(3):964-969, (1992).

Igaki et al., "Effects of Intravenously Administered C-type Natriuretic Peptide in Humans: Comparison with Atrial Natriuretic Peptide," Hypertens Res, 21:7-13, (1998).

Jiang, et al., "Effect of Sialylated O-Glycans in Pro-Brain Natriuretic Peptide Stability," Clin Chem, 56(6): 959-966, (Jun. 2010).

Klag, et al., "Advances in treatment of achondroplasia and osteoarthritis," Human Molecular Genetics, vol. 25, No. R1, (2016).

Lorget et al., "Evaluation of the Therapeutic Potential of a CNP Analog in a Fgfr3 Mouse Model Recapitulating Achondroplasia," AJHG, 91(6):1108-1114, (2012).

Martz et al., "sFGFR for achondroplasia," SciBX, 6(40), 2 pages, doi:10.1038/scibx.2013.1120, (2013).

Martz et al., "sFGFR for achondroplasia," SciBX, Nature Publishing Group, 2 pages, (2013).

Mehta, et al., "The Use of Somatropin (Recombinant Growth Hormone) in Children of Short Stature," Pediatr Drugs, 4(1): 37-47, (2002).

(56) References Cited

OTHER PUBLICATIONS

Merrifield, "Solid Phase Peptide Synthesis. I. The Synthesis of a Tetrapeptide," J. Am. Chem. Soc., 85(14):2149-2154, doi: 10.1021/ja00897a025, (1963).
Molina Clinical Policy, Subject: Recombinant Human Growth Hormone: Pediatric Conditions Without GHD, Policy No. MCP-004-C, 24 pages, (2010).
NOF America Corporation, Sunbright® CS, GS, AS, HS, TS and PS Series (NHS active esters/Carbonate), retreived from the internet at: www.nofamerica.com/store/index.php?dispatch=categories.view&category_id=7 on Mar. 19, 2021.
Oefner, et al., "Structure of Human Neutral Endopeptidase (Neprilysin) Complexed with Phosphoramindon," J. Mol. Biol., 296, 341-349, (2000).
Pejchalova, et al., "C-natriuretic peptide: An important regulator of cartilage," Molecular Genetics and Metabolism, 92, 210-215, (2007).
Potter et al., "Natriuretic peptide metabolism, clearance and degradation," FEBS J, 278(11):1808-1817, doi: 10.1111/j.1742-4658.2011.08082.x, (2011).
Ramaswami, et al., "Treatment of Achondroplasia with Growth hormones: Six Year of Experience," Pediatric Research, 22 pages, (1999).
Sakaguchi, et al., "Characterisation of C-type natriuretic peptide receptors in the gill of dogfish *Triakis scyllia*," Journal of Endocrinology, 156, 127-124, (1998).
Samson et al., "C-type natriuretic peptide mediates the hypothalamic actions of the natriuretic peptides to inhibit luteinizing hormone secretion," Endocrinology, 132(2):504-509, doi: 10.1210/END0.132.2.8425472, (1993).
STNext search notes for U.S. Pat. No. 10,052,366, Accession No. 2013:644347, Dated Feb. 11, 2021.
Takano, et al., "Molecular evolution of shark C-type natriuretic peptides," Zoolog Sci, 11 (3):441-454, (1994).
Tallarida, "Quantitative Methods for Assessing Drug Synergism," Genes & Cancer, 2(11) pp. 1003-1008, (2011).
Wang et al., "Effect of liposome-encapsulated C-type natriuretic peptide on vascular response," Database Chemabs, 1 page, Accession No. 1999:790321, (1999).
Wendt et al., "Neutral Endopeptidase-Resistant C-Type Natriuretic Peptide Variant Represents a New Therapeutic Approach for Treatment of Fibroblast Growth Factor Receptor 3-Related Dwarfism," J Pharmacol Exp Ther, 353(1):132-149, (2015).
Yamashita, et al., "Statin treatment rescues FGFR3 skeletal dysplasia phenotypes," Nature, 513, 507-511, (2014).
Yampolsky, et al., "The Exchangeability of Amino Acids in Proteins," Genetics, 170: 1459-1472, (Aug. 2005).
SG 11202107446Q Search Report mailed Nov. 17, 2022.
SG 11202107446Q Written Opinion mailed Nov. 21, 2022.
U.S. Appl. No. 15/538,641, Non-Final Office Action mailed Sep. 6, 2018.
U.S. Appl. No. 15/538,641, Requirement for Restriction/Election mailed Jun. 14, 2018.
U.S. Appl. No. 16/066,058, Non-Final Office Action mailed Feb. 23, 2021.
U.S. Appl. No. 16/066,058, Non-Final Office Action mailed Dec. 31, 2019.
U.S. Appl. No. 16/066,058, Notice of Allowance and Interview Summary mailed Mar. 11, 2022.
U.S. Appl. No. 16/066,058, Requirement for Restriction/Election mailed Oct. 4, 2019.
U.S. Appl. No. 16/066,980, Non-Final Office Action mailed Apr. 19, 2021.
U.S. Appl. No. 16/066,980, Notice of Allowance mailed Dec. 13, 2021.
U.S. Appl. No. 16/066,980, Requirement for Restriction/Election mailed Dec. 28, 2020.
U.S. Appl. No. 16/067,057, Corrected Notice of Allowance mailed Sep. 18, 2020.
U.S. Appl. No. 16/067,057, Final Office Action mailed Dec. 2, 2019.
U.S. Appl. No. 16/067,057, Non-Final Office Action mailed Jun. 25, 2019.
U.S. Appl. No. 16/067,057, Notice of Allowance mailed Apr. 9, 2020.
U.S. Appl. No. 16/067,057, Notice of Allowance mailed Jul. 29, 2020.
U.S. Appl. No. 16/067,070, Final Office Action mailed Aug. 28, 2020.
U.S. Appl. No. 16/067,070, Non-Final Office Action mailed Jan. 26, 2021.
U.S. Appl. No. 16/067,070, Non-Final Office Action mailed Dec. 30, 2019.
U.S. Appl. No. 16/067,070, Notice of Allowance mailed Feb. 24, 2022.
U.S. Appl. No. 16/067,070, Notice of Allowance mailed Oct. 18, 2021.
U.S. Appl. No. 16/067,070, Requirement for Restriction/Election mailed Aug. 21, 2019.
U.S. Appl. No. 16/067,095, Final Office Action mailed Nov. 10, 2020.
U.S. Appl. No. 16/067,095, Non-Final Office Action mailed Mar. 20, 2020.
U.S. Appl. No. 16/067,095, Non-Final Office Action mailed Apr. 5, 2021.
U.S. Appl. No. 16/067,095, Non-Final Office Action mailed Nov. 19, 2021.
U.S. Appl. No. 16/067,095, Notice of Allowance and Interview Summary mailed Mar. 16, 2022.
U.S. Appl. No. 16/067,095, Notice of Allowance mailed Jul. 28, 2021.
U.S. Appl. No. 16/067,095, Requirement for Restriction/Election mailed Oct. 10, 2019.
U.S. Appl. No. 16/067,111, Final Office Action mailed Sep. 17, 2020.
U.S. Appl. No. 16/067,111, Non-Final Office Action mailed Feb. 5, 2020.
U.S. Appl. No. 16/067,111, Notice of Allowability mailed Dec. 6, 2021.
U.S. Appl. No. 16/067,111, Notice of Allowance mailed Sep. 1, 2021.
U.S. Appl. No. 16/067,111, Requirement for Restriction/Election mailed Aug. 30, 2019.
U.S. Appl. No. 16/269,097, Non-Final Office Action mailed Feb. 14, 2020.
U.S. Appl. No. 16/338,185, Final Office Action mailed Apr. 7, 2021.
U.S. Appl. No. 16/338,185, Non-Final Office Action mailed Oct. 25, 2021.
U.S. Appl. No. 16/338,185, Non-Final Office Action mailed Nov. 18, 2020.
U.S. Appl. No. 16/338,185, Notice of Allowance mailed May 25, 2022.
U.S. Appl. No. 16/338,185, Requirement for Restriction/Election mailed Jul. 6, 2020.
U.S. Appl. No. 16/933,127, Non-Final Office Action mailed Dec. 27, 2021.
U.S. Appl. No. 16/993,127, Requirement for Restriction/Election mailed Jul. 28, 2021.
U.S. Appl. No. 17/005,272, Non-Final Office Action mailed Aug. 16, 2021.
U.S. Appl. No. 17/184,561, Corrected Notice of Allowance mailed Sep. 23, 2021.
U.S. Appl. No. 17/184,561, Non-Final Office Action mailed May 3, 2021.
U.S. Appl. No. 17/184,561, Notice of Allowance mailed Aug. 18, 2021.
U.S. Appl. No. 17/752,664, Non-Final Office Action mailed Mar. 23, 2023.
U.S. Appl. No. 17/752,664, Requirement for Restriction/Election mailed Oct. 14, 2022.
U.S. Appl. No. 17/842,436, Final Office Action mailed Mar. 3, 2023.
U.S. Appl. No. 17/842,436, Non-Final Office Action mailed Nov. 21, 2022.

(56) References Cited

OTHER PUBLICATIONS

U.S. Appl. No. 16/066,058, Final Office Action mailed Aug. 20, 2020.
U.S. Appl. No. 16/067,070, Notice of Allowance mailed Jun. 3, 2021.
U.S. Appl. No. 16/067,111, Notice of Allowance mailed Feb. 5, 2021.
U.S. Appl. No. 16/067,111, Notice of Allowance mailed May 12, 2021.
U.S. Appl. No. 16/338,185, Notice of Allowance mailed Sep. 27, 2022.
WIPO Application No. PCT/EP2016/050298, PCT International Preliminary Report on Patentability issued Jul. 11, 2017.
WIPO Application No. PCT/EP2016/050298, PCT International Search Report mailed Apr. 8, 2017.
WIPO Application No. PCT/EP2016/050298, PCT Written Opinion of the International Searching Authority mailed Apr. 8, 2017.
WIPO Application No. PCT/EP2017/050201, PCT International Preliminary Report on Patentability issued Jul. 10, 2018.
WIPO Application No. PCT/EP2017/050201, PCT International Search Report mailed Apr. 12, 2017.
WIPO Application No. PCT/EP2017/050201, PCT Written Opinion of the International Searching Authority mailed Apr. 12, 2017.
WIPO Application No. PCT/EP2017/0502091, PCT International Preliminary Report on Patentability issued Jul. 10, 2018.
WIPO Application No. PCT/EP2017/0502091, PCT Written Opinion of the International Searching Authority mailed Apr. 11, 2017.
WIPO Application No. PCT/EP2017/050213, PCT International Preliminary Report on Patentability issued Jul. 10, 2018.
WIPO Application No. PCT/EP2017/050213, PCT International Search Report mailed May 11, 2017.
WIPO Application No. PCT/EP2017/050213, PCT Written Opinion of the International Searching Authority mailed May 11, 2017.
WIPO Application No. PCT/EP2017/050217, PCT International Preliminary Report on Patentability issued Jul. 10, 2018.
WIPO Application No. PCT/EP2017/050217, PCT International Search Report mailed Apr. 4, 2017.
WIPO Application No. PCT/EP2017/050217, PCT Written Opinion of the International Searching Authority mailed Apr. 4, 2017.
WIPO Application No. PCT/EP2017/050220, PCT International Preliminary Report on Patentability issued Jul. 10, 2018.
WIPO Application No. PCT/EP2017/050220, PCT International Search Report mailed Apr. 10, 2017.
WIPO Application No. PCT/EP2017/050220, PCT Written Opinion of the International Searching Authority mailed Apr. 10, 2017.
WIPO Application No. PCT/EP2017/050224, PCT International Preliminary Report on Patentability issued Jul. 10, 2018.
WIPO Application No. PCT/EP2017/050224, PCT International Search Report mailed Mar. 23, 2017.
WIPO Application No. PCT/EP2017/050224, PCT Written Opinion of the International Searching Authority mailed Mar. 23, 2017.
WIPO Application No. PCT/EP2017/074596, PCT International Preliminary Report on Patentability issued Apr. 2, 2019.
WIPO Application No. PCT/EP2020/053304, PCT International Search Report and Written Opinion of the International Searching Authority mailed Aug. 4, 2020.
WIPO Application No. PCT/EP2017/0502091, PCT International Search Report mailed Apr. 11, 2017.
U.S. Appl. No. 17/538,971, Notice of Allowance mailed May 9, 2024.
EudraCT No. 2019-002754-22v1 Clinical trial results, Apr. 11, 2023.
U.S. Appl. No. 17/538,971, Notice of Allowance mailed Jan. 18, 2024.
U.S. Appl. No. 17/696,769, Requirement for Restriction/Election mailed Mar. 16, 2022.
U.S. Appl. No. 17/752,664, Non-Final Office Action mailed Mar. 14, 2024.
U.S. Appl. No. 17/842,436, Notice of Allowance mailed Apr. 5, 2024.
U.S. Appl. No. 17/848, 180, Non-Final Office Action mailed Feb. 26, 2024.
Abassi et al., "Metabolism of endothelin-1 and big endothelin-1 by recombinant neutral endopeptidase EC.3.4.24.11," Br. J. Pharmacol., 109:1024-1028, (1993).
Abbey et al., "Lysophosphatidic Acid Inhibits C-Type Natriuretic Peptide Activation of Guanylyl Cyclase-B," Endocrinology, 144(1):240-246, (2003).
Barrett et al., "Oligopeptidases, and the Emergence of the Prolyl Oligopeptidase Family," Biol. Chem. Hoppe-Seyler, 373:353-360, (Jul. 1992).
Bartels et al., "Mutations in the Transmembrane Natriuretic Peptide Receptor NPR-B Impair Skeletal Growth and cause Acromesomelic Dysplasia, Type Maroteaux," Am. J. Hum. Genet., 75:27-34, (2004).
Bhatia et al., "Mitochondrial Dysfunction in Alzheimer's Disease: Opportunities for Drug Development," Current Neuropharmacology, 20:675-692, (2022).
Biering-Sørensen, "Physical Measurements as Risk Indicators for Low-Back Trouble Over a One-Year Period," Spine 9(2):106-119, (1984).
Biomarin Pharmaceutical Inc., Annex I—Summary of Product Characteristics, VOXZOGO, 52 pgs., (Dec. 2021).
Biomarin Pharmaceutical Inc., Highlights of Prescribing Information, VOXZOGO, 22 pgs., (Nov. 2021).
Block et al., "The Role of Remote Monitoring in Evaluation Fatigue in Multiple Sclerosis: A Review," Frontiers in Neurology, 13:878613, (Jun. 2022).
Borsche et al., "Mitochondria and Parkinson's Disease: Clinical, Molecular, and Translational Aspects," Journal of Parkinson's Disease, 11:45-60, (2021).
Breinholt et al., "Phase 1 safety, tolerability, pharmacokinetics and pharmacodynamics results of a long-acting C-type natriuretic peptide prodrug, TransCon CNP," Br J Clin Pharmacol., 88:4763-4772, (2022).
Brusse et al., "Testing Functional Performance in People with Parkinson Disease," Physical Therapy, 85(2):134-141, (Feb. 2005).
Caliceti et al., "Improvement of the physicochemical and biopharmaceutical properties of insulin by poly(ethylene glycol) conjugation," S.T.P. Pharma Sciences, 9(1):107-113, (1999).
Carpenter et al., "Rational Design of Stable Lyophilized Protein Formulations: Theory and Practice," Rational Design of Stable Protein Formulations, 109-133, (2002).
Chusho et al., "Dwarfism and early death in mice lacking C-type natriuretic peptide," PNAS, 98(7):4016-4021, (Mar. 27, 2001).
Clael et al., "Association of Strength and Physical Functions in People with Parkinson's Disease," Neuroscience Journal, 2018(8507018):1-5, (Dec. 2018).
Danielsen et al., "A neutral endopeptidase in the microvillar membrane of pig intestine," Biochem J., 191:645-648, (1980).
De Plater, et al., "A C-type natriuretic peptide from the venom of the platypus (*Ornithorhynchus anatinus*): Structure and pharmacology," Comparative Biochemistry and Physiology Part C, 120, 99-110, (1998).
Declaration of Daniel Wendt, 3 pgs., (Jan. 20, 2023).
Declaration of Dr. Ulrich Hersel, 5 pgs., (Aug. 25, 2022).
Domondon et al., "Regulation of mitochondria function by natriuretic peptides," Am J Physiol Renal Physiol, 317:F1164-1168, (2019).
Edman, "Method for determination of the amino acid sequence in peptides," Acta Chemica Scandinavica, 4:282-293, (1950).
Elmore, "Peptide Synthesis," Techniques in Molecular Biology, 32-54, (1987).
EP Application No. 16192229.9, Grounds for the Decision Annex dated Sep. 23, 2024.
EP Application No. 16192229.9, Summons to Attend Oral Proceedings dated Jun. 18, 2024.
EP Application No. 16192229.9, Transmittal of Decision dated Jun. 19, 2023.
EP Application No. 3 175 863, Written Submissions dated Mar. 28, 2024, 25 pgs.
EP Application No. 96 114 549.7, Applicant submission to EPO dated Nov. 14, 2006.

(56) References Cited

OTHER PUBLICATIONS

Erdös et al., "Neutral endopeptidase 24.11 (enkephalinase) and related regulators of peptide hormones," The FASEB Journal, 3:154-151, (Feb. 1989).
Espiner et al., "C-type natriuretic peptide in Parkinson's disease: reduced secretion and response to deprenyl," J. Neural Transm., 121:371-378, (2014).
Felix, Site-Specific Poly(ethlene glycol)ylation Peptides, Poly(ethylene glycol), Chemistry and Biological Applications, American Chemical Society, Edited by Harris & Zalipsky, Chap. 16, 218-238, (1997).
Genentech, Inc. XOLAIR® highlights of prescribing information, revised Sep. 2014.
Goncalves et al., "In vitro and in vivo characterization of Recifercept, a soluble fibroblast growth factor receptor 3, as treatment for achondroplasia," PLOS One, 15(12):e0244368, (2020).
Graven-Nielsen et al., "Induction and Assessment of Muscle Pain, Referred Pain, and Muscular Hyperalgesia," Current Pain and Headache Reports, 443-451, (2003).
Greenwald et al., "A New Aliphatic Amino Prodrug System for the Delivery of Small Molecules and Proteins Utilizing Novel PEG Derivatives," J. Med. Chem., 47:726-734, (2004).
Greenwald et al., "Drug delivery systems based on trimethyl lock lactonization poly(ethylene glycol) prodrugs of amino-containing compounds," J. Med. Chem., 43:475-487, (2000).
Greenwald et al., "Drug delivery systems employing 1,4- or 1,6-elimination: Poly(ethylene glycol) prodrugs of amine-containing compounds," J. Med. Chem., 42:3657-3667, (1999).
Hinds et al., "Effects of PEG conjugation on insulin properties," Advanced Drug Delivery Reviews, 54:505-530, (2002).
Hinds et al., "Synthesis and Characterization of Poly(ethlene glycol)-Insulin Conjugates," Bioconjugate Chem., 11:195-201, (2000).
Hunt et al., "Bioactivity and Metabolism of C-Type Natriuretic Peptide in Normal Man," Journal of Clinical Endocrinology and Metabolism, 78(5):1428-1435, (1994).
Ishizaka et al., "Isolation and identification of C-type natriuretic peptide in human monocytic cell line, THP-1," Biochemical and Biophysical Research Communications, 189(2):697-704, (Dec. 15, 1992).
Itaba et al., "Presence of C-type natriuretic peptide (CNP) in guinea pig caecum: role and mechanisms of CNP in circular smooth muscle relaxation," Neurogastroenterol Motil, 16:375-382, (2004).
Iwata et al., "Metabolic Regulation of Brain Aβ by Neprilysin," Science, 292:1550-1552, (May 25, 2001).
Kenny et al., "Hydrolysis of human and pig brain natriuretic peptides, urodilatin, C-type natriuretic peptide and some C-receptor ligands by endopeptidase-24.11," Biochem J., 291:83-88, (1993).
Kitoh et al., "Pharmacokinetics and safety after once and twice a day doses of meclizine hydrochloride administered to children with achondroplasia," PLOS One, 15(4):e0229639, (2020).
Lebel et al., "Role of the neutral endopeptidase 24.11 in the conversion of big endothelins in guinea-pig lung parenchyma," Brit Jour of Pharmacol., 117:184-188, (1996).
Lisy et al., "Neutral endopeptidase inhibition potentiates the natriuretic actions of adrenomedullin," Physiology, F410-414, (Apr. 25, 2024).
Mackler et al., "Oxidative Energy Deficiency. II. Human Achondroplasia," Archives of Biochemistry and Biophysics, 159:885-888, (1973).
Macours et al., "Structure, Evolutionary Conservation, and Functions of Angiotensin- and Endothelin-Converting Enzymes," International Review of Cytology, 239:47-97, (2004).
Mahesh et al., "Amide bond activation of biological molecules," Molecules, 23:1-43, (2018).
Marra et al., "An Overview of Mitochondrial Protein Defects in Neuromuscular Diseases," Biomolecules, 11:1-39, (2021).
Medeiros et al., "Processing and Metabolism of Peptide-YY: Pivotal Roles of Dipeptidyl peptidase-IV, Aminopeptidase-P and Endopeptidase-24.11*," Endocrinology, 134(5):2088-2094, (1994).
Minamino et al., "Characterization of immunoreactive human C-type natruiretic peptide in brain and heart," Biochemical and Biophysical Research Communications, 149(1):535-542, (Aug. 30, 1991).
Minamino et al., "Natriuretic Peptides in the Cardiovascular System," Handbook of Biologically Active Peptides, Chap. 165, 1199-1207, (2006).
Minamino et al., "N-Terminally Extended Form of C-Type Natriuretic Peptide (CNP-53) Identified in Porcine Brain," 170(2):973-979, (Jul. 31, 1990).
Miyashita et al., "Natriuretic Peptides/cGMP/cGMP-Dependent Protein Kinase Cascades Promote Muscle Mitochondrial Biogenesis and Prevent Obesity," Diabetes, 58:2880-2892, (2009).
Muraresku et al., "Mitochondrial Disease: Advances in clinical diagnosis, management, therapeutic development, and preventative strategies," Curr Genet Med Rep., 6(2):62-72, (2018).
Murayama et al., "Cloning and sequence analysis of a Bothrops jararaca cDNA encoding a precursor of seven bradykinin-potentiating peptides and a C-type natriuretic peptide," PNAS, 94:1189-1193, (Feb. 1997).
Nakagawa et al., "Roles of Natriuretic Peptides and the Significance of Neprilysin in Cardiovascular Diseases," Biology, 11:1017, (2022).
Naqvi et al., "Muscle Strength Grading," StatPearls—NCBI Bookshelf, 3 pgs., (2025).
Nesher et al., "Reversible pegylation prolongs the hypotensive effect of atrial natriuretic peptide," Bioconjgate Chem., 19:342-348, (2008).
Norman et al., "Degradation of brain natriuretic peptide by neutral endopeptidase: species specific sites of proteolysis determined by mass spectrometry," Biochemical and Biophysical Research Communications, 175(1):22-30, (Feb. 28, 1991).
Pasut et al., "Protein, peptide and non-peptide drug PEGylation for therapeutic application," Expert Opin. Ther. Patents, 14(6):859-894, (2004).
Peixoto De Barcelos et al., "Mitochondrial Dysfunction and Multiple Sclerosis," Biology, 8(37):1-17, (2019).
Perez-Ternero et al., "C-type natriuretic peptide is a pivotal regulator of metabolic homeostasis," PNAS, 119(13):e2116470119, (2022).
Perez-Ternero et al., "C-type natriuretic peptide preserves central neurological function by maintaining blood-brain barrier integrity," Front. Mol. Neurosci., 15:991112, (2022).
Pierart et al., "Effect of human endopeptidase 24.11 ("enkephalinase") on IL-1-induced thymocyte proliferation activity," Journal of Immunology, 140(11):3808-3811, (1988).
Piccinin et al., "PGC-1s in the Spotlight with Parkinson's Disease," International Journal of Molecular Sciences, 22(3847):1-20, (2021).
Potter et al., "Natriuretic Peptides: Their Structures, Receptors, Physiologic Functions and Therapeutic Applications," Handb Exp Pharmacol., 191:341-366, (2009).
Potter et al., "Natriuretic peptides, their receptors, and cyclic guanosine monophosphate-dependent signaling functions," Endocrine Reviews, 27(1):47-72, (2006).
Rauen, "The RASopathies," Annu Rev Genomics Hum Genet., 14:355-369, (2013).
Roberts et al., "Chemistry for peptide and protein PEGylation," Advanced Drug Delivery Reviews, 64:116-127, (2012).
Roche Data Sheet Herceptin® Trastuzumab 150 mg and 440 mg powder for concentrate for solution for infusion, 140625, (Jun. 2014).
Rose et al., "Neuropeptide Y Fragments Derived by Neprilysin Processing Are Neuroprotective in a Transgenic Model of Alzheimer's Disease," The Journal of Neuroscience, 29(4):1115-1125, (Jan. 28, 2009).
Rosenkranz et al., "Enhancing mitochondrial activity in neurons protects against neurodegeneration in a mouse model of multiple sclerosis," dLife, 10:e61798, (2021).
Saint-Laurent et al., "Obesity in achondroplasia patients: from evidence to medical monitoring," Orphanet Journal of Rare Diseases, 14:253, (2019).
Savarirayan et al., "Infigratinib in children with achondroplasia: the PROPEL and PROPEL 2 studies," Ther Adv Musculoskel Dis, 14:1-13, (2022).
Second Declaration of Dr. Ulrich Hersel, 4 pgs., (Mar. 27, 2024).

(56) References Cited

OTHER PUBLICATIONS

Shirotani et al., "Neprilysin Degrades Both Amyloid β Peptides 1-40 and 1-42 Most Rapidly and Efficiently among Thiorphan- and Phosphor Amidon-sensitive Endopeptidases," Journal of Biological Chemistry, 276(24)21895-21901, (2001).
Smith, "Peptide Sequencing by Edman Degradation," Encyclopedia of Life Sciences, 1-3, (2001).
Sponseller et al., "Patient Guide to Achondroplasia Kyphosis," Johns Hopkins Orthopaedic Surgery, 3 pgs., (2003).
Stawikowski et al., "Introduction to Peptide Synthesis," Curr Protoc Protein Sci, 1-17, (Feb. 2002).
Stewart et al., "Pediatric Disorders of Orthostatic Intolerance," Pediatrics, 141:e20171673, (Jan. 2018).
Stuart et al., "Physical activity monitoring to assess disability progression in multiple sclerosis," Multiple Sclerosis Journal—Experimental, Translational and Clinical, 1-12, (2020).
Sudoh et al., "C-type natriuretic peptide (CNP): A new member of natriuretic peptide family identified in porcine brain," Biochemical and Biophysical Research Communications, 168(2):863-870, (Apr. 30, 1990).
Suzuki et al., Isolation of high-molecular-weight C-type natriuretic peptide from the heart of a cartilaginous fish (European dogfish, *Scyliorhinus canicula*), FEBS, 282(2):321-325, (May 1991).
Taraldsen et al., "Gait, physical function, and physical activity in three groups of home-dwelling older adults with diferent severity of cognitive impairment—a cross-sectional study," BMC Geriatrics, 21:670, (2021).
Tawaragi et al., "Gene and Precursor Structures of Human C-Type Natriuretic Peptide," Biochemical and Biophysical Research Communications, 175(2):645-651, (Mar. 15, 1991).
Tsubery et al., "Prolonging the Action of Protein and Peptide Drugs by a Novel Approach of Reversible Polyethylene Glycol Modification," The Journal of Biological Chemistry, 279(37):38118-38124, (Sep. 10, 2004).
U.S. Appl. No. 15/646,822, Protest under 37 CFR 1.291 dated Mar. 3, 2018.
U.S. Appl. No. 17/428,604, Non-Final Office Action mailed Sep. 24, 2024.
U.S. Appl. No. 17/428,604, Final Office Action mailed Dec. 2, 2024.
U.S. Appl. No. 17/752,664, Final Office Action mailed Nov. 1, 2024.
U.S. Appl. No. 17/839,390, Notice of Allowance mailed Aug. 21, 2024.
U.S. Appl. No. 17/842,436, Corrected Notice of Allowance mailed Sep. 26, 2024.
U.S. Appl. No. 17/842,436, Notice of Allowance mailed Jul. 23, 2024.
U.S. Appl. No. 18/145,676, Non-Final Office Action mailed Oct. 17, 2024.
U.S. Appl. No. 61/180,112, Certified copy of priority document mailed Jun. 3, 2010.
U.S. Appl. No. 61/180,112, Notice of Recordation and Assignment dated Jan. 22, 2010.
U.S. Appl. No. 61/254,563, Filing Receipt mailed Nov. 20, 2009. 287.
U.S. Appl. No. 61/254,563, Certified copy of priority document mailed Jun. 3, 2010.
U.S. Appl. No. 61/254,563, Assignment and Notice of Recordation dated Jun. 9, 2010.
Uchio et al., "Site-specific insulin conjugates with enhanced stability and extended action profile," Advanced Drug Delivery Reviews, 35:289-306, (1999).
Veronese, "Peptide and protein PEGylation: a review of problems and solutions," Biomaterials, 22:405-417, (2001).
Veronese, "The Impact of PEGylation on Biological Therapies" Biodrugs, 22:315-329, (2008).
Vidovic et al., "Production and isotope labeling of antimicrobial peptides in *Escherichia coli* by means of a novel fusion partner that enables high-yield insoluble expression and fast purification," J. Pept. Sci., 15:278-284, (2009).
Wang, "Lyophilization and development of solid protein pharmaceuticals," International Journal of Pharmaceutics, 203, 1-60, (2000).
Wiedlocha et al., "Roles of the FGF-FGFR Signaling System in Cancer Development and Inflammation," Cells, 10:2231, (2021).
Witte et al., "Reduced expression of PGC-1a partly underlies mitochondrial changes and correlates with neuronal loss in multiple sclerosis cortex," Acta Neuropathol, 125:231-243, (2013).
Woodward et al., "Central and systematic C-type Natriuretic Peptide are both reduced in Parkinson's Disease," Parkinsonism and Related Disorders, 1-5, (2017).
Wu et al., "Furin-mediated Processing of Pro-C-type Natriuretic Peptide," The Journal of Biological Chemistry, 278(28):25847-25852, (2003).
Yasoda et al., "Overexpression of CNP in chondrocytes rescues achondroplasia through a MAPK-dependent pathway," Nature Medicine, 10(1):80-86, (Jan. 2004).
Yasoda et al., "Systemic Administration of C-Type Natriuretic Peptide as a Novel Therapeutic Strategy for Skeletal Dysplasias," Endocrinology, 150(7):3138-3144, (Jul. 2009).
Youn et al., "High-yield production of biologically active mono-PEGylated salmon calcitonin by site-specific PEGylation," Journal of Controlled Release, 117:371-379, (2007).
Youn et al., "Improved intestinal delivery of salmon calcitonin by Lys18-amine specific PEGylation: Stability, permeability, pharmacokinetic behavior and in vivo hypo calcemic efficacy," Journal of Controlled Release, 114:334-342, (2006).
Zappe et al., "PEGylation of cyanovirin-N, an entry inhibitor of HIV," Advanced Drug Delivery, 60:79-87, (2000).
Zhao et al., "Peroxisome proliferator activator receptor gamma coactivator-1alpha (PGC-1a) improves motor performance and survival in a mouse model of amyotrophic lateral sclerosis," Molecular Neurodegeneration, 6:51, (2011).
Zhao et al., "The Impact of Mitochondrial Dysfunction in Amyotrophic Lateral Sclerosis," Cells, 11:2049, (2022).
Zheng et al., "PGC-1α, A Potential Therapeutic Target for Early Intervention in Parkinson's Disease," Sci Transl Med., 2(52):1-29, (Oct. 2010).
Zhou et al., "Identification of the G protein-activating sequence of the single-transmembrane natriuretic peptide receptor C (NPR-C)," Am J. Physiol Cell Physiol, 284:C1255-1261, (2003).
Kimura et al., "Neutral endopeptidase (ES 3.4.24.11) does not hydrolyze recombinant human interleukin-1β," Immunology Letters, 21:109-114, (1991).
EP Patent No. 31758963, Communication of the Board Appeal pursuant to Article 15(1) of the Rules of Procedure of the Boards of Appeal mailed Aug. 7, 2025.
EP Patent No. 31758963, Decision of the Board of Appeals mailed Dec. 1, 2025.
EP Patent No. 31758963, Minutes of the Oral Proceedings mailed Oct. 22, 2025.
EP Patent No. 31758963, Response to Statement of Grounds of Appeal mailed May 27, 2025.
EP Patent No. 31758963, Submissions Responsive to Opponent 1's Reply to Patentee's Appeal mailed Jun. 27, 2025.

* cited by examiner

SEQUENCE LISTING

```
Sequence total quantity: 99
SEQ ID NO: 1            moltype = AA  length = 22
FEATURE                 Location/Qualifiers
DISULFID                6..22
                        note = intrachain disulfide bond
source                  1..22
                        mol_type = protein
                        organism = Homo sapiens
SEQUENCE: 1
GLSKGCFGLK LDRIGSMSGL GC                                             22

SEQ ID NO: 2            moltype = AA  length = 53
FEATURE                 Location/Qualifiers
DISULFID                37..53
                        note = intrachain disulfide bond
source                  1..53
                        mol_type = protein
                        organism = Homo sapiens
SEQUENCE: 2
DLRVDTKSRA AWARLLQEHP NARKYKGANK KGLSKGCFGL KLDRIGSMSG LGC           53

SEQ ID NO: 3            moltype = AA  length = 54
FEATURE                 Location/Qualifiers
REGION                  1..54
```

```
                        note = G-CNP-53
DISULFID                38..54
                        note = intrachain disulfide bond
source                  1..54
                        mol_type = protein
                        organism = synthetic construct
SEQUENCE: 3
GDLRVDTKSR AAWARLLQEH PNARKYKGAN KKGLSKGCFG LKLDRIGSMS GLGC        54

SEQ ID NO: 4            moltype = AA  length = 54
FEATURE                 Location/Qualifiers
REGION                  1..54
                        note = M-CNP-53
DISULFID                38..54
                        note = intrachain disulfide bond
source                  1..54
                        mol_type = protein
                        organism = synthetic construct
SEQUENCE: 4
MDLRVDTKSR AAWARLLQEH PNARKYKGAN KKGLSKGCFG LKLDRIGSMS GLGC        54

SEQ ID NO: 5            moltype = AA  length = 54
FEATURE                 Location/Qualifiers
REGION                  1..54
                        note = P-CNP-53
DISULFID                38..54
                        note = intrachain disulfide bond
source                  1..54
                        mol_type = protein
                        organism = synthetic construct
SEQUENCE: 5
PDLRVDTKSR AAWARLLQEH PNARKYKGAN KKGLSKGCFG LKLDRIGSMS GLGC        54

SEQ ID NO: 6            moltype = AA  length = 53
FEATURE                 Location/Qualifiers
REGION                  1..53
                        note = CNP-53 M48N
DISULFID                37..53
                        note = intrachain disulfide bond
source                  1..53
                        mol_type = protein
                        organism = synthetic construct
SEQUENCE: 6
DLRVDTKSRA AWARLLQEHP NARKYKGANK KGLSKGCFGL KLDRIGSNSG LGC         53

SEQ ID NO: 7            moltype = AA  length = 36
FEATURE                 Location/Qualifiers
REGION                  1..36
                        note = CNP-53 with deletion of amino acids 15-31
DISULFID                20..36
                        note = intrachain disulfide bond
source                  1..36
                        mol_type = protein
                        organism = synthetic construct
SEQUENCE: 7
DLRVDTKSRA AWARGLSKGC FGLKLDRIGS MSGLGC                            36

SEQ ID NO: 8            moltype = AA  length = 52
FEATURE                 Location/Qualifiers
REGION                  1..52
                        note = CNP-52
DISULFID                36..52
                        note = intrachain disulfide bond
source                  1..52
                        mol_type = protein
                        organism = synthetic construct
SEQUENCE: 8
LRVDTKSRAA WARLLQEHPN ARKYKGANKK GLSKGCFGLK LDRIGSMSGL GC          52

SEQ ID NO: 9            moltype = AA  length = 51
FEATURE                 Location/Qualifiers
REGION                  1..51
                        note = CNP-51
DISULFID                35..51
                        note = intrachain disulfide bond
source                  1..51
                        mol_type = protein
                        organism = synthetic construct
SEQUENCE: 9
```

```
RVDTKSRAAW ARLLQEHPNA RKYKGANKKG LSKGCFGLKL DRIGSMSGLG C           51

SEQ ID NO: 10          moltype = AA  length = 50
FEATURE                Location/Qualifiers
REGION                 1..50
                       note = CNP-50
DISULFID               34..50
                       note = intrachain disulfide bond
source                 1..50
                       mol_type = protein
                       organism = synthetic construct
SEQUENCE: 10
VDTKSRAAWA RLLQEHPNAR KYKGANKKGL SKGCFGLKLD RIGSMSGLGC             50

SEQ ID NO: 11          moltype = AA  length = 49
FEATURE                Location/Qualifiers
REGION                 1..49
                       note = CNP-49
DISULFID               33..49
                       note = intrachain disulfide bond
source                 1..49
                       mol_type = protein
                       organism = synthetic construct
SEQUENCE: 11
DTKSRAAWAR LLQEHPNARK YKGANKKGLS KGCFGLKLDR IGSMSGLGC              49

SEQ ID NO: 12          moltype = AA  length = 48
FEATURE                Location/Qualifiers
REGION                 1..48
                       note = CNP-48
DISULFID               32..48
                       note = intrachain disulfide bond
source                 1..48
                       mol_type = protein
                       organism = synthetic construct
SEQUENCE: 12
TKSRAAWARL LQEHPNARKY KGANKKGLSK GCFGLKLDRI GSMSGLGC               48

SEQ ID NO: 13          moltype = AA  length = 47
FEATURE                Location/Qualifiers
REGION                 1..47
                       note = CNP-47
DISULFID               31..47
                       note = intrachain disulfide bond
source                 1..47
                       mol_type = protein
                       organism = synthetic construct
SEQUENCE: 13
KSRAAWARLL QEHPNARKYK GANKKGLSKG CFGLKLDRIG SMSGLGC                47

SEQ ID NO: 14          moltype = AA  length = 46
FEATURE                Location/Qualifiers
REGION                 1..46
                       note = CNP-46
DISULFID               30..46
                       note = intrachain disulfide bond
source                 1..46
                       mol_type = protein
                       organism = synthetic construct
SEQUENCE: 14
SRAAWARLLQ EHPNARKYKG ANKKGLSKGC FGLKLDRIGS MSGLGC                 46

SEQ ID NO: 15          moltype = AA  length = 45
FEATURE                Location/Qualifiers
REGION                 1..45
                       note = CNP-45
DISULFID               29..45
                       note = intrachain disulfide bond
source                 1..45
                       mol_type = protein
                       organism = synthetic construct
SEQUENCE: 15
RAAWARLLQE HPNARKYKGA NKKGLSKGCF GLKLDRIGSM SGLGC                  45

SEQ ID NO: 16          moltype = AA  length = 44
FEATURE                Location/Qualifiers
REGION                 1..44
                       note = CNP-44
DISULFID               28..44
```

```
                        note = intrachain disulfide bond
source                  1..44
                        mol_type = protein
                        organism = synthetic construct
SEQUENCE: 16
AAWARLLQEH PNARKYKGAN KKGLSKGCFG LKLDRIGSMS GLGC                    44

SEQ ID NO: 17           moltype = AA  length = 35
FEATURE                 Location/Qualifiers
REGION                  1..35
                        note = CNP-44 with a deletion of amino acids 14-22
DISULFID                19..35
                        note = intrachain disulfide bond
source                  1..35
                        mol_type = protein
                        organism = synthetic construct
SEQUENCE: 17
AAWARLLQEH PNAGLSKGCF GLKLDRIGSM SGLGC                              35

SEQ ID NO: 18           moltype = AA  length = 36
FEATURE                 Location/Qualifiers
REGION                  1..36
                        note = CNP-44 with a deletion of amino acids 15-22
DISULFID                20..36
                        note = intrachain disulfide bond
source                  1..36
                        mol_type = protein
                        organism = synthetic construct
SEQUENCE: 18
AAWARLLQEH PNARGLSKGC FGLKLDRIGS MSGLGC                             36

SEQ ID NO: 19           moltype = AA  length = 43
FEATURE                 Location/Qualifiers
REGION                  1..43
                        note = CNP-43
DISULFID                27..43
                        note = intrachain disulfide bond
source                  1..43
                        mol_type = protein
                        organism = synthetic construct
SEQUENCE: 19
AWARLLQEHP NARKYKGANK KGLSKGCFGL KLDRIGSMSG LGC                     43

SEQ ID NO: 20           moltype = AA  length = 42
FEATURE                 Location/Qualifiers
REGION                  1..42
                        note = CNP-42
DISULFID                26..42
                        note = intrachain disulfide bond
source                  1..42
                        mol_type = protein
                        organism = synthetic construct
SEQUENCE: 20
WARLLQEHPN ARKYKGANKK GLSKGCFGLK LDRIGSMSGL GC                      42

SEQ ID NO: 21           moltype = AA  length = 41
FEATURE                 Location/Qualifiers
REGION                  1..41
                        note = CNP-41
DISULFID                25..41
                        note = intrachain disulfide bond
source                  1..41
                        mol_type = protein
                        organism = synthetic construct
SEQUENCE: 21
ARLLQEHPNA RKYKGANKKG LSKGCFGLKL DRIGSMSGLG C                       41

SEQ ID NO: 22           moltype = AA  length = 40
FEATURE                 Location/Qualifiers
REGION                  1..40
                        note = CNP-40
DISULFID                24..40
                        note = intrachain disulfide bond
source                  1..40
                        mol_type = protein
                        organism = synthetic construct
SEQUENCE: 22
RLLQEHPNAR KYKGANKKGL SKGCFGLKLD RIGSMSGLGC                         40
```

-continued

```
SEQ ID NO: 23          moltype = AA  length = 39
FEATURE                Location/Qualifiers
REGION                 1..39
                       note = CNP-39
DISULFID               23..39
                       note = intrachain disulfide bond
source                 1..39
                       mol_type = protein
                       organism = synthetic construct
SEQUENCE: 23
LLQEHPNARK YKGANKKGLS KGCFGLKLDR IGSMSGLGC                       39

SEQ ID NO: 24          moltype = AA  length = 38
FEATURE                Location/Qualifiers
REGION                 1..38
                       note = CNP-38
DISULFID               22..38
                       note = intrachain disulfide bond
source                 1..38
                       mol_type = protein
                       organism = synthetic construct
SEQUENCE: 24
LQEHPNARKY KGANKKGLSK GCFGLKLDRI GSMSGLGC                        38

SEQ ID NO: 25          moltype = AA  length = 37
FEATURE                Location/Qualifiers
REGION                 1..37
                       note = CNP-37
DISULFID               21..37
                       note = intrachain disulfide bond
source                 1..37
                       mol_type = protein
                       organism = synthetic construct
SEQUENCE: 25
QEHPNARKYK GANKKGLSKG CFGLKLDRIG SMSGLGC                         37

SEQ ID NO: 26          moltype = AA  length = 37
FEATURE                Location/Qualifiers
REGION                 1..37
                       note = CNP-37 mit Q1pQ (pQ = pyroglutamate)
SITE                   1
                       note = MISC_FEATURE - X = pyroglutamate
DISULFID               21..37
                       note = intrachain disulfide bond
source                 1..37
                       mol_type = protein
                       organism = synthetic construct
SEQUENCE: 26
XEHPNARKYK GANKKGLSKG CFGLKLDRIG SMSGLGC                         37

SEQ ID NO: 27          moltype = AA  length = 38
FEATURE                Location/Qualifiers
REGION                 1..38
                       note = G-CNP-37
DISULFID               22..38
                       note = intrachain disulfide bond
source                 1..38
                       mol_type = protein
                       organism = synthetic construct
SEQUENCE: 27
GQEHPNARKY KGANKKGLSK GCFGLKLDRI GSMSGLGC                        38

SEQ ID NO: 28          moltype = AA  length = 38
FEATURE                Location/Qualifiers
REGION                 1..38
                       note = P-CNP-37
DISULFID               22..38
                       note = intrachain disulfide bond
source                 1..38
                       mol_type = protein
                       organism = synthetic construct
SEQUENCE: 28
PQEHPNARKY KGANKKGLSK GCFGLKLDRI GSMSGLGC                        38

SEQ ID NO: 29          moltype = AA  length = 38
FEATURE                Location/Qualifiers
REGION                 1..38
                       note = M-CNP-37
DISULFID               22..38
```

```
                        note = intrachain disulfide bond
source                  1..38
                        mol_type = protein
                        organism = synthetic construct
SEQUENCE: 29
MQEHPNARKY KGANKKGLSK GCFGLKLDRI GSMSGLGC                     38

SEQ ID NO: 30           moltype = AA  length = 39
FEATURE                 Location/Qualifiers
REGION                  1..39
                        note = PG-CNP-37
DISULFID                23..39
                        note = intrachain disulfide bond
source                  1..39
                        mol_type = protein
                        organism = synthetic construct
SEQUENCE: 30
PGQEHPNARK YKGANKKGLS KGCFGLKLDR IGSMSGLGC                    39

SEQ ID NO: 31           moltype = AA  length = 39
FEATURE                 Location/Qualifiers
REGION                  1..39
                        note = MG-CNP-37
DISULFID                23..39
                        note = intrachain disulfide bond
source                  1..39
                        mol_type = protein
                        organism = synthetic construct
SEQUENCE: 31
MGQEHPNARK YKGANKKGLS KGCFGLKLDR IGSMSGLGC                    39

SEQ ID NO: 32           moltype = AA  length = 37
FEATURE                 Location/Qualifiers
REGION                  1..37
                        note = CNP-37 M32N
DISULFID                21..37
                        note = intrachain disulfide bond
source                  1..37
                        mol_type = protein
                        organism = synthetic construct
SEQUENCE: 32
QEHPNARKYK GANKKGLSKG CFGLKLDRIG SNSGLGC                      37

SEQ ID NO: 33           moltype = AA  length = 38
FEATURE                 Location/Qualifiers
REGION                  1..38
                        note = G-CNP-37 M32N
DISULFID                22..38
                        note = intrachain disulfide bond
source                  1..38
                        mol_type = protein
                        organism = synthetic construct
SEQUENCE: 33
GQEHPNARKY KGANKKGLSK GCFGLKLDRI GSNSGLGC                     38

SEQ ID NO: 34           moltype = AA  length = 38
FEATURE                 Location/Qualifiers
REGION                  1..38
                        note = G-CNP-37 K14Q
DISULFID                22..38
                        note = intrachain disulfide bond
source                  1..38
                        mol_type = protein
                        organism = synthetic construct
SEQUENCE: 34
GQEHPNARKY KGANQKGLSK GCFGLKLDRI GSMSGLGC                     38

SEQ ID NO: 35           moltype = AA  length = 38
FEATURE                 Location/Qualifiers
REGION                  1..38
                        note = G-CNP-37 K14P
DISULFID                22..38
                        note = intrachain disulfide bond
source                  1..38
                        mol_type = protein
                        organism = synthetic construct
SEQUENCE: 35
GQEHPNARKY KGANPKGLSK GCFGLKLDRI GSMSGLGC                     38
```

-continued

```
SEQ ID NO: 36          moltype = AA  length = 37
FEATURE                Location/Qualifiers
REGION                 1..37
                       note = G-CNP-37 K14Q, deletion of amino acid 15
DISULFID               21..37
                       note = intrachain disulfide bond
source                 1..37
                       mol_type = protein
                       organism = synthetic construct
SEQUENCE: 36
GQEHPNARKY KGANQGLSKG CFGLKLDRIG SMSGLGC                        37

SEQ ID NO: 37          moltype = AA  length = 38
FEATURE                Location/Qualifiers
REGION                 1..38
                       note = G-CNP-37 K14Q, K15Q
DISULFID               22..38
                       note = intrachain disulfide bond
source                 1..38
                       mol_type = protein
                       organism = synthetic construct
SEQUENCE: 37
GQEHPNARKY KGANQQGLSK GCFGLKLDRI GSMSGLGC                       38

SEQ ID NO: 38          moltype = AA  length = 36
FEATURE                Location/Qualifiers
REGION                 1..36
                       note = CNP-36
DISULFID               20..36
                       note = intrachain disulfide bond
source                 1..36
                       mol_type = protein
                       organism = synthetic construct
SEQUENCE: 38
EHPNARKYKG ANKKGLSKGC FGLKLDRIGS MSGLGC                         36

SEQ ID NO: 39          moltype = AA  length = 35
FEATURE                Location/Qualifiers
REGION                 1..35
                       note = CNP-35
DISULFID               19..35
                       note = intrachain disulfide bond
source                 1..35
                       mol_type = protein
                       organism = synthetic construct
SEQUENCE: 39
HPNARKYKGA NKKGLSKGCF GLKLDRIGSM SGLGC                          35

SEQ ID NO: 40          moltype = AA  length = 34
FEATURE                Location/Qualifiers
REGION                 1..34
                       note = CNP-34
DISULFID               18..34
                       note = intrachain disulfide bond
source                 1..34
                       mol_type = protein
                       organism = synthetic construct
SEQUENCE: 40
PNARKYKGAN KKGLSKGCFG LKLDRIGSMS GLGC                           34

SEQ ID NO: 41          moltype = AA  length = 33
FEATURE                Location/Qualifiers
REGION                 1..33
                       note = CNP-33
DISULFID               17..33
                       note = intrachain disulfide bond
source                 1..33
                       mol_type = protein
                       organism = synthetic construct
SEQUENCE: 41
NARKYKGANK KGLSKGCFGL KLDRIGSMSG LGC                            33

SEQ ID NO: 42          moltype = AA  length = 32
FEATURE                Location/Qualifiers
REGION                 1..32
                       note = CNP-32
DISULFID               16..32
                       note = intrachain disulfide bond
source                 1..32
```

```
                        mol_type = protein
                        organism = synthetic construct
SEQUENCE: 42
ARKYKGANKK GLSKGCFGLK LDRIGSMSGL GC                                  32

SEQ ID NO: 43           moltype = AA  length = 31
FEATURE                 Location/Qualifiers
REGION                  1..31
                        note = CNP-31
DISULFID                15..31
                        note = intrachain disulfide bond
source                  1..31
                        mol_type = protein
                        organism = synthetic construct
SEQUENCE: 43
RKYKGANKKG LSKGCFGLKL DRIGSMSGLG C                                   31

SEQ ID NO: 44           moltype = AA  length = 30
FEATURE                 Location/Qualifiers
REGION                  1..30
                        note = CNP-30
DISULFID                14..30
                        note = intrachain disulfide bond
source                  1..30
                        mol_type = protein
                        organism = synthetic construct
SEQUENCE: 44
KYKGANKKGL SKGCFGLKLD RIGSMSGLGC                                     30

SEQ ID NO: 45           moltype = AA  length = 29
FEATURE                 Location/Qualifiers
REGION                  1..29
                        note = CNP-29
DISULFID                13..29
                        note = intrachain disulfide bond
source                  1..29
                        mol_type = protein
                        organism = synthetic construct
SEQUENCE: 45
YKGANKKGLS KGCFGLKLDR IGSMSGLGC                                      29

SEQ ID NO: 46           moltype = AA  length = 28
FEATURE                 Location/Qualifiers
REGION                  1..28
                        note = CNP-28
DISULFID                12..28
                        note = intrachain disulfide bond
source                  1..28
                        mol_type = protein
                        organism = synthetic construct
SEQUENCE: 46
KGANKKGLSK GCFGLKLDRI GSMSGLGC                                       28

SEQ ID NO: 47           moltype = AA  length = 38
FEATURE                 Location/Qualifiers
REGION                  1..38
                        note = GHKSEVAHRF-CNP-28
DISULFID                22..38
                        note = intrachain disulfide bond
source                  1..38
                        mol_type = protein
                        organism = synthetic construct
SEQUENCE: 47
GHKSEVAHRF KGANKKGLSK GCFGLKLDRI GSMSGLGC                            38

SEQ ID NO: 48           moltype = AA  length = 27
FEATURE                 Location/Qualifiers
REGION                  1..27
                        note = CNP-27
DISULFID                11..27
                        note = intrachain disulfide bond
source                  1..27
                        mol_type = protein
                        organism = synthetic construct
SEQUENCE: 48
GANKKGLSKG CFGLKLDRIG SMSGLGC                                        27

SEQ ID NO: 49           moltype = AA  length = 27
FEATURE                 Location/Qualifiers
```

-continued

```
REGION               1..27
                     note = CNP-27 K4Q, K5Q
DISULFID             11..27
                     note = intrachain disulfide bond
source               1..27
                     mol_type = protein
                     organism = synthetic construct
SEQUENCE: 49
GANQQGLSKG CFGLKLDRIG SMSGLGC                                          27

SEQ ID NO: 50        moltype = AA  length = 27
FEATURE              Location/Qualifiers
REGION               1..27
                     note = CNP-27 K4R, K5R
DISULFID             11..27
                     note = intrachain disulfide bond
source               1..27
                     mol_type = protein
                     organism = synthetic construct
SEQUENCE: 50
GANRRGLSKG CFGLKLDRIG SMSGLGC                                          27

SEQ ID NO: 51        moltype = AA  length = 27
FEATURE              Location/Qualifiers
REGION               1..27
                     note = CNP-27 K4P, K5R
DISULFID             11..27
                     note = intrachain disulfide bond
source               1..27
                     mol_type = protein
                     organism = synthetic construct
SEQUENCE: 51
GANPRGLSKG CFGLKLDRIG SMSGLGC                                          27

SEQ ID NO: 52        moltype = AA  length = 27
FEATURE              Location/Qualifiers
REGION               1..27
                     note = CNP-27 K4S, K5S
DISULFID             11..27
                     note = intrachain disulfide bond
source               1..27
                     mol_type = protein
                     organism = synthetic construct
SEQUENCE: 52
GANSSGLSKG CFGLKLDRIG SMSGLGC                                          27

SEQ ID NO: 53        moltype = AA  length = 30
FEATURE              Location/Qualifiers
REGION               1..30
                     note = GAN-CNP-27 K4P, K5R
DISULFID             14..30
                     note = intrachain disulfide bond
source               1..30
                     mol_type = protein
                     organism = synthetic construct
SEQUENCE: 53
GANGANPRGL SRGCFGLKLD RIGSMSGLGC                                       30

SEQ ID NO: 54        moltype = AA  length = 27
FEATURE              Location/Qualifiers
REGION               1..27
                     note = CNP-27 K4R, K5R, K9R
DISULFID             11..27
                     note = intrachain disulfide bond
source               1..27
                     mol_type = protein
                     organism = synthetic construct
SEQUENCE: 54
GANRRGLSRG CFGLKLDRIG SMSGLGC                                          27

SEQ ID NO: 55        moltype = AA  length = 27
FEATURE              Location/Qualifiers
REGION               1..27
                     note = CNP-27 K4R, K5R, K9R, M22N
DISULFID             11..27
                     note = intrachain disulfide bond
source               1..27
                     mol_type = protein
                     organism = synthetic construct
```

-continued

```
SEQUENCE: 55
GANRRGLSRG CFGLKLDRIG SNSGLGC                                   27

SEQ ID NO: 56          moltype = AA  length = 28
FEATURE                Location/Qualifiers
REGION                 1..28
                       note = P-CNP-27 K4R, K5R, K9R
DISULFID               12..28
                       note = intrachain disulfide bond
source                 1..28
                       mol_type = protein
                       organism = synthetic construct
SEQUENCE: 56
PGANRRGLSR GCFGLKLDRI GSMSGLGC                                  28

SEQ ID NO: 57          moltype = AA  length = 28
FEATURE                Location/Qualifiers
REGION                 1..28
                       note = M-CNP-27 K4R, K5R, K9R
DISULFID               12..28
                       note = intrachain disulfide bond
source                 1..28
                       mol_type = protein
                       organism = synthetic construct
SEQUENCE: 57
MGANRRGLSR GCFGLKLDRI GSMSGLGC                                  28

SEQ ID NO: 58          moltype = AA  length = 38
FEATURE                Location/Qualifiers
REGION                 1..38
                       note = Human Serum Albumine Fragment - CNP-27
DISULFID               22..38
                       note = intrachain disulfide bond
source                 1..38
                       mol_type = protein
                       organism = synthetic construct
SEQUENCE: 58
GHKSEVAHRF KGANKKGLSK GCFGLKLDRI GSMSGLGC                       38

SEQ ID NO: 59          moltype = AA  length = 38
FEATURE                Location/Qualifiers
REGION                 1..38
                       note = Human Serum Albumine Fragment - CNP-27 M22N
DISULFID               22..38
                       note = intrachain disulfide bond
source                 1..38
                       mol_type = protein
                       organism = synthetic construct
SEQUENCE: 59
GHKSEVAHRF KGANKKGLSK GCFGLKLDRI GSNSGLGC                       38

SEQ ID NO: 60          moltype = AA  length = 39
FEATURE                Location/Qualifiers
REGION                 1..39
                       note = methionine - Human Serum Albumine Fragment - CNP-27
DISULFID               23..39
                       note = intrachain disulfide bond
source                 1..39
                       mol_type = protein
                       organism = synthetic construct
SEQUENCE: 60
MGHKSEVAHR FKGANKKGLS KGCFGLKLDR IGSMSGLGC                      39

SEQ ID NO: 61          moltype = AA  length = 39
FEATURE                Location/Qualifiers
REGION                 1..39
                       note = proline - Human Serum Albumine Fragment - CNP-27
DISULFID               23..39
                       note = intrachain disulfide bond
source                 1..39
                       mol_type = protein
                       organism = synthetic construct
SEQUENCE: 61
PGHKSEVAHR FKGANKKGLS KGCFGLKLDR IGSMSGLGC                      39

SEQ ID NO: 62          moltype = AA  length = 26
FEATURE                Location/Qualifiers
REGION                 1..26
                       note = CNP-26
```

-continued

```
DISULFID               10..26
                       note = intrachain disulfide bond
source                 1..26
                       mol_type = protein
                       organism = synthetic construct
SEQUENCE: 62
ANKKGLSKGC FGLKLDRIGS MSGLGC                                      26

SEQ ID NO: 63          moltype = AA  length = 25
FEATURE                Location/Qualifiers
REGION                 1..25
                       note = CNP-25
DISULFID               9..25
                       note = intrachain disulfide bond
source                 1..25
                       mol_type = protein
                       organism = synthetic construct
SEQUENCE: 63
NKKGLSKGCF GLKLDRIGSM SGLGC                                       25

SEQ ID NO: 64          moltype = AA  length = 24
FEATURE                Location/Qualifiers
REGION                 1..24
                       note = CNP-24
DISULFID               8..24
                       note = intrachain disulfide bond
source                 1..24
                       mol_type = protein
                       organism = synthetic construct
SEQUENCE: 64
KKGLSKGCFG LKLDRIGSMS GLGC                                        24

SEQ ID NO: 65          moltype = AA  length = 23
FEATURE                Location/Qualifiers
REGION                 1..23
                       note = CNP-23
DISULFID               7..23
                       note = intrachain disulfide bond
source                 1..23
                       mol_type = protein
                       organism = synthetic construct
SEQUENCE: 65
KGLSKGCFGL KLDRIGSMSG LGC                                         23

SEQ ID NO: 66          moltype = AA  length = 23
FEATURE                Location/Qualifiers
REGION                 1..23
                       note = R-CNP-22
DISULFID               7..23
                       note = intrachain disulfide bond
source                 1..23
                       mol_type = protein
                       organism = synthetic construct
SEQUENCE: 66
RGLSKGCFGL KLDRIGSMSG LGC                                         23

SEQ ID NO: 67          moltype = AA  length = 24
FEATURE                Location/Qualifiers
REGION                 1..24
                       note = ER-CNP-22
DISULFID               8..24
                       note = intrachain disulfide bond
source                 1..24
                       mol_type = protein
                       organism = synthetic construct
SEQUENCE: 67
ERGLSKGCFG LKLDRIGSMS GLGC                                        24

SEQ ID NO: 68          moltype = AA  length = 23
FEATURE                Location/Qualifiers
REGION                 1..23
                       note = R-CNP-22 K4R
DISULFID               7..23
                       note = intrachain disulfide bond
source                 1..23
                       mol_type = protein
                       organism = synthetic construct
SEQUENCE: 68
RGLSRGCFGL KLDRIGSMSG LGC                                         23
```

-continued

```
SEQ ID NO: 69          moltype = AA  length = 24
FEATURE                Location/Qualifiers
REGION                 1..24
                       note = ER-CNP-22 4KR
DISULFID               8..24
                       note = intrachain disulfide bond
source                 1..24
                       mol_type = protein
                       organism = synthetic construct
SEQUENCE: 69
ERGLSRGCFG LKLDRIGSMS GLGC                                        24

SEQ ID NO: 70          moltype = AA  length = 24
FEATURE                Location/Qualifiers
REGION                 1..24
                       note = RR-CNP-22
DISULFID               8..24
                       note = intrachain disulfide bond
source                 1..24
                       mol_type = protein
                       organism = synthetic construct
SEQUENCE: 70
RRGLSRGCFG LKLDRIGSMS GLGC                                        24

SEQ ID NO: 71          moltype = AA  length = 37
FEATURE                Location/Qualifiers
REGION                 1..37
                       note = HRGP fragment - CNP-22
DISULFID               21..37
                       note = intrachain disulfide bond
source                 1..37
                       mol_type = protein
                       organism = synthetic construct
SEQUENCE: 71
GHHSHEQHPH GANQQGLSKG CFGLKLDRIG SMSGLGC                          37

SEQ ID NO: 72          moltype = AA  length = 38
FEATURE                Location/Qualifiers
REGION                 1..38
                       note = HRGP fragment - CNP-22
DISULFID               22..38
                       note = intrachain disulfide bond
source                 1..38
                       mol_type = protein
                       organism = synthetic construct
SEQUENCE: 72
GAHHPHEHDT HGANQQGLSK GCFGLKLDRI GSMSGLGC                         38

SEQ ID NO: 73          moltype = AA  length = 37
FEATURE                Location/Qualifiers
REGION                 1..37
                       note = HRGP fragment - CNP-22
DISULFID               21..37
                       note = intrachain disulfide bond
source                 1..37
                       mol_type = protein
                       organism = synthetic construct
SEQUENCE: 73
GHHSHEQHPH GANPRGLSKG CFGLKLDRIG SMSGLGC                          37

SEQ ID NO: 74          moltype = AA  length = 36
FEATURE                Location/Qualifiers
REGION                 1..36
                       note = IgG1(FC) fragment - CNP-22
DISULFID               20..36
                       note = intrachain disulfide bond
source                 1..36
                       mol_type = protein
                       organism = synthetic construct
SEQUENCE: 74
GQPREPQVYT LPPSGLSKGC FGLKLDRIGS MSGLGC                           36

SEQ ID NO: 75          moltype = AA  length = 39
FEATURE                Location/Qualifiers
REGION                 1..39
                       note = Human Serum Albumine - CNP-22
DISULFID               23..39
                       note = intrachain disulfide bond
```

-continued

```
source                  1..39
                        mol_type = protein
                        organism = synthetic construct
SEQUENCE: 75
GQHKDDNPNL PRGANPRGLS KGCFGLKLDR IGSMSGLGC                           39

SEQ ID NO: 76           moltype = AA  length = 37
FEATURE                 Location/Qualifiers
REGION                  1..37
                        note = Human Serum Albumine - CNP-22
DISULFID                21..37
                        note = intrachain disulfide bond
source                  1..37
                        mol_type = protein
                        organism = synthetic construct
SEQUENCE: 76
GERAFKAWAV ARLSQGLSKG CFGLKLDRIG SMSGLGC                             37

SEQ ID NO: 77           moltype = AA  length = 35
FEATURE                 Location/Qualifiers
REGION                  1..35
                        note = osteocrin NPR C inhibitor fragment - CNP-22
DISULFID                19..35
                        note = intrachain disulfide bond
source                  1..35
                        mol_type = protein
                        organism = synthetic construct
SEQUENCE: 77
FGIPMDRIGR NPRGLSKGCF GLKLDRIGSM SGLGC                               35

SEQ ID NO: 78           moltype = AA  length = 40
FEATURE                 Location/Qualifiers
REGION                  1..40
                        note = FGF2 heparin-binding domain fragment - CNP-22
DISULFID                24..40
                        note = intrachain disulfide bond
source                  1..40
                        mol_type = protein
                        organism = synthetic construct
SEQUENCE: 78
GKRTGQYKLG SKTGPGPKGL SKGCFGLKLD RIGSMSGLGC                          40

SEQ ID NO: 79           moltype = AA  length = 37
FEATURE                 Location/Qualifiers
REGION                  1..37
                        note = IgG1(FC) fragment - CNP-22 K4R
DISULFID                21..37
                        note = intrachain disulfide bond
source                  1..37
                        mol_type = protein
                        organism = synthetic construct
SEQUENCE: 79
GQPREPQVYT GANQQGLSRG CFGLKLDRIG SMSGLGC                             37

SEQ ID NO: 80           moltype = AA  length = 36
FEATURE                 Location/Qualifiers
REGION                  1..36
                        note = Human Serum Albumine fragment - CNP-22 K4R
DISULFID                20..36
                        note = intrachain disulfide bond
source                  1..36
                        mol_type = protein
                        organism = synthetic construct
SEQUENCE: 80
GVPQVSTSTG ANQQGLSRGC FGLKLDRIGS MSGLGC                              36

SEQ ID NO: 81           moltype = AA  length = 37
FEATURE                 Location/Qualifiers
REGION                  1..37
                        note = fibronectin fragment - CNP-22
DISULFID                21..37
                        note = intrachain disulfide bond
source                  1..37
                        mol_type = protein
                        organism = synthetic construct
SEQUENCE: 81
GQPSSSSQST GANQQGLSRG CFGLKLDRIG SMSGLGC                             37

SEQ ID NO: 82           moltype = AA  length = 37
```

-continued

```
FEATURE                Location/Qualifiers
REGION                 1..37
                       note = fibronectin fragment - CNP-22 K4R
DISULFID               21..37
                       note = intrachain disulfide bond
source                 1..37
                       mol_type = protein
                       organism = synthetic construct
SEQUENCE: 82
GQTHSSGTQS GANQQGLSRG CFGLKLDRIG SMSGLGC                            37

SEQ ID NO: 83          moltype = AA  length = 37
FEATURE                Location/Qualifiers
REGION                 1..37
                       note = fibronectin fragment - CNP-22 K4R
DISULFID               21..37
                       note = intrachain disulfide bond
source                 1..37
                       mol_type = protein
                       organism = synthetic construct
SEQUENCE: 83
GSTGQWHSES GANQQGLSRG CFGLKLDRIG SMSGLGC                            37

SEQ ID NO: 84          moltype = AA  length = 37
FEATURE                Location/Qualifiers
REGION                 1..37
                       note = zinc finger fragment - CNP-22 K4R
DISULFID               21..37
                       note = intrachain disulfide bond
source                 1..37
                       mol_type = protein
                       organism = synthetic construct
SEQUENCE: 84
GSSSSSSSSS GANQQGLSRG CFGLKLDRIG SMSGLGC                            37

SEQ ID NO: 85          moltype = AA  length = 21
FEATURE                Location/Qualifiers
REGION                 1..21
                       note = CNP-21
DISULFID               5..21
                       note = intrachain disulfide bond
source                 1..21
                       mol_type = protein
                       organism = synthetic construct
SEQUENCE: 85
LSKGCFGLKL DRIGSMSGLG C                                             21

SEQ ID NO: 86          moltype = AA  length = 20
FEATURE                Location/Qualifiers
REGION                 1..20
                       note = CNP-20
DISULFID               4..20
                       note = intrachain disulfide bond
source                 1..20
                       mol_type = protein
                       organism = synthetic construct
SEQUENCE: 86
SKGCFGLKLD RIGSMSGLGC                                               20

SEQ ID NO: 87          moltype = AA  length = 19
FEATURE                Location/Qualifiers
REGION                 1..19
                       note = CNP-19
DISULFID               3..19
                       note = intrachain disulfide bond
source                 1..19
                       mol_type = protein
                       organism = synthetic construct
SEQUENCE: 87
KGCFGLKLDR IGSMSGLGC                                                19

SEQ ID NO: 88          moltype = AA  length = 18
FEATURE                Location/Qualifiers
REGION                 1..18
                       note = CNP-18
DISULFID               2..18
                       note = intrachain disulfide bond
source                 1..18
                       mol_type = protein
```

```
                       organism = synthetic construct
SEQUENCE: 88
GCFGLKLDRI GSMSGLGC                                                18

SEQ ID NO: 89          moltype = AA  length = 17
FEATURE                Location/Qualifiers
REGION                 1..17
                       note = CNP-17
DISULFID               1..17
                       note = intrachain disulfide bond
source                 1..17
                       mol_type = protein
                       organism = synthetic construct
SEQUENCE: 89
CFGLKLDRIG SMSGLGC                                                 17

SEQ ID NO: 90          moltype = AA  length = 32
FEATURE                Location/Qualifiers
REGION                 1..32
                       note = BNP fragment - CNP-17 - BNP- fragment
DISULFID               10..26
                       note = intrachain disulfide bond
source                 1..32
                       mol_type = protein
                       organism = synthetic construct
SEQUENCE: 90
SPKMVQGSGC FGLKLDRIGS MSGLGCKVLR RH                                32

SEQ ID NO: 91          moltype = AA  length = 38
FEATURE                Location/Qualifiers
REGION                 1..38
                       note = CNP-38 L1G
DISULFID               22..38
                       note = intrachain disulfide bond
source                 1..38
                       mol_type = protein
                       organism = synthetic construct
SEQUENCE: 91
GQEHPNARKY KGANKKGLSK GCFGLKLDRI GSMSGLGC                          38

SEQ ID NO: 92          moltype = AA  length = 37
FEATURE                Location/Qualifiers
REGION                 1..37
                       note = Ac-CNP-37
MOD_RES                1
                       note = ACETYLATION
DISULFID               21..37
                       note = intrachain disulfide bond
source                 1..37
                       mol_type = protein
                       organism = synthetic construct
SEQUENCE: 92
QEHPNARKYK GANKKGLSKG CFGLKLDRIG SMSGLGC                           37

SEQ ID NO: 93          moltype = AA  length = 37
FEATURE                Location/Qualifiers
REGION                 1..37
                       note = CNP-37, Xaa = K or R, with the provision that at
                        least one Xaa is R
SITE                   8
                       note = MISC_FEATURE - Xaa = Lys, Arg, Pro, Ser or Gln, with
                        the provision that at least one of amino acids 8, 10, 14,
                        15, 19 or 25 is selected from the group consisting of Arg,
                        Pro, Ser and Gln
SITE                   10
                       note = MISC_FEATURE - Xaa = Lys, Arg, Pro, Ser or Gln, with
                        the provision that at least one of amino acids 8, 10, 14,
                        15, 19 or 25 is selected from the group consisting of Arg,
                        Pro, Ser and Gln
SITE                   14
                       note = MISC_FEATURE - Xaa = Lys, Arg, Pro, Ser or Gln, with
                        the provision that at least one of amino acids 8, 10, 14,
                        15, 19 or 25 is selected from the group consisting of Arg,
                        Pro, Ser and Gln
SITE                   15
                       note = MISC_FEATURE - Xaa = Lys, Arg, Pro, Ser or Gln, with
                        the provision that at least one of amino acids 8, 10, 14,
                        15, 19 or 25 is selected from the group consisting of Arg,
                        Pro, Ser and Gln
```

-continued

```
SITE                    19
                        note = MISC_FEATURE - Xaa = Lys, Arg, Pro, Ser or Gln, with
                         the provision that at least one of amino acids 8, 10, 14,
                         15, 19 or 25 is selected from the group consisting of Arg,
                         Pro, Ser and Gln
DISULFID                21..37
                        note = intrachain disulfide bond
SITE                    25
                        note = MISC_FEATURE - Xaa = Lys, Arg, Pro, Ser or Gln, with
                         the provision that at least one of amino acids 8, 10, 14,
                         15, 19 or 25 is selected from the group consisting of Arg,
                         Pro, Ser and Gln
source                  1..37
                        mol_type = protein
                        organism = synthetic construct
SEQUENCE: 93
QEHPNARXYX GANXXGLSXG CFGLXLDRIG SMSGLGC                             37

SEQ ID NO: 94           moltype = AA  length = 37
FEATURE                 Location/Qualifiers
REGION                  1..37
                        note = mutated CNP-37
SITE                    14
                        note = MISC_FEATURE - X is selected from the group
                         consising of Lys, Arg, Pro, Ser and Gln, with the
                         provision that at least one of the amino acids at position
                         14, 15, 19 and 25 is selected from the group consisting of
                         Arg, Pro, Ser and Gln
SITE                    15
                        note = MISC_FEATURE - X is selected from the group
                         consising of Lys, Arg, Pro, Ser and Gln, with the
                         provision that at least one of the amino acids at position
                         14, 15, 19 and 25 is selected from the group consisting of
                         Arg, Pro, Ser and Gln
SITE                    19
                        note = MISC_FEATURE - X is selected from the group
                         consising of Lys, Arg, Pro, Ser and Gln, with the
                         provision that at least one of the amino acids at position
                         14, 15, 19 and 25 is selected from the group consisting of
                         Arg, Pro, Ser and Gln
DISULFID                21..37
                        note = intrachain disulfide bond
SITE                    25
                        note = MISC_FEATURE - X is selected from the group
                         consising of Lys, Arg, Pro, Ser and Gln, with the
                         provision that at least one of the amino acids at position
                         14, 15, 19 and 25 is selected from the group consisting of
                         Arg, Pro, Ser and Gln
source                  1..37
                        mol_type = protein
                        organism = synthetic construct
SEQUENCE: 94
QEHPNARKYK GANXXGLSXG CFGLXLDRIG SMSGLGC                             37

SEQ ID NO: 95           moltype = AA  length = 37
FEATURE                 Location/Qualifiers
REGION                  1..37
                        note = mutated CNP-37
REGION                  14..15
                        note = MISC_FEATURE - Xaa Xaa is selected from the group
                         consisting of Lys Arg, Arg Lys, Lys Pro, Pro Lys, Ser Ser,
                         Arg Ser, Ser Arg, Gln Lys, Gln Arg, Lys Gln, Arg Gln, Arg
                         Arg and Gln Gln
DISULFID                21..37
                        note = intrachain disulfide bond
source                  1..37
                        mol_type = protein
                        organism = synthetic construct
SEQUENCE: 95
QEHPNARKYK GANXXGLSKG CFGLKLDRIG SMSGLGC                             37

SEQ ID NO: 96           moltype = AA  length = 15
FEATURE                 Location/Qualifiers
source                  1..15
                        mol_type = protein
                        organism = Homo sapiens
SEQUENCE: 96
FGLKLDRIGS MSGLG                                                     15
```

-continued

```
SEQ ID NO: 97          moltype = AA  length = 20
FEATURE                Location/Qualifiers
REGION                 1..20
                       note = Artificial random coil
source                 1..20
                       mol_type = protein
                       organism = synthetic construct
SEQUENCE: 97
GGPGGPGPGG PGGPGPGGPG                                          20

SEQ ID NO: 98          moltype = AA  length = 13
FEATURE                Location/Qualifiers
REGION                 1..13
                       note = NPR-C inhibitor
source                 1..13
                       mol_type = protein
                       organism = synthetic construct
SEQUENCE: 98
FGIPMDRIGR NPR                                                 13

SEQ ID NO: 99          moltype = AA  length = 191
FEATURE                Location/Qualifiers
source                 1..191
                       mol_type = protein
                       organism = Homo sapiens
SEQUENCE: 99
FPTIPLSRLF DNAMLRAHRL HQLAFDTYQE FEEAYIPKEQ KYSFLQNPQT SLCFSESIPT  60
PSNREETQQK SNLELLRISL LLIQSWLEPV QFLRSVFANS LVYGASDSNV YDLLKDLEEG  120
IQTLMGRLED GSPRTGQIFK QTYSKFDTNS HNDDALLKNY GLLYCFRKDM DKVETFLRIV  180
QCRSVEGSCG F                                                   191
```

COMBINATION THERAPY WITH CONTROLLED-RELEASE CNP AGONISTS

CROSS-REFERENCE TO RELATED APPLICATIONS

This application is a divisional of U.S. Ser. No. 16/338,185, filed Mar. 29, 2019, which is a national stage entry of PCT/EP2017/074596, filed Sep. 28, 2017, incorporated by reference in its entirety for all purposes, which claims the benefit of EP 16191456.9 filed Sep. 29, 2016.

SEQUENCE LISTING

This application includes sequences in file 586555SEQL-ST.XML of 168908 bytes, created Apr. 11, 2023, which is incorporated by reference.

BACKGROUND

The present invention relates to a combination of a CNP agonist and at least one further biologically active moiety or drug for use in a method for the treatment or prevention of disorders that benefit from stimulating growth, pharmaceutical compositions comprising at least one CNP agonist, preferably controlled-release CNP agonist, wherein the pharmaceutical composition comprises at least one further biologically active moiety or drug, to using these pharmaceutical compositions as a medicament, to their use in the treatment of disorders that benefit from stimulating growth and to methods of preventing or treating a patient having a disorder that benefits from stimulating growth.

Skeletal development starts in the early embryo and continues postnatally until adulthood when peak bone mass is reached. The key process controlling longitudinal growth is endochondral bone formation. This process occurs at growth plates in the axial and appendicular skeleton as chondrocytes proliferate, differentiate, increase in size, synthesize collagen, calcify matrix, and become apoptotic, ultimately leading to the recruitment of osteoblasts that replace the calcified cartilage matrix with bone. Endochondral growth is regulated by endocrine, paracrine, and autocrine factors.

One disorder that benefits from stimulating growth is achondroplasia. Achondroplasia (ACH) is caused by a gain-of-function mutation in fibroblast growth factor receptor 3 (FGFR3) gene. The normal function of FGFR3 is to slow down formation of bone by inhibiting the proliferation and differentiation of chondrocytes, the cells that produce cartilage. The mutation increases the activity of FGFR3, severely limiting bone growth. Growth hormone treatment, directly increasing linear growth by stimulating proliferation of epiphyseal growth plate precursor cells and enhancing local production of IGF-1 followed by clonal expansion of differentiating chondrocytes, has demonstrated moderate improvement of the height velocity of children with achondroplasia without obvious side effects. A greater increase in spinal height, compared to the length of the legs accentuated the existing disproportion. As a result, to restore proportionate adult stature within the normal range, addition of later surgical leg lengthening was proposed (Ramaswami et al. *Pediatric Research* (1999) 46, 435-435).

Binding of CNP to its receptor, natriuretic peptide receptor B (NPR-B) expressed in proliferating and prehypertrophic chondrocytes, inhibits FGFR3 downstream signaling at the level of Raf-1 and thus triggers endochondral growth and skeletal overgrowth, as observed in both mice and humans overexpressing CNP (Lorget et al, The American Journal of Human Genetics 91, 1108-1114, Dec. 7, 2012).

Administration of a CNP variant to normal mice, normal growing monkeys, or achondroplasia mice resulted in growth of the axial and appendicular skeletons (Wendt et al. J Pharmacol Exp Ther 353:132-149, April 2015).

SUMMARY OF THE INVENTION

In summary, there is a need for a more efficacious and safer treatment, which avoids the cardiovascular side effects, such as hypotension.

It is therefore an object of the present invention to provide improved treatments of various growth-related disorders.

This object is achieved with a combination of a CNP agonist and at least one further biologically active moiety or drug for use in a method for the treatment or prevention of disorders that benefit from stimulating growth.

It is a further object of the present invention to provide a pharmaceutical composition comprising at least one CNP agonist, preferably controlled-release CNP agonist, wherein the pharmaceutical composition comprises at least one further biologically active moiety or drug.

It is a further object of the present invention to provide a method of treating or preventing a patient having a disorder that benefits from stimulating growth, the method comprising administering to the patient an effective amount of a combination of a CNP agonist and at least one further biologically active moiety or drug It was surprisingly found that co-treatment, preferably co-administration of at least one CNP agonist, preferably controlled-release CNP agonist, and at least one further biologically active moiety or drug provides beneficial effects in the treatment of certain diseases.

In a preferred embodiment the present invention relates to a combination of a CNP agonist, preferably a controlled-release CNP agonist, and an hGH, preferably a controlled-release hGH, for use in a method for the treatment or prevention of disorders. Accordingly, it also relates to pharmaceutical compositions comprising a CNP agonist, preferably controlled-release agonist, and an hGH, preferably controlled-release hGH and to a method of treating or preventing a patient having a disorder that benefits from stimulating growth, the method comprising administering to the patient an effective amount of a combination of a CNP agonist, preferably a controlled-release CNP agonist, and a hGH, preferably a controlled-release hGH.

A combination of a controlled-release CNP agonist and hGH has resulted in a better response in all treated individuals which provides a suitable treatment also for patients that would not respond to CNP alone. It was further found that a combination of a controlled-release CNP agonist and hGH required lower doses than required for the controlled-release CNP agonist or the hGH alone to achieve the same effect. This is advantageous, because lower doses reduce the risk of side effects.

DETAILED DESCRIPTION

Within the present invention the terms are used having the meaning as follows.

As used herein the term “CNP agonist” refers to any compound that activates natriuretic peptide receptor B (NPR-B) and has an $EC_{50}$ that is at most 50-fold higher than the NPR-B activity of CNP-22 (SEQ ID NO:1).

As used herein the term “controlled-release CNP agonist” refers to any compound, conjugate, crystal or admixture that comprises at least one CNP agonist and from which the at least one CNP agonist is released with a release half-life of at least 6 hours. Accordingly, in general a “controlled-release compound” refers to any compound, conjugate, crystal or admixture that comprises at least one biologically active moiety or drug and from which at least one drug or modified biologically active moiety, preferably drug, is released with a half-life of at least 6 hours.

As used herein the term “stable conjugate” refers to any covalent conjugate of at least one biologically active moiety to another moiety, wherein the at least one biologically active moiety is connected to said other moiety through a stable linkage.

As used herein the term “unit dose” refers to the dose of the pharmaceutical composition comprising at least one CNP agonist or controlled-release CNP agonist and at least one further biologically active moiety or drug to be administered to a patient in one administration.

As used herein the term “release half-life” refers to the time needed until half of all CNP agonist molecules are released from the controlled-release CNP agonist. Such release may for example occur through diffusion, hydrolysis or enzymatic cleavage.

As used herein the term “CNP” refers all CNP polypeptides, preferably from mammalian species, more preferably from human and mammalian species, more preferably from human and murine species, as well as their variants, analogs, orthologs, homologs, and derivatives and fragments thereof, that are characterized by regulating the growth, proliferation and differentiation of cartilaginous growth plate chondrocytes. Preferably, the term “CNP” refers to the CNP polypeptide of SEQ ID NO:24 as well as its variants, homologs and derivatives exhibiting essentially the same biological activity, i.e. regulating the growth, proliferation and differentiation of cartilaginous growth plate chondrocytes. More preferably, the term “CNP” refers to the polypeptide of SEQ ID NO:24.

Figure 1:
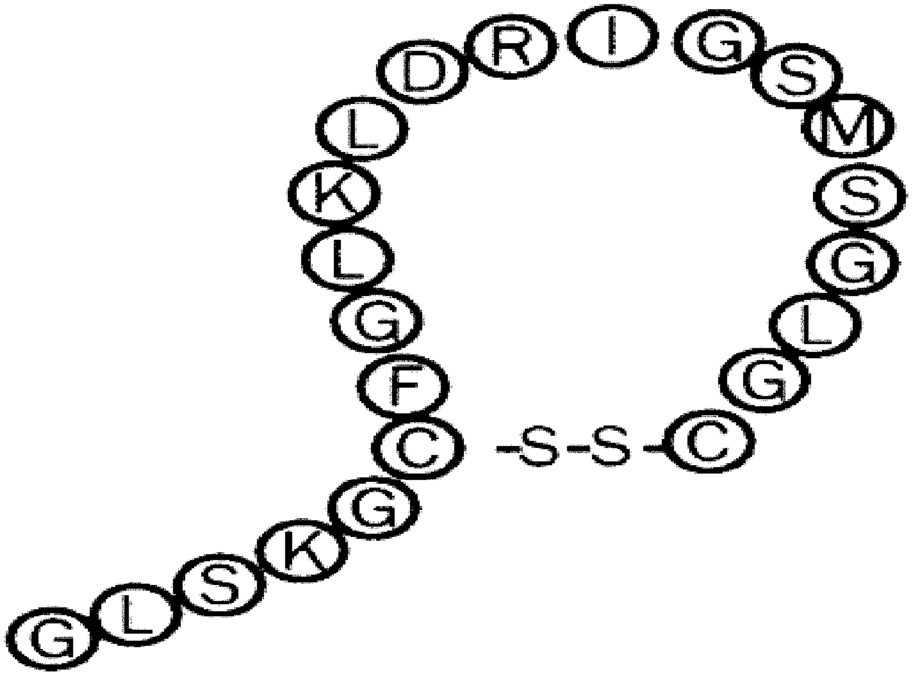
FIG. 1: Structure of CNP according to SEQ ID NO:1.

Naturally occurring CNP-22 (SEQ ID NO: 1) has the following sequence:

GLSKGCFGLKLDRIGSMSGLGC, wherein the cysteines at position 6 and 22 are connected through a disulfide-bridge, as illustrated in FIG. 1.

SEQ ID NO:24 has the following sequence:

LQEHPNARKYKGANKKGLSKGCFGLKLDRIGSMSGLGC, wherein the cysteines at position 22 and 38 are connected through a disulfide-bride.

The term “CNP” also includes all CNP variants, analogs, orthologs, homologs and derivatives and fragments thereof as disclosed in WO 2009/067639 A2 and WO 2010/135541 A2, which are herewith incorporated by reference.

Accordingly, the term “CNP” also refers preferably to the following peptide sequences:

(CNP-53): SEQ ID NO: 2
DLRVDTKSRAAWARLLQEHPNARKYKGANKKGLSKGCFGLKLDRIGSMSG
LGC;

(G-CNP-53): SEQ ID NO: 3
GDLRVDTKSRAAWARLLQEHPNARKYKGANKKGLSKGCFGLKLDRIGSMS
GLGC;

(M-CNP-53): SEQ ID NO: 4
MDLRVDTKSRAAWARLLQEHPNARKYKGANKKGLSKGCFGLKLDRIGSMS
GLGC;

(P-CNP-53): SEQ ID NO: 5
PDLRVDTKSRAAWARLLQEHPNARKYKGANKKGLSKGCFGLKLDRIGSMS
GLGC;

(CNP-53 M48N): SEQ ID NO. 6
DLRVDTKSRAAWARLLQEHPNARKYKGANKKGLSKGCFGLKLDRIGSNSG
LGC;

(CNP-53 Δ15-31): SEQ ID NO: 7
DLRVDTKSRAAWARGLSKGCFGLKLDRIGSMSGLGC;

(CNP-52): SEQ ID NO: 8
LRVDTKSRAAWARLLQEHPNARKYKGANKKGLSKGCFGLKLDRIGSMSGL
GC;

(CNP-51): SEQ ID NO: 9
RVDTKSRAAWARLLQEHPNARKYKGANKKGLSKGCFGLKLDRIGSMSGLG
C;

(CNP-50): SEQ ID NO: 10
VDTKSRAAWARLLQEHPNARKYKGANKKGLSKGCFGLKLDRIGSMSGLG
C;

(CNP-49): SEQ ID NO: 11
DTKSRAAWARLLQEHPNARKYKGANKKGLSKGCFGLKLDRIGSMSGLGC;

(CNP-48): SEQ ID NO: 12
TKSRAAWARLLQEHPNARKYKGANKKGLSKGCFGLKLDRIGSMSGLGC;

(CNP-47): SEQ ID NO: 13
KSRAAWARLLQEHPNARKYKGANKKGLSKGCFGLKLDRIGSMSGLGC;

(CNP-46): SEQ ID NO: 14
SRAAWARLLQEHPNARKYKGANKKGLSKGCFGLKLDRIGSMSGLGC;

(CNP-45): SEQ ID NO: 15
RAAWARLLQEHPNARKYKGANKKGLSKGCFGLKLDRIGSMSGLGC;

(CNP-44): SEQ ID NO: 16
AAWARLLQEHPNARKYKGANKKGLSKGCFGLKLDRIGSMSGLGC;

-continued (CNP-44 Δ14-22): SEQ ID NO: 17
AAWARLLQEHPNAGLSKGCFGLKLDRIGSMSGLGC;

(CNP-44 Δ15-22): SEQ ID NO: 18
AAWARLLQEHPNARGLSKGCFGLKLDRIGSMSGLGC;

(CNP-43): SEQ ID NO: 19
AWARLLQEHPNARKYKGANKKGLSKGCFGLKLDRIGSMSGLGC;

(CNP-42): SEQ ID NO: 20
WARLLQEHPNARKYKGANKKGLSKGCFGLKLDRIGSMSGLGC;

(CNP-41): SEQ ID NO: 21
ARLLQEHPNARKYKGANKKGLSKGCFGLKLDRIGSMSGLGC;

(CNP-40): SEQ ID NO: 22
RLLQEHPNARKYKGANKKGLSKGCFGLKLDRIGSMSGLGC;

(CNP-39): SEQ ID NO: 23
LLQEHPNARKYKGANKKGLSKGCFGLKLDRIGSMSGLGC;

(CNP-38): SEQ ID NO: 24
LQEHPNARKYKGANKKGLSKGCFGLKLDRIGSMSGLGC;

(CNP-37): SEQ ID NO: 25
QEHPNARKYKGANKKGLSKGCFGLKLDRIGSMSGLGC;

(CNP-37 Q1pQ, wherein pQ = pyroglutamate): SEQ ID NO: 26
pQEHPNARKYKGANKKGLSKGCFGLKLDRIGSMSGLGC;

(G-CNP-37): SEQ ID NO: 27
GQEHPNARKYKGANKKGLSKGCFGLKLDRIGSMSGLGC;

(P-CNP-37): SEQ ID NO: 28
PQEHPNARKYKGANKKGLSKGCFGLKLDRIGSMSGLGC;

(M-CNP-37): SEQ ID NO: 29
MQEHPNARKYKGANKKGLSKGCFGLKLDRIGSMSGLGC;

(PG-CNP-37; vosoritide): SEQ ID NO: 30
PGQEHPNARKYKGANKKGLSKGCFGLKLDRIGSMSGLGC;

(MG-CNP-37): SEQ ID NO: 31
MGQEHPNARKYKGANKKGLSKGCFGLKLDRIGSMSGLGC;

(CNP-37 M32N): SEQ ID NO: 32
QEHPNARKYKGANKKGLSKGCFGLKLDRIGSNSGLGC;

(G-CNP-37 M32N): SEQ ID NO: 33
GQEHPNARKYKGANKKGLSKGCFGLKLDRIGSNSGLGC;

(G-CNP-37 K14Q): SEQ ID NO: 34
GQEHPNARKYKGANQKGLSKGCFGLKLDRIGSMSGLGC;

(G-CNP-37 K14P): SEQ ID NO: 35
GQEHPNARKYKGANPKGLSKGCFGLKLDRIGSMSGLGC;

(G-CNP-37 K14Q, Δ15): SEQ ID NO: 36
GQEHPNARKYKGANQGLSKGCFGLKLDRIGSMSGLGC;

-continued (G-CNP-37 K14Q, K15Q): SEQ ID NO: 37
GQEHPNARKYKGANQQGLSKGCFGLKLDRIGSMSGLGC;

(CNP-36): SEQ ID NO: 38
EHPNARKYKGANKKGLSKGCFGLKLDRIGSMSGLGC;

(CNP-35): SEQ ID NO: 39
HPNARKYKGANKKGLSKGCFGLKLDRIGSMSGLGC;

(CNP-34): SEQ ID NO: 40
PNARKYKGANKKGLSKGCFGLKLDRIGSMSGLGC;

(CNP-33): SEQ ID NO: 41
NARKYKGANKKGLSKGCFGLKLDRIGSMSGLGC;

(CNP-32): SEQ ID NO: 42
ARKYKGANKKGLSKGCFGLKLDRIGSMSGLGC;

(CNP-31): SEQ ID NO: 43
RKYKGANKKGLSKGCFGLKLDRIGSMSGLGC;

(CNP-30): SEQ ID NO: 44
KYKGANKKGLSKGCFGLKLDRIGSMSGLGC;

(CNP-29): SEQ ID NO: 45
YKGANKKGLSKGCFGLKLDRIGSMSGLGC;

(CNP-28): SEQ ID NO: 46
KGANKKGLSKGCFGLKLDRIGSMSGLGC;

(GHKSEVAHRF-CNP-28): SEQ ID NO: 47
GHKSEVAHRFKGANKKGLSKGCFGLKLDRIGSMSGLGC;

(CNP-27): SEQ ID NO: 48
GANKKGLSKGCFGLKLDRIGSMSGLGC;

(CNP-27 K4Q, K5Q): SEQ ID NO: 49
GANQQGLSKGCFGLKLDRIGSMSGLGC;

(CNP-27 K4R, K5R): SEQ ID NO: 50
GANRRGLSKGCFGLKLDRIGSMSGLGC;

(CNP-27 K4P, K5R): SEQ ID NO: 51
GANPRGLSKGCFGLKLDRIGSMSGLGC;

(CNP-27 K4S, K5S): SEQ ID NO: 52
GANSSGLSKGCFGLKLDRIGSMSGLGC;

(CNP-27 K4P, K5R): SEQ ID NO: 53
GANGANPRGLSRGCFGLKLDRIGSMSGLGC;

(CNP-27 K4R, K5R, K9R): SEQ ID NO: 54
GANRRGLSRGCFGLKLDRIGSMSGLGC;

(CNP-27 K4R, K5R, K9R, M22N): SEQ ID NO: 55
GANRRGLSRGCFGLKLDRIGSNSGLGC;

(P-CNP-27 K4R, K5R, K9R): SEQ ID NO: 56
PGANRRGLSRGCFGLKLDRIGSMSGLGC;

-continued (M-CNP-27 K4R, K5R, K9R):
SEQ ID NO: 57
MGANRRGLSRGCFGLKLDRIGSMSGLGC;

(HSA fragment-CNP-27):
SEQ ID NO: 58
GHKSEVAHRFKGANKKGLSKGCFGLKLDRIGSMSGLG;

(HSA fragment-CNP-27 M22N):
SEQ ID NO: 59
GHKSEVAHRFKGANKKGLSKGCFGLKLDRIGSNSGLGC;

(M-HSA fragment-CNP-27):
SEQ ID NO: 60
MGHKSEVAHRFKGANKKGLSKGCFGLKLDRIGSMSGLGC;

(P-HSA fragment-CNP-27):
SEQ ID NO: 61
PGHKSEVAHRFKGANKKGLSKGCFGLKLDRIGSMSGLGC;

(CNP-26):
SEQ ID NO: 62
ANKKGLSKGCFGLKLDRIGSMSGLGC;

(CNP-25):
SEQ ID NO: 63
NKKGLSKGCFGLKLDRIGSMSGLGC;

(CNP-24):
SEQ ID NO: 64
KKGLSKGCFGLKLDRIGSMSGLGC;

(CNP-23):
SEQ ID NO: 65
KGLSKGCFGLKLDRIGSMSGLGC;

(R-CNP-22):
SEQ ID NO: 66
RGLSKGCFGLKLDRIGSMSGLGC;

(ER-CNP-22):
SEQ ID NO: 67
ERGLSKGCFGLKLDRIGSMSGLGC;

(R-CNP-22 K4R):
SEQ ID NO: 68
RGLSRGCFGLKLDRIGSMSGLGC;

(ER-CNP-22 4KR):
SEQ ID NO: 69
ERGLSRGCFGLKLDRIGSMSGLGC;

(RR-CNP-22):
SEQ ID NO: 70
RRGLSRGCFGLKLDRIGSMSGLGC;

(HRGP fragment-CNP-22):
SEQ ID NO: 71
GHHSHEQHPHGANQQGLSKGCFGLKLDRIGSMSGLGC;

(HRGP fragment-CNP-22):
SEQ ID NO. 72
GAHHPHEHDTHGANQQGLSKGCFGLKLDRIGSMSGLGC;

(HRGP fragment-CNP-22):
SEQ ID NO: 73
GHHSHEQHPHGANPRGLSKGCFGLKLDRIGSMSGLGC;

($IgG_1(F_c)$ fragment-CNP-22):
SEQ ID NO: 74
GQPREPQVYTLPPSGLSKGCFGLKLDRIGSMSGLGC;

(HSA fragment-CNP-22):
SEQ ID NO: 75
GQHKDDNPNLPRGANPRGLSKGCFGLKLDRIGSMSGLGC;

(HSA fragment-CNP-22):
SEQ ID NO: 76
GERAFKAWAVARLSQGLSKGCFGLKLDRIGSMSGLGC;

-continued (osteocrin NPR C inhibitor fragment-CNP22):
SEQ ID NO: 77
FGIPMDRIGRNPRGLSKGCFGLKLDRIGSMSGLGC;

(FGF2 heparin-binding domain fragment-CNP22):
SEQ ID NO: 78
GKRTGQYKLGSKTGPGPKGLSKGCFGLKLDRIGSMSGLGC;

($IgG_1(F_c)$ fragment-CNP-22 K4R):
SEQ ID NO: 79
GQPREPQVYTGANQQGLSRGCFGLKLDRIGSMSGLGC;

(HSA fragment-CNP-22 K4R):
SEQ ID NO: 80
GVPQVSTSTGANQQGLSRGCFGLKLDRIGSMSGLGC;

(fibronectin fragment-CNP-22 K4R):
SEQ ID NO: 81
GQPSSSSQSTGANQQGLSRGCFGLKLDRIGSMSGLGC;

(fibronectin fragment-CNP-22 K4R):
SEQ ID NO: 82
GQTHSSGTQSGANQQGLSRGCFGLKLDRIGSMSGLGC;

(fibronectin fragment-CNP-22 K4R):
SEQ ID NO: 83
GSTGQWHSESGANQQGLSRGCFGLKLDRIGSMSGLGC;

(zinc finger fragment-CNP-22 K4R):
SEQ ID NO: 84
GSSSSSSSSGANQQGLSRGCFGLKLDRIGSMSGLGC;

(CNP-21):
SEQ ID NO: 85
LSKGCFGLKLDRIGSMSGLGC;

(CNP-20):
SEQ ID NO: 86
SKGCFGLKLDRIGSMSGLGC;

(CNP-19):
SEQ ID NO: 87
KGCFGLKLDRIGSMSGLGC;

(CNP-18):
SEQ ID NO: 88
GCFGLKLDRIGSMSGLGC;

(CNP-17):
SEQ ID NO: 89
CFGLKLDRIGSMSGLGC;

(BNP fragment-CNP-17-BNP fragment):
SEQ ID NO: 90
SPKMVQGSGCFGLKLDRIGSMSGLGCKVLRRH;

(CNP-38 L1G):
SEQ ID NO: 91
GQEHPNARKYKGANKKGLSKGCFGLKLDRIGSMSGLGC;

(Ac-CNP-37; wherein Ac = acetyl):
SEQ ID NO: 92
Ac-QEHPNARKYKGANKKGLSKGCFGLKLDRIGSMSGLGC;

It is understood that the equivalents of the cysteines in positions 22 and 38 of SEQ ID NO:24 are also connected through a disulfide-bridge in SEQ ID NOs: 2 to 92.

More preferably, the term “CNP” refers to the sequence of SEQ ID: NOs 2, 19, 20, 21, 22, 23, 24, 25, 26, 30, 32, 38, 39, 40, 41, 42, 43, 91, 92. Even more preferably, the term “CNP” refers to the sequence of SEQ ID: NOs 23, 24, 25, 26, 38, 39, 91 and 92. In a particularly preferred embodiment the term “CNP” refers to the sequence of SEQ ID NO:24. In another preferred embodiment the term “CNP” refers to the sequence of SEQ ID NO:26.

In another preferred embodiment the term "CNP" refers to a sequence of SEQ ID NO:93

$QEHPNARX_1YX_2GANX_3X_4GLSX_5GCFGLX_6LDRIGSMSGLGC$, wherein $X_1$, $X_2$, $X_3$, $X_4$, $X_5$ and $X_6$ are independently of each other selected from the group consisting of K, R, P, S and Q, with the provision that at least one of $X_1$, $X_2$, $X_3$, $X_4$, $X_5$ and $X_6$ is selected from the group consisting of R, P, S and Q; preferably $X_1$, $X_2$, $X_3$, $X_4$, $X_5$ and $X_6$ are selected from the group consisting of K and R, with the provision that at least one of $X_1$, $X_2$, $X_3$, $X_4$, $X_5$ and $X_6$ is R;

even more preferably to a sequence of SEQ ID NO:94

$QEHPNARKYKGANX_1X_2GLSX_3GCFGLX_4LDRIGSMSGLGC$, wherein $X_1$, $X_2$, $X_3$ and $X_4$ are independently of each other selected from the group consisting of K, R, P, S and Q, with the provision that at least one of $X_1$, $X_2$, $X_3$ and $X_4$ is selected from the group consisting of R, P, S and Q; preferably $X_1$, $X_2$, $X_3$ and $X_4$ are selected from K and R, with the provision that at least one of $X_1$, $X_2$, $X_3$ and $X_4$ is R;

and most preferably to a sequence of SEQ ID NO:95

$QEHPNARKYKGANX_1X_2GLSKGCFGLKLDRIGSMSGLGC$, wherein $X_1X_2$ are selected from the group consisting of KR, RK, KP, PK, SS, RS, SR, QK, QR, KQ, RQ, RR and QQ.

It is understood that in all CNP sequences given in this specification the equivalents of the cysteines in positions 22 and 38 of SEQ ID NO:24 are also connected through a disulfide-bridge in SEQ ID NOs: 93 to 95.

It is understood that the present invention also encompasses CNP variants in which any one or more, up to all, residues susceptible to deamidation or a deamidation-like reaction (e.g., isomerization) may be converted to other residue(s) via deamidation or a deamidation-like reaction to any extent, up to 100% conversion per converted residue. In certain embodiments, the disclosure encompasses CNP variants in which:

(1) any one or more, up to all, asparagine (Asn/N) residues may be converted to aspartic acid or aspartate, and/or to isoaspartic acid or isoaspartate, via deamidation up to about 5%, 10%, 20%, 30%, 40%, 50%, 60%, 70%, 80%, 90% or 100% conversion per converted residue; or (2) any one or more, up to all, glutamine (Gln/Q) residues may be converted to glutamic acid or glutamate, and/or to isoglutamic acid or isoglutamate, via deamidation up to about 5%, 10%, 20%, 30%, 40%, 50%, 60%, 70%, 80%, 90% or 100% conversion per converted residue; or (3) any one or more, up to all, aspartic acid or aspartate (Asp/D) residues may be converted to isoaspartic acid or isoaspartate via a deamidation-like reaction (also called isomerization) up to about 5%, 10%, 20%, 30%, 40%, 50%, 60%, 70%, 80%, 90% or 100% conversion per converted residue; or (4) any one or more, up to all, glutamic acid or glutamate (Glu/E) residues may be converted to isoglutamic acid or isoglutamate via a deamidation-like reaction (also called isomerization) up to about 5%, 10%, 20%, 30%, 40%, 50%, 60%, 70%, 80%, 90% or 100% conversion per converted residue;

(5) the N-terminal glutamine (if present) may be converted into pyroglutamate up to about 5%, 10%, 20%, 30%, 40%, 50%, 60%, 70%, 80%, 90% or 100% conversion; or (5) a combination of the above.

As used herein, the term "CNP polypeptide variant" refers to a polypeptide from the same species that differs from a reference CNP polypeptide. Preferably, such reference CNP polypeptide sequence is the sequence of SEQ ID NO:24. Generally, differences are limited so that the amino acid sequence of the reference and the variant are closely similar overall and, in many regions, identical. Preferably, CNP polypeptide variants are at least 70%, 80%, 90%, or 95% identical to a reference CNP polypeptide, preferably the CNP polypeptide of SEQ ID NO:24. By a polypeptide having an amino acid sequence at least, for example, 95% "identical" to a query amino acid sequence, it is intended that the amino acid sequence of the subject polypeptide is identical to the query sequence except that the subject polypeptide sequence may include up to five amino acid alterations per each 100 amino acids of the query amino acid sequence. These alterations of the reference sequence may occur at the amino (N-terminal) or carboxy terminal (C-terminal) positions of the reference amino acid sequence or anywhere between those terminal positions, interspersed either individually among residues in the reference sequence or in one or more contiguous groups within the reference sequence. The query sequence may be an entire amino acid sequence of the reference sequence or any fragment specified as described herein. Preferably, the query sequence is the sequence of SEQ ID NO:24.

Such CNP polypeptide variants may be naturally occurring variants, such as naturally occurring allelic variants encoded by one of several alternate forms of a CNP occupying a given locus on a chromosome or an organism, or isoforms encoded by naturally occurring splice variants originating from a single primary transcript. Alternatively, a CNP polypeptide variant may be a variant that is not known to occur naturally and that can be made mutagenesis techniques known in the art.

It is known in the art that one or more amino acids may be deleted from the N-terminus and/or C-terminus of a bioactive peptide or protein without substantial loss of biological function. Such N- and/or C-terminal deletions are also encompassed by the term CNP polypeptide variant.

It is also recognized by one of ordinary skill in the art that some amino acid sequences of CNP polypeptides can be varied without significant effect of the structure or function of the peptide. Such mutants include deletions, insertions, inversions, repeats, and substitutions selected according to general rules known in the art so as to have little effect on activity. For example, guidance concerning how to make phenotypically silent amino acid substitutions is provided in Bowie et al. (1990), Science 247:1306-1310, which is hereby incorporated by reference in its entirety, wherein the authors indicate that there are two main approaches for studying the tolerance of the amino acid sequence to change.

The term CNP polypeptide also encompasses all CNP polypeptides encoded by CNP analogs, orthologs, and/or species homologs. As used herein, the term "CNP analog" refers to CNP of different and unrelated organisms which perform the same functions in each organism but which did not originate from an ancestral structure that the organisms' ancestors had in common. Instead, analogous CNPs arose separately and then later evolved to perform the same or similar functions. In other words, analogous CNP polypeptides are polypeptides with quite different amino acid sequences but that perform the same biological activity, namely regulating the growth, proliferation and differentiation of cartilaginous growth plate chondrocytes.

As used herein the term “CNP ortholog” refers to CNP within two different species which sequences are related to each other via a common homologous CNP in an ancestral species, but which have evolved to become different from each other.

As used herein, the term “CNP homolog” refers to CNP of different organisms which perform the same functions in each organism and which originate from an ancestral structure that the organisms' ancestors had in common. In other words, homologous CNP polypeptides are polypeptides with quite similar amino acid sequences that perform the same biological activity, namely regulating the growth, proliferation and differentiation of cartilaginous growth plate chondrocytes. Preferably, CNP polypeptide homologs may be defined as polypeptides exhibiting at least 40%, 50%, 60%, 70%, 80%, 90% or 95% identity to a reference CNP polypeptide, preferably the CNP polypeptide of SEQ ID NO:24.

Thus, a CNP polypeptide according to the invention may be, for example: (i) one in which at least one of the amino acids residues is substituted with a conserved or non-conserved amino acid residue, preferably a conserved amino acid residue, and such substituted amino acid residue may or may not be one encoded by the genetic code; and/or (ii) one in which at least one of the amino acid residues includes a substituent group; and/or (iii) one in which the CNP polypeptide is fused with another compound, such as a compound to increase the half-life of the polypeptide (for example, polyethylene glycol); and/or (iv) one in which additional amino acids are fused to the CNP polypeptide, such as an IgG Fc fusion region peptide or leader or secretory sequence or a sequence which is employed for purification of the above form of the polypeptide or a pre-protein sequence.

As used herein, the term “CNP polypeptide fragment” refers to any peptide comprising a contiguous span of a part of the amino acid sequence of a CNP polypeptide, preferably the polypeptide of SEQ ID NO:24.

More specifically, a CNP polypeptide fragment comprises at least 6, such as at least 8, at least 10 or at least 17 consecutive amino acids of a CNP polypeptide, more preferably of the polypeptide of SEQ ID NO:24. A CNP polypeptide fragment may additionally be described as sub-genuses of CNP polypeptides comprising at least 6 amino acids, wherein “at least 6” is defined as any integer between 6 and the integer representing the C-terminal amino acid of a CNP polypeptide, preferably of the polypeptide of SEQ ID No:24. Further included are species of CNP polypeptide fragments at least 6 amino acids in length, as described above, that are further specified in terms of their N-terminal and C-terminal positions. Also encompassed by the term “CNP polypeptide fragment” as individual species are all CNP polypeptide fragments, at least 6 amino acids in length, as described above, that may be particularly specified by a N-terminal and C-terminal position. That is, every combination of a N-terminal and C-terminal position that a fragment at least 6 contiguous amino acid residues in length could occupy, on any given amino acid sequence of a CNP polypeptide, preferably the CNP polypeptide of SEQ ID: NO24 is included in the present invention.

The term “CNP” also includes poly(amino acid) conjugates which have a sequence as described above, but having a backbone that comprises both amide and non-amide linkages, such as ester linkages, like for example depsipeptides. Depsipeptides are chains of amino acid residues in which the backbone comprises both amide (peptide) and ester bonds. Accordingly, the term “side chain” as used herein refers either to the moiety attached to the alpha-carbon of an amino acid moiety, if the amino acid moiety is connected through amine bonds such as in polypeptides, or to any carbon atom-comprising moiety attached to the backbone of a poly(amino acid) conjugate, such as for example in the case of depsipeptides. Preferably, the term “CNP” refers to polypeptides having a backbone formed through amide (peptide) bonds.

As the term CNP includes the above-described variants, analogs, orthologs, homologs, derivatives and fragments of CNP, all references to specific positions within a reference sequence also include the equivalent positions in variants, analogs, orthologs, homologs, derivatives and fragments of a CNP moiety, even if not specifically mentioned.

As used herein, the term “ring moiety” refers to the stretch of consecutive amino acid residues of the CNP drug or moiety that is located between two cysteine residues that form an intramolecular disulphide bridge or between homologous amino acid residues which are connected through a chemical linker. Preferably, the ring moiety is located between two cysteine residues that form an intramolecular disulphide bridge. These two cysteines correspond to the cysteines at position 22 and position 38 in the sequence of CNP-38 (SEQ ID NO:24). Accordingly, amino acids 23 to 37 are located in said ring moiety, if the CNP drug or moiety has the sequence of CNP-22.

Independently of the length of the CNP moiety, the sequence of the ring moiety of wild-type CNP is FGLKLDRIGSMSGLG (SEQ ID NO:96).

As described above, the term “CNP” relates to CNP drugs or moieties having different numbers of amino acids. The person skilled in the art understands that in CNP drugs or moieties of different lengths the positions of equivalent amino acids vary and the skilled artisan will have no difficulty identifying the two cysteines forming the disulphide bridge or their two homologous amino acid residues connected to each other through a chemical linker in longer, shorter and/or otherwise modified CNP versions.

As the term CNP includes the above-described variants, analogs, orthologs, homologs, derivatives and fragments of CNP, the term “ring moiety” also includes the corresponding variants, analogs, orthologs, homologs, derivatives and fragments of the sequence of SEQ ID NO:96. Accordingly, all references to specific positions within a reference sequence also include the equivalent positions in variants, analogs, orthologs, homologs, derivatives and fragments of a CNP moiety, even if not explicitly mentioned.

As used herein, the term “random coil” refers to a peptide or protein adopting/having/forming, preferably having, a conformation which substantially lacks a defined secondary and tertiary structure as determined by circular dichroism spectroscopy performed in aqueous buffer at ambient temperature, and pH 7.4. Preferably, ambient temperature is about 20° C., i.e. between 18° C. and 22° C., most preferably ambient temperature is 20° C.

As used herein the term “micelle” means an aggregate of amphiphilic molecules dispersed in a liquid colloid. In aqueous solution a typical micelle forms an aggregate with the hydrophilic moiety of the surfactant molecules facing the surrounding solvent and the hydrophobic moiety of the surfactant molecule facing inwards, also called “normal-phase micelle". "Invers micelles" have the hydrophilic moiety facing inwards and the hydrophobic moiety facing the surrounding solvent.

As used herein the term "liposome" refers to a vesicle, preferably a spherical vesicle, having at least one lipid bilayer. Preferably, liposomes comprise phospholipids, even more preferably phosphatidylcholine. The term "liposome" refers to various structures and sizes, such as, for example, to multilamellar liposome vesicles (MLV) having more than one concentric lipid bilayer with an average diameter of 100 to 1000 nm, small unilamellar liposome vesicles (SUV) having one lipid bilayer and an average diameter of 25 to 100 nm, large unilamellar liposome vesicles (LUV) having one lipid bilayer and an average diameter of about 1000 μm and giant unilamellar vesicles (GUV) having one lipid bilayer and an average diameter of 1 to 100 μm. The term "liposome" also includes elastic vesicles such as transferosomes and ethosomes, for example.

As used herein the term "aquasome" refers to spherical nanoparticles having a diameter of 60 to 300 nm that comprise at least three layers of self-assembled structure, namely a solid phase nanocrystalline core coated with an oligomeric film to which drug molecules are adsorbed with or without modification of the drug.

As used herein the term "ethosome" refers to lipid vesicles comprising phospholipids and ethanol and/or isopropanol in relatively high concentration and water, having a size ranging from tens of nanometers to micrometers.

As used herein the term "LeciPlex" refers to positively charged phospholipid-based vesicular system which comprises soy PC, a cationic agent, and a bio-compatible solvent like PEG 300, PEG 400, diethylene glycol monoethyl ether, tetrahydrofurfuryl alcohol polyethylene glycol ether or 2-pyrrolidone or N-methyl-2-pyrrolidone.

As used herein the term "niosome" refers to unilamellar or multilamellar vesicles comprising non-ionic surfactants.

As used herein the term "pharmacosome" refers to ultrafine vesicular, micellar or hexagonal aggregates from lipids covalently bound to biologically active moieties.

As used herein the term "proniosome" refers to dry formulations of surfactant-coated carrier which on rehydration and mild agitation gives niosomes.

As used herein the term "polymersome" refers to an artificial spherical vesicle comprising a membrane formed from amphiphilic synthetic block copolymers and may optionally comprise an aqueous solution in its core. A polymersome has a diameter ranging from 50 nm to 5 μm and larger. The term also includes syntosomes, which are polymersomes engineered to comprise channels that allow certain chemicals to pass through the membrane into or out of the vesicle.

As used herein the term "sphingosome" refers to a concentric, bilayered vesicle in which an aqueous volume is entirely enclosed by a membranous lipid bilayer mainly composed of natural or synthetic sphingolipid.

As used herein the term "transferosome" refers to ultraflexible lipid vesicles comprising an aqueous core that are formed from a mixture of common polar and suitable edge-activated lipids which facilitate the formation of highly curved bilayers which render the transferosome highly deformable.

As used herein the term "ufasome" refers to a vesicle comprising unsaturated fatty acids.

As used herein the term "aptamer" refers to an oligonucleotide or peptide molecule that binds a specific molecule. The term "aptamer" includes DNA, RNA, XNA and peptide aptamers.

As used herein, the term "oligonucleotide" refers to a short nucleic acid polymer of up to 100 bases.

As used herein the term "polypeptide" refers to a peptide comprising up to and including 50 amino acid monomers.

As used herein the term "protein" refers to a peptide of more than 50 amino acid residues. Preferably a protein comprises at most 20000 amino acid residues, such as at most 15000 amino acid residues, such as at most 10000 amino acid residues, such as at most 5000 amino acid residues, such as at most 4000 amino acid residues, such as at most 3000 amino acid residues, such as at most 2000 amino acid residues, such as at most 1000 amino acid residues.

As used herein the terms "small molecule drug" and "small molecule biologically active moiety" refer to drugs and biologically active moieties that are organic compounds having a molecular weight of no more than 1 kDa, such as up to 900 Da.

As used herein the term "natural product" refers to purified organic compounds isolated from natural sources that are produced by the pathways of primary or secondary metabolism.

As used herein the term "physiological conditions" refers to an aqueous buffer at pH 7.4, 37° C.

As used herein the term "pharmaceutical composition" refers to a composition containing one or more active ingredients, such as for example the CNP agonist or controlled-release CNP agonists of the present invention, and one or more excipients, as well as any product which results, directly or indirectly, from combination, complexation or aggregation of any two or more of the ingredients of the composition, or from dissociation of one or more of the ingredients, or from other types of reactions or interactions of one or more of the ingredients. Accordingly, the pharmaceutical compositions of the present invention encompass any composition made by admixing one or more CNP agonist or controlled-release CNP agonists of the present invention and a pharmaceutically acceptable excipient.

As used herein the term "liquid composition" refers to a mixture comprising water-soluble CNP agonist or controlled-release CNP agonist, at least one water-soluble further drug or biologically active moiety and one or more solvents, such as water.

The term "suspension composition" relates to a mixture comprising water-insoluble controlled-release CNP agonist and/or water-insoluble further drug or biologically active moiety and one or more solvents, such as water.

As used herein, the term "dry composition" means that a pharmaceutical composition is provided in a dry form. Suitable methods for drying are spray-drying and lyophilization, i.e. freeze-drying. Such dry composition of prodrug has a residual water content of a maximum of 10%, preferably less than 5% and more preferably less than 2%, determined according to Karl Fischer. Preferably, the pharmaceutical composition of the present invention is dried by lyophilization.

The term "drug" as used herein refers to a substance used in the treatment, cure, prevention, or diagnosis of a disease or used to otherwise enhance physical or mental well-being. If a drug is conjugated to another moiety, the moiety of the resulting product that originated from the drug is referred to as "biologically active moiety".

As used herein the term "prodrug" refers to a biologically active moiety reversibly and covalently connected to a specialized protective group through a reversible prodrug linker moiety which is a linker moiety comprising a reversible linkage with the biologically active moiety and wherein the specialized protective group alters or eliminates undesirable properties in the parent molecule. This also includes the enhancement of desirable properties in the drug and the suppression of undesirable properties. The specialized non-toxic protective group is referred to as “carrier”. A prodrug releases the reversibly and covalently bound biologically active moiety in the form of its corresponding drug. In other words, a prodrug is a conjugate comprising a biologically active moiety which is covalently and reversibly conjugated to a carrier moiety via a reversible prodrug linker moiety, which covalent and reversible conjugation of the carrier to the reversible prodrug linker moiety is either directly or through a spacer. Such conjugate releases the formerly conjugated biologically active moiety in the form of a free drug.

A “biodegradable linkage” or a “reversible linkage” is a linkage that is hydrolytically degradable, i.e. cleavable, in the absence of enzymes under physiological conditions (aqueous buffer at pH 7.4, 37° C.) with a half-life ranging from one hour to six months, preferably from one hour to four months, even more preferably from one hour to three months, even more preferably from one hour to two months, even more preferably from one hour to one month. Accordingly, a stable linkage is a linkage having a half-life under physiological conditions (aqueous buffer at pH 7.4, 37° C.) of more than six months.

Accordingly, a “reversible prodrug linker moiety” is a moiety which is covalently conjugated to a biologically active moiety, such as a CNP agonist moiety, through a reversible linkage and is also covalently conjugated to a carrier moiety, such as —Z or —Z', wherein the covalent conjugation to said carrier moiety is either directly or through a spacer moiety, such as $-L^2-$. Preferably the linkage between —Z or —Z' and $-L^2-$ is a stable linkage.

As used herein, the term “traceless prodrug linker” means a reversible prodrug linker which upon cleavage releases the drug in its free form. As used herein, the term “free form” of a drug means the drug in its unmodified, pharmacologically active form.

As used herein, the terms “effective amount” and “pharmacologically effective amount” refers to a dosage that is medically effective.

As used herein, the term “excipient” refers to a diluent, adjuvant, or vehicle with which the therapeutic, such as a drug or prodrug, is administered. Such pharmaceutical excipient can be sterile liquids, such as water and oils, including those of petroleum, animal, vegetable or synthetic origin, including but not limited to peanut oil, soybean oil, mineral oil, sesame oil and the like. Water is a preferred excipient when the pharmaceutical composition is administered orally. Saline and aqueous dextrose are preferred excipients when the pharmaceutical composition is administered intravenously. Saline solutions and aqueous dextrose and glycerol solutions are preferably employed as liquid excipients for injectable solutions. Suitable pharmaceutical excipients include starch, glucose, lactose, sucrose, mannitol, trehalose, gelatin, malt, rice, flour, chalk, silica gel, sodium stearate, glycerol monostearate, talc, sodium chloride, dried skim milk, glycerol, propylene, glycol, water, ethanol and the like. The pharmaceutical composition, if desired, can also contain minor amounts of wetting or emulsifying agents, pH buffering agents, like, for example, acetate, succinate, tris, carbonate, phosphate, HEPES (4-(2-hydroxyethyl)-1-piperazineethanesulfonic acid), MES (2-(N-morpholino)ethanesulfonic acid), or can contain detergents, like Tween, poloxamers, poloxamines, CHAPS, Igepal, or amino acids like, for example, glycine, lysine, or histidine. These pharmaceutical compositions can take the form of solutions, suspensions, emulsions, tablets, pills, capsules, powders, sustained-release formulations and the like. The pharmaceutical composition can be formulated as a suppository, with traditional binders and excipients such as triglycerides. Oral formulation can include standard excipients such as pharmaceutical grades of mannitol, lactose, starch, magnesium stearate, sodium saccharine, cellulose, magnesium carbonate, etc. Such compositions will contain a therapeutically effective amount of the drug or biologically active moiety, together with a suitable amount of excipient so as to provide the form for proper administration to the patient. The formulation should suit the mode of administration.

As used herein, the term “reagent” means a chemical compound which comprises at least one functional group for reaction with the functional group of another chemical compound or drug. It is understood that a drug comprising a functional group (such as a primary or secondary amine or hydroxyl functional group) is also a reagent.

As used herein, the term “moiety” means a part of a molecule, which lacks one or more atom(s) compared to the corresponding reagent. If, for example, a reagent of the formula “H—X—H” reacts with another reagent and becomes part of the reaction product, the corresponding moiety of the reaction product has the structure “H—X—” or “—X—”, whereas each “—” indicates attachment to another moiety. Accordingly, a biologically active moiety is released from a prodrug as a drug.

It is understood that if the sequence or chemical structure of a group of atoms is provided which group of atoms is attached to two moieties or is interrupting a moiety, said sequence or chemical structure can be attached to the two moieties in either orientation, unless explicitly stated otherwise. For example, a moiety “—C(O)N($R^1$)—” can be attached to two moieties or interrupting a moiety either as “—C(O)N($R^1$)—” or as “—N($R^1$)C(O)—”. Similarly, a moiety

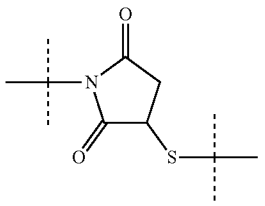

can be attached to two moieties or can interrupt a moiety either as

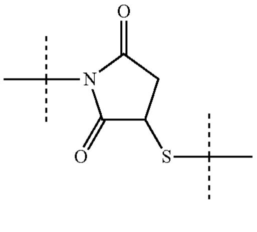

or as

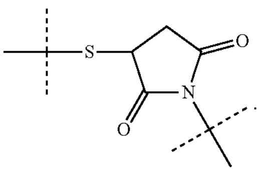

As used herein, the term “functional group” means a group of atoms which can react with other groups of atoms. Functional groups include but are not limited to the following groups: carboxylic acid (—(C═O)OH), primary or secondary amine (—$NH_2$, —NH—), maleimide, thiol (—SH), sulfonic acid (—(O═S═O)OH), carbonate, carbamate (—O(C═O)N<), hydroxyl (—OH), aldehyde (—(C═O)H), ketone (—(C═O)—), hydrazine (>N—N<), isocyanate, isothiocyanate, phosphoric acid (—O(P═O) OHOH), phosphonic acid (—O(P═O)OHH), haloacetyl, alkyl halide, acryloyl, aryl fluoride, hydroxylamine, disulfide, sulfonamides, sulfuric acid, vinyl sulfone, vinyl ketone, diazoalkane, oxirane, and aziridine.

In case the CNP agonist or controlled-release CNP agonists of the present invention comprise one or more acidic or basic groups, the invention also comprises their corresponding pharmaceutically or toxicologically acceptable salts, in particular their pharmaceutically utilizable salts. Thus, the CNP agonist or controlled-release CNP agonists of the present invention comprising acidic groups can be used according to the invention, for example, as alkali metal salts, alkaline earth metal salts or as ammonium salts. More precise examples of such salts include sodium salts, potassium salts, calcium salts, magnesium salts or salts with ammonia or organic amines such as, for example, ethylamine, ethanolamine, triethanolamine or amino acids. CNP agonists or controlled-release CNP agonists of the present invention comprising one or more basic groups, i.e. groups which can be protonated, can be present and can be used according to the invention in the form of their addition salts with inorganic or organic acids. Examples for suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, and other acids known to the person skilled in the art. For the person skilled in the art further methods are known for converting the basic group into a cation like the alkylation of an amine group resulting in a positively-charge ammonium group and an appropriate counterion of the salt. If the CNP agonist or controlled-release CNP agonists of the present invention simultaneously comprise acidic and basic groups, the invention also includes, in addition to the salt forms mentioned, inner salts or betaines (zwitterions). The respective salts can be obtained by customary methods which are known to the person skilled in the art like, for example by contacting these prodrugs with an organic or inorganic acid or base in a solvent or dispersant, or by anion exchange or cation exchange with other salts. The present invention also includes all salts of the prodrugs of the present invention which, owing to low physiological compatibility, are not directly suitable for use in pharmaceuticals but which can be used, for example, as intermediates for chemical reactions or for the preparation of pharmaceutically acceptable salts.

The term "pharmaceutically acceptable" means a substance that does cause harm when administered to a patient and preferably means approved by a regulatory agency, such as the EMA (Europe) and/or the FDA (US) and/or any other national regulatory agency for use in animals, preferably for use in humans.

As used herein the term "about" in combination with a numerical value is used to indicate a range ranging from and including the numerical value plus and minus no more than 10% of said numerical value, more preferably no more than 8% of said numerical value, even more preferably no more than 5% of said numerical value and most preferably no more than 2% of said numerical value. For example, the phrase "about 200" is used to mean a range ranging from and including 200+/−10%, i.e. ranging from and including 180 to 220; preferably 200+/−8%, i.e. ranging from and including 184 to 216; even more preferably ranging from and including 200+/−5%, i.e. ranging from and including 190 to 210; and most preferably 200+/−2%, i.e. ranging from and including 196 to 204. It is understood that a percentage given as "about 20%" does not mean "20%+/−10%", i.e. ranging from and including 10 to 30%, but "about 20%" means ranging from and including 18 to 22%, i.e. plus and minus 10% of the numerical value which is 20.

As used herein, the term "polymer" means a molecule comprising repeating structural units, i.e. the monomers, connected by chemical bonds in a linear, circular, branched, crosslinked or dendrimeric way or a combination thereof, which may be of synthetic or biological origin or a combination of both. It is understood that a polymer may also comprise one or more other chemical groups and/or moieties, such as, for example, one or more functional groups. Preferably, a soluble polymer has a molecular weight of at least 0.5 kDa, e.g. a molecular weight of at least 1 kDa, a molecular weight of at least 2 kDa, a molecular weight of at least 3 kDa or a molecular weight of at least 5 kDa. If the polymer is soluble, it preferable has a molecular weight of at most 1000 kDa, such as at most 750 kDa, such as at most 500 kDa, such as at most 300 kDa, such as at most 200 kDa, such as at most 100 kDa. It is understood that for insoluble polymers, such as hydrogels, no meaningful molecular weight ranges can be provided. It is understood that also a protein is a polymer in which the amino acids are the repeating structural units, even though the side chains of each amino acid may be different.

As used herein, the term "polymeric" means a reagent or a moiety comprising one or more polymers or polymer moieties. A polymeric reagent or moiety may optionally also comprise one or more other moiety/moieties, which are preferably selected from the group consisting of:

$C_{1-50}$ alkyl, $C_{2-50}$ alkenyl, $C_{2-50}$ alkynyl, $C_{3-10}$ cycloalkyl, 3- to 10-membered heterocyclyl, 8- to 11-membered heterobicyclyl, phenyl, naphthyl, indenyl, indanyl, and tetralinyl; and linkages selected from the group comprising

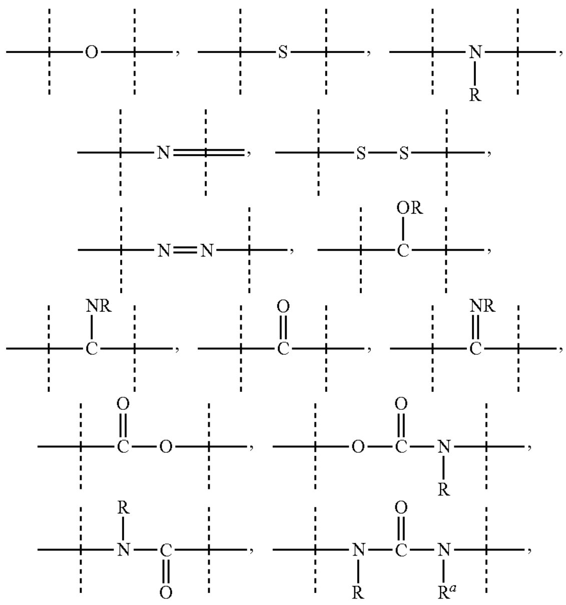

-continued

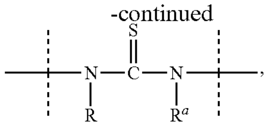

and

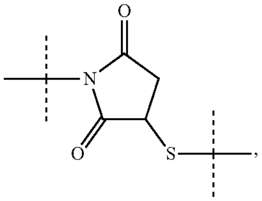

wherein dashed lines indicate attachment to the remainder of the moiety or reagent, and —R and —$R^a$ are independently of each other selected from the group consisting of —H, methyl, ethyl, propyl, butyl, pentyl and hexyl.

The person skilled in the art understands that the polymerization products obtained from a polymerization reaction do not all have the same molecular weight, but rather exhibit a molecular weight distribution. Consequently, the molecular weight ranges, molecular weights, ranges of numbers of monomers in a polymer and numbers of monomers in a polymer as used herein, refer to the number average molecular weight and number average of monomers, i.e. to the arithmetic mean of the molecular weight of the polymer or polymeric moiety and the arithmetic mean of the number of monomers of the polymer or polymeric moiety.

Accordingly, in a polymeric moiety comprising "x" monomer units any integer given for "x" therefore corresponds to the arithmetic mean number of monomers. Any range of integers given for "x" provides the range of integers in which the arithmetic mean numbers of monomers lies. An integer for "x" given as "about x" means that the arithmetic mean numbers of monomers lies in a range of integers of x+/−10%, preferably x+/−8%, more preferably x+/−5% and most preferably x+/−2%.

As used herein, the term "number average molecular weight" means the ordinary arithmetic mean of the molecular weights of the individual polymers.

As used herein the term "water-soluble" with reference to a carrier means that when such carrier is part of the controlled-release CNP agonists of the present invention at least 1 g of the controlled-release CNP agonists comprising such water-soluble carrier can be dissolved in one liter of water at 20° C. to form a homogeneous solution. Accordingly, the term "water-insoluble" with reference to a carrier means that when such carrier is part of a controlled-release CNP agonists of the present invention less than 1 g of the controlled-release CNP agonists comprising such water-insoluble carrier can be dissolved in one liter of water at 20° C. to form a homogeneous solution.

As used herein, the term "hydrogel" means a hydrophilic or amphiphilic polymeric network composed of homopolymers or copolymers, which is insoluble due to the presence of covalent chemical crosslinks. The crosslinks provide the network structure and physical integrity.

As used herein the term "thermogelling" means a compound that is a liquid or a low viscosity solution having a viscosity of less than 500 cps at 25° C. at a shear rate of about 0.1/second at a low temperature, which low temperature ranges between about 0° C. to about 10° C., but which is a higher viscosity compound of less than 10000 cps at 25° C. at a shear rate of about 0.1/second at a higher temperature, which higher temperature ranges between about 30° C. to about 40° C., such as at about 37° C.

As used herein, the term "PEG-based" in relation to a moiety or reagent means that said moiety or reagent comprises PEG. Preferably, a PEG-based moiety or reagent comprises at least 10% (w/w) PEG, such as at least 20% (w/w) PEG, such as at least 30% (w/w) PEG, such as at least 40% (w/w) PEG, such as at least 50% (w/w), such as at least 60 (w/w) PEG, such as at least 70% (w/w) PEG, such as at least 80% (w/w) PEG, such as at least 90% (w/w) PEG, such as at least 95%. The remaining weight percentage of the PEG-based moiety or reagent are other moieties preferably selected from the following moieties and linkages:

$C_{1-50}$ alkyl, $C_{2-50}$ alkenyl, $C_{2-50}$ alkynyl, $C_{3-10}$ cycloalkyl, 3- to 10-membered heterocyclyl, 8- to 11-membered heterobicyclyl, phenyl, naphthyl, indenyl, indanyl, and tetralinyl; and linkages selected from the group comprising

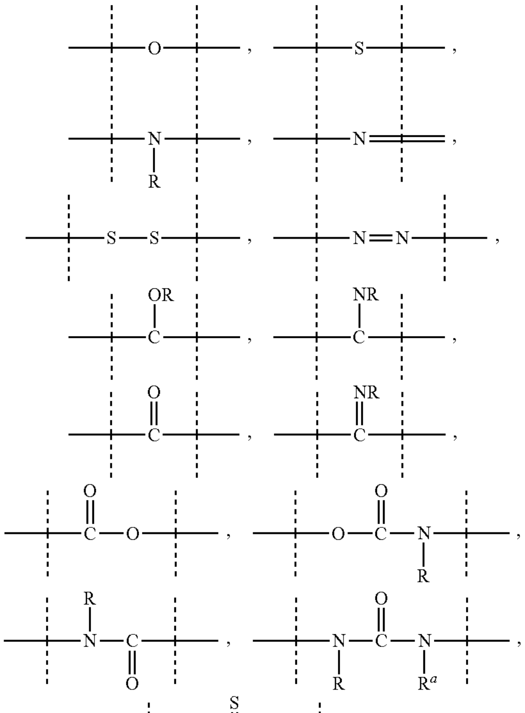

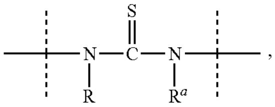

and

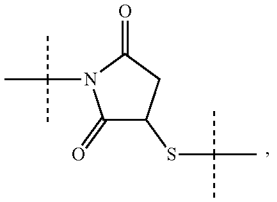

wherein dashed lines indicate attachment to the remainder of the moiety or reagent, and —R and —$R^a$ are independently of each other selected from the group consisting of —H, methyl, ethyl, propyl, butyl, pentyl and hexyl.

As used herein, the term "PEG-based comprising at least X % PEG" in relation to a moiety or reagent means that said moiety or reagent comprises at least X % (w/w) ethylene glycol units (—$CH_2CH_2O$—), wherein the ethylene glycol units may be arranged blockwise, alternating or may be randomly distributed within the moiety or reagent and preferably all ethylene glycol units of said moiety or reagent are present in one block; the remaining weight percentage of the PEG-based moiety or reagent are other moieties preferably selected from the following moieties and linkages:

$C_{1-50}$ alkyl, $C_{2-50}$ alkenyl, $C_{2-50}$ alkynyl, $C_{3-10}$ cycloalkyl, 3- to 10-membered heterocyclyl, 8- to 11-membered heterobicyclyl, phenyl, naphthyl, indenyl, indanyl, and tetralinyl; and linkages selected from the group comprising

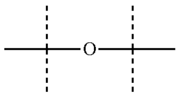, 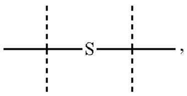,

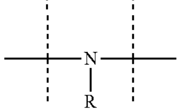, 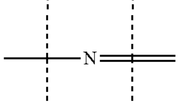,

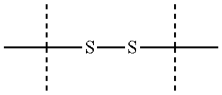, 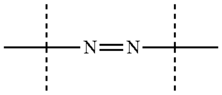,

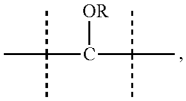, 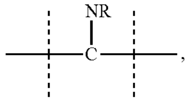,

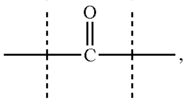, 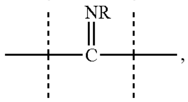,

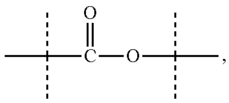, 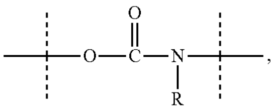,

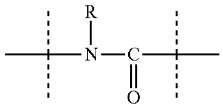, 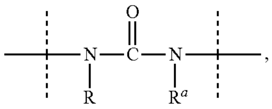,

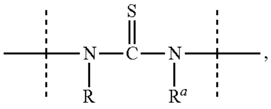, and

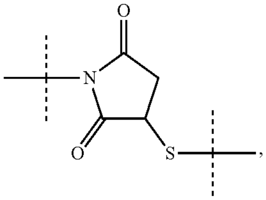, wherein dashed lines indicate attachment to the remainder of the moiety or reagent, and —R and —$R^a$ are independently of each other selected from the group consisting of —H, methyl, ethyl, propyl, butyl, pentyl and hexyl.

The term "hyaluronic acid-based comprising at least X % hyaluronic acid" is used accordingly.

The term "substituted" as used herein means that one or more —H atom(s) of a molecule or moiety are replaced by a different atom or a group of atoms, which are referred to as "substituent".

Preferably, the one or more further optional substituents are independently of each other selected from the group consisting of halogen, —CN, —$COOR^{x1}$, —$OR^{x1}$, —C(O)$R^{x1}$, —C(O)N($R^{x1}R^{x1a}$), —$S(O)_2N(R^{x1}R^{x1a})$, —S(O)N($R^{x1}R^{x1a}$), —$S(O)_2R^{x1}$, —S(O)$R^{x1}$, —N($R^{x1}$)$S(O)_2N(R^{x1a}R^{x1b})$, —$SR^{x1}$, —N($R^{x1}R^{x1a}$), —$NO_2$, —OC(O)$R^{x1}$, —N($R^{x1}$)C(O)$R^{x1a}$, —N($R^{x1}$)$S(O)_2R^{x1a}$, —N($R^{x1}$)S(O)$R^{x1a}$, —N($R^{x1}$)C(O)O$R^{x1a}$, —N($R^{x1}$)C(O)N($R^{x1a}R^{x1b}$), —OC(O)N($R^{x1}R^{x1a}$), -$T^0$, $C_{1-50}$ alkyl, $C_{2-50}$ alkenyl, and $C_{2-50}$ alkynyl; wherein -$T^0$, $C_{1-50}$ alkyl, $C_{2-50}$ alkenyl, and $C_{2-50}$ alkynyl are optionally substituted with one or more —$R^{x2}$, which are the same or different and wherein $C_{1-50}$ alkyl, $C_{2-50}$ alkenyl, and $C_{2-50}$ alkynyl are optionally interrupted by one or more groups selected from the group consisting of -$T^0$-, —C(O)O—, —O—, —C(O)—, —C(O)N($R^{x3}$)—, —$S(O)_2N(R^{x3})$—, —S(O)N($R^{x3}$)—, —$S(O)_2$—, —S(O)—, —N($R^{x3}$)$S(O)_2N(R^{x3a})$—, —S—, —N($R^{x3}$)—, —OC($OR^{x3}$)($R^{x3a}$)—, —N($R^{x3}$)C(O)N($R^{x3a}$)—, and —OC(O)N($R^{x3}$)—;

$R^{x1}$, —$R^{x1a}$, —$R^{x1b}$ are independently of each other selected from the group consisting of —H, -$T^0$, $C_{1-50}$ alkyl, $C_{2-50}$ alkenyl, and $C_{2-50}$ alkynyl; wherein -$T^0$, $C_{1-50}$ alkyl, $C_{2-50}$ alkenyl, and $C_{2-50}$ alkynyl are optionally substituted with one or more —$R^{x2}$, which are the same or different and wherein $C_{1-50}$ alkyl, $C_{2-50}$ alkenyl, and $C_{2-50}$ alkynyl are optionally interrupted by one or more groups selected from the group consisting of -$T^0$-, —C(O)O—, —O—, —C(O)—, —C(O)N($R^{x3}$)—, —$S(O)_2N(R^{x3})$—, —S(O)N($R^{x3}$)—; —$S(O)_2$—, —S(O)—, —N($R^{x3}$)$S(O)_2N(R^{x3a})$—, —S—, —N($R^{x3}$)—, —OC($OR^{x3}$)($R^{x3a}$)—, —N($R^{x3}$)C(O)N($R^{x3a}$)—, and —OC(O)N($R^{x3}$)—;

each $T^0$ is independently selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each $T^0$ is independently optionally substituted with one or more —$R^{x2}$, which are the same or different;

each —$R^{x2}$ is independently selected from the group consisting of halogen, —CN, oxo (=O), —$COOR^{x4}$, —$OR^{x4}$, —C(O)$R^{x4}$, —C(O)N($R^{x4}R^{x4a}$), —$S(O)_2N(R^{x4}R^{x4a})$, —S(O)N($R^{x4}R^{x4a}$), —$S(O)_2R^{x4}$, —S(O)$R^{x4}$, —N($R^{x4}$)$S(O)_2N(R^{x4a}R^{x4b})$, —$SR^{x4}$, —N($R^{x4}R^{x4a}$), —$NO_2$, —OC(O)$R^{x4}$, —N($R^{x4}$)C(O)$R^{x4a}$, —N($R^{x4}$)$S(O)_2R^{x4a}$, —N($R^{x4}$)S(O)$R^{x4a}$, —N($R^{x4}$)C(O)O$R^{x4a}$, —N($R^{x4}$)C(O)N($R^{x4a}R^{x4b}$), —OC(O)N($R^{x4}R^{x4a}$), and $C_{1-6}$ alkyl; wherein $C_{1-6}$ alkyl is optionally substituted with one or more halogen, which are the same or different;

each —$R^{x3}$, —$R^{x3a}$, —$R^{x4}$, —$R^{x4a}$, —$R^{x4b}$ is independently selected from the group consisting of —H and $C_{1-6}$ alkyl; wherein $C_{1-6}$ alkyl is optionally substituted with one or more halogen, which are the same or different.

More preferably, the one or more further optional substituents are independently of each other selected from the group consisting of halogen, —CN, —$COOR^{x1}$, —$OR^{x1}$, —C(O)$R^{x1}$, —C(O)N($R^{x1}R^{x1a}$), —$S(O)_2N(R^{x1}R^{x1a})$, —S(O)N($R^{x1}R^{x1a}$), —$S(O)_2R^{x1}$, —S(O)$R^{x1}$, —N($R^{x1}$)$S(O)_2N(R^{x1a}R^{x1b})$, —$SR^{x1}$, —N($R^{x1}R^{x1a}$), —$NO_2$, —OC(O)$R^{x1}$, —N($R^{x1}$)C(O)$R^{x1a}$, —N($R^{x1}$)$S(O)_2R^{x1a}$, —N($R^{x1}$)S(O)$R^{x1a}$, —N($R^{x1}$)C(O)O$R^{x1a}$, —N($R^{x1}$)C(O)N($R^{x1a}R^{x1b}$), —OC(O)N($R^{x1}R^{x1a}$), -$T^0$, $C_{1-10}$ alkyl, $C_{2-10}$ alkenyl, and $C_{2-10}$ alkynyl; wherein -$T^0$, $C_{1-10}$ alkyl, $C_{2-10}$ alkenyl, and $C_{2-10}$ alkynyl are optionally substituted with one or more —$R^{x2}$, which are the same or different and wherein $C_{1-10}$ alkyl, $C_{2-10}$ alkenyl, and $C_{2-10}$ alkynyl are optionally interrupted by one or more groups selected from the group consisting of -$T^0$-, —C(O)O—, —O—, —C(O)—, —C(O)N($R^{x3}$)—, —$S(O)_2N(R^{x3})$—, —S(O)N($R^{x3}$)—, —$S(O)_2$—, —S(O)—, —N($R^{x3}$)S(O)$_2$N($R^{x3a}$)—, —S—, —N($R^{x3}$)—, —OC(O$R^{x3}$)($R^{x3a}$)—, —N($R^{x3}$)C(O)N($R^{x3a}$)—, and —OC(O)N($R^{x3}$)—;

each —$R^{x1}$, —$R^{x1a}$, —$R^{x1b}$, —$R^{x3}$, —$R^{x3a}$ is independently selected from the group consisting of —H, halogen, $C_{1-6}$ alkyl, $C_{2-6}$ alkenyl, and $C_{2-6}$ alkynyl;

each $T^0$ is independently selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each $T^0$ is independently optionally substituted with one or more —$R^{x2}$ which are the same or different;

each —$R^{x2}$ is independently selected from the group consisting of halogen, —CN, oxo (=O), —COO$R^{x4}$, —O$R^{x4}$, —C(O)$R^{x4}$, —C(O)N($R^{x4}R^{x4a}$), —S(O)$_2$N($R^{x4}R^{x4a}$), —S(O)N($R^{x4}R^{x4a}$), —S(O)$_2R^{x4}$, —S(O)$R^{x4}$, —N($R^{x4}$)S(O)$_2$N($R^{x4a}R^{x4b}$), —S$R^{x4}$, —N($R^{x4}R^{x4a}$), —NO$_2$, —OC(O)$R^{x4}$, —N($R^{x4}$)C(O)$R^{x4a}$, —N($R^{x4}$)S(O)$_2R^{x4a}$, —N($R^{x4}$)S(O)$R^{x4a}$, —N($R^{x4}$)C(O)O$R^{x4a}$, —N($R^{x4}$)C(O)N($R^{x4a}R^{x4b}$), —OC(O)N($R^{x4}R^{x4a}$), and $C_{1-6}$ alkyl; wherein $C_{1-6}$ alkyl is optionally substituted with one or more halogen, which are the same or different;

each —$R^{x4}$, —$R^{x4a}$, —$R^{x4b}$ is independently selected from the group consisting of —H, halogen, $C_{1-6}$ alkyl, $C_{2-6}$ alkenyl, and $C_{2-6}$ alkynyl;

Even more preferably, the one or more further optional substituents are independently of each other selected from the group consisting of halogen, —CN, —COO$R^{x1}$, —O$R^{x1}$, —C(O)$R^{x1}$, —C(O)N($R^{x1}R^{x1a}$), —S(O)$_2$N($R^{x1}R^{x1a}$), —S(O)N($R^{x1}R^{x1a}$), —S(O)$_2R^{x1}$, —S(O)$R^{x1}$, —N($R^{x1}$)S(O)$_2$N($R^{x1a}R^{x1b}$), —S$R^{x1}$, —N($R^{x1}R^{x1a}$), —NO$_2$, —OC(O)$R^{x1}$, —N($R^{x1}$)C(O)$R^{x1a}$, —N($R^{x1}$)S(O)$_2R^{x1a}$, —N($R^{x1}$)S(O)$R^{x1a}$, —N($R^{x1}$)C(O)O$R^{x1a}$, —N($R^{x1}$)C(O)N($R^{x1a}R^{x1b}$), —OC(O)N($R^{x1}R^{x1a}$), -$T^0$, $C_{1-6}$ alkyl, $C_{2-6}$ alkenyl, and $C_{2-6}$ alkynyl; wherein -$T^0$, $C_{1-6}$ alkyl, $C_{2-6}$ alkenyl, and $C_{2-6}$ alkynyl are optionally substituted with one or more —$R^{x2}$, which are the same or different and wherein $C_{1-6}$ alkyl, $C_{2-6}$ alkenyl, and $C_{2-6}$ alkynyl are optionally interrupted by one or more groups selected from the group consisting of -$T^0$-, —C(O)O—, —O—, —C(O)—, —C(O)N($R^{x3}$)—, —S(O)$_2$N($R^{x3}$)—, —S(O)N($R^{x3}$)—, —S(O)$_2$—, —S(O)—, —N($R^{x3}$)S(O)$_2$N($R^{x3a}$)—, —S—, —N($R^{x3}$)—, —OC(ORx)($R^{x3a}$)—, —N($R^{x3}$)C(O)N($R^{x3a}$)—, and —OC(O)N($R^{x3}$)—;

each —$R^{x1}$, —$R^{x1a}$, —$R^{x1b}$, —$R^{x2}$, —$R^{x3}$, —$R^{x3a}$ is independently selected from the group consisting of —H, halogen, $C_{1-6}$ alkyl, $C_{2-6}$ alkenyl, and $C_{2-6}$ alkynyl;

each $T^0$ is independently selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each $T^0$ is independently optionally substituted with one or more —$R^{x2}$ which are the same or different.

Preferably, a maximum of 6 —H atoms of an optionally substituted molecule are independently replaced by a substituent, e.g. 5 —H atoms are independently replaced by a substituent, 4 —H atoms are independently replaced by a substituent, 3 —H atoms are independently replaced by a substituent, 2 —H atoms are independently replaced by a substituent, or 1 —H atom is replaced by a substituent.

The term "interrupted" means that a moiety is inserted between two carbon atoms or—if the insertion is at one of the moiety's ends—between a carbon or heteroatom and a hydrogen atom, preferably between a carbon and a hydrogen atom.

As used herein, the term "$C_{1-4}$ alkyl" alone or in combination means a straight-chain or branched alkyl moiety having 1 to 4 carbon atoms. If present at the end of a molecule, examples of straight-chain or branched $C_{1-4}$ alkyl are methyl, ethyl, n-propyl, isopropyl, n-butyl, isobutyl, sec-butyl and tert-butyl. When two moieties of a molecule are linked by the $C_{1-4}$ alkyl, then examples for such $C_{1-4}$ alkyl groups are —CH$_2$—, —CH$_2$—CH$_2$—, —CH(CH$_3$)—, —CH$_2$—CH$_2$—CH$_2$—, —CH(C$_2$H$_5$)—, —C(CH$_3$)$_2$—. Each hydrogen of a $C_{1-4}$ alkyl carbon may optionally be replaced by a substituent as defined above. Optionally, a $C_{1-4}$ alkyl may be interrupted by one or more moieties as defined below.

As used herein, the term "$C_{1-6}$ alkyl" alone or in combination means a straight-chain or branched alkyl moiety having 1 to 6 carbon atoms. If present at the end of a molecule, examples of straight-chain and branched $C_{1-6}$ alkyl groups are methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl. When two moieties of a molecule are linked by the $C_{1-6}$ alkyl group, then examples for such $C_{1-6}$ alkyl groups are —CH$_2$—, —CH$_2$—CH$_2$—, —CH(CH$_3$)—, —CH$_2$—CH$_2$—CH$_2$—, —CH(C$_2$H$_5$)— and —C(CH$_3$)$_2$—. Each hydrogen atom of a $C_{1-6}$ carbon may optionally be replaced by a substituent as defined above. Optionally, a $C_{1-6}$ alkyl may be interrupted by one or more moieties as defined below.

Accordingly, "$C_{1-10}$ alkyl", "$C_{1-20}$ alkyl" or "$C_{1-50}$ alkyl" means an alkyl chain having 1 to 10, 1 to 20 or 1 to 50 carbon atoms, respectively, wherein each hydrogen atom of the $C_{1-10}$, $C_{1-20}$ or $C_{1-50}$ carbon may optionally be replaced by a substituent as defined above. Optionally, a $C_{1-10}$ or $C_{1-50}$ alkyl may be interrupted by one or more moieties as defined below.

As used herein, the term "$C_{2-6}$ alkenyl" alone or in combination means a straight-chain or branched hydrocarbon moiety comprising at least one carbon-carbon double bond having 2 to 6 carbon atoms. If present at the end of a molecule, examples are —CH=CH$_2$, —CH=CH—CH$_3$, —CH$_2$—CH=CH$_2$, —CH=CHCH$_2$—CH$_3$ and —CH=CH—CH=CH$_2$. When two moieties of a molecule are linked by the $C_{2-6}$ alkenyl group, then an example for such $C_{2-6}$ alkenyl is —CH=CH—. Each hydrogen atom of a $C_{2-6}$ alkenyl moiety may optionally be replaced by a substituent as defined above. Optionally, a $C_{2-6}$ alkenyl may be interrupted by one or more moieties as defined below.

Accordingly, the term "$C_{2-10}$ alkenyl", "$C_{2-20}$ alkenyl" or "$C_{2-50}$ alkenyl" alone or in combination means a straight-chain or branched hydrocarbon moiety comprising at least one carbon-carbon double bond having 2 to 10, 2 to 20 or 2 to 50 carbon atoms. Each hydrogen atom of a $C_{2-10}$ alkenyl, $C_{2-20}$ alkenyl or $C_{2-50}$ alkenyl group may optionally be replaced by a substituent as defined above. Optionally, a $C_{2-10}$ alkenyl, $C_{2-20}$ alkenyl or $C_{2-50}$ alkenyl may be interrupted by one or more moieties as defined below.

As used herein, the term "$C_{2-6}$ alkynyl" alone or in combination means straight-chain or branched hydrocarbon moiety comprising at least one carbon-carbon triple bond having 2 to 6 carbon atoms. If present at the end of a molecule, examples are —C≡CH, —CH$_2$—C≡CH, CH$_2$—CH$_2$—C≡CH and CH$_2$—C≡C—CH$_3$. When two moieties of a molecule are linked by the alkynyl group, then an example is —C≡C—. Each hydrogen atom of a $C_{2-6}$ alkynyl group may optionally be replaced by a substituent as defined above. Optionally, one or more double bond(s) may occur. Optionally, a $C_{2-6}$ alkynyl may be interrupted by one or more moieties as defined below.

Accordingly, as used herein, the term "$C_{2-10}$ alkynyl", "$C_{2-20}$ alkynyl" and "$C_{2-50}$ alkynyl" alone or in combination means a straight-chain or branched hydrocarbon moiety comprising at least one carbon-carbon triple bond having 2 to 10, 2 to 20 or 2 to 50 carbon atoms, respectively. Each hydrogen atom of a $C_{2-10}$ alkynyl, $C_{2-20}$ alkynyl or $C_{2-50}$ alkynyl group may optionally be replaced by a substituent as defined above. Optionally, one or more double bond(s) may occur. Optionally, a $C_{2-10}$ alkynyl, $C_{2-20}$ alkynyl or $C_{2-50}$ alkynyl may be interrupted by one or more moieties as defined below.

As mentioned above, a $C_{1-4}$ alkyl, $C_{1-6}$ alkyl, $C_{1-10}$ alkyl, $C_{1-20}$ alkyl, $C_{1-50}$ alkyl, $C_{2-6}$ alkenyl, $C_{2-10}$ alkenyl, $C_{2-20}$ alkenyl, $C_{2-50}$ alkenyl, $C_{2-6}$ alkynyl, $C_{2-10}$ alkynyl, $C_{2-20}$ alkenyl or $C_{2-50}$ alkynyl may optionally be interrupted by one or more moieties which are preferably selected from the group consisting of

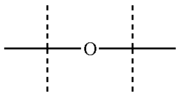 , 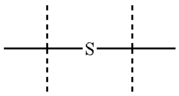 ,

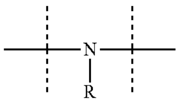 , 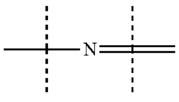 ,

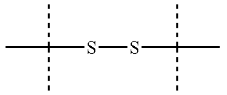 , 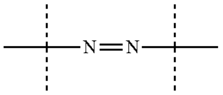 ,

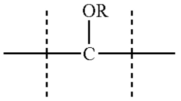 , 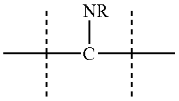 ,

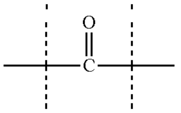 , 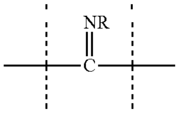 ,

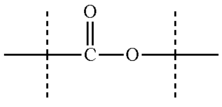 , 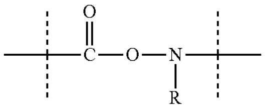 ,

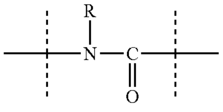 , 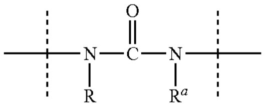 ,

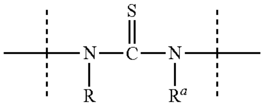 , and

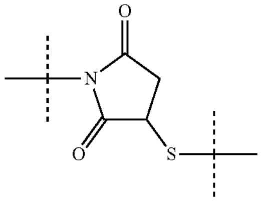 , wherein dashed lines indicate attachment to the remainder of the moiety or reagent; and —R and —$R^a$ are independently of each other selected from the group consisting of —H, methyl, ethyl, propyl, butyl, pentyl and hexyl.

As used herein, the term "$C_{3-10}$ cycloalkyl" means a cyclic alkyl chain having 3 to 10 carbon atoms, which may be saturated or unsaturated, e.g. cyclopropyl, cyclobutyl, cyclopentyl, cyclohexyl, cyclohexenyl, cycloheptyl, cyclooctyl, cyclononyl or cyclodecyl. Each hydrogen atom of a $C_{3-10}$ cycloalkyl carbon may be replaced by a substituent as defined above. The term "$C_{3-10}$ cycloalkyl" also includes bridged bicycles like norbornane or norbornene.

The term "8- to 30-membered carbopolycyclyl" or "8- to 30-membered carbopolycycle" means a cyclic moiety of two or more rings with 8 to 30 ring atoms, where two neighboring rings share at least one ring atom and that may contain up to the maximum number of double bonds (aromatic or non-aromatic ring which is fully, partially or un-saturated). Preferably a 8- to 30-membered carbopolycyclyl means a cyclic moiety of two, three, four or five rings, more preferably of two, three or four rings.

As used herein, the term "3- to 10-membered heterocyclyl" or "3- to 10-membered heterocycle" means a ring with 3, 4, 5, 6, 7, 8, 9 or 10 ring atoms that may contain up to the maximum number of double bonds (aromatic or non-aromatic ring which is fully, partially or un-saturated) wherein at least one ring atom up to 4 ring atoms are replaced by a heteroatom selected from the group consisting of sulfur (including —S(O)—, —$S(O)_2$—), oxygen and nitrogen (including =N(O)—) and wherein the ring is linked to the rest of the molecule via a carbon or nitrogen atom. Examples for 3- to 10-membered heterocycles include but are not limited to aziridine, oxirane, thiirane, azirine, oxirene, thiirene, azetidine, oxetane, thietane, furan, thiophene, pyrrole, pyrroline, imidazole, imidazoline, pyrazole, pyrazoline, oxazole, oxazoline, isoxazole, isoxazoline, thiazole, thiazoline, isothiazole, isothiazoline, thiadiazole, thiadiazoline, tetrahydrofuran, tetrahydrothiophene, pyrrolidine, imidazolidine, pyrazolidine, oxazolidine, isoxazolidine, thiazolidine, isothiazolidine, thiadiazolidine, sulfolane, pyran, dihydropyran, tetrahydropyran, imidazolidine, pyridine, pyridazine, pyrazine, pyrimidine, piperazine, piperidine, morpholine, tetrazole, triazole, triazolidine, tetrazolidine, diazepane, azepine and homopiperazine. Each hydrogen atom of a 3- to 10-membered heterocyclyl or 3- to 10-membered heterocyclic group may be replaced by a substituent as defined below.

As used herein, the term "8- to 11-membered heterobicyclyl" or "8- to 11-membered heterobicycle" means a heterocyclic moiety of two rings with 8 to 11 ring atoms, where at least one ring atom is shared by both rings and that may contain up to the maximum number of double bonds (aromatic or non-aromatic ring which is fully, partially or un-saturated) wherein at least one ring atom up to 6 ring atoms are replaced by a heteroatom selected from the group consisting of sulfur (including —S(O)—, —$S(O)_2$—), oxygen and nitrogen (including =N(O)—) and wherein the ring is linked to the rest of the molecule via a carbon or nitrogen atom. Examples for an 8- to 11-membered heterobicycle are indole, indoline, benzofuran, benzothiophene, benzoxazole, benzisoxazole, benzothiazole, benzisothiazole, benzimidazole, benzimidazoline, quinoline, quinazoline, dihydroquinazoline, quinoline, dihydroquinoline, tetrahydroquinoline, decahydroquinoline, isoquinoline, decahydroisoquinoline, tetrahydroisoquinoline, dihydroisoquinoline, benzazepine, purine and pteridine. The term 8- to 11-membered heterobicycle also includes spiro structures of two rings like 1,4-dioxa-8-azaspiro[4.5]decane or bridged heterocycles like 8-aza-bicyclo[3.2.1]octane. Each hydrogen atom of an 8- to 11-membered heterobicyclyl or 8- to 11-membered heterobicycle carbon may be replaced by a substituent as defined below.

Similarly, the term “8- to 30-membered heteropolycyclyl” or “8- to 30-membered heteropolycycle” means a heterocyclic moiety of more than two rings with 8 to 30 ring atoms, preferably of three, four or five rings, where two neighboring rings share at least one ring atom and that may contain up to the maximum number of double bonds (aromatic or non-aromatic ring which is fully, partially or unsaturated), wherein at least one ring atom up to 10 ring atoms are replaced by a heteroatom selected from the group of sulfur (including —S(O)—, —$S(O)_2$—), oxygen and nitrogen (including =N(O)—) and wherein the ring is linked to the rest of a molecule via a carbon or nitrogen atom.

It is understood that the phrase “the pair $R^x/R^y$ is joined together with the atom to which they are attached to form a $C_{3-10}$ cycloalkyl or a 3- to 10-membered heterocyclyl” in relation with a moiety of the structure

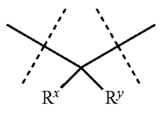

means that $R^x$ and $R^y$ form the following structure:

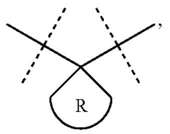

wherein R is $C_{3-10}$ cycloalkyl or 3- to 10-membered heterocyclyl.

It is also understood that the phrase “the pair $R^x/R^y$ is joint together with the atoms to which they are attached to form a ring A” in relation with a moiety of the structure

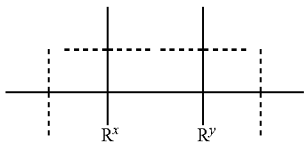

means that $R^x$ and $R^y$ form the following structure:

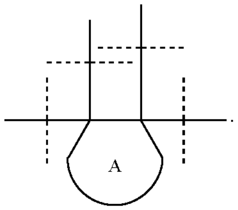

As used herein, “halogen” means fluoro, chloro, bromo or iodo. It is generally preferred that halogen is fluoro or chloro.

In general, the term “comprise” or “comprising” also encompasses “consist of” or “consisting of”.

The at least one further biologically active moiety or drug may be in its free form (i.e in the form of a free drug), may be in the form of a stable conjugate or may be in the form of a controlled-release compound.

In one embodiment, the at least one further biologically active moiety or drug is a drug in its free form.

Preferably, the at least one further drug is selected from the group consisting of antihistamines; human anti-FGFR3 antibodies; soluble forms of human fibroblast growth factor receptor 3; tyrosine kinase inhibitors; statins; CNP agonists; growth hormone; IGF-1; ANP; BNP; inhibitors of peptidases and proteases; and inhibitors of NPR—C.

A preferred antihistamine is meclozine. A typical dose of meclozine administered to a human patient ranges from 0.05 mg/day to 5000 mg/day and is preferably 50 mg/day.

A preferred tyrosine kinase inhibitor is NVP-BGJ398. A typical dose of NVP-BGJ398 administered to a human patient ranges from 0.02 mg/kg/day to 200 mg/kg/day and is preferably 2 mg/kg/day.

A preferred statin is rosuvastatin. Preferred ranges for rosuvastatin are provided in table 1.

A preferred CNP agonist for the at least one further drug is vosoritide. A typical dose of vosoritide administered to a human patient ranges from 2.5 μg/kg/day to 60 μg/kg/day and is preferably 15 μg/kg/day.

Preferred inhibitors of peptidases and proteases are NEP and furin.

A preferred inhibitor for NEP are thiorphan and candoxatril. A typical dose administered to a human patient ranges from 0.01 mg/day to 1000 mg/day for thiorphan and from 1 mg/day to 1000 mg/day for candoxatril and is preferably 50 mg/day for thiorphan and 200 mg/day for candoxatril.

Preferred inhibitors of NPR—C are the fragment of SEQ ID NO:98 (FGIPMDRIGRNPR) and antibody B701. A typical dose of antibody B701 administered to a human patient ranges from 0.25 mg/kg/month to 250 mg/kg/month and is preferably 25 mg/kg/months, administered either in one or multiple injections.

Preferred inhibitors of tyrosine kinases are as disclosed in U.S. Pat. Nos. 6,329,375 and 6,344,459, which are herewith incorporated by reference.

In one embodiment the at least one further drug is an antihistamine.

In another embodiment the at least one further drug is a human anti-FGFR3 antibody.

In another embodiment the at least one further drug is a soluble form of human fibroblast growth factor receptor 3 (sFGFR3). A typical dose of sFGFR3 administered to a human patient ranges from 0.002 mg/kg over one week to 2 mg/kg over one week, preferably from 0.02 mg/kg over one week to 0.2 mg/kg over one week and most preferably is about 1 mg/kg over one week.

In another embodiment the at least one further drug is a tyrosine kinase inhibitor.

In another embodiment the at least one further drug is a statin.

In another embodiment the at least one further drug is a growth hormone, preferably a human growth hormone (hGH) and most preferably a human growth hormone having the sequence of SEQ ID NO:99:

```
FPTIPLSRLFDNAMLRAHRLHQLAFDTYQEFEEAYIPKEQKYSFLQNPQT

SLCFSESIPTPSNREETQQKSNLELLRISLLLIQSWLEPVQFLRSVFANS
```

-continued

LVYGASDSNVYDLLKDLEEGIQTLMGRLEDGSPRTGQIFKQTYSKFDTNS

HNDDALLKNYGLLYCFRKDMDKVETFLRIVQCRSVEGSCGF

A typical dose of hGH, preferably of hGH having the sequence of SEQ ID NO:99, administered to a human patient ranges from 0.021 mg/kg/week to 0.7 mg/kg/week and is preferably 0.21 mg/kg/week.

In another embodiment the at least one further drug is a CNP agonist. A typical dose of CNP agonist administered to a human patient ranges from 1.5 μg/kg/day to 1.5 mg/kg/day and is preferably 15 μg/kg/day.

In another embodiment the at least one further drug is IGF-1. A typical dose of IGF-1 administered to a human patient ranges from 10 μg/kg/day to 1 mg/kg/day and is preferably 100 μg/kg/day.

In another embodiment the at least one further drug is ANP. A typical dose of ANP administered to a human patient ranges from 1 μg/kg/day to 1 mg/kg/day and is preferably 15 μg/kg/day.

In another embodiment the at least one further is BNP. A typical dose of BNP administered to a human patient ranges from 1 μg/kg/day to 1 mg/kg/day and is preferably 15 μg/kg/day.

In another embodiment the at least one further drug is an inhibitor of peptidases and proteases.

In another embodiment the at least one further drug is an inhibitor of NPR—C.

In another embodiment the at least one further biologically active moiety in its free form is PTH. Preferred PTH sequences are SEQ ID Nos:1 to 121 of WO2017/148883A1, most preferably the PTH having the SEQ ID NO: 51, which are herewith incorporated by reference. In another embodiment, the at least one further biologically active moiety or drug is in the form of a stable conjugate.

In one embodiment the at least one further biologically active moiety in the form of a stable conjugate comprises at least one biologically active moiety covalently conjugated through a stable linkage to a polymeric moiety, preferably to a water-soluble polymeric moiety, either directly or through a spacer moiety.

Preferably, such polymeric moiety, even more preferably water-soluble polymeric moiety, comprises a polymer selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

In another embodiment the at least one further biologically active moiety in the form of a stable conjugate is covalently conjugated through a stable linkage to an albumin-binding moiety. Preferably, said albumin-binding moiety is a $C_{8-24}$ alkyl moiety or fatty acid derivative. Preferred fatty acid derivatives are those disclosed in WO 2005/027978 A2 and WO 2014/060512 A1 which are herewith incorporated by reference.

Preferably, the at least one further biologically active moiety in the form of a stable conjugate comprises a biologically active moiety selected from the group consisting of antihistamins; human anti-FGFR3 antibodies; soluble forms of human fibroblast growth factor receptor 3 (sFGFR3); tyrosine kinase inhibitors; statins; CNP agonists; growth hormone; IGF-1; ANP; BNP; inhibitors of peptidases and proteases; and inhibitors of NPR—C.

A preferred antihistamin is meclozine. Doses of meclozine typically and preferably administered to a human patient are as described above for free meclizine converted into the equivalent doses of the stable conjugate.

A preferred tyrosine kinase inhibitor is NVP-BGJ398. Doses of NVP-BGJ398 typically and preferably administered to a human patient are as described above for free NVP-BGJ398 converted into the equivalent amounts of the stable conjugate.

A preferred statin is rosuvastatin. Preferred ranges of rosuvastatin are provided in table 1 converted into the equivalent doses of the stable conjugate.

A preferred CNP agonist for the at least one further biologically active moiety is vosoritide. Doses of vosoritide typically and preferably administered to a human patient are as described above for free vosoritide converted into the equivalent doses of the stable conjugate.

Preferred inhibitors of peptidases and proteases are NEP and furin.

A preferred inhibitor for NEP are thiorphan and candoxatril. Doses of thiorphan and candoxatril typically and preferably administered to a human patient are as described above for free thiorphan and candoxatril converted into the equivalent doses of the stable conjugate.

Preferred inhibitors of NPR—C are the fragment of SEQ ID NO:98 (FGIPMDRIGRNPR) and antibody B701. Doses of B701 typically and preferably administered to a human patient are as described above for free B701 converted into the equivalent doses of the stable conjugate.

Preferred inhibitors of tyrosine kinases are as disclosed in U.S. Pat. Nos. 6,329,375 and 6,344,459, which are herewith incorporated by reference.

In one embodiment the at least one further biologically active moiety in the form of a stable conjugate comprises an antihistamin moiety.

In another embodiment the at least one further biologically active moiety in the form of a stable conjugate comprises a human anti-FGFR3 antibody moiety.

In another embodiment the at least one further biologically active moiety in the form of a stable conjugate comprises a soluble forms of human fibroblast growth factor receptor 3 (sFGFR3) moiety. Doses of sFGFR3 typically and preferably administered to a human patient are as described above for free sFGFR3 converted into the equivalent doses of the stable conjugate.

In another embodiment the at least one further biologically active moiety in the form of a stable conjugate comprises a tyrosine kinase inhibitor moiety.

In another embodiment the at least one further biologically active moiety in the form of a stable conjugate comprises a statin moiety.

In another embodiment the at least one further biologically active moiety in the form of a stable conjugate comprises a growth hormone moiety, preferably a human growth hormone (hGH) and most preferably a human growth hormone having the sequence of SEQ ID NO:99. Doses of hGH, preferably having the sequence of SEQ ID NO:99, typically and preferably administered to a human patient are as described above for free hGH converted of the equivalent doses for the stable conjugate.

In another embodiment the at least one further biologically active moiety in the form of a stable conjugate comprises a CNP agonist moiety. Doses of the CNP agonist typically and preferably administered to a human patient are as described above for free CNP agonist converted into the equivalent doses of the stable conjugate.

In another embodiment the at least one further biologically active moiety in the form of a stable conjugate comprises an IGF-1 moiety. Doses of the IGF-1 typically and preferably administered to a human patient are as described above for free IGF-1 converted into the equivalent doses of the stable conjugate.

In another embodiment the at least one further biologically active moiety in the form of a stable conjugate comprises an ANP moiety. Doses of ANP typically and preferably administered to a human patient are as described above for free ANP converted into the equivalent doses of the stable conjugate.

In another embodiment the at least one further biologically active moiety in the form of a stable conjugate comprises a BNP moiety. Doses of BNP typically and preferably administered to a human patient are as described above for free BNP converted into the equivalent doses of the stable conjugate.

In another embodiment the at least one further biologically active moiety in the form of a stable conjugate comprises an inhibitor of peptidases and proteases moiety.

In another embodiment the at least one further biologically active moiety in the form of a stable conjugate comprises an inhibitor of NPR—C moiety.

In another embodiment the at least one further biologically active moiety in the form of a stable conjugate comprises PTH. Preferred PTH sequences are SEQ ID NOs:1 to 121 of WO2017/148883A1, most preferably the PTH having the SEQ ID NO: 51, which are herewith incorporated by reference.

In another embodiment the at least one further biologically active moiety or drug is in the form of a controlled-release compound.

Preferably, the at least one further biologically active moiety or drug in the form of a controlled-release compound comprises at least one biologically active moiety or drug selected from the group consisting of antihistamins; human anti-FGFR3 antibodies; soluble forms of human fibroblast growth factor receptor 3; statins; CNP agonists; growth hormone; IGF-1; ANP; BNP; inhibitors of peptidases and proteases; inhibitors of tyrosine kinases; and inhibitors of NPR—C.

A preferred antihistamin is meclozine. Doses of meclozine typically and preferably administered to a human patient are as described above for free meclizine converted into the equivalent doses of the controlled-release compound.

A preferred tyrosine kinase inhibitor is NVP-BGJ398. Doses of NVP-BGJ398 typically and preferably administered to a human patient are as described above for free NVP-BGJ398 converted into the equivalent doses of the controlled-release compound.

A preferred statin is rosuvastatin. Preferred ranges of rosuvastatin are provided in table 1 converted into the equivalent doses of the controlled-release compound.

A preferred CNP agonist for the at least one further drug is vosoritide. Doses of vosoritide typically and preferably administered to a human patient are as described above for free vosoritide converted into the equivalent doses of the controlled-release compound.

Preferred inhibitors of peptidases and proteases are NEP and furin.

A preferred inhibitor for NEP are thiorphan and candoxatril. Doses of thiorphan and candoxatril typically and preferably administered to a human patient are as described above for free thiorphan and candoxatril converted into the equivalent amounts of the controlled-release compound.

Preferred inhibitors of NPR—C are the fragment of SEQ ID NO:98 (FGIPMDRIGRNPR) and antibody B701. Doses of B701 typically and preferably administered to a human patient are as described above for free B701 converted into the equivalent doses of the controlled-release compound.

Preferred inhibitors of tyrosine kinases are as disclosed in U.S. Pat. Nos. 6,329,375 and 6,344,459, which are herewith incorporated by reference.

In one embodiment the at least one further biologically active moiety or drug in the form of a controlled-release compound comprises an antihistamin moiety or drug.

In another embodiment the at least one further biologically active moiety or drug in the form of a controlled-release compound comprises a human anti-FGFR3 antibody moiety or drug.

In another embodiment the at least one further biologically active moiety or drug in the form of a controlled-release compound comprises a soluble forms of human fibroblast growth factor receptor 3 (sFGFR3) moiety or drug. Doses of sFGFR3 typically and preferably administered to a human patient are as described above for free sFGFR3 converted into the equivalent doses of the controlled-release compound.

In another embodiment the at least one further biologically active moiety or drug in the form of a controlled-release compound comprises a tyrosine kinase inhibitor moiety or drug.

In another embodiment the at least one further biologically active moiety or drug in the form of a controlled-release compound comprises a statin moiety or drug.

In another embodiment the at least one further biologically active moiety or drug in the form of a controlled-release compound comprises a growth hormone moiety or drug, preferably a human growth hormone (hGH) and most preferably a human growth hormone having the sequence of SEQ ID NO:99. Doses of hGH, preferably having the sequence of SEQ ID NO:99, typically and preferably administered to a human patient are as described above for free hGH converted into the equivalent doses of the stable conjugate.

In another embodiment the at least one further biologically active moiety or drug in the form of a controlled-release compound comprises a CNP agonist moiety. Doses of the CNP agonist typically and preferably administered to a human patient are as described above for free CNP agonist converted into the equivalent doses of the controlled-release compound.

In another embodiment the at least one further biologically active moiety or drug in the form of a controlled-release compound comprises an IGF-1 moiety or drug. Doses of the IGF-1 typically and preferably administered to a human patient are as described above for free IGF-1 converted into the equivalent doses of the controlled-release compound.

In another embodiment the at least one further biologically active moiety or drug in the form of a controlled-release compound comprises an ANP moiety or drug. Doses of ANP typically and preferably administered to a human patient are as described above for free ANP converted into the equivalent doses of the controlled-release compound.

In another embodiment the at least one further biologically active moiety or drug in the form of a controlled-release compound comprises a BNP moiety or drug. Doses of BNP typically and preferably administered to a human patient are as described above for free BNP converted into the equivalent doses of the controlled-release compound.

In another embodiment the at least one further biologically active moiety or drug in the form of a controlled-release compound comprises an inhibitor of peptidases and proteases moiety or drug.

In another embodiment the at least one further biologically active moiety or drug in the form of a controlled-release compound comprises an inhibitor of NPR—C moiety or drug.

In another embodiment the at least one further biologically active moiety in the form of a controlled-release compound comprises PTH. Preferred PTH sequences are SEQ ID NOs:1 to 121 of WO2017/148883A1, most preferably the PTH having the SEQ ID NO: 51, which are herewith incorporated by reference.

In one embodiment the at least one further biologically active moiety or drug in the form of a controlled-release compound is water-insoluble.

Preferably, such water-insoluble controlled-release compound is selected from the group consisting of crystals, nanoparticles, microparticles, nanospheres and microspheres.

In one embodiment the at least one further biologically active moiety or drug in the form of a water-insoluble controlled-release compound is a crystal comprising at least one drug or biologically active moiety.

In another embodiment the at least one further biologically active moiety or drug in the form of a water-insoluble controlled-release compound is a nanoparticle comprising at least one drug or biologically active moiety.

In another embodiment the at least one further biologically active moiety or drug in the form of a water-insoluble controlled-release compound is a microparticle comprising at least one drug or biologically active moiety.

In another embodiment the at least one further biologically active moiety or drug in the form of a water-insoluble controlled-release compound is a nanosphere comprising at least one drug or biologically active moiety.

In another embodiment the at least one further biologically active moiety or drug in the form of a water-insoluble controlled-release compound is a microsphere comprising at least one drug or biologically active moiety.

In one embodiment the at least one further biologically active moiety or drug in the form of a water-insoluble controlled-release compound is a vesicle comprising at least one drug or biologically active moiety. Preferably, such vesicle comprising at least one drug or biologically active moiety is a micelle, liposome or polymersome.

In one embodiment the at least one further biologically active moiety or drug in the form of a water-insoluble controlled-release compound is a micelle comprising at least one drug or biologically active moiety.

In another embodiment the at least one further biologically active moiety or drug in the form of a water-insoluble controlled-release compound is a liposome comprising at least one drug or biologically active moiety. Preferably, such liposome is selected from the group consisting of aquasomes; non-ionic surfactant vesicles, such as niosomes and proniosomes; cationic liposomes, such as LeciPlex; transfersomes; ethosomes; ufasomes; sphingosomes; and pharmacosomes.

In another embodiment the at least one further biologically active moiety or drug in the form of a water-insoluble controlled-release compound is a polymersome at least one drug or biologically active moiety.

In another embodiment the at least one further biologically active moiety or drug in the form of a water-insoluble controlled-release compound comprises at least one biologically active moiety or drug non-covalently embedded in a water-insoluble polymer. Preferably, such water-insoluble polymer comprises a polymer selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

In a preferred embodiment the at least one further biologically active moiety or drug in the form of a water-insoluble controlled-release compound comprises at least one drug or biologically active moiety non-covalently embedded in poly(lactic-co-glycolic acid) (PLGA).

In another embodiment the at least one further biologically active moiety or drug in the form of a water-insoluble controlled-release compound comprises at least one biologically active moiety covalently and reversibly conjugated to a water-insoluble polymer. Preferably such water-insoluble polymer comprises a polymer selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly (ethylenes), poly(ethyleneglycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly (methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

Preferably, the at least one further biologically active moiety or drug in the form of a water-insoluble controlled-release compound comprises at least one biologically active moiety or drug selected from the group consisting of antihistamins; human anti-FGFR3 antibodies; soluble forms of human fibroblast growth factor receptor 3; tyrosine kinase inhibitors; statins; CNP agonists; growth hormone; IGF-1; ANP; BNP; inhibitors of peptidases and proteases; and inhibitors of NPR—C.

A preferred antihistamin is meclozine. Doses of meclozine typically and preferably administered to a human patient are as described above for free meclizine converted into the equivalent doses of the water-insoluble controlled-release compound.

A preferred tyrosine kinase inhibitor is NVP-BGJ398. Doses of NVP-BGJ398 typically and preferably administered to a human patient are as described above for free NVP-BGJ398 converted into the equivalent doses of the water-insoluble controlled-release compound.

A preferred statin is rosuvastatin. Preferred ranges of rosuvastatin are provided in table 1 converted into the equivalent doses of the water-insoluble controlled-release compound.

A preferred CNP agonist for the at least one further drug is vosoritide. Doses of vosoritide typically and preferably administered to a human patient are as described above for free vosoritide converted into the equivalent doses of the water-insoluble controlled-release compound.

Preferred inhibitors of peptidases and proteases are NEP and furin.

A preferred inhibitor for NEP are thiorphan and candoxatril. Doses of thiorphan and candoxatril typically and preferably administered to a human patient are as described above for free thiorphan and candoxatril converted into the equivalent doses of the water-insoluble controlled-release compound.

Preferred inhibitors of NPR—C are the fragment of SEQ ID NO:98 (FGIPMDRIGRNPR) and antibody B701. Doses of B701 typically and preferably administered to a human patient are as described above for free B701 converted into the equivalent doses of the water-insoluble controlled-release compound.

Preferred inhibitors of tyrosine kinases are as disclosed in U.S. Pat. Nos. 6,329,375 and 6,344,459, which are herewith incorporated by reference.

In one embodiment the at least one further biologically active moiety or drug in the form of a water-insoluble controlled-release compound comprises an antihistamin moiety or drug.

In another embodiment the at least one further biologically active moiety or drug in the form of a water-insoluble controlled-release compound comprises a human anti-FGFR3 antibody moiety or drug.

In another embodiment the at least one further biologically active moiety or drug in the form of a water-insoluble controlled-release compound comprises a soluble forms of human fibroblast growth factor receptor 3 (sFGFR3) moiety or drug. Doses of sFGFR3 typically and preferably administered to a human patient are as described above for free sFGFR3 converted into the equivalent doses of the water-insoluble controlled-release compound.

In another embodiment the at least one further biologically active moiety or drug in the form of a water-insoluble controlled-release compound comprises a tyrosine kinase inhibitor moiety or drug.

In another embodiment the at least one further biologically active moiety or drug in the form of a water-insoluble controlled-release compound comprises a statin moiety or drug.

In another embodiment the at least one further biologically active moiety or drug in the form of a water-insoluble controlled-release compound comprises a growth hormone moiety or drug, preferably a human growth hormone (hGH) and most preferably a human growth hormone having the sequence of SEQ ID NO:99. Doses of hGH typically and preferably administered to a human patient are as described above for free hGH converted into the equivalent doses of the water-insoluble controlled-release compound.

In another embodiment the at least one further biologically active moiety or drug in the form of a water-insoluble controlled-release compound comprises a CNP agonist moiety. Doses of the CNP agonist moiety typically and preferably administered to a human patient are as described above for free CNP agonist converted into the equivalent doses of the water-insoluble controlled-release compound.

In another embodiment the at least one further biologically active moiety or drug in the form of a water-insoluble controlled-release compound comprises an IGF-1 moiety or drug. Doses of the IGF-1 typically and preferably administered to a human patient are as described above for free IGF-1 converted into the equivalent doses of the water-insoluble controlled-release compound.

In another embodiment the at least one further biologically active moiety or drug in the form of a water-insoluble controlled-release compound comprises an ANP moiety or drug. Doses of the ANP typically and preferably administered to a human patient are as described above for free ANP converted into the equivalent doses of the water-insoluble controlled-release compound.

In another embodiment the at least one further biologically active moiety or drug in the form of a water-insoluble controlled-release compound comprises a BNP moiety or drug. Doses of the BNP typically and preferably administered to a human patient are as described above for free BNP converted into the equivalent doses of the water-insoluble controlled-release compound.

In another embodiment the at least one further biologically active moiety or drug in the form of a water-insoluble controlled-release compound comprises an inhibitor of peptidases and proteases moiety or drug.

In another embodiment the at least one further biologically active moiety or drug in the form of a water-insoluble controlled-release compound comprises an inhibitor of NPR—C moiety or drug.

In another embodiment the at least one further biologically active moiety in the form of a water-insoluble controlled-release compound is PTH. Preferred PTH sequences are SEQ ID NOs:1 to 121 of WO2017/148883A1, most preferably the PTH having the SEQ ID NO: 51, which are herewith incorporated by reference.

In another embodiment the at least one further biologically active moiety or drug in the form of a controlled-release compound is water-soluble.

In one embodiment the at least one further biologically active moiety or drug in the form of a water-soluble controlled-release compound comprises at least one biologically active moiety covalently conjugated through a reversible linkage to a water-soluble polymeric moiety, either directly or through a spacer moiety.

Preferably, such water-soluble polymeric moiety comprises a polymer selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly(ethylene oxides), poly (ethyl phosphates), poly(ethyloxazolines), poly(glycolic acids), poly(hydroxyethyl acrylates), poly(hydroxyethyloxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly(methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

In another embodiment the at least one further biologically active moiety in the form of a water-soluble controlled-release compound is covalently conjugated through a stable linkage to an albumin-binding moiety. Preferably, said albumin-binding moiety is a $C_{8-24}$ alkyl moiety or fatty acid derivative. Preferred fatty acid derivatives are those disclosed in WO 2005/027978 A2 and WO 2014/060512 A1 which are herewith incorporated by reference.

Preferably, the at least one further biologically active moiety in the form of a water-soluble controlled-release compound comprises a biologically active moiety selected from the group consisting of antihistamins; human anti-FGFR3 antibodies; soluble forms of human fibroblast growth factor receptor 3; tyrosine kinase inhibitors; statins; CNP agonists; growth hormone; IGF-1; ANP; BNP; inhibitors of peptidases and proteases; and inhibitors of NPR—C.

A preferred antihistamin is meclozine. Doses of meclozine typically and preferably administered to a human patient are as described above for free meclizine converted into the equivalent doses of the water-soluble controlled-release compound.

A preferred tyrosine kinase inhibitor is NVP-BGJ398. Doses of NVP-BGJ398 typically and preferably administered to a human patient are as described above for free NVP-BGJ398 converted into the equivalent doses of the water-soluble controlled-release compound.

A preferred statin is rosuvastatin. Preferred ranges of rosuvastatin are provided in table 1 converted into the equivalent doses of the water-soluble controlled-release compound.

A preferred CNP agonist for the at least one further drug is vosoritide. Doses of vosoritide typically and preferably administered to a human patient are as described above for free vosoritide converted into the equivalent doses of the water-soluble controlled-release compound.

Preferred inhibitors of peptidases and proteases are NEP and furin.

A preferred inhibitor for NEP are thiorphan and candoxatril. Doses of thiorphan and candoxatril typically and preferably administered to a human patient are as described above for free thiorphan and candoxatril converted into the equivalent doses of the water-soluble controlled-release compound.

Preferred inhibitors of NPR—C are the fragment of SEQ ID NO:98 (FGIPMDRIGRNPR) and antibody B701. Doses of B701 typically and preferably administered to a human patient are as described above for free B701 converted into the equivalent doses of the water-soluble controlled-release compound.

Preferred inhibitors of tyrosine kinases are as disclosed in U.S. Pat. Nos. 6,329,375 and 6,344,459, which are herewith incorporated by reference.

In one embodiment the at least one further biologically active moiety or drug in the form of a water-soluble controlled-release compound comprises an antihistamin moiety or drug.

In another embodiment the at least one further biologically active moiety or drug in the form of a water-soluble controlled-release compound comprises a human anti-FGFR3 antibody moiety or drug.

In another embodiment the at least one further biologically active moiety or drug in the form of a water-soluble controlled-release compound comprises a soluble forms of human fibroblast growth factor receptor 3 (sFGFR3) moiety or drug. Doses of sFGFR3 typically and preferably administered to a human patient are as described above for free sFGFR3 converted into the equivalent doses of the water-soluble controlled-release compound.

In another embodiment the at least one further biologically active moiety or drug in the form of a water-soluble controlled-release compound comprises a tyrosine kinase inhibitor moiety or drug.

In another embodiment the at least one further biologically active moiety or drug in the form of a water-soluble controlled-release compound comprises a statin moiety or drug.

In another embodiment the at least one further biologically active moiety or drug in the form of a water-soluble controlled-release compound comprises a growth hormone moiety or drug, preferably a human growth hormone (hGH), and most preferably a human growth hormone having the sequence of SEQ ID NO:99. Doses of hGH typically and preferably administered to a human patient are as described above for free hGH converted into the equivalent doses of the water-soluble controlled-release compound.

In one embodiment such water-soluble controlled-release compound comprising a growth hormone moiety, preferably an hGH moiety, most preferably an hGH moiety having the sequence of SEQ ID NO:99, is of formula (1a) or (1b):

(1a)

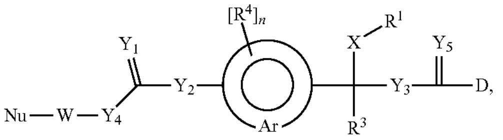

(1b)

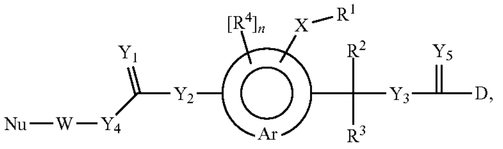

wherein

D is an hGH moiety connected to the rest of the compound through a nitrogen of an amine functional group of said hGH moiety;

n is 0, 1, 2, 3, or 4;

—X— is a chemical bond or a spacer;

$=Y_1$ is selected from the group consisting of =O and =S;

$-Y_2-$ is selected from the group consisting of —O— and —S—;

$-Y_3-$, $-Y_5-$ are independently of each other selected from the group consisting of —O— and —S—;

$Y_4-$ is selected from the group consisting of —O—, $-NR^5-$ and $-C(R^6R^{6a})-$;

$-R^1$ is a carrier, preferably a water-soluble PEG-based moiety comprising at least 40% PEG;

$-R^2$, $-R^3$, $-R^5$, $-R^6$, and $-R^{6a}$ are independently of each other selected from the group consisting of —H, methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl;

$-R^4$ is selected from the group consisting of methyl, ethyl, n-propyl, isopropyl, n-butyl, isobutyl, sec-butyl, tert-butyl, n-pentyl, 2-methylbutyl, 2,2-dimethylpropyl, n-hexyl, 2-methylpentyl, 3-methylpentyl, 2,2-dimethylbutyl, 2,3-dimethylbutyl and 3,3-dimethylpropyl;

—W— is selected from the group consisting of $C_{1-20}$ alkyl optionally interrupted by one or more groups selected from the group consisting of $C_{3-10}$ cycloalkyl, 8- to 30-membered carbopolycyclyl, 3- to 10-membered heterocyclyl, —C(O)—, $-C(O)N(R^7)-$, —O—, —S— and $-N(R^7)-$;

Nu is a nucleophile selected from the group consisting of $-N(R^7R^{7a})$, $-N(R^7OH)$, $-N(R^7)-N(R^{7a}R^{7b})$, $-S(R^7)$, —COOH,

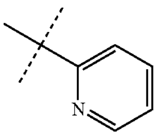, 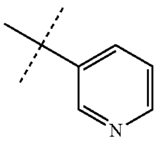, 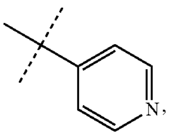,

-continued

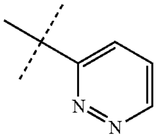, 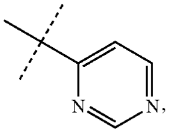, 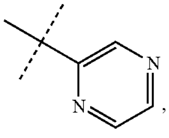,

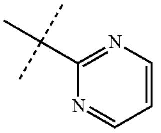, 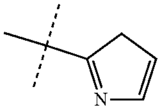, 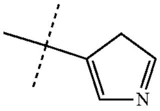,

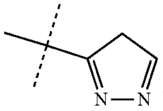, 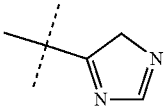 and

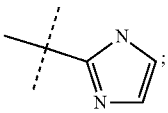;

—Ar— is selected from the group consisting of

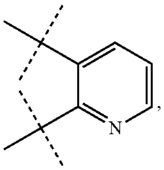, 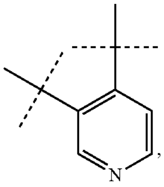,

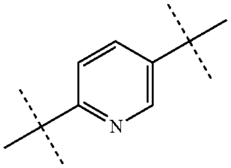, 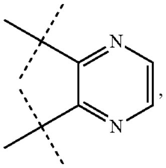,

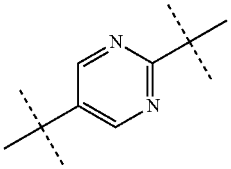, 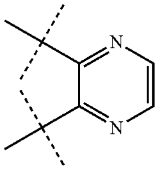,

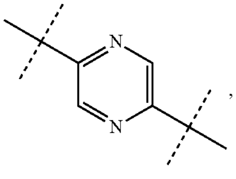, 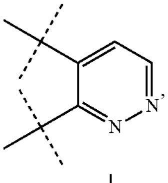,

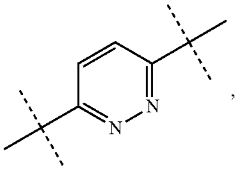, 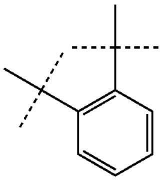,

-continued

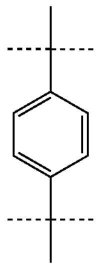,
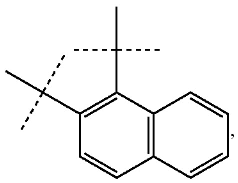,
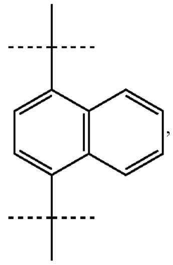,
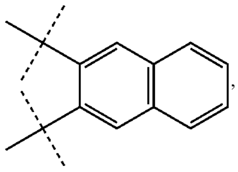,
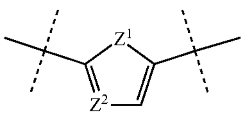,
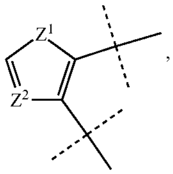,
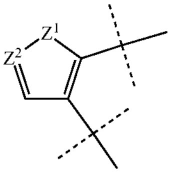, and
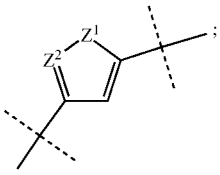;

wherein dashed lines indicate attachment to the rest of the compound,

—$Z^1$— is selected from the group consisting of —O—, —S— and —N($R^7$)—,

—$Z^2$— is —N($R^7$)—; and

—$R^7$, —$R^{7a}$ and —$R^{7b}$ are independently of each other selected from the group consisting of —H, $C_{1-6}$ alkyl, $C_{2-6}$ alkenyl and $C_{2-6}$ alkynyl;

wherein the compound of formula (1a) or (1b) is optionally further substituted.

-D of formula (1a) or (1b) is attached to the rest of the compound through the nitrogen of a primary or secondary amine, preferably through the nitrogen of the N-terminal amine or through a nitrogen of an amine of a lysine side chain. Preferably, -D of formula (1a) or (1b) is a moiety having the sequence of SEQ ID NO:99.

In one embodiment =$Y^1$ of formula (1a) or (1b) is =O.

In one embodiment —$Y^2$— of formula (1a) or (1b) is —O—.

In one embodiment —$Y^3$— of formula (1a) or (1b) is —O—.

In one embodiment —$Y^4$— of formula (1a) or (1b) is —$NR^5$—.

In one embodiment =$Y^5$ of formula (1a) or (1b) is =O.

In one embodiment n of formula (1a) or (1b) is 0 or 1. Most preferably, n of formula (1a) or (1b) is 0.

Preferably, $R^1$ of formula (1a) or (1b) has a molecular weight ranging from 10 to 250 kDa, even more preferably from 15 to 150 kDa.

In a preferred embodiment $R^1$ of formula (1a) or (1b) has a molecular weight ranging from 30 to 50 kDa, even more preferably from 35 to 45 kDa, even more preferably from 38 to 42 kDa and most preferably has a molecular weight of about 40 kDa.

In another equally preferred embodiment $R^1$ of formula (1a) or (1b) has a molecular weight ranging from 60 to 100 kDa, even more preferably from 70 to 90 kDa, even more preferably from 75 to 85 kDa and most preferably has a molecular weight of about 80 kDa.

Preferably, $R^1$ of formula (1a) or (1b) is branched and comprises at least three polymeric moieties which may also be referred to as polymeric arms or polymeric chains.

More preferably, $R^1$ of formula (1a) or (1b) comprises at least one branching point, preferably at least two branching points, and at least three polymeric chains which polymeric chains are preferably PEG-based, wherein each branching point is preferably selected from the group consisting of —N<, —$CR^8$< and >C<, wherein $R^8$ is selected from the group consisting of —H, $C_{1-6}$ alkyl, $C_{2-6}$ alkenyl and $C_{2-6}$ alkynyl; wherein $C_{1-6}$ alkyl, $C_{2-6}$ alkenyl and $C_{2-6}$ alkynyl are optionally substituted with one or more $R^9$, which are the same or different, and wherein $C_{1-6}$ alkyl, $C_{2-6}$ alkenyl and $C_{2-6}$ alkynyl are optionally interrupted with —C(O)O—, —O—, —C(O)—, —C(O)N($R^{10}$)—, —$S(O)_2$N($R^{10}$)—, —S(O)N($R^{10}$)—, —$S(O)_2$—, —S(O)—, —N($R^{10}$)$S(O)_2$N($R^{10a}$)—, —S—, —N($R^{10}$)—, —OC($OR^{10}$)($R^{10a}$)—, —N($R^{10}$)C(O)N($R^{10a}$)—, and —OC(O)N($R^{10}$)—; wherein $R^9$, $R^{10}$ and $R^{10a}$ are selected from —H, $C_{1-6}$ alkyl, $C_{2-6}$ alkenyl and $C_{2-6}$ alkynyl.

In one preferred embodiment $R^1$ of formula (1a) or (1b) comprises a first branching point $BP^1$ from which at least two spacer moieties $C^1$ and $C^2$ extend of which at least one spacer moiety is connected to an at least second branching point $BP^2$, from which second branching point $BP^2$ at least two polymeric moieties extend. More preferably, $R^1$ comprises a first branching point $BP^1$ from which two spacer moieties $C^1$ and $C^2$ extend, which spacer moiety $C^1$ is connected to a second branching point $BP^2$, from which second branching point $BP^2$ at least two polymeric moieties extend, and which spacer moiety $C^2$ is connected to a third branching point $BP^3$, from which third branching point $BP^3$ at least two polymeric moieties extend. It is understood that $BP^1$, $BP^2$, $BP^3$, $C^1$, $C^2$ and the polymeric moieties are part of $R^1$.

In another preferred embodiment $R^1$ comprises a spacer moiety $C^1$, which spacer moiety $C^1$ comprises a first branching point $BP^1$, a second branching point $BP^2$ and a third branching point $BP^3$, wherein at least one polymeric moiety extends from $BP^1$, at least one polymeric moiety extends from $BP^2$ and at least one polymeric moiety extends from $BP^3$. More preferably, $R^1$ comprises a spacer moiety $C^1$, which spacer moiety $C^1$ comprises a first branching point $BP^1$, a second branching point $BP^2$, a third branching point $BP^3$ and a forth branching point $BP^4$, wherein at least one polymeric moiety extends from $BP^1$, at least one polymeric moiety extends from $BP^2$, at least one polymeric moiety extends from $BP^3$ and at least one polymeric moiety $P^4$ extends from $BP^4$. It is understood that $BP^1$, $BP^2$, $BP^3$, $BP^4$, $C^1$ and the polymeric moieties are part of $R^1$.

Preferably, $BP^1$, $BP^2$, $BP^3$ and $BP^4$ are independently of each other selected from the group consisting of —$CR^8$<, >C< and —N<, wherein $R^8$ is selected from the group consisting of —H, $C_{1-6}$ alkyl, $C_{2-6}$ alkenyl and $C_{2-6}$ alkynyl; wherein $C_{1-6}$ alkyl, $C_{2-6}$ alkenyl and $C_{2-6}$ alkynyl are optionally substituted with one or more $R^9$, which are the same or different, and wherein $C_{1-6}$ alkyl, $C_{2-6}$ alkenyl and $C_{2-6}$ alkynyl are optionally interrupted with —C(O)O—, —O—, —C(O)—, —C(O)N($R^{10}$)—, —$S(O)_2$N($R^{10}$)—, —S(O)N($R^{10}$)—, —$S(O)_2$—, —S(O)—, —N($R^{10}$)$S(O)_2$N($R^{10a}$)—, —S—, —N($R^{10}$)—, —OC($OR^{10}$)($R^{10a}$)—, —N($R^{10}$)C(O)

$N(R^{10a})$—, and —$OC(O)N(R^{10})$—; wherein $R^9$, $R^{10}$ and $R^{10a}$ are selected from —H, $C_{1-6}$ alkyl, $C_{2-6}$ alkenyl and $C_{2-6}$ alkynyl.

Preferably, $C^1$ and $C^2$ are independently of other selected from the group consisting of $C_{1-50}$ alkyl, $C_{2-50}$ alkenyl and $C_{2-50}$ alkynyl; wherein $C_{1-50}$ alkyl, $C_{2-50}$ alkenyl and $C_{2-50}$ alkynyl are optionally substituted with one or more $R^{11}$, which are the same or different, and wherein $C_{1-50}$ alkyl, $C_{2-50}$ alkenyl and $C_{2-50}$ alkynyl are optionally interrupted with one or more groups selected from the group consisting of -T-, —C(O)O—, —O—, —C(O)—, —$C(O)N(R^{12})$—, —$S(O)_2N(R^{12})$—, —$S(O)N(R^{12})$—, —$S(O)_2$—, —S(O)—, —$N(R^{12})S(O)_2N(R^{12a})$—, —S—, —$N(R^{12})$—, —$OC(OR^{12})(R^{12a})$—, —$N(R^{12})C(O)N(R^{12a})$—, and —$OC(O)N(R^{12})$—;

wherein -T- is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl, and wherein each -T- is independently optionally substituted with one or more $R^{11}$, which are the same or different;

wherein each $R^{11}$ is independently selected from the group consisting of halogen, —CN, oxo (=O), —$COOR^{12}$, —$OR^{12}$, —$C(O)R^{12}$, —$C(O)N(R^{12}R^{12a})$, —$S(O)_2N(R^{12}R^{12a})$, —$S(O)N(R^{12}R^{12a})$, —$S(O)_2R^{12}$, —$S(O)R^{12}$, —$N(R^{12})S(O)_2N(R^{12a}R^{12b})$, —$SR^{12}$, —$N(R^{12}R^{12a})$, —$NO_2$, —$OC(O)R^{12}$, —$N(R^{12})C(O)R^{12a}$, —$N(R^{12})S(O)_2R^{12a}$, —$N(R^{12})S(O)R^{12a}$, —$N(R^{12})C(O)OR^{12a}$, —$N(R^{12})C(O)N(R^{12a}R^{12b})$, —$OC(O)N(R^{12}R^{12a})$, and $C_{1-6}$ alkyl; wherein $C_{1-6}$ alkyl is optionally substituted with one or more halogen, which are the same or different;

and wherein each $R^{12}$, $R^{12a}$ and $R^{12b}$ are independently of each other selected from the group consisting of —H, $C_{1-6}$ alkyl, $C_{2-6}$ alkenyl and $C_{2-6}$ alkynyl, wherein $C_{1-6}$ alkyl, $C_{2-6}$ alkenyl and $C_{2-6}$ alkynyl is optionally substituted with one or more halogen, which are the same or different.

Preferably, $P^1$, $P^2$, $P^3$, $P^4$ are independently of each other a polymeric moiety, more preferably a PEG-based chain comprising at least 40% PEG, even more preferably at least 50% PEG, even more preferably at least 60% PEG, even more preferably at least 70% PEG, even more preferably at least 80% PEG, even more preferably at least 90% PEG and most preferably at least 95% PEG.

In one preferred embodiment $P^1$, $P^2$, $P^3$ and $P^4$ have independently of each other a molecular weight ranging from 5 kDa to 20 kDa, more preferably ranging from 7 to 15 kDa, even more preferably ranging from 8 to 12 kDa and most preferably have a molecular weight of about 10 kDa.

In an equally preferred embodiment $P^1$, $P^2$, $P^3$ and $P^4$ have independently of each other a molecular weight ranging from 10 to 30 kDa, more preferably ranging from 15 to 25 kDa, even more preferably ranging from 17 to 23 kDa and most preferably have a molecular weight of about 20 kDa.

In a preferred embodiment —$R^1$ of formula (1a) or (1b) comprises a moiety of formula (2)

(2)

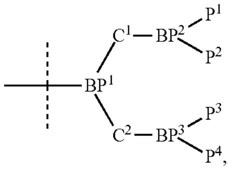

wherein

—$BP^1$<, —$BP^2$< and —$BP^3$< are independently of each other selected from the group consisting of —N< and —$C(R^8)$<;

$R^8$ is selected from the group consisting of H, $C_{1-6}$ alkyl, $C_{2-6}$ alkenyl and $C_{2-6}$ alkynyl;

—$P^1$, —$P^2$ —$P^3$ and —$P^4$ are independently of each other a PEG-based chain comprising at least 40% PEG and having a molecular weight ranging from 5 to 30 kDa;

$C^1$— and —$C^2$— are independently of each other selected from the group consisting of $C_{1-50}$ alkyl, $C_{2-50}$ alkenyl, and $C_{2-50}$ alkynyl; wherein $C_{1-50}$ alkyl, $C_{2-50}$ alkenyl, and $C_{2-50}$ alkynyl are optionally substituted with one or more $R^9$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —$C(O)N(R^{10})$—, —$S(O)_2N(R^{10})$—, —$S(O)N(R^{10})$—, —$S(O)_2$—, —S(O)—, —$N(R^{10})S(O)_2N(R^{10a})$—, —S—, —$N(R^{10})$—, —$OC(OR^{10})(R^{10a})$—, —$N(R^{10})C(O)N(R^{10a})$—, and —$OC(O)N(R^{10})$—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more $R^9$, which are the same or different;

each $R^9$ is independently selected from the group consisting of halogen, —CN, oxo (=O), —$COOR^{11}$, —$OR^{11}$, —$C(O)R^{11}$, —$C(O)N(R^{11}R^{11a})$, —$S(O)_2N(R^{11}R^{11a})$, —$S(O)N(R^{11}R^{11a})$, —$S(O)_2R^{11}$, —$S(O)R^{11}$, —$N(R^{11})S(O)_2N(R^{11a}R^{11b})$, —$SR^{11}$, —$N(R^{11}R^{11a})$, —$NO_2$, —$OC(O)R^{11}$, —$N(R^{11})C(O)R^{11a}$, —$N(R^{11})S(O)_2R^{11a}$, —$N(R^{11})S(O)R^{11a}$, —$N(R^{11})C(O)OR^{11a}$, —$N(R^{11})C(O)N(R^{11a}R^{11b})$, —$OC(O)N(R^{11}R^{11a})$, and $C_{1-6}$ alkyl; wherein $C_{1-6}$ alkyl is optionally substituted with one or more halogen, which are the same or different; and each $R^{10}$, $R^{10a}$, $R^{11}$, $R^{11a}$ and $R^{11b}$ is independently selected from the group consisting of —H, and $C_{1-6}$ alkyl, wherein $C_{1-6}$ alkyl is optionally substituted with one or more halogen, which are the same or different.

In a preferred embodiment $BP^1$ of formula (2) is —N<.

In a preferred embodiment $BP^2$ and $BP^2$ of formula (2) are both —CH<.

It is advantageous if the first branching point $BP^1$ and the attachment site of X are separated by no more than a certain number of atoms.

Preferably, the critical distance in the compounds of formula (1a) or (1b) is less than 60 atoms, more preferably less than 50 atoms, even more preferably less than 40 atoms, even more preferably less than 30 atoms, even more preferably less than 20 atoms and most preferably less than 10 atoms.

The term "critical distance" refers to the shortest distance measured as the number of atoms between the first branching point $BP^1$ comprised in $R^1$ and the atom marked with the asterisk in formula (a), if the compound is of formula (1a), or refers to the number of atoms between the first branching point $BP^1$ comprised in $R^1$ and the atom marked with the asterisk in formula (b), if the compound is of formula (1b):

(a)

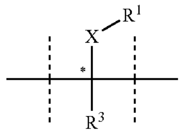

(b)

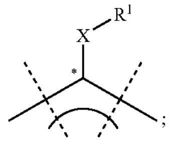

wherein the dashed lines indicate attachment to the remainder of the compound of formula (1a) in the case of (a) and to the remainder of the compound of formula (1b) in the case of (b).

In a preferred embodiment $-P^1$, $-P^2$, $-P^3$ and $-P^4$ of formula (2) independently of each other have a molecular weight ranging from 5 kDa to 20 kDa, more preferably ranging from 7 to 15 kDa, even more preferably ranging from 8 to 12 kDa and most preferably have a molecular weight of about 10 kDa.

In an equally preferred embodiment $-P^1$, $-P^2$, $-P^3$ and $-P^4$ of formula (2) independently of each other have a molecular weight ranging from 10 to 30 kDa, more preferably ranging from 15 to kDa, even more preferably ranging from 17 to 23 kDa and most preferably have a molecular weight of about 20 kDa.

In a preferred embodiment $-C^1-$ and $-C^2-$ of formula (2) are $C_{1-50}$ alkyl, which $C_{1-50}$ alkyl is interrupted by one or more of the groups selected from the group consisting of $-O-$, $-C(O)N(R^{10})-$ and 3- to 10 membered heterocyclyl; wherein the 3- to 10 membered heterocyclyl is substituted with at least one oxo (=O).

Most preferably, $-C^1-$ and $-C^2-$ of formula (2) are of formula (2a)

(2a)

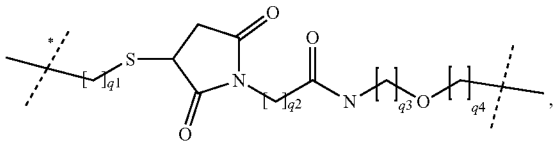

wherein the dashed line marked with the asterisk indicates attachment to $BP^1$;

the unmarked dashed line indicates attachment to $BP^2$ or $BP^3$, respectively;

q1 is 1, 2, 3, 4, 5, 6, 7 or 8; preferably q1 is 4, 5, 6, 7, or 8; more preferably q1 is 5, 6 or 7; most preferably q1 is 6;

q2 is 1, 2, 3, 4, or 5; preferably q2 is 1, 2 or 3; most preferably q2 is 2;

q3 is 1, 2, 3, 4, 5, 6, 7 or 8; preferably q3 is 2, 3, 4, or 5; more preferably q3 is 2, 3 or 4; most preferably q3 is 3;

q4 is 1, 2 or 3; most preferably, q4 is 1.

In a preferred embodiment $P^1$, $P^2$, $P^3$ and $P^4$ of formula (2) are independently of each other of formula (2b)

(2b)

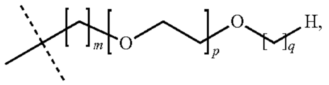

wherein the dashed line indicates attachment the rest of $R^1$, i.e. to $BP^2$ or $BP^3$, respectively, m is 0, 1, 2, 3, 4, 5 or 6; preferably 0 or 1, p is an integer ranging from 57 to 1420, more preferably from 85 to 850; and q is 1, 2, 3, 4, 5 or 6.

In a preferred embodiment p of formula (2b) ranges from 170 to 284, even more preferably from 198 to 255 and most preferably from 215 to 238.

In an equally preferred embodiment p of formula (2b) ranges from 340 to 568, even more preferably from 398 to 510 and most preferably from 426 to 482.

More preferably, $-R^1$ comprises a moiety of formula (2c):

(2c)

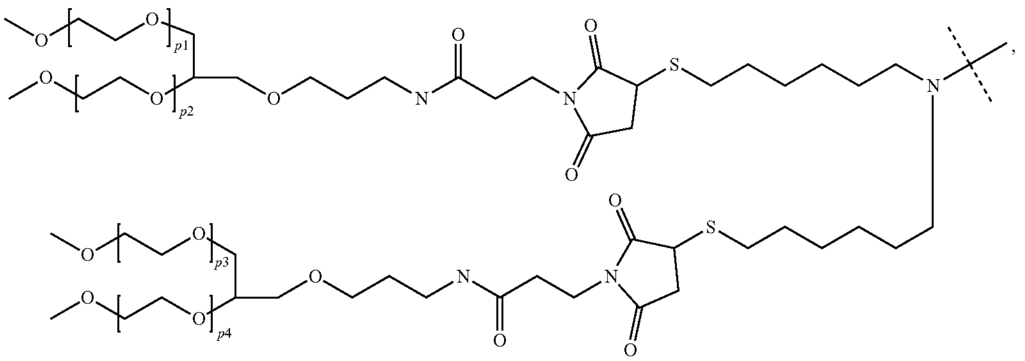

wherein p1, p2, p3 and p4 are independently an integer ranging from 57 to 1420, even more preferably from 85 to 850.

In a preferred embodiment p1, p2, p3 and p4 of formula (2c) are an integer independently selected from 170 to 284, even more preferably from 198 to 255 and most preferably from 215 to 238.

In an equally preferred embodiment p1, p2, p3 and p4 of formula (2c) are an integer independently selected from 340 to 568, even more preferably from 398 to 510 and most preferably from 426 to 482.

In a preferred embodiment —$R^2$ of formula (1b) is selected from the group consisting of —H, methyl, ethyl, n-propyl, isopropyl, n-butyl, isobutyl, sec-butyl and tert-butyl. More preferably, —$R^2$ of formula (1b) is selected from the group consisting of —H, methyl, ethyl, n-propyl and isopropyl. Even more preferably —$R^2$ of formula (1b) is selected from —H, methyl and ethyl. Most preferably, —$R^2$ of formula (1b) is —H.

In a preferred embodiment —$R^3$ of formula (1a) and (1b) is selected from the group consisting of —H, methyl, ethyl, n-propyl, isopropyl, n-butyl, isobutyl, sec-butyl and tert-butyl. More preferably, —$R^3$ of formula (1a) and (1b) is selected from the group consisting of —H, methyl, ethyl, n-propyl and isopropyl. Even more preferably —$R^3$ of formula (1a) and (1b) is selected from —H, methyl and ethyl. Most preferably, —$R^3$ of formula (1a) and (1b) is —H.

In a preferred embodiment, each —$R^4$ of formula (1a) or (1b) is independently selected from methyl, ethyl, n-propyl, isopropyl, n-butyl, isobutyl, sec-butyl and tert-butyl. More preferably, —$R^4$ of formula (1a) or (1b) is selected from the group consisting of methyl, ethyl, n-propyl and isopropyl. Even more preferably —$R^4$ of formula (1a) or (1b) is selected from methyl and ethyl.

In a preferred embodiment —$R^5$ of formula (1a) or (1b) is selected from the group consisting of —H, methyl, ethyl, n-propyl, isopropyl, n-butyl, isobutyl, sec-butyl and tert-butyl. More preferably, —$R^5$ of formula (1a) or (1b) is selected from the group consisting of —H, methyl, ethyl, n-propyl and isopropyl. Even more preferably —$R^5$ of formula (1a) or (1b) is selected from methyl and ethyl. Most preferably, —$R^5$ of formula (1a) or (1b) is methyl.

In a preferred embodiment —$R^6$ and —$R^{6a}$ of formula (1a) or (1b) are independently selected from the group consisting of —H, methyl, ethyl, n-propyl, isopropyl, n-butyl, isobutyl, sec-butyl and tert-butyl. More preferably, —$R^6$ and —$R^{6a}$ of formula (1a) or (1b) are independently selected from the group consisting of —H, methyl, ethyl, n-propyl and isopropyl. Even more preferably —$R^6$ and —$R^{6a}$ of formula (1a) or (1b) are independently selected from —H, methyl and ethyl. Most preferably, —$R^6$ and —$R^{6a}$ of formula (1a) or (1b) are both —H.

In a preferred embodiment X of formula (1a) or (1b) is preferably selected from the group consisting of -T-, —C(O)O—, —O—, —C(O)—, —C(O)N($R^{z1}$)—, —S(O)$_2$N($R^{z1}$)—, —S(O)N($R^{z1}$)—, —S(O)$_2$—, —S(O)—, —N($R^{z1}$)S(O)$_2$N($R^{z1a}$)—, —S—, —N($R^{z1}$)—, —OC(O$R^{z1}$)($R^{z1a}$)—, —N($R^{z1}$)C(O)N($R^{z1a}$)—, —OC(O)N($R^{z1}$)—, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more $R^{z2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{z3}$)—, —S(O)$_2$N($R^{z3}$)—, —S(O)N($R^{z3}$)—, —S(O)$_2$—, —S(O)—, —N($R^{z3}$)S(O)$_2$N($R^{z3a}$)—, —S—, —N($R^{z3}$)—, —OC(O$R^{z3}$)($R^{z3a}$)—, —N($R^{z3}$)C(O)N($R^{z3a}$)—, and —OC(O)N($R^{z3}$)—;

$R^{z1}$ and $R^{z1a}$ are independently of each other selected from the group consisting of —H, -T, $C_{1-50}$ alkyl, $C_{2-50}$ alkenyl, and $C_{2-50}$ alkynyl; wherein -T, $C_{1-50}$ alkyl, $C_{2-50}$ alkenyl, and $C_{2-50}$ alkynyl are optionally substituted with one or more $R^{z2}$, which are the same or different, and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{z4}$)—, —S(O)$_2$N($R^{z4}$)—, —S(O)N($R^{z4}$)—, —S(O)$_2$—, —S(O)—, —N($R^{z4}$)S(O)$_2$N($R^{z4a}$)—, —S—, —N($R^{z4}$)—, —OC(O$R^{z4}$)($R^{z4a}$)—, —N($R^{z4}$)C(O)N($R^{z4a}$)—, and —OC(O)N($R^{z4}$)—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more $R^{z2}$, which are the same or different;

each $R^{z2}$ is independently selected from the group consisting of halogen, —CN, oxo (=O), —COO$R^{z5}$, —O$R^{z5}$, —C(O)$R^{z5}$, —C(O)N($R^{z5}R^{z5a}$), —S(O)$_2$N($R^{z5}R^{z5a}$), —S(O)N($R^{z5}R^{z5a}$), —S(O)$_2R^{z5}$, —S(O)$R^{z5}$, —N($R^{z5}$)S(O)$_2$N($R^{z5a}R^{z5b}$), —S$R^{z5}$, —N($R^{z5}R^{z5a}$), —NO$_2$, —OC(O)$R^{z5}$, —N($R^{z5}$)C(O)$R^{z5a}$, —N($R^{z5}$)S(O)$_2R^{z5a}$, —N($R^{z5}$)S(O)$R^{z5a}$, —N($R^{z5}$)C(O)O$R^{z5a}$, —N($R^{z5}$)C(O)N($R^{z5a}R^{z5b}$), —OC(O)N($R^{z5}R^{z5a}$), and $C_{1-6}$ alkyl; wherein $C_{1-6}$ alkyl is optionally substituted with one or more halogen, which are the same or different;

each $R^{z3}$, $R^{z3a}$, $R^{z4}$, $R^{z4a}$, $R^{z5}$, $R^{z5a}$ and $R^{z5b}$ is independently selected from the group consisting of —H, and $C_{1-6}$ alkyl; wherein $C_{1-6}$ alkyl is optionally substituted with one or more halogen, which are the same or different.

More preferably, X of formula (1a) or (1b) is selected from the group consisting of $C_{1-10}$ alkyl, $C_{2-10}$ alkenyl, and $C_{2-10}$ alkynyl; wherein $C_{1-10}$ alkyl, $C_{2-10}$ alkenyl, and $C_{2-10}$ alkynyl are optionally substituted with one or more $R^{z2}$, which are the same or different and wherein $C_{1-10}$ alkyl, $C_{2-10}$ alkenyl, and $C_{2-10}$ alkynyl are optionally interrupted by one or more groups selected from the group consisting of -T-, —C(O)O—, —O—, —C(O)—, —C(O)N($R^{z3}$)—, —S(O)$_2$N($R^{z3}$)—, —S(O)N($R^{z3}$)—, —S(O)$_2$—, —S(O)—, —N($R^{z3}$)S(O)$_2$N($R^{z3a}$)—, —S—, —N($R^{z3}$)—, —OC(O$R^{z3}$)($R^{z3a}$)—, —N($R^{z3}$)C(O)N($R^{z3a}$)—, and —OC(O)N($R^{z3}$)—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more $R^{z2}$, which are the same or different;

each $R^{z2}$ is independently selected from $C_{1-6}$ alkyl, wherein $C_{1-6}$ alkyl is optionally substituted with one or more halogen, which are the same or different;

each $R^{z3}$, $R^{z3a}$ is independently selected from the group consisting of —H, and $C_{1-6}$ alkyl, wherein $C_{1-6}$ alkyl is optionally substituted with one or more halogen, which are the same or different.

Even more preferably, X of formula (1a) or (1b) is $C_{1-10}$ alkyl which is optionally interrupted by one or more groups selected from the group consisting of —C(O)O—, —O—, —C(O)—, —C(O)N($R^{z3}$)—, —S—, —N($R^{z3}$)—, —OC($OR^{z3}$)($R^{z3a}$)— and —OC(O)N($R^{z3}$)—;

each $R^{z3}$, $R^{z3}$ is independently selected from —H and $C_{1-6}$ alkyl.

Most preferably, X of formula (1a) or (1b) is of formula (3)

(3)

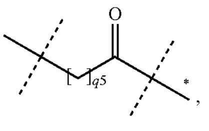

wherein the dashed line marked with the asterisk indicates attachment to the $R^1$;

the unmarked dashed line indicates attachment to remainder of the compound;

q5 is 1, 2, 3, 4, 5, 6, 7 or 8; preferably q5 is 1, 2, 3, 4, or 5; more preferably q5 is 2, 3 or 4; most preferably q5 is 3;

Preferably, Ar of formula (1a) or (1b) is phenyl. Most preferably Ar of formula (1a) or (1b) is

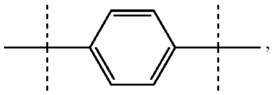

wherein the dashed lines indicate attachment to the remainder of the compound of formula (1a) or (1b).

Preferably W of formula (1a) or (1b) is $C_{1-20}$ alkyl, optionally interrupted with $C_{3-10}$ cycloalkyl, —C(O)—, —C(O)N($R^7$)—, —O—, —S— and —N($R^7$)—. Even more preferably, W of formula (1a) and (1b) is $C_{1-10}$ alkyl, optionally interrupted with $C_{3-10}$ cycloalkyl, —C(O)—, —C(O)N($R^7$)—, —O—, —S— and —N($R^7$)—. Even more preferably, W of formula (1a) and (1b) is $C_{1-6}$ alkyl, optionally interrupted with $C_{3-10}$ cycloalkyl, —C(O)—, —C(O)N($R^7$)—, —O—, —S— and —N($R^7$)—. Most preferably, W of formula (1a) or (1b) is

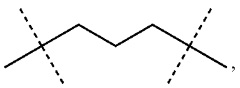

wherein the dashed lines indicate attachment to the rest of the molecule.

Preferably, -Nu of formula (1a) or (1b) is —N($R^7R^{7a}$).

Preferably, —$R^7$ and —$R^{7a}$ of formula (1a) or (1b) are independently of each other selected from the group consisting of —H, methyl, ethyl, n-propyl, isopropyl, n-butyl, isobutyl, sec-butyl and tert-butyl. More preferably, —$R^7$ and —$R^{7a}$ of formula (1a) or (1b) are independently of each other selected from —H, methyl, ethyl, n-propyl and isopropyl. Even more preferably, —$R^7$ and —$R^{7a}$ of formula (1a) or (1b) are independently of each other selected from methyl or ethyl. Most preferably, —$R^7$ and —$R^{7a}$ of formula (1a) or (1b) are both methyl.

Preferably, the water-soluble controlled-release growth hormone compound is compound 2 of example 2 of WO2016/079114A1. Accordingly, a preferred water-soluble controlled-release growth hormone compound has structure of formula (A1):

(A1)

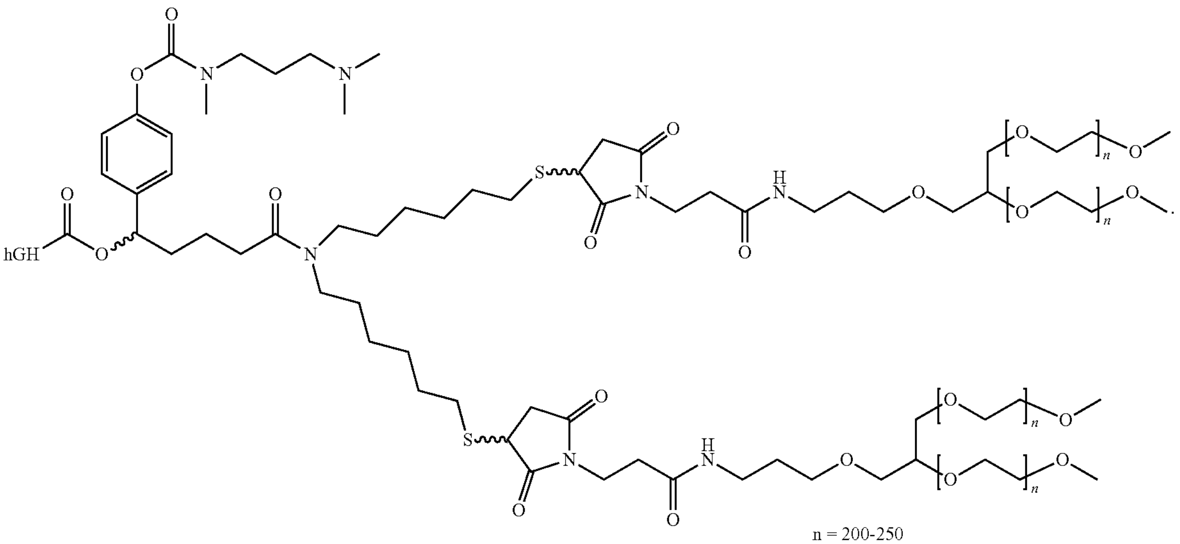

n = 200-250

In another embodiment the at least one further biologically active moiety or drug in the form of a water-soluble controlled-release compound comprises a CNP agonist moiety. Doses of the CNP agonist moiety typically and preferably administered to a human patient are as described above for free CNP agonist converted into the equivalent doses of the water-soluble controlled-release compound.

In another embodiment the at least one further biologically active moiety or drug in the form of a water-soluble controlled-release compound comprises an IGF-1 moiety or drug. Doses of IGF-1 typically and preferably administered to a human patient are as described above for free IGF-1 converted into the equivalent doses of the water-soluble controlled-release compound.

In another embodiment the at least one further biologically active moiety or drug in the form of a water-soluble controlled-release compound comprises an ANP moiety or drug. Doses of ANP typically and preferably administered to a human patient are as described above for free ANP converted into the equivalent doses of the water-soluble controlled-release compound.

In another embodiment the at least one further biologically active moiety or drug in the form of a water-soluble controlled-release compound comprises a BNP moiety or drug. Doses of BNP typically and preferably administered to a human patient are as described above for free BNP converted into the equivalent doses of the water-soluble controlled-release compound.

In another embodiment the at least one further biologically active moiety or drug in the form of a water-soluble controlled-release compound comprises an inhibitor of peptidases and proteases moiety or drug.

In another embodiment the at least one further biologically active moiety or drug in the form of a water-soluble controlled-release compound comprises an inhibitor of NPR—C moiety or drug.

In another embodiment the at least one further biologically active moiety in the form of a water-soluble controlled-release compound is PTH. Preferred PTH sequences are SEQ ID NOs:1 to 121 of WO2017/148883A1, most preferably the PTH having the SEQ ID NO: 51, which are herewith incorporated by reference.

The CNP agonist is or comprises a CNP agonist selected from the group consisting of small molecules, natural products, oligonucleotides, polypeptides and proteins.

In one embodiment the CNP agonist is or comprises a small molecule. In one embodiment the CNP agonist comprises a small molecule. In another embodiment the CNP agonist is a small molecule.

In another embodiment the CNP agonist is or comprises a natural product. In one embodiment the CNP agonist comprises a natural product. In another embodiment the CNP agonist is a natural product.

In another embodiment the CNP agonist is or comprises an oligonucleotide. Preferably, such oligonucleotide is selected from the group consisting of antisense oligonucleotides, aptamers, RNAi and siRNA. In one embodiment the CNP agonist comprises an oligonucleotide, more preferably selected from the group consisting of antisense oligonucleotides, aptamers, RNAi and siRNA. In another embodiment the CNP agonist is an oligonucleotide, more preferably selected from the group consisting of antisense oligonucleotides, aptamers, RNAi and siRNA.

In another embodiment the CNP agonist is or comprises a protein. In one embodiment the CNP agonist comprises a protein. In another embodiment the CNP agonist is a protein.

In one embodiment the CNP agonist comprises a polypeptide. In another embodiment the CNP agonist is a polypeptide. Preferably the CNP agonist comprises a CNP molecule or moiety. More preferably the CNP agonist is CNP. Even more preferably the CNP agonist comprises a CNP molecule or moiety having the sequence of SEQ ID NO:24, SEQ ID NO:25 or SEQ ID NO:30. Even more preferably the CNP agonist is CNP having the sequence of SEQ ID NO:24, SEQ ID NO:25 or SEQ ID NO:30. Even more preferably the CNP agonist comprises a CNP molecule or moiety CNP having the sequence of SEQ ID NO:24. Most preferably the CNP agonist is a CNP having the sequence of SEQ ID NO:24.

Preferably, the CNP agonist is a controlled-release CNP agonist. In the following sections the controlled-release CNP agonist comprised in the pharmaceutical composition of the present invention is described in further detail.

The controlled-release CNP agonist releases at least one CNP agonist under physiological conditions with a release half-life of at least 6 hours. Preferably the controlled-release CNP agonist releases at least one CNP agonist under physiological conditions with a release half-life of at least 12 hours. Even more preferably the controlled-release CNP agonist releases at least one CNP agonist under physiological conditions with a release half-life of at least 24 hours. Even more preferably the controlled-release CNP agonist releases at least one CNP agonist under physiological conditions with a release half-life of at least 48 hours. Even more preferably the controlled-release CNP agonist releases at least one CNP agonist under physiological conditions with a release half-life of at least 72 hours. Even more preferably the controlled-release CNP agonist releases at least one CNP agonist under physiological conditions with a release half-life of at least 96 hours. Even more preferably the controlled-release CNP agonist releases at least one CNP agonist under physiological conditions with a release half-life of at least 120 hours. Even more preferably the controlled-release CNP agonist releases at least one CNP agonist under physiological conditions with a release half-life of at least 144 hours.

The controlled-release CNP agonist preferably comprises a CNP agonist selected from the group consisting of small molecules, natural products, oligonucleotides, polypeptides and proteins.

In one embodiment the CNP agonist comprises a small molecule. Preferably, the CNP agonist is a small molecule.

In another embodiment the CNP agonist comprises a natural product. Preferably, the CNP agonist is a natural product.

In another embodiment the CNP agonist comprises an oligonucleotide. Preferably, such oligonucleotide is selected from the group consisting of antisense oligonucleotides, aptamers, RNAi and siRNA. Preferably, the CNP agonist is an oligonucleotide, more preferably selected from the group consisting of antisense oligonucleotides, aptamers, RNAi and siRNA.

In another embodiment the CNP agonist comprises a protein. Preferably, the CNP agonist is a protein.

In a preferred embodiment the CNP agonist comprises a polypeptide. More preferably the CNP agonist is a polypeptide. Preferably the CNP agonist comprises a CNP molecule or moiety. More preferably the CNP agonist is CNP. Even more preferably the CNP agonist comprises a CNP molecule or moiety having the sequence of SEQ ID NO:24, SEQ ID NO:25 or SEQ ID NO:30. Even more preferably the CNP agonist is CNP having the sequence of SEQ ID NO:24, SEQ ID NO:25 or SEQ ID NO:30. Even more preferably the CNP agonist comprises a CNP molecule or moiety CNP having the sequence of SEQ ID NO:24. Most preferably the CNP agonist is a CNP having the sequence of SEQ ID NO:24.

In one embodiment the controlled-release CNP agonist is water-insoluble.

Preferably, the controlled-release CNP agonist is selected from the group consisting of crystals, nanoparticles, microparticles, nanospheres and microspheres.

In one embodiment the controlled-release CNP agonist is a crystal comprising at least one CNP agonist.

In another embodiment the controlled-release CNP agonist is a nanoparticle comprising at least one CNP agonist.

In another embodiment the controlled-release CNP agonist is a microparticle comprising at least one CNP agonist.

In another embodiment the controlled-release CNP agonist is a nanosphere comprising at least one CNP agonist.

In another embodiment the controlled-release CNP agonist is a microsphere comprising at least one CNP agonist.

In one embodiment the controlled-release CNP agonist is a vesicle comprising at least one CNP agonist. Preferably, such vesicle comprising at least one CNP agonist is a micelle, liposome or polymersome.

In one embodiment the controlled-release CNP agonist is a micelle comprising at least one CNP agonist.

In another embodiment the controlled-release CNP agonist is a liposome comprising at least one CNP agonist. Preferably, such liposome is selected from the group consisting of aquasomes; non-ionic surfactant vesicles, such as niosomes and proniosomes; cationic liposomes, such as LeciPlex; transfersomes; ethosomes; ufasomes; sphingosomes; and pharmacosomes.

In another embodiment the controlled-release CNP agonist is a polymersome comprising at least one CNP agonist.

In another embodiment the controlled-release CNP agonist comprises at least one CNP agonist non-covalently embedded in a water-insoluble polymer. Preferably, such water-insoluble polymer comprises a polymer selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly (ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly (lactic-co-glycolic acids), poly(methacrylamides), poly (methacrylates), poly(methyloxazolines), poly (organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

In a preferred embodiment the controlled-release CNP comprises at least one CNP agonist non-covalently embedded in poly(lactic-co-glycolic acid) (PLGA).

In another embodiment the controlled-release CNP agonist comprises at least one CNP agonist covalently and reversibly conjugated to a water-insoluble polymer. Preferably such water-insoluble polymer comprises a polymer selected from the group consisting of 2-methacryloyl-oxyethyl phosphoyl cholins, poly(acrylic acids), poly(acrylates), poly(acrylamides), poly(alkyloxy) polymers, poly (amides), poly(amidoamines), poly(amino acids), poly (anhydrides), poly(aspartamides), poly(butyric acids), poly (glycolic acids), polybutylene terephthalates, poly (caprolactones), poly(carbonates), poly(cyanoacrylates), poly(dimethylacrylamides), poly(esters), poly(ethylenes), poly(ethyleneglycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly (hydroxypropyloxazolines), poly(iminocarbonates), poly (lactic acids), poly(lactic-co-glycolic acids), poly (methacrylamides), poly(methacrylates), poly (methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

Preferably such controlled-release CNP agonist comprising at least one CNP agonist covalently and reversibly conjugated to a water-insoluble polymer is a CNP agonist prodrug comprising a conjugate D-L, wherein -D is a CNP agonist moiety; and -L comprises a reversible prodrug linker moiety $-L^1-$;

wherein $-L^1-$ is substituted with $-L^2-Z'$ and is optionally further substituted; wherein $-L^2-$ is a single chemical bond or a spacer moiety; and —Z' is a water-insoluble carrier moiety.

It is understood that a multitude of moieties $-L^2-L^1-D$ is connected to a water-insoluble carrier —Z'.

The water-insoluble carrier —Z' is preferably a hydrogel. Preferably, such hydrogel comprises a polymer selected from the group consisting of 2-methacryloyl-oxyethyl phosphoyl cholins, poly(acrylic acids), poly(acrylates), poly (acrylamides), poly(alkyloxy) polymers, poly(amides), poly (amidoamines), poly(amino acids), poly(anhydrides), poly (aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly (ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly (lactic-co-glycolic acids), poly(methacrylamides), poly (methacrylates), poly(methyloxazolines), poly (organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

If the carrier —Z' is a hydrogel, it is preferably a hydrogel comprising PEG or hyaluronic acid. Most preferably such hydrogel comprises PEG.

Even more preferably, the carrier —Z' is a hydrogel as described in WO 2006/003014 A2, WO 2011/012715 A1 or WO 2014/056926 A1, which are herewith incorporated by reference in their entirety.

In another embodiment —Z' is a polymer network formed through the physical aggregation of polymer chains, which physical aggregation is preferably caused by hydrogen bonds, crystallization, helix formation or complexation. In one embodiment such polymer network is a thermogelling polymer.

In another embodiment the controlled-release CNP agonist is water soluble.

In one embodiment the CNP agonist is a polypeptide or protein and the controlled-release CNP agonist is a fusion protein comprising such polypeptide or protein CNP agonist moiety fused to one or more further polypeptide or protein moiety. Preferably, the CNP agonist is released from the fusion protein through enzymatic cleavage. Preferably, such at least one or more further polypeptide or protein moieties are selected from the group consisting of carboxyl-terminal peptide of the chorionic gonadotropin as described in US 2012/0035101 A1 which are herewith incorporated by reference; albumin; XTEN sequences as described in WO 2011123813 A2 which are herewith incorporated by reference; proline/alanine random coil sequences as described in WO 2011/144756 A1 which are herewith incorporated by reference; proline/alanine/serine random coil sequences as described in WO 2008/155134 A1 and WO 2013/024049 A1 which are herewith incorporated by reference; and Fc fusion proteins.

In a preferred embodiment the controlled-release CNP agonist is a CNP agonist compound of formula (Ia) or (Ib)

$$Z{-}(L^2{-}L^1{-}D)_x, \quad (Ia)$$

$$D{-}(L^1{-}L^2{-}Z)_y, \quad (Ib)$$

wherein

-D is a CNP agonist moiety;

-$L^1$- is a reversible prodrug linker moiety;

-$L^2$- is a single chemical bond or a spacer moiety; —Z is a water-soluble carrier moiety;

x is an integer selected from the group consisting of 1, 2, 3, 4, 5, 6, 7, 8, 9, 10, 11, 12, 13, 14, 15 or 16; and y is an integer selected from the group consisting of 1, 2, 3, 4 and 5.

It is understood that the compounds of (Ia) and (Ib) are prodrugs.

Preferably, x of formula (Ia) is an integer selected from the group consisting of 1, 2, 3, 4, 6 and 8. More preferably x of formula (Ia) is an integer selected from the group consisting of 1, 2, 4, and 6. Even more preferably x of formula (Ia) is an integer selected from the group consisting of 1, 4 and 6 and most preferably x of formula (Ia) is 1.

Preferably, y of formula (Ib) is an integer selected from the group consisting of 1, 2 or 3. In one preferred embodiment y of formula (Ib) is 1. In an equally preferred embodiment y of formula (Ib) is 2.

Preferably the controlled-release CNP agonist is a CNP agonist prodrug of formula (Ia) with x=1.

The moiety -$L^1$- is a reversible prodrug linker from which the drug, i.e. the CNP agonist, is released in its free form, i.e. -$L^1$- is a traceless prodrug linker. Suitable prodrug linkers are known in the art, such as for example the reversible prodrug linker moieties disclosed in WO 2005/099768 A2, WO 2006/136586 A2, WO 2011/089216 A1 and WO 2013/024053 A1, which are incorporated by reference herewith.

In another embodiment -$L^1$- is a reversible prodrug linker as described in WO 2011/012722 A1, WO 2011/089214 A1, WO 2011/089215 A1, WO 2013/024052 A1 and WO 2013/160340 A1 which are incorporated by reference herewith.

The moiety -$L^1$- can be connected to -D through any type of linkage, provided that it is reversible. Preferably, -$L^1$- is connected to -D through a linkage selected from the group consisting of amide, ester, carbamate, acetal, aminal, imine, oxime, hydrazone, disulfide and acylguanidine. Even more preferably -$L^1$- is connected to -D through a linkage selected from the group consisting of amide, ester, carbamate and acylguanidine. It is understood that these linkages may not per se be reversible, but that neighboring groups comprised in -$L^1$- may render the linkage reversible.

In a preferred embodiment, the moiety -$L^1$- is connected to -D through an amide linkage.

A particularly preferred moiety -$L^1$- is disclosed in WO 2009/095479 A2. Accordingly, in one preferred embodiment the moiety -$L^1$- is of formula (II):

(II)

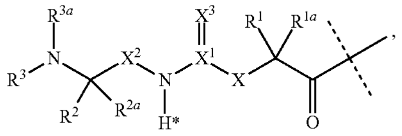

wherein the dashed line indicates the attachment to a nitrogen of -D which is a CNP agonist moiety by forming an amide bond;

—X— is —$C(R^4R^{4a})$—; —$N(R^4)$—; —O—; —$C(R^4R^{4a})$—$C(R^5R^{5a})$—; —$C(R^5R^{5a})$—$C(R^4R^{4a})$—; —$C(R^4R^{4a})$—$N(R^6)$—; —$N(R^6)$—$C(R^4R^{4a})$—; —$C(R^4R^{4a})$—O—; —O—$C(R^4R^{4a})$—; or —$C(R^7R^{7a})$—;

$X^1$ is C; or S(O);

$X^2$— is —$C(R^8R^{8a})$—; or —$C(R^8R^{8a})$—$C(R^9R^{9a})$—;

=$X^3$ is =O; =S; or =N—CN;

—$R^1$, —$R^{1a}$, —$R^2$, —$R^{2a}$, —$R^4$, —$R^{4a}$, —$R^5$, —$R^{5a}$, —$R^6$, —$R^8$, —$R^{8a}$, —$R^9$, —$R^{9a}$ are independently selected from the group consisting of —H; and $C_{1-6}$ alkyl;

—$R^3$, —$R^{3a}$ are independently selected from the group consisting of —H; and $C_{1-6}$ alkyl, provided that in case one of —$R^3$, —$R^{3a}$ or both are other than —H they are connected to N to which they are attached through an $SP^3$-hybridized carbon atom;

—$R^7$ is —$N(R^{10}R^{10a})$; or —$NR^{10}$—(C=O)—$R^{11}$;

—$R^{7a}$, —$R^{10}$, —$R^{10a}$, —$R^{11}$ are independently of each other —H; or $C_{1-6}$ alkyl;

optionally, one or more of the pairs —$R^{1a}$/—$R^{4a}$, —$R^{1a}$/—$R^{5a}$, —$R^{1a}$/—$R^{7a}$, —$R^{4a}$/—$R^{5a}$, —$R^{8a}$/—$R^{9a}$ form a chemical bond;

optionally, one or more of the pairs —$R^1$/—$R^{1a}$, —$R^2$/—$R^{2a}$, —$R^4$/—$R^{4a}$, —$R^5$/—$R^{5a}$, —$R^8$/—$R^{8a}$, —$R^9$/—$R^{9a}$ are joined together with the atom to which they are attached to form a $C_{3-10}$ cycloalkyl; or 3- to 10-membered heterocyclyl;

optionally, one or more of the pairs —$R^1$/—$R^4$, —$R^1$/—$R^5$, —$R^1$/—$R^6$, —$R^1$/—$R^{7a}$, —$R^4$/—$R^5$, —$R^4$/—$R^6$, —$R^8$/—$R^9$, —$R^2$/—$R^3$ are joined together with the atoms to which they are attached to form a ring A;

optionally, $R^3/R^{3a}$ are joined together with the nitrogen atom to which they are attached to form a 3- to 10-membered heterocycle;

A is selected from the group consisting of phenyl; naphthyl; indenyl; indanyl; tetralinyl; $C_{3-10}$ cycloalkyl; 3- to 10-membered heterocyclyl; and 8- to 11-membered heterobicyclyl; and wherein $-L^1-$ is substituted with $-L^2-Z$ or $-L^2-Z'$ and wherein $-L^1-$ is optionally further substituted, provided that the hydrogen marked with the asterisk in formula (II) is not replaced by $-L^2-Z$ or $-L^2-Z'$ or a substituent; wherein $L^2$- is a single chemical bond or a spacer;

—Z is a water-soluble carrier; and

Z' is a water-insoluble carrier.

Preferably $-L^1-$ of formula (II) is substituted with one moiety $-L^2-Z$ or $-L^2-Z'$.

In one embodiment $-L^1-$ of formula (II) is not further substituted.

It is understood that if $—R^3/—R^{3a}$ of formula (II) are joined together with the nitrogen atom to which they are attached to form a 3- to 10-membered heterocycle, only such 3- to 10-membered heterocycles may be formed in which the atoms directly attached to the nitrogen are $SP^3$-hybridized carbon atoms. In other words, such 3- to 10-membered heterocycle formed by $—R^3/—R^{3a}$ together with the nitrogen atom to which they are attached has the following structure:

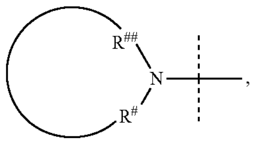

wherein the dashed line indicates attachment to the rest of $-L^1-$;

the ring comprises 3 to 10 atoms comprising at least one nitrogen; and $R^{\#}$ and $R^{\#\#}$ represent an $SP^3$-hydridized carbon atom.

It is also understood that the 3- to 10-membered heterocycle may be further substituted.

Exemplary embodiments of suitable 3- to 10-membered heterocycles formed by $—R^3/—R^{3a}$ of formula (II) together with the nitrogen atom to which they are attached are the following:

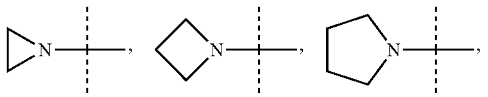

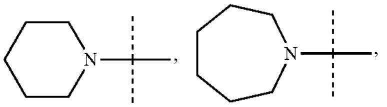

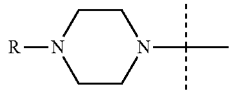
and
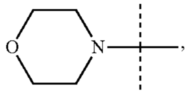

wherein dashed lines indicate attachment to the rest of the molecule; and

—R is selected from the group consisting of —H and $C_{1-6}$ alkyl.

$-L^1-$ of formula (II) may optionally be further substituted. In general, any substituent may be used as far as the cleavage principle is not affected, i.e. the hydrogen marked with the asterisk in formula (II) is not replaced and the nitrogen of the moiety

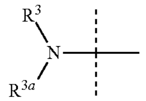

of formula (II) remains part of a primary, secondary or tertiary amine, i.e. $—R^3$ and $—R^{3a}$ are independently of each other —H or are connected to —N< through an $SP^3$-hybridized carbon atom.

In one embodiment $—R^1$ or $—R^{1a}$ of formula (II) is substituted with $-L^2-Z$ or $-L^2-Z'$. In another embodiment $—R^2$ or $—R^{2a}$ of formula (II) is substituted with $-L^2-Z$ or $-L^2-Z'$. In another embodiment $—R^3$ or $—R^{3a}$ of formula (II) is substituted with $-L^2-Z$ or $-L^2-Z'$. In another embodiment $—R^4$ of formula (II) is substituted with $-L^2-Z$ or $-L^2-Z'$. In another embodiment $—R^5$ or $—R^{5a}$ of formula (II) is substituted with $-L^2-Z$ or $-L^2-Z'$. In another embodiment $—R^6$ of formula (II) is substituted with $-L^2-Z$ or $-L^2-Z'$. In another embodiment $—R^7$ or $—R^{7a}$ of formula (II) is substituted with $-L^2-Z$ or $-L^2-Z'$. In another embodiment $—R^8$ or $—R^{8a}$ of formula (II) is substituted with $-L^2-Z$ or $-L^2-Z'$. In another embodiment $—R^9$ or $—R^{9a}$ of formula (II) is substituted with $-L^2-Z$ or $-L^2-Z'$.

Most preferably $—R^4$ of formula (II) is substituted with $-L^2-Z$ or $-L^2-Z'$.

Preferably, —X— of formula (II) is $—C(R^4R^{4a})—$ or $—N(R^4)—$. Most preferably, —X— of formula (II) is $—C(R^4R^{4a})—$.

Preferably, $X^1$ of formula (II) is C.

Preferably, $=X^3$ of formula (II) is $=O$.

Preferably, $—X^2—$ of formula (II) is $—C(R^8R^{8a})—$.

Preferably $—R^8$ and $—R^{8a}$ of formula (II) are independently selected from the group consisting of —H, methyl and ethyl. More preferably at least one of $—R^8$ and $—R^{8a}$ of formula (II) is —H. Even more preferably both $—R^8$ and $—R^{8a}$ of formula (II) are —H.

Preferably, $—R^1$ and $—R^{1a}$ of formula (II) are independently selected from the group consisting of —H, methyl and ethyl. More preferably, at least one of $—R^1$ and $—R^{1a}$ of formula (II) is —H. Even more preferably both $—R^1$ and $—R^{1a}$ of formula (II) are —H.

Preferably, $—R^2$ and $—R^{2a}$ of formula (II) are independently selected from the group consisting of —H, methyl and ethyl. More preferably, at least one of $—R^2$ and $—R^{2a}$ of formula (II) is —H. Even more preferably both $—R^2$ and $—R^{2a}$ of formula (II) are H.

Preferably, $—R^3$ and $—R^{3a}$ of formula (II) are independently selected from the group consisting of —H, methyl, ethyl, propyl and butyl. Even more preferably at least one of $—R^3$ and $—R^{3a}$ of formula (II) is methyl. In an equally preferred embodiment $—R^3$ and $—R^{3a}$ of formula (II) are both —H. In another equally preferred embodiment $—R^3$ and $—R^{3a}$ of formula (II) are both methyl.

Preferably, $—R^3$ of formula (II) is —H and $—R^{3a}$ of formula (II) is methyl.

Preferably, $—R^4$ and $—R^{4a}$ of formula (II) are independently selected from the group consisting of —H, methyl and ethyl. More preferably, at least one of $—R^4$ and $—R^{4a}$ of formula (II) is —H. Even more preferably both —$R^4$ and —$R^{4a}$ of formula (II) are —H.

Preferably the moiety -$L^1$- is of formula (IIa):

(IIa)

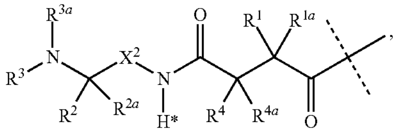

wherein the dashed line indicates the attachment to a nitrogen of -D which is a CNP agonist moiety by forming an amide bond;

—$R^1$, —$R^{1a}$, —$R^2$, —$R^{2a}$, —$R^3$, —$R^{3a}$, —$R^4$, —$R^{4a}$ and —$X^2$— are used as defined in formula (II); and wherein -$L^1$- is substituted with -$L^2$-Z or -$L^2$-Z' and wherein -$L^1$- is optionally further substituted, provided that the hydrogen marked with the asterisk in formula (IIa) is not replaced by -$L^2$-Z or -$L^2$-Z' or a substituent.

Preferably -$L^1$- of formula (IIa) is substituted with one moiety -$L^2$-Z or -$L^2$-Z'.

Preferably the moiety -$L^1$- of formula (IIa) is not further substituted.

Preferably, —$R^1$ and —$R^{1a}$ of formula (IIa) are independently selected from the group consisting of —H, methyl and ethyl. More preferably, at least one of —$R^1$ and —$R^{1a}$ of formula (IIa) is —H. Even more preferably both —$R^1$ and —$R^{1a}$ of formula (IIa) are —H.

Preferably, —$R^4$ and —$R^{4a}$ of formula (IIa) are independently selected from the group consisting of —H, methyl and ethyl. More preferably, at least one of —$R^4$ and —$R^{4a}$ of formula (IIa) is —H. Even more preferably both —$R^4$ and —$R^{4a}$ of formula (IIa) are —H.

Preferably, —$X^2$— of formula (IIa) is —$C(R^8R^{8a})$—.

Preferably —$R^8$ and —$R^{8a}$ of formula (IIa) are independently selected from the group consisting of —H, methyl and ethyl. More preferably at least one of —$R^8$ and —$R^{8a}$ of formula (IIa) is —H. Even more preferably both —$R^8$ and —$R^{8a}$ of formula (IIa) are —H.

Preferably, —$R^2$ and —$R^{2a}$ of formula (IIa) are independently selected from the group consisting of —H, methyl and ethyl. More preferably, at least one of —$R^2$ and —$R^{2a}$ of formula (IIa) is —H. Even more preferably both —$R^2$ and —$R^{2a}$ of formula (IIa) are H.

Preferably, —$R^3$ and —$R^{3a}$ of formula (IIa) are independently selected from the group consisting of —H, methyl, ethyl, propyl and butyl. Even more preferably at least one of —$R^3$ and —$R^{3a}$ of formula (IIa) is methyl. In an equally preferred embodiment —$R^3$ and —$R^{3a}$ of formula (IIa) are both —H. In another equally preferred embodiment —$R^3$ and —$R^{3a}$ of formula (IIa) are both methyl.

Preferably, —$R^3$ of formula (IIa) is —H and —$R^{3a}$ of formula (IIa) is methyl.

Preferably the moiety -$L^1$- is of formula (IIb):

(IIb)

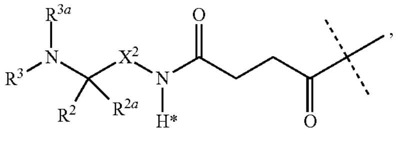

wherein the dashed line indicates the attachment to a nitrogen of -D which is a CNP agonist moiety by forming an amide bond;

—$R^2$, —$R^{2a}$, —$R^3$, —$R^{3a}$ and —$X^2$— are used as defined in formula (II); and wherein -$L^1$- is substituted with -$L^2$-Z or -$L^2$-Z' and wherein -$L^1$- is optionally further substituted, provided that the hydrogen marked with the asterisk in formula (IIb) is not replaced by -$L^2$-Z or -$L^2$-Z' or a substituent.

Preferably -$L^1$- of formula (IIb) is substituted with one moiety -$L^2$-Z or -$L^2$-Z'.

Preferably the moiety -$L^1$- of formula (IIb) is not further substituted.

Preferably, —$X^2$— of formula (IIb) is —$C(R^8R^{8a})$—.

Preferably —$R^8$ and —$R^{8a}$ of formula (IIb) are independently selected from the group consisting of —H, methyl and ethyl. More preferably at least one of —$R^8$ and —$R^{8a}$ of formula (IIb) is —H. Even more preferably both —$R^8$ and —$R^{8a}$ of formula (IIb) are —H.

Preferably, —$R^2$ and —$R^{2a}$ of formula (IIb) are independently selected from the group consisting of —H, methyl and ethyl. More preferably, at least one of —$R^2$ and —$R^{2a}$ of formula (IIb) is —H. Even more preferably both —$R^2$ and —$R^{2a}$ of formula (IIb) are H.

Preferably, —$R^3$ and —$R^{3a}$ of formula (IIb) are independently selected from the group consisting of —H, methyl, ethyl, propyl and butyl. Even more preferably at least one of —$R^3$ and —$R^{3a}$ of formula (IIb) is methyl. In an equally preferred embodiment —$R^3$ and —$R^{3a}$ of formula (IIb) are both —H. In another equally preferred embodiment —$R^3$ and —$R^{3a}$ of formula (IIb) are both methyl.

Most preferably, —$R^3$ of formula (IIb) is —H and —$R^{3a}$ of formula (IIb) is methyl.

Even more preferably the moiety -$L^1$- is of formula (IIb'):

(IIb')

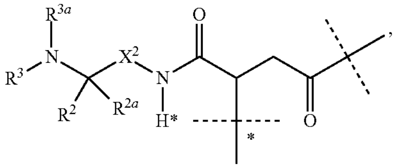

wherein wherein the dashed line indicates the attachment to a nitrogen of D which is a CNP agonist moiety by forming an amide bond;

the dashed line marked with the asterisk indicates attachment to -$L^2$-;

—$R^2$, —$R^{2a}$, —$R^3$, —$R^{3a}$ and —$X^2$— are used as defined in formula (II); and wherein -$L^1$- is optionally further substituted, provided that the hydrogen marked with the asterisk in formula (IIb') is not replaced by a substituent.

Preferably the moiety -$L^1$- of formula (IIb') is not further substituted.

Preferably, —$X^2$— of formula (IIb') is —$C(R^8R^{8a})$—.

Preferably —$R^8$ and —$R^{8a}$ of formula (IIb') are independently selected from the group consisting of —H, methyl and ethyl. More preferably at least one of —$R^8$ and —$R^{8a}$ of formula (IIb') is —H. Even more preferably both —$R^8$ and —$R^{8a}$ of formula (IIb') are —H.

Preferably, —$R^2$ and —$R^{2a}$ of formula (IIb') are independently selected from the group consisting of —H, methyl and ethyl. More preferably, at least one of —$R^2$ and —$R^{2a}$ of formula (IIb') is —H. Even more preferably both —$R^2$ and —$R^{2a}$ of formula (IIb') are —H.

Preferably, —$R^3$ and —$R^{3a}$ of formula (IIb') are independently selected from the group consisting of —H, methyl, ethyl, propyl and butyl. Even more preferably at least one of —$R^3$ and —$R^{3a}$ of formula (IIb') is methyl. In an equally preferred embodiment —$R^3$ and —$R^{3a}$ of formula (IIb') are both —H. In another equally preferred embodiment —$R^3$ and —$R^{3a}$ of formula (IIb') are both methyl.

Most preferably, —$R^3$ of formula (IIb') is —H and —$R^{3a}$ of formula (IIb') is methyl.

Preferably the moiety -$L^1$- is of formula (IIc):

(IIc)

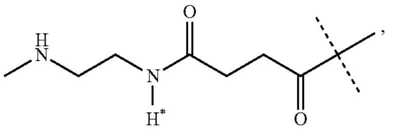

wherein the dashed line indicates the attachment to a nitrogen of -D which is a CNP agonist moiety by forming an amide bond; and wherein -$L^1$- is substituted with -$L^2$-Z or -$L^2$-Z' and wherein -$L^1$- is optionally further substituted, provided that the hydrogen marked with the asterisk in formula (IIc) is not replaced by -$L^2$-Z or -$L^2$-Z' or a substituent.

Preferably -$L^1$- of formula (IIc) is substituted with one moiety -$L^2$-Z or -$L^2$-Z'.

Preferably the moiety -$L^1$- of formula (IIc) is not further substituted.

In another preferred embodiment the moiety -$L^1$- is of formula (IIc-a):

(IIc-a)

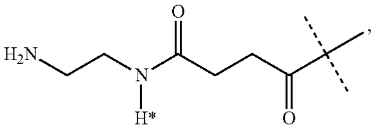

wherein the dashed line indicates the attachment to a nitrogen of -D which is a CNP agonist moiety by forming an amide bond; and wherein -$L^1$- is substituted with -$L^2$-Z or -$L^2$-Z' and wherein -$L^1$- is optionally further substituted, provided that the hydrogen marked with the asterisk in formula (IIc) is not replaced by -$L^2$-Z or -$L^2$-Z' or a substituent.

Preferably -$L^1$- of formula (IIc-a) is substituted with one moiety -$L^2$-Z or -$L^2$-Z'.

Preferably the moiety -$L^1$- of formula (IIc-a) is not further substituted.

In another preferred embodiment the moiety -$L^1$- is of formula (IIc-b):

(IIc-b)

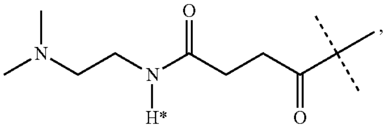

wherein the dashed line indicates the attachment to a nitrogen of -D which is a CNP agonist moiety by forming an amide bond; and wherein -$L^1$- is substituted with -$L^2$-Z or -$L^2$-Z' and wherein -$L^1$- is optionally further substituted, provided that the hydrogen marked with the asterisk in formula (IIc) is not replaced by -$L^2$-Z or -$L^2$-Z' or a substituent.

Preferably -$L^1$- of formula (IIc-b) is substituted with one moiety -$L^2$-Z or -$L^2$-Z'.

Preferably the moiety -$L^1$- of formula (IIc-b) is not further substituted.

Even more preferably the moiety -$L^1$- is selected from the group consisting of formula (IIc-i), (IIc-ii), (IIc-iii), (IIc-iv) and (IIc-v):

(IIc-i)

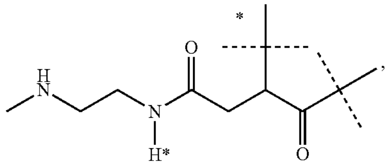

(IIc-ii)

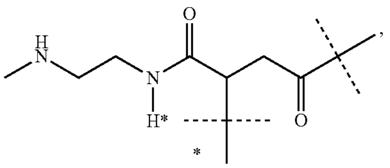

(IIc-iii)

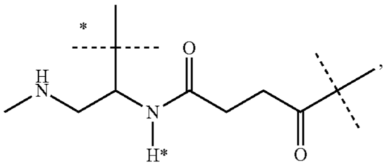

(IIc-iv)

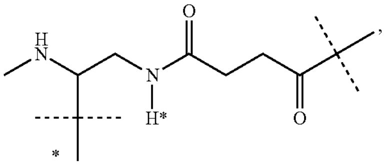

and (IIc-v)

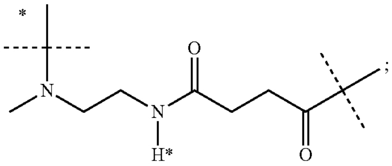

wherein the unmarked dashed line indicates the attachment to a nitrogen of -D which is a CNP agonist moiety by forming an amide bond; and the dashed line marked with the asterisk indicates attachment to -$L^2$-Z or -$L^2$-Z'; and $L^1$- is optionally further substituted, provided that the hydrogen marked with the asterisk in formula (IIc-i), (IIc-ii), (IIc-iii), (IIc-iv) and (IIc-v) is not replaced by a substituent.

Preferably, the moiety -$L^1$- of formula (IIc-i), (IIc-ii), (IIc-iii), (IIc-iv) and (IIc-v) is not further substituted.

In a particularly preferred embodiment the moiety $-L^1-$ is (IIc-ii)

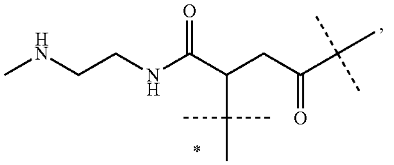

wherein the unmarked dashed line indicates the attachment to a nitrogen of -D which is a CNP agonist moiety by forming an amide bond; and the dashed line marked with the asterisk indicates attachment to $-L^2$-Z or $-L^2$-Z'.

Preferably $-L^1-$ of formula (IIc-ii) is substituted with one moiety $-L^2$-Z or $-L^2$-Z'.

In an equally preferred embodiment the moiety $-L^1-$ is selected from the group consisting of formula (IIc-i'), (IIc-ii'), (IIc-iii'), (IIc-iv') and (IIc-v'):

(IIc-i')

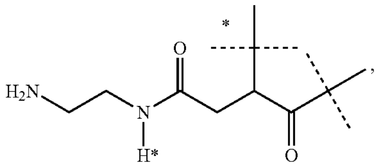

(IIc-ii')

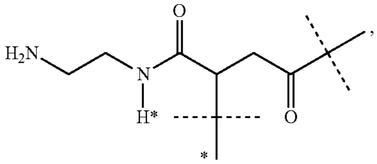

(IIc-iii')

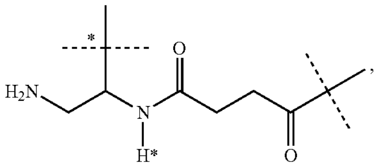

(IIc-iv')

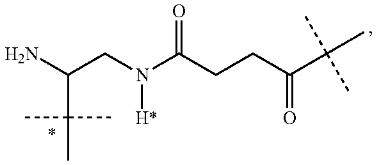

and (IIc-v')

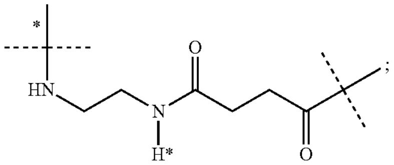

wherein the unmarked dashed line indicates the attachment to a nitrogen of -D which is a CNP agonist moiety by forming an amide bond; and the dashed line marked with the asterisk indicates attachment to $-L^2$-Z or $-L^2$-Z'; and $L^1$- is optionally further substituted, provided that the hydrogen marked with the asterisk in formula (IIc-i'), (IIc-ii'), (IIc-iii'), (IIc-iv') and (IIc-v') is not replaced by a substituent.

Preferably, the moiety $-L^1-$ of formula (IIc-i'), (IIc-ii'), (IIc-iii'), (IIc-iv') and (IIc-v') is not further substituted.

In another particularly preferred embodiment the moiety $-L^1-$ is (IIc-ii')

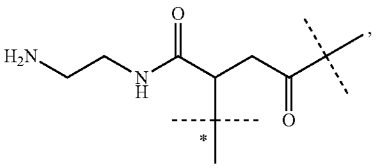

wherein the unmarked dashed line indicates the attachment to a nitrogen of -D which is a CNP agonist moiety by forming an amide bond; and the dashed line marked with the asterisk indicates attachment to $-L^2$-Z or $-L^2$-Z'.

Preferably $-L^1-$ of formula (IIc-ii') is substituted with one moiety $-L^2$-Z or $-L^2$-Z'.

In an equally preferred embodiment the moiety $-L^1-$ is selected from the group consisting of formula (IIc-i''), (IIc-ii''), (IIc-iii'') and (IIc-iv''):

(IIc-i'')

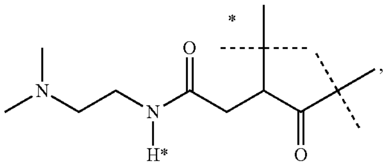

(IIc-ii'')

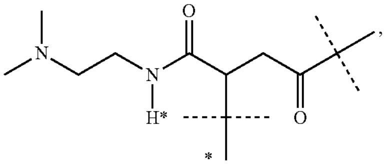

(IIc-iii'')

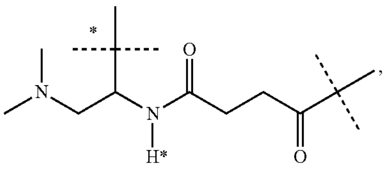

and (IIc-iv'')

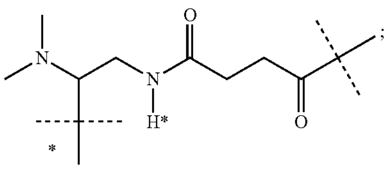

wherein the unmarked dashed line indicates the attachment to a nitrogen of -D which is a CNP agonist moiety by forming an amide bond; and the dashed line marked with the asterisk indicates attachment to $-L^2$-Z or $-L^2$-Z'; and $L^1$- is optionally further substituted, provided that the hydrogen marked with the asterisk in formula (IIc-i"), (IIc-ii"), (IIc-iii") and (IIc-iv") is not replaced by a substituent.

Preferably, the moiety -$L^1$- of formula (IIc-i"), (IIc-ii"), (IIc-iii") and (IIc-iv") is not further substituted.

In another particularly preferred embodiment the moiety -$L^1$- is (IIc-ii")

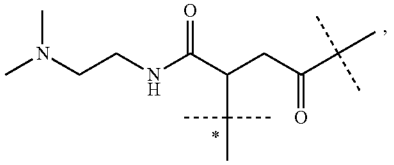

wherein the unmarked dashed line indicates the attachment to a nitrogen of -D which is a CNP agonist moiety by forming an amide bond; and the dashed line marked with the asterisk indicates attachment to -$L^2$-Z or -$L^2$-Z'.

Preferably -$L^1$- of formula (IIc-ii") is substituted with one moiety -$L^2$-Z or -$L^2$-Z'.

The optional further substituents of -$L^1$- of formula (II), (IIa), (IIb), (IIb'), (IIc), (IIc-i), (IIc-ii), (IIc-iii), (IIc-iv), (IIc-v), (IIc-i'), (IIc-ii'), (IIc-iii'), (IIc-iv'), (IIc-v'), (IIc-i"), (IIc-ii"), (IIc-iii) and (IIc-iv") are preferably as described above.

Another preferred moiety -$L^1$- is disclosed in unpublished European patent application 14180004, which corresponds to the international application with the application number PCT/EP2015/067929. Accordingly, in another preferred embodiment the moiety -$L^1$- is of formula (III):

(III)

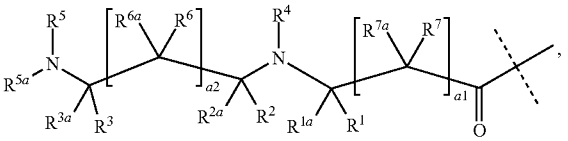

wherein the dashed line indicates attachment to a primary or secondary amine or hydroxyl of -D by forming an amide or ester linkage, respectively;

—$R^1$, —$R^{1a}$, —$R^2$, —$R^{2a}$, —$R^3$ and —$R^{3a}$ are independently of each other selected from the group consisting of —H, —$C(R^8R^{8a}R^{8b})$, —$C(=O)R^8$, —C≡N, —$C(=NR^8)R^{8a}$, —$CR^8(=CR^{8a}R^{8b})$, —C≡$CR^8$ and -T;

—$R^4$, —$R^5$ and —$R^{5a}$ are independently of each other selected from the group consisting of —H, —$C(R^9R^{9a}R^{9b})$ and -T;

a1 and a2 are independently of each other 0 or 1;

each —$R^6$, —$R^{6a}$, —$R^7$, —$R^{7a}$, —$R^8$, —$R^{8a}$, —$R^{8b}$, —$R^9$, —$R^{9a}$, —$R^{9b}$ are independently of each other selected from the group consisting of —H, halogen, —CN, —$COOR^{10}$, —$OR^{10}$, —$C(O)R^{10}$, —$C(O)N(R^{10}R^{10a})$, —$S(O)_2N(R^{10}R^{10a})$, —$S(O)N(R^{10}R^{10a})$, —$S(O)_2R^{10}$, —$S(O)R^{10}$, —$N(R^{10})S(O)_2N(R^{10a}R^{10b})$, —$SR^{10}$, —$N(R^{10}R^{10a})$, —$NO_2$, —$OC(O)R^{10}$, —$N(R^{10})C(O)R^{10a}$, —$N(R^{10})S(O)_2R^{10a}$, —$N(R^{10})S(O)R^{10a}$, —$N(R^{10})C(O)OR^{10a}$, —$N(R^{10})C(O)N(R^{10a}R^{10b})$, —$OC(O)N(R^{10}R^{10a})$, -T, $C_{1-20}$ alkyl, $C_{2-20}$ alkenyl, and $C_{2-20}$ alkynyl; wherein -T, $C_{1-20}$ alkyl, $C_{2-20}$ alkenyl, and $C_{2-20}$ alkynyl are optionally substituted with one or more —$R^{11}$, which are the same or different and wherein $C_{1-20}$ alkyl, $C_{2-20}$ alkenyl, and $C_{2-20}$ alkynyl are optionally interrupted by one or more groups selected from the group consisting of -T-, —C(O)O—, —O—, —C(O)—, —$C(O)N(R^{12})$—, —$S(O)_2N(R^{12})$—, —$S(O)N(R^{12})$—, —$S(O)_2$—, —S(O)—, —$N(R^{12})S(O)_2N(R^{12a})$—, —S—, —$N(R^{12})$—, —$OC(OR^{12})(R^{12a})$—, —$N(R^{12})C(O)N(R^{12a})$—, and —$OC(O)N(R^{12})$—;

each —$R^{10}$, —$R^{10a}$, —$R^{10b}$ is independently selected from the group consisting of —H, -T, $C_{1-20}$ alkyl, $C_{2-20}$ alkenyl, and $C_{2-20}$ alkynyl; wherein -T, $C_{1-20}$ alkyl, $C_{2-20}$ alkenyl, and $C_{2-20}$ alkynyl are optionally substituted with one or more —$R^{11}$, which are the same or different and wherein $C_{1-20}$ alkyl, $C_{2-20}$ alkenyl, and $C_{2-20}$ alkynyl are optionally interrupted by one or more groups selected from the group consisting of -T-, —C(O)O—, —O—, —C(O)—, —$C(O)N(R^{12})$—, —$S(O)_2N(R^{12})$—, —$S(O)N(R^{12})$—, —$S(O)_2$—, —S(O)—, —$N(R^{12})S(O)_2N(R^{12a})$—, —S—, —$N(R^{12})$—, —$OC(OR^{12})(R^{12a})$—, —$N(R^{12})C(O)N(R^{12a})$—, and —$OC(O)N(R^{12})$—;

each T is independently of each other selected from the group consisting of phenyl, naphthyl, indenyl, indanyl, tetralinyl, $C_{3-10}$ cycloalkyl, 3- to 10-membered heterocyclyl, and 8- to 11-membered heterobicyclyl; wherein each T is independently optionally substituted with one or more —$R^{11}$, which are the same or different;

each —$R^{11}$ is independently of each other selected from halogen, —CN, oxo (=O), —$COOR^{13}$, —$OR^{13}$, —$C(O)R^{13}$, —$C(O)N(R^{13}R^{13a})$, —$S(O)_2N(R^{13}R^{13a})$, —$S(O)N(R^{13}R^{13a})$, —$S(O)_2R^{13}$, —$S(O)R^{13}$, —$N(R^{13})S(O)_2N(R^{13a}R^{13b})$, —$SR^{13}$, —$N(R^{13}R^{13a})$, —$NO_2$, —$OC(O)R^{13}$, —$N(R^{13})C(O)R^{13a}$, —$N(R^{13})S(O)_2R^{13a}$, —$N(R^{13})S(O)R^{13a}$, —$N(R^{13})C(O)OR^{13a}$, —$N(R^{13})C(O)N(R^{13a}R^{13b})$, —$OC(O)N(R^{13}R^{13a})$, and $C_{1-6}$ alkyl; wherein $C_{1-6}$ alkyl is optionally substituted with one or more halogen, which are the same or different;

each —$R^{12}$, —$R^{12a}$, —$R^{13}$, —$R^{13a}$, —$R^{13b}$ is independently selected from the group consisting of —H, and $C_{1-6}$ alkyl; wherein $C_{1-6}$ alkyl is optionally substituted with one or more halogen, which are the same or different;

optionally, one or more of the pairs —$R^1$/—$R^{1a}$, —$R^2$/—$R^{2a}$, —$R^3$/—$R^{3a}$, —$R^6$/—$R^{6a}$, —$R^7$/—$R^{7a}$ are joined together with the atom to which they are attached to form a $C_{3-10}$ cycloalkyl or a 3- to 10-membered heterocyclyl;

optionally, one or more of the pairs —$R^1$/—$R^2$, —$R^1$/—$R^3$, —$R^1$/—$R^4$, —$R^1$/—$R^5$, —$R^1$/—$R^6$, —$R^1$/—$R^7$, —$R^2$/—$R^3$, —$R^2$/—$R^4$, —$R^2$/—$R^5$, —$R^2$/—$R^6$, —$R^2$/—$R^7$, —$R^3$/—$R^4$, —$R^3$/—$R^5$, —$R^3$/—$R^6$, —$R^3$/—$R^7$, —$R^4$/—$R^5$, —$R^4$/—$R^6$, —$R^4$/—$R^7$, —$R^5$/—$R^6$, —$R^5$/—$R^7$, —$R^6$/—$R^7$ are joint together with the atoms to which they are attached to form a ring A;

A is selected from the group consisting of phenyl; naphthyl; indenyl; indanyl; tetralinyl; $C_{3-10}$ cycloalkyl; 3- to 10-membered heterocyclyl; and 8- to 11-membered heterobicyclyl;

wherein $-L^1-$ is substituted with $-L^2-Z$ or $-L^2-Z'$ and wherein $-L^1-$ is optionally further substituted;

wherein $L^2-$ is a single chemical bond or a spacer;

—Z is a water-soluble carrier; and

Z' is a water-insoluble carrier.

The optional further substituents of $-L^1-$ of formula (III) are preferably as described above.

Preferably $-L^1-$ of formula (III) is substituted with one moiety $-L^2-Z$ or $-L^2-Z'$.

In one embodiment $-L^1-$ of formula (III) is not further substituted.

Additional preferred embodiments for $-L^1-$ are disclosed in EP1536334B1, WO2009/009712A1, WO2008/034122A1, WO2009/143412A2, WO2011/082368A2, and U.S. Pat. No. 8,618,124B2, which are herewith incorporated by reference in their entirety.

Additional preferred embodiments for $-L^1-$ are disclosed in U.S. Pat. No. 8,946,405B2 and U.S. Pat. No. 8,754,190B2, which are herewith incorporated by reference in their entirety. Accordingly, a preferred moiety $-L^1-$ is of formula (IV):

(IV)

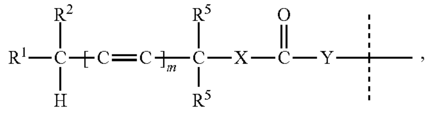

wherein the dashed line indicates attachment to -D which is a CNP agonist moiety and wherein attachment is through a functional group of -D selected from the group consisting of —OH, —SH and $—NH_2$;

m is 0 or 1;

at least one or both of $—R^1$ and $—R^2$ is/are independently of each other selected from the group consisting of —CN, $—NO_2$, optionally substituted aryl, optionally substituted heteroaryl, optionally substituted alkenyl, optionally substituted alkynyl, $—C(O)R^3$, $—S(O)R^3$, $—S(O)_2R^3$, and $—SR^4$, one and only one of $—R^1$ and $—R^2$ is selected from the group consisting of —H, optionally substituted alkyl, optionally substituted arylalkyl, and optionally substituted heteroarylalkyl;

$—R^3$ is selected from the group consisting of —H, optionally substituted alkyl, optionally substituted aryl, optionally substituted arylalkyl, optionally substituted heteroaryl, optionally substituted heteroarylalkyl, $—OR^9$ and $—N(R^9)_2$;

$—R^4$ is selected from the group consisting of optionally substituted alkyl, optionally substituted aryl, optionally substituted arylalkyl, optionally substituted heteroaryl, and optionally substituted heteroarylalkyl;

each $—R^5$ is independently selected from the group consisting of —H, optionally substituted alkyl, optionally substituted alkenylalkyl, optionally substituted alkynylalkyl, optionally substituted aryl, optionally substituted arylalkyl, optionally substituted heteroaryl and optionally substituted heteroarylalkyl;

$—R^9$ is selected from the group consisting of —H and optionally substituted alkyl;

—Y— is absent and —X— is —O— or —S—; or

—Y— is $—N(Q)CH_2—$ and —X— is —O—;

Q is selected from the group consisting of optionally substituted alkyl, optionally substituted aryl, optionally substituted arylalkyl, optionally substituted heteroaryl and optionally substituted heteroarylalkyl;

optionally, $—R^1$ and $—R^2$ may be joined to form a 3 to 8-membered ring; and optionally, both $—R^9$ together with the nitrogen to which they are attached form a heterocyclic ring;

wherein $-L^1-$ is substituted with $-L^2-Z$ or $-L^2-Z'$ and wherein $-L^1-$ is optionally further substituted;

wherein $L^2-$ is a single chemical bond or a spacer;

—Z is a water-soluble carrier; and

Z' is a water-insoluble carrier.

Only in the context of formula (IV) the terms used have the following meaning:

The term "alkyl" as used herein includes linear, branched or cyclic saturated hydrocarbon groups of 1 to 8 carbons, or in some embodiments 1 to 6 or 1 to 4 carbon atoms.

The term "alkoxy" includes alkyl groups bonded to oxygen, including methoxy, ethoxy, isopropoxy, cyclopropoxy, cyclobutoxy, and similar.

The term "alkenyl" includes non-aromatic unsaturated hydrocarbons with carbon-carbon double bonds.

The term "alkynyl" includes non-aromatic unsaturated hydrocarbons with carbon-carbon triple bonds.

The term "aryl" includes aromatic hydrocarbon groups of 6 to 18 carbons, preferably 6 to 10 carbons, including groups such as phenyl, naphthyl, and anthracenyl. The term "heteroaryl" includes aromatic rings comprising 3 to 15 carbons containing at least one N, O or S atom, preferably 3 to 7 carbons containing at least one N, O or S atom, including groups such as pyrrolyl, pyridyl, pyrimidinyl, imidazolyl, oxazolyl, isoxazolyl, thiazolyl, isothiazolyl, quinolyl, indolyl, indenyl, and similar.

In some instance, alkenyl, alkynyl, aryl or heteroaryl moieties may be coupled to the remainder of the molecule through an alkylene linkage. Under those circumstances, the substituent will be referred to as alkenylalkyl, alkynylalkyl, arylalkyl or heteroarylalkyl, indicating that an alkylene moiety is between the alkenyl, alkynyl, aryl or heteroaryl moiety and the molecule to which the alkenyl, alkynyl, aryl or heteroaryl is coupled.

The term "halogen" includes bromo, fluoro, chloro and iodo.

The term "heterocyclic ring" refers to a 4 to 8 membered aromatic or non-aromatic ring comprising 3 to 7 carbon atoms and at least one N, O, or S atom. Examples are piperidinyl, piperazinyl, tetrahydropyranyl, pyrrolidine, and tetrahydrofuranyl, as well as the exemplary groups provided for the term "heteroaryl" above.

When a ring system is optionally substituted, suitable substituents are selected from the group consisting of alkyl, alkenyl, alkynyl, or an additional ring, each optionally further substituted. Optional substituents on any group, including the above, include halo, nitro, cyano, —OR, —SR, $—NR_2$, —OCOR, —NRCOR, —COOR, $—CONR_2$, —SOR, $—SO_2R$, $—SONR_2$, $—SO_2N R_2$, wherein each R is independently alkyl, alkenyl, alkynyl, aryl or heteroaryl, or two R groups taken together with the atoms to which they are attached form a ring.

Preferably $-L^1-$ of formula (IV) is substituted with one moiety $-L^2-Z$ or $-L^2-Z'$.

An additional preferred embodiment for $-L^1-$ is disclosed in WO2013/036857A1, which is herewith incorporated by reference in its entirety. Accordingly, a preferred moiety $-L^1-$ is of formula (V):

(V)

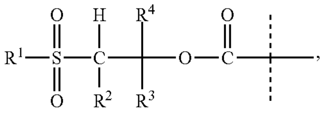

wherein the dashed line indicates attachment to -D which is a CNP agonist moiety and wherein attachment is through an amine functional group of -D;

—$R^1$ is selected from the group consisting of optionally substituted $C_1$-$C_6$ linear, branched, or cyclic alkyl; optionally substituted aryl; optionally substituted heteroaryl; alkoxy; and —$NR^5{}_2$;

—$R^2$ is selected from the group consisting of —H; optionally substituted $C_1$-$C_6$ alkyl; optionally substituted aryl; and optionally substituted heteroaryl;

—$R^3$ is selected from the group consisting of —H; optionally substituted $C_1$-$C_6$ alkyl; optionally substituted aryl; and optionally substituted heteroaryl;

—$R^4$ is selected from the group consisting of —H; optionally substituted $C_1$-$C_6$ alkyl; optionally substituted aryl; and optionally substituted heteroaryl;

each —$R^5$ is independently of each other selected from the group consisting of —H; optionally substituted $C_1$-$C_6$ alkyl; optionally substituted aryl; and optionally substituted heteroaryl; or when taken together two —$R^5$ can be cycloalkyl or cycloheteroalkyl;

wherein -$L^1$- is substituted with -$L^2$-Z or -$L^2$-Z' and wherein -$L^1$- is optionally further substituted;

wherein

-$L^2$- is a single chemical bond or a spacer;

—Z is a water-soluble carrier; and

—Z' is a water-insoluble carrier.

Only in the context of formula (V) the terms used have the following meaning:

"Alkyl", "alkenyl", and "alkynyl" include linear, branched or cyclic hydrocarbon groups of 1-8 carbons or 1-6 carbons or 1-4 carbons wherein alkyl is a saturated hydrocarbon, alkenyl includes one or more carbon-carbon double bonds and alkynyl includes one or more carbon-carbon triple bonds. Unless otherwise specified these contain 1-6 C.

"Aryl" includes aromatic hydrocarbon groups of 6-18 carbons, preferably 6-10 carbons, including groups such as phenyl, naphthyl, and anthracene "Heteroaryl" includes aromatic rings comprising 3-15 carbons containing at least one N, O or S atom, preferably 3-7 carbons containing at least one N, O or S atom, including groups such as pyrrolyl, pyridyl, pyrimidinyl, imidazolyl, oxazolyl, isoxazolyl, thiszolyl, isothiazolyl, quinolyl, indolyl, indenyl, and similar.

The term "substituted" means an alkyl, alkenyl, alkynyl, aryl, or heteroaryl group comprising one or more substituent groups in place of one or more hydrogen atoms. Substituents may generally be selected from halogen including F, Cl, Br, and I; lower alkyl including linear, branched, and cyclic; lower haloalkyl including fluoroalkyl, chloroalkyl, bromoalkyl, and iodoalkyl; OH; lower alkoxy including linear, branched, and cyclic; SH; lower alkylthio including linear, branched and cyclic; amino, alkylamino, dialkylamino, silyl including alkylsilyl, alkoxysilyl, and arylsilyl; nitro; cyano; carbonyl; carboxylic acid, carboxylic ester, carboxylic amide, aminocarbonyl; aminoacyl; carbamate; urea; thiocarbamate; thiourea; ketne; sulfone; sulfonamide; aryl including phenyl, naphthyl, and anthracenyl; heteroaryl including 5-member heteroaryls including as pyrrole, imidazole, furan, thiophene, oxazole, thiazole, isoxazole, isothiazole, thiadiazole, triazole, oxadiazole, and tetrazole, 6-member heteroaryls including pyridine, pyrimidine, pyrazine, and fused heteroaryls including benzofuran, benzothiophene, benzoxazole, benzimidazole, indole, benzothiazole, benzisoxazole, and benzisothiazole.

Preferably -$L^1$- of formula (V) is substituted with one moiety -$L^2$-Z or -$L^2$-Z'.

A further preferred embodiment for -$L^1$- is disclosed in U.S. Pat. No. 7,585,837B2, which is herewith incorporated by reference in its entirety. Accordingly, a preferred moiety -$L^1$- is of formula (VI):

(VI)

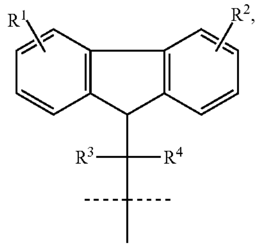

wherein the dashed line indicates attachment to -D which is a CNP agonist moiety and wherein attachment is through an amine functional group of -D;

$R^1$ and $R^2$ are independently selected from the group consisting of hydrogen, alkyl, alkoxy, alkoxyalkyl, aryl, alkaryl, aralkyl, halogen, nitro, —$SO_3H$, —$SO_2NHR^5$, amino, ammonium, carboxyl, $PO_3H_2$, and $OPO_3H_2$;

$R^3$, $R^4$, and $R^5$ are independently selected from the group consisting of hydrogen, alkyl, and aryl;

wherein -$L^1$- is substituted with -$L^2$-Z or -$L^2$-Z' and wherein -$L^1$- is optionally further substituted;

wherein

-$L^2$- is a single chemical bond or a spacer;

—Z is a water-soluble carrier; and

—Z' is a water-insoluble carrier.

Suitable substituents for formulas (VI) are alkyl (such as $C_{1-6}$ alkyl), alkenyl (such as $C_{2-6}$ alkenyl), alkynyl (such as $C_{2-6}$ alkynyl), aryl (such as phenyl), heteroalkyl, heteroalkenyl, heteroalkynyl, heteroaryl (such as aromatic 4 to 7 membered heterocycle) or halogen moieties.

Only in the context of formula (VI) the terms used have the following meaning:

The terms "alkyl", "alkoxy", "alkoxyalkyl", "aryl", "alkaryl" and "aralkyl" mean alkyl radicals of 1-8, preferably 1-4 carbon atoms, e.g. methyl, ethyl, propyl, isopropyl and butyl, and aryl radicals of 6-10 carbon atoms, e.g. phenyl and naphthyl. The term "halogen" includes bromo, fluoro, chloro and iodo.

Preferably -$L^1$- of formula (VI) is substituted with one moiety -$L^2$-Z or -$L^2$-Z'.

A further preferred embodiment for -$L^1$- is disclosed in WO2002/089789A1, which is herewith incorporated by reference in its entirety. Accordingly, a preferred moiety -$L^1$- is of formula (VII):

(VII)

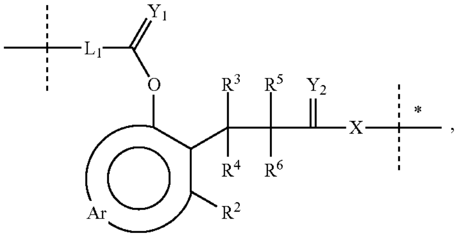

wherein the dashed line indicates attachment to -D which is a CNP agonist moiety and wherein attachment is through an amine functional group of -D;

$L_1$ is a bifunctional linking group, $Y_1$ and $Y_2$ are independently O, S or $NR^7$;

$R^2$, $R^3$, $R^4$, $R^5$, $R^6$ and $R^7$ are independently selected from the group consisting of hydrogen, $C_{1-6}$ alkyls, $C_{3-12}$ branched alkyls, $C_{3-8}$ cycloalkyls, $C_{1-6}$ substituted alkyls, $C_{3-8}$ substituted cycloalkyls, aryls, substituted aryls, aralkyls, $C_{1-6}$ heteroalkyls, substituted $C_{1-6}$ heteroalkyls, $C_{1-6}$ alkoxy, phenoxy, and $C_{1-6}$ heteroalkoxy;

Ar is a moiety which when included in formula (VII) forms a multisubstituted aromatic hydrocarbon or a multi-substituted heterocyclic group;

X is a chemical bond or a moiety that is actively transported into a target cell, a hydrophobic moiety, or a combination thereof, y is 0 or 1;

wherein $-L^1-$ is substituted with $-L^2-Z$ or $-L^2-Z'$ and wherein $-L^1-$ is optionally further substituted;

wherein $-L^2-$ is a single chemical bond or a spacer;

—Z is a water-soluble carrier; and

—Z' is a water-insoluble carrier.

Only in the context of formula (VII) the terms used have the following meaning:

The term "alkyl" shall be understood to include, e.g. straight, branched, substituted $C_{1-12}$ alkyls, including alkoxy, $C_{3-8}$ cycloalkyls or substituted cycloalkyls, etc.

The term "substituted" shall be understood to include adding or replacing one or more atoms contained within a functional group or compounds with one or more different atoms.

Substituted alkyls include carboxyalkyls, aminoalkyls, dialkylaminos, hydroxyalkyls and mercaptoalkyls; substituted cycloalkyls include moieties such as 4-chlorocyclohexyl; aryls include moieties such as napthyl; substituted aryls include moieties such as 3-bromo-phenyl; aralkyls include moieties such as toluyl; heteroalkyls include moieties such as ethylthiophene; substituted heteroalkyls include moieties such as 3-methoxythiophone; alkoxy includes moeities such as methoxy; and phenoxy includes moieties such as 3-nitrophenoxy. Halo-shall be understood to include fluoro, chloro, iodo and bromo.

Preferably $-L^1-$ of formula (VII) is substituted with one moiety $-L^2-Z$ or $-L^2-Z'$.

In another preferred embodiment $-L^1-$ comprises a substructure of formula (VIII)

(VIII)

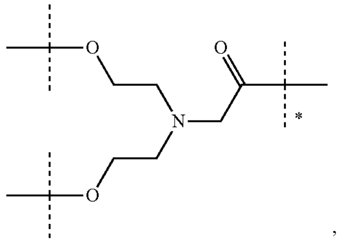

wherein the dashed line marked with the asterisk indicates attachment to a nitrogen of -D which is a CNP agonist moiety by forming an amide bond;

the unmarked dashed lines indicate attachment to the remainder of $-L^1-$; and wherein $-L^1-$ is substituted with $-L^2-Z$ or $-L^2-Z'$ and wherein $-L^1-$ is optionally further substituted;

wherein $L^2-$ is a single chemical bond or a spacer;

—Z is a water-soluble carrier; and

—Z' is a water-insoluble carrier.

Preferably $-L^1-$ of formula (VIII) is substituted with one moiety $-L^2-Z$ or $-L^2-Z'$.

In one embodiment $-L^1-$ of formula (VIII) is not further substituted.

In another preferred embodiment $-L^1-$ comprises a substructure of formula (IX)

(IX)

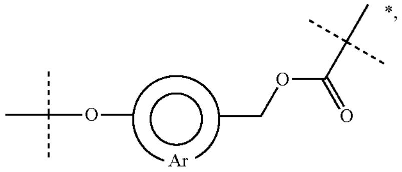

wherein the dashed line marked with the asterisk indicates attachment to a nitrogen of -D which is a CNP agonist moiety by forming a carbamate bond;

the unmarked dashed lines indicate attachment to the remainder of $-L^1-$; and wherein $-L^1-$ is substituted with $-L^2-Z$ or $-L^2-Z'$ and wherein $-L^1-$ is optionally further substituted;

wherein $-L^2-$ is a single chemical bond or a spacer;

—Z is a water-soluble carrier; and

—Z' is a water-insoluble carrier.

Preferably $-L^1-$ of formula (IX) is substituted with one moiety $-L^2-Z$ or $-L^2-Z'$.

In one embodiment $-L^1-$ of formula (IX) is not further substituted.

Preferably -D of formula (Ia), (Ib), (II), (IIa), (IIb), (IIb'), (IIc), (IIc-i), (IIc-ii), (IIc-iii), (IIc-iv), (IIc-iv), (III), (IV), (V), (VI), (VII), (VIII) and (IX) is a CNP moiety. The moiety -D may be connected to $-L^1-$ through any functional group of D-H and is preferably connected to $-L^1-$ through an amine functional group of D-H. This may be the N-terminal amine functional group or an amine functional group provided by a lysine side chain, i.e. by the lysines at position 9, 11, 15, 16, 20 and 26, if the CNP has the sequence of SEQ ID NO:24.

It was surprisingly found that attachment of -$L^1$- to the ring of a CNP moiety significantly reduces the CNP prodrug's affinity to NPR—B compared to attachment at the N-terminus or to the non-ring part of CNP, which reduced affinity to NPR—B in turn reduces the risk of cardiovascular side effects, such as hypotension.

Accordingly, -$L^1$- is preferably conjugated to the side chain of an amino acid residue of said ring moiety of -D or to the backbone of said ring moiety of -D. Even more preferably, -$L^1$- is covalently and reversibly conjugated to the side chain of an amino acid residue of said ring moiety of -D. If -D is a CNP moiety with the sequence of SEQ ID NO:24, -$L^1$- is preferably conjugated to the amine functional group provided by the lysine at position 26 of the corresponding drug D-H.

The moiety -$L^2$- is a chemical bond or a spacer moiety.

In one embodiment -$L^2$- is a chemical bond.

In another embodiment -$L^2$- is a spacer moiety.

When -$L^2$- is other than a single chemical bond, -$L^2$- is preferably selected from the group consisting of -T-, —C(O)O—, —O—, —C(O)—, —C(O)N($R^{y1}$)—, —$S(O)_2$N($R^{y1}$)—, —S(O)N($R^{y1}$)—, —$S(O)_2$—, —S(O)—, —N($R^{y1}$)$S(O)_2$N($R^{y1a}$)—, —S—, —N($R^{y1}$)—, —OC(O$R^{y1}$)($R^{y1a}$)—, —N($R^{y1}$)C(O)N($R^{y1a}$)—, —OC(O)N($R^{y1}$)—, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more —$R^{y2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{y3}$)—, —$S(O)_2$N($R^{y3}$)—, —S(O)N($R^{y3}$)—, —$S(O)_2$—, —S(O)—, —N($R^{y3}$)$S(O)_2$N($R^{y3a}$)—, —S—, —N($R^{y3}$)—, —OC(O$R^{y3}$)($R^{y3a}$)—, —N($R^{y3}$)C(O)N($R^{y3a}$)—, and —OC(O)N($R^{y3}$)—;

—$R^{y1}$ and —$R^{y1a}$ are independently of each other selected from the group consisting of —H, -T, $C_{1-50}$ alkyl, $C_{2-50}$ alkenyl, and $C_{2-50}$ alkynyl; wherein -T, $C_{1-50}$ alkyl, $C_{2-50}$ alkenyl, and $C_{2-50}$ alkynyl are optionally substituted with one or more —$R^{y2}$, which are the same or different, and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{y4}$)—, —$S(O)_2$N($R^{y4}$)—, —S(O)N($R^{y4}$)—, —$S(O)_2$—, —S(O)—, —N($R^{y4}$)$S(O)_2$N($R^{y4a}$)—, —S—, —N($R^{y4}$)—, —OC(O$R^{y4}$)($R^{y4a}$)—, —N($R^{y4}$)C(O)N($R^{y4a}$)—, and —OC(O)N($R^{y4}$)—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more —$R^{y2}$, which are the same or different;

each —$R^{y2}$ is independently selected from the group consisting of halogen, —CN, oxo (═O), —COO$R^{y5}$, —O$R^{y5}$, —C(O)$R^{y5}$, —C(O)N($R^{y5}R^{y5a}$), —$S(O)_2$N($R^{y5}R^{y5a}$), —S(O)N($R^{y5}R^{y5a}$), —$S(O)_2R^{y5}$, —S(O)$R^{y5}$, —N($R^{y5}$)$S(O)_2$N($R^{y5a}R^{y5b}$), —S$R^{y5}$, —N($R^{y5}R^{y5a}$), —$NO_2$, —OC(O)$R^{y5}$, —N($R^{y5}$)C(O)$R^{y5a}$, —N($R^{y5}$)$S(O)_2R^{y5a}$, —N($R^{y5}$)S(O)$R^{y5a}$, —N($R^{y5}$)C(O)O$R^{y5a}$, —N($R^{y5}$)C(O)N($R^{y5a}R^{y5b}$), —OC(O)N($R^{y5}R^{y5a}$), and $C_{1-6}$ alkyl; wherein $C_{1-6}$ alkyl is optionally substituted with one or more halogen, which are the same or different; and each —$R^{y3}$, —$R^{y3a}$, —$R^{y4}$, —$R^{y4a}$, —$R^{y5}$, —$R^{y5a}$ and —$R^{y5b}$ is independently selected from the group consisting of —H, and $C_{1-6}$ alkyl, wherein $C_{1-6}$ alkyl is optionally substituted with one or more halogen, which are the same or different.

When -$L^2$- is other than a single chemical bond, -$L^2$- is even more preferably selected from -T-, —C(O)O—, —O—, —C(O)—, —C(O)N($R^{y1}$)—, —$S(O)_2$N($R^{y1}$)—, —S(O)N($R^{y1}$)—, —$S(O)_2$—, —S(O)—, —N($R^{y1}$)$S(O)_2$N($R^{y1a}$)—, —S—, —N($R^{y1}$)—, —OC(O$R^{y1}$)($R^{y1a}$)—, —N($R^{y1}$)C(O)N($R^{y1a}$)—, —OC(O)N($R^{y1}$)—, $C_{1-50}$ alkyl, $C_{2-50}$ alkenyl, and $C_{2-50}$ alkynyl; wherein -T-, $C_{1-20}$ alkyl, $C_{2-20}$ alkenyl, and $C_{2-20}$ alkynyl are optionally substituted with one or more —$R^{y2}$, which are the same or different and wherein $C_{1-20}$ alkyl, $C_{2-20}$ alkenyl, and $C_{2-20}$ alkynyl are optionally interrupted by one or more groups selected from the group consisting of -T-, —C(O)O—, —O—, —C(O)—, —C(O)N($R^{y3}$)—, —$S(O)_2$N($R^{y3}$)—, —S(O)N($R^{y3}$)—, —$S(O)_2$—, —S(O)—, —N($R^{y3}$)$S(O)_2$N($R^{y3a}$)—, —S—, —N($R^{y3}$)—, —OC(O$R^{y3}$)($R^{y3a}$)—, —N($R^{y3}$)C(O)N($R^{y3a}$)—, and —OC(O)N($R^{y3}$)—;

—$R^{y1}$ and —$R^{y1a}$ are independently of each other selected from the group consisting of —H, -T, $C_{1-10}$ alkyl, $C_{2-10}$ alkenyl, and $C_{2-10}$ alkynyl; wherein -T, $C_{1-10}$ alkyl, $C_{2-10}$ alkenyl, and $C_{2-10}$ alkynyl are optionally substituted with one or more —$R^{y2}$, which are the same or different, and wherein $C_{1-10}$ alkyl, $C_{2-10}$ alkenyl, and $C_{2-10}$ alkynyl are optionally interrupted by one or more groups selected from the group consisting of -T-, —C(O)O—, —O—, —C(O)—, —C(O)N($R^{y4}$)—, —$S(O)_2$N($R^{y4}$)—, —S(O)N($R^{y4}$)—, —$S(O)_2$—, —S(O)—, —N($R^{y4}$)$S(O)_2$N($R^{y4a}$)—, —S—, —N($R^{y4}$)—, —OC(O$R^{y4}$)($R^{y4a}$)—, —N($R^{y4}$)C(O)N($R^{y4a}$)—, and —OC(O)N($R^{y4}$)—;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each T is independently optionally substituted with one or more —$R^{y2}$, which are the same or different;

$R^{y2}$ is selected from the group consisting of halogen, —CN, oxo (═O), —COO$R^{y5}$, —O$R^{y5}$, —C(O)$R^{y5}$, —C(O)N($R^{y5}R^{y5a}$), —$S(O)_2$N($R^{y5}R^{y5a}$), —S(O)N($R^{y5}R^{y5a}$), —$S(O)_2R^{y5}$, —S(O)$R^{y5}$, —N($R^{y5}$)$S(O)_2$N($R^{y5a}R^{y5b}$), —S$R^{y5}$, —N($R^{y5}R^{y5a}$), —$NO_2$, —OC(O)$R^{y5}$, —N($R^{y5}$)C(O)$R^{y5a}$, —N($R^{y5}$)$S(O)_2R^{y5a}$, —N($R^{y5}$)S(O)$R^{y5a}$, —N($R^{y5}$)C(O)O$R^{y5a}$, —N($R^{y5}$)C(O)N($R^{y5a}R^{y5b}$), —OC(O)N($R^{y5}R^{y5a}$), and $C_{1-6}$ alkyl; wherein $C_{1-6}$ alkyl is optionally substituted with one or more halogen, which are the same or different; and each —$R^{y3}$, —$R^{y3a}$, —$R^{y4}$, —$R^{y4a}$, —$R^{y5}$, —$R^{y5a}$ and —$R^{y5b}$ is independently of each other selected from the group consisting of —H, and $C_{1-6}$ alkyl; wherein $C_{1-6}$ alkyl is optionally substituted with one or more halogen, which are the same or different.

When -$L^2$- is other than a single chemical bond, -$L^2$- is even more preferably selected from the group consisting of -T-, —C(O)O—, —O—, —C(O)—, —C(O)N($R^{y1}$)—, —$S(O)_2$N($R^{y1}$)—, —S(O)N($R^{y1}$)—, —$S(O)_2$—, —S(O)—, —N($R^{y1}$)$S(O)_2$N($R^{y1a}$)—, —S—, —N($R^{y1}$)—, —OC(O$R^{y1}$)($R^{y1a}$)—, —N($R^{y1}$)C(O)N($R^{y1a}$)—, —OC(O)N($R^{y1}$)—, $C_{1-50}$ alkyl, $C_{2-50}$ alkenyl, and $C_{2-50}$ alkynyl; wherein -T-, $C_{1-50}$ alkyl, $C_{2-50}$ alkenyl, and $C_{2-50}$ alkynyl are optionally substituted with one or more —$R^{y2}$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^{y3}$)—, —S(O)$_2$N($R^{y3}$)—, —S(O)N($R^{y3}$)—, —S(O)$_2$—, —S(O)—, —N($R^{y3}$)S(O)$_2$N($R^{y3a}$)—, —S—, —N($R^{y3}$)—, —OC(O$R^{y3}$)($R^{y3a}$)—, —N($R^{y3}$)C(O)N($R^{y3a}$)—, and —OC(O)N($R^{y3}$)—;

—$R^{y1}$ and —$R^{y1a}$ are independently selected from the group consisting of —H, -T, $C_{1-10}$ alkyl, $C_{2-10}$ alkenyl, and $C_{2-10}$ alkynyl;

each T is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl;

each —$R^{y2}$ is independently selected from the group consisting of halogen, and $C_{1-6}$ alkyl; and each —$R^{y3}$, —$R^{y3a}$, —$R^{y4}$, —$R^{y4a}$, —$R^{y5}$, —$R^{y5a}$ and —$R^{y5b}$ is independently of each other selected from the group consisting of —H, and $C_{1-6}$ alkyl; wherein $C_{1-6}$ alkyl is optionally substituted with one or more halogen, which are the same or different.

Even more preferably, -$L^2$- is a $C_{1-20}$ alkyl chain, which is optionally interrupted by one or more groups independently selected from —O—, -T- and —C(O)N($R^{y1}$)—; and which $C_{1-20}$ alkyl chain is optionally substituted with one or more groups independently selected from —OH, -T and —C(O)N($R^{y6}R^{y6a}$); wherein —$R^{y1}$, —$R^{y6}$, —$R^{y6a}$ are independently selected from the group consisting of H and $C_{1-4}$ alkyl and wherein T is selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl.

Preferably, -$L^2$- has a molecular weight in the range of from 14 g/mol to 750 g/mol.

Preferably, -$L^2$- comprises a moiety selected from

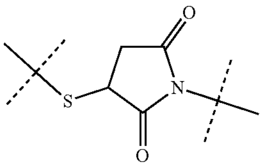
,
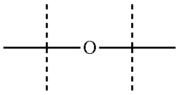
,
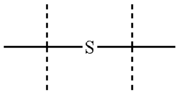
,
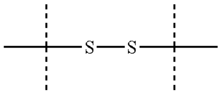
,
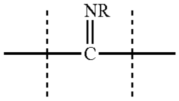
,
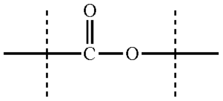
,
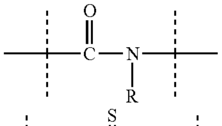
,
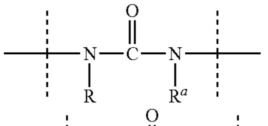
,
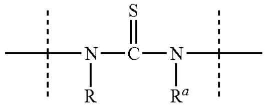
,
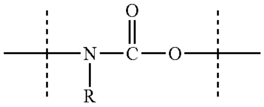
,
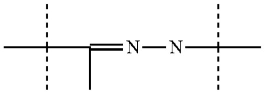
,
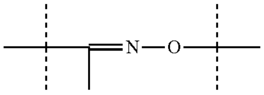
, -continued

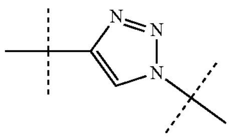
,
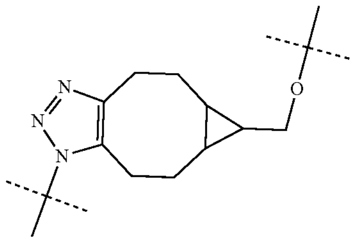
,
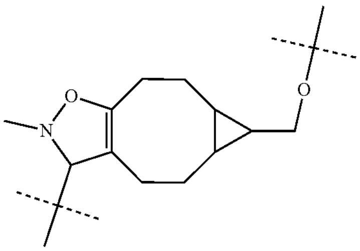
,
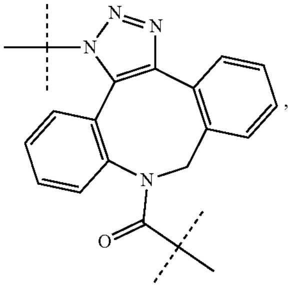
,
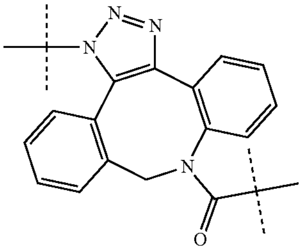
,
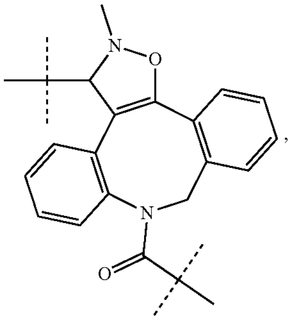
, -continued

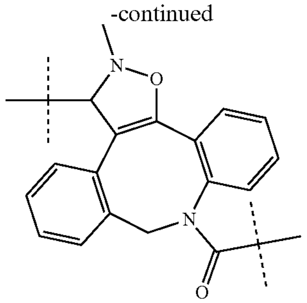

,

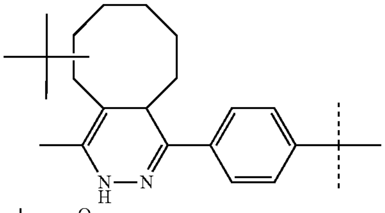

,

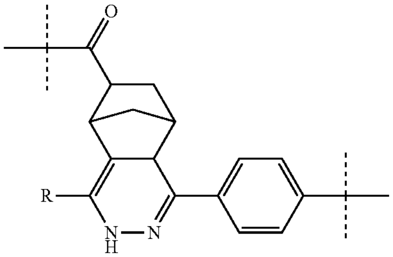

, and

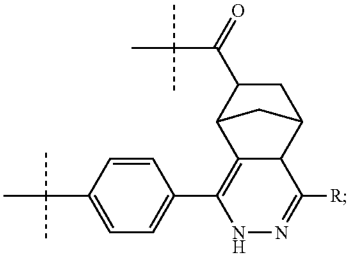

wherein dashed lines indicate attachment to the rest of $-L^2-$, $-L^1-$, —Z and/or —Z', respectively; and —R and $—R^a$ are independently of each other selected from the group consisting of —H, methyl, ethyl, propyl, butyl, pentyl and hexyl.

In one preferred embodiment $-L^2-$ has a chain lengths of 1 to 20 atoms.

As used herein the term "chain length" with regard to the moiety $-L^2-$ refers to the number of atoms of $-L^2-$ present in the shortest connection between $-L^1-$ and —Z.

Preferably, $-L^2-$ is of formula (i)

(i)

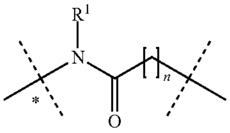

, wherein the dashed line marked with the asterisk indicates attachment to $-L^1-$;

the unmarked dashed line indicates attachment to —Z or —Z';

$—R^1$ is selected from the group consisting of —H, $C_{1-6}$ alkyl, $C_{2-6}$ alkenyl and $C_{2-6}$ alkynyl;

n is selected from the group consisting of 0, 1, 2, 3, 4, 5, 6, 7, 8, 9, 10, 11, 12, 13, 14, 15, 16, 17 and 18; and wherein the moiety of formula (i) is optionally further substituted.

Preferably $—R^1$ of formula (i) is selected from the group consisting of —H, methyl, ethyl, propyl, and butyl. Even more preferably $—R^1$ of formula (i) is selected from the group consisting of —H, methyl, ethyl and propyl. Even more preferably $—R^1$ of formula (i) is selected from the group consisting of —H and methyl. Most preferably $—R^1$ of formula (i) is methyl.

Preferably n of formula (i) is selected from the group consisting of 0, 1, 2, 3, 4, 5, 6, 7, 8, 9 and 10. Even more preferably n of formula (i) is selected from the group consisting of 0, 1, 2, 3, 4 and 5. Even more preferably n of formula (i) is selected from the group consisting of 0, 1, 2 and 3. Even more preferably n of formula (i) is selected from the group consisting of 0 and 1. Most preferably n of formula (i) is 0.

In one preferred embodiment $-L^2-$ is a moiety selected from the group consisting of (ii)

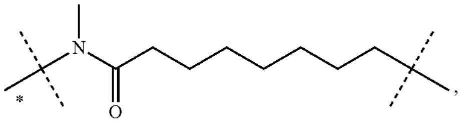

, (iii)

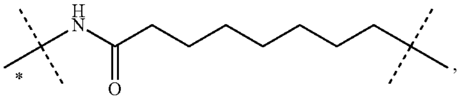

, (iv)

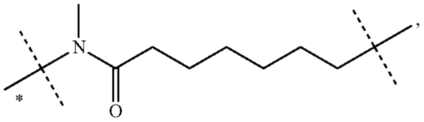

, (v)

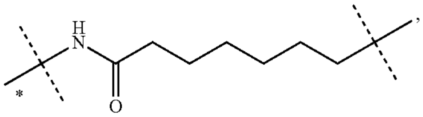

, (vi)

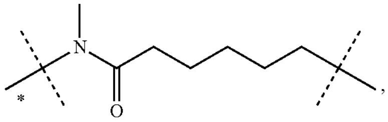

, (vii)

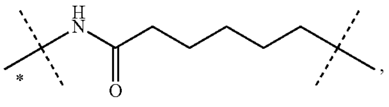

, (viii)

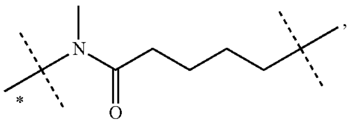

, (ix)

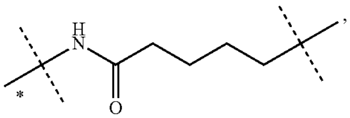

,

-continued (x)

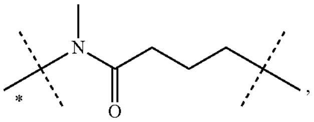

, (xi)

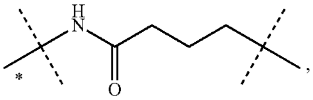

, (xii)

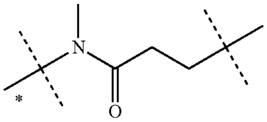

, (xiii)

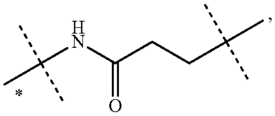

, (xiv)

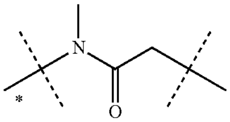

, (xv)

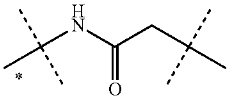

, (xvi)

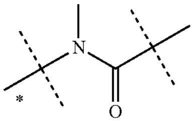

and (xvii)

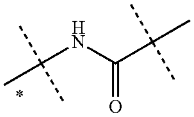

;

wherein the dashed line marked with the asterisk indicates attachment to -$L^1$-;

the unmarked dashed line indicates attachment to —Z or —Z'; and wherein the moieties (ii), (iii), (iv), (v), (vi), (vii), (viii), (ix), (x), (xi), (xii), (xiii), (xiv), (xv), (xvi) and (xvii) are optionally further substituted.

In a preferred embodiment -$L^2$- is selected from the group consisting of (xiv)

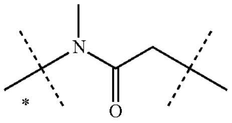

, (xv)

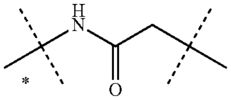

,

-continued (xvi)

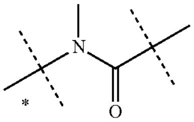

, and (xvii)

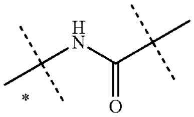

;

wherein the dashed line marked with the asterisk indicates attachment to -$L^1$-; and the unmarked dashed line indicates attachment to —Z or —Z'.

Even more preferred -$L^2$- is selected from the group consisting of (xiv)

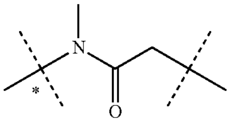

and (xvi)

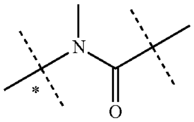

wherein the dashed line marked with the asterisk indicates attachment to -$L^1$-; and the unmarked dashed line indicates attachment to —Z or —Z'.

Even more preferably -$L^2$- is (xvi)

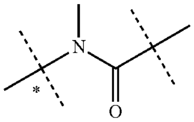

, wherein the dashed line marked with the asterisk indicates attachment to -$L^1$-; and the unmarked dashed line indicates attachment to —Z or —Z'.

In one preferred embodiment the moiety -$L^1$-$L^2$- is selected from the group consisting of (IId-i)

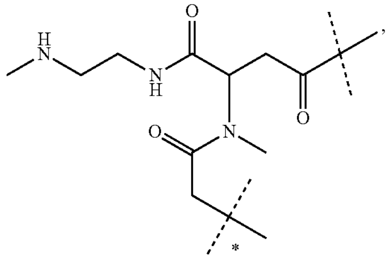

(IId-ii)

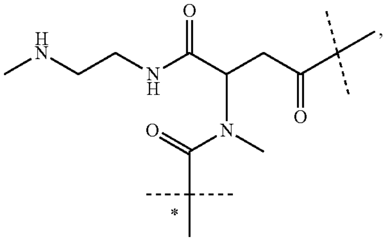

(IId-iii)

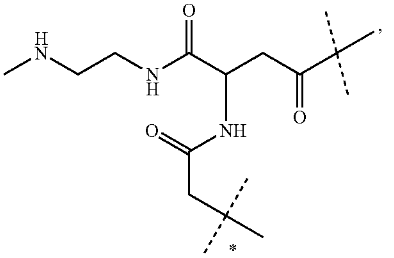

(IId-iv)

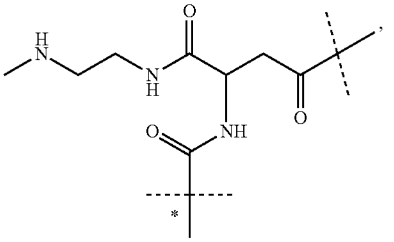

wherein the unmarked dashed line indicates the attachment to a nitrogen of -D which is a CNP agonist moiety by forming an amide bond; and the dashed line marked with the asterisk indicates attachment to —Z or —Z'.

In an even more preferred embodiment the moiety $-L^1-L^2-$ is (IId-ii)

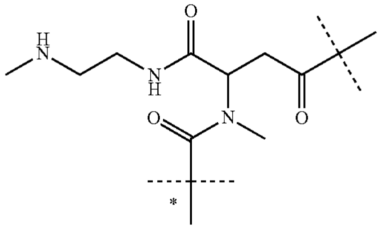

, wherein the unmarked dashed line indicates the attachment to a nitrogen of -D which is a CNP agonist moiety by forming an amide bond; and the dashed line marked with the asterisk indicates attachment to —Z or —Z'.

In a most preferred embodiment the moiety $-L^1-L^2-$ is of formula (IId-ii')

(IId-ii')

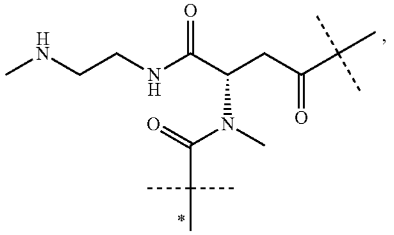

wherein the unmarked dashed line indicates the attachment to a nitrogen of -D which is a CNP agonist moiety by forming an amide bond; and the dashed line marked with the asterisk indicates attachment to —Z or —Z'.

In another preferred embodiment the moiety $-L^1-L^2-$ is selected from the group consisting of (IId-ia)

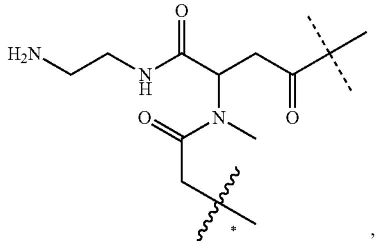

, (IId-iia)

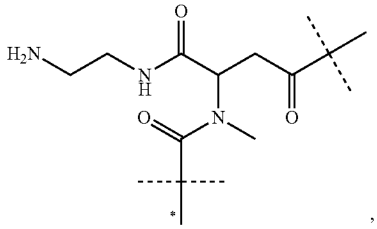

, (IId-iiia)

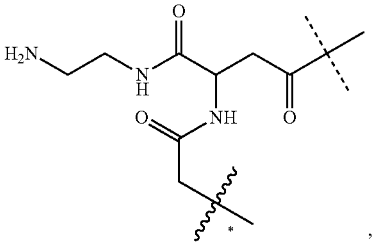

,

-continued (IId-iva)

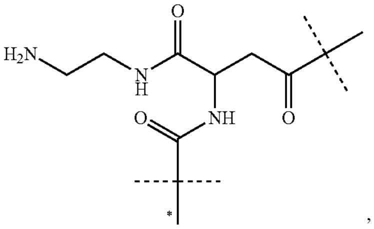

, wherein the unmarked dashed line indicates the attachment to a nitrogen of -D which is a CNP agonist moiety by forming an amide bond; and the dashed line marked with the asterisk indicates attachment to —Z or —Z'.

In an even more preferred embodiment the moiety $-L^1-L^2-$ is (IId-iia')

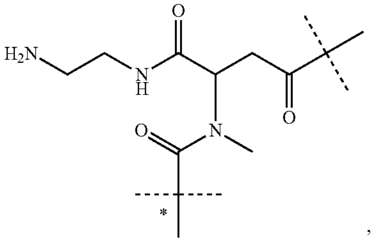

, wherein the unmarked dashed line indicates the attachment to a nitrogen of -D which is a CNP agonist moiety by forming an amide bond; and the dashed line marked with the asterisk indicates attachment to —Z or —Z'.

In a most preferred embodiment the moiety $-L^1-L^2-$ is of formula (IId-iia')

(IId-iia')

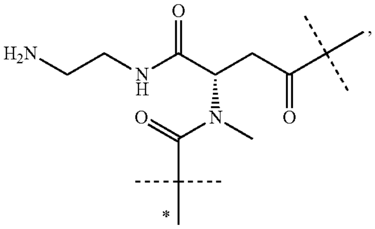

, wherein the unmarked dashed line indicates the attachment to a nitrogen of -D which is a CNP agonist moiety by forming an amide bond; and the dashed line marked with the asterisk indicates attachment to —Z or —Z'.

In another preferred embodiment the moiety $-L^1-L^2-$ is selected from the group consisting of (IId-ib)

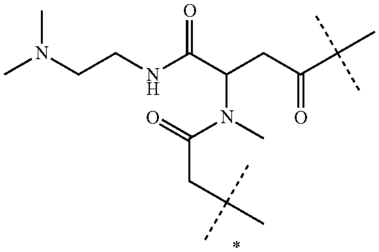

, (IId-iib)

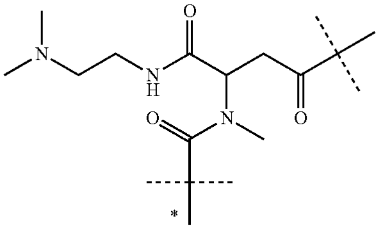

, (IId-iiib)

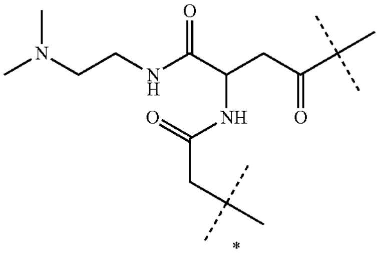

, (IId-ivb)

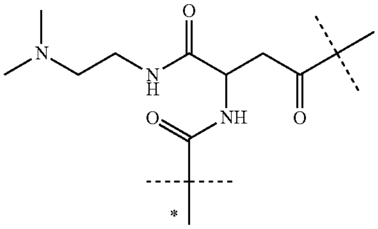

, wherein the unmarked dashed line indicates the attachment to a nitrogen of -D which is a CNP agonist moiety by forming an amide bond; and the dashed line marked with the asterisk indicates attachment to —Z or —Z'.

In an even more preferred embodiment the moiety $-L^1-L^2-$ is (IId-iib)

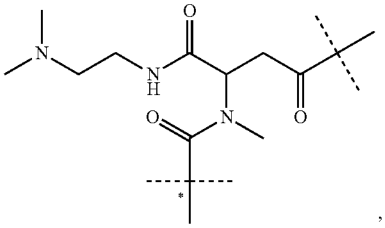

, wherein the unmarked dashed line indicates the attachment to a nitrogen of -D which is a CNP agonist moiety by forming an amide bond; and the dashed line marked with the asterisk indicates attachment to —Z or —Z'.

In a most preferred embodiment the moiety $-L^1-L^2-$ is of formula (IId-iib')

(IId-iib')

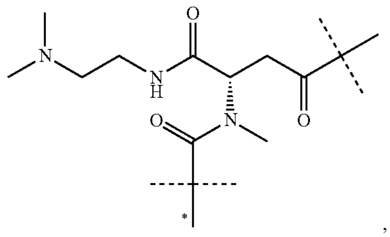

, wherein the unmarked dashed line indicates the attachment to a nitrogen of -D which is a CNP agonist moiety by forming an amide bond; and the dashed line marked with the asterisk indicates attachment to —Z or —Z'.

Preferably, —Z of formula (Ia) or (Ib) has a molecular weight ranging from 5 to 200 kDa. Even more preferably, —Z of formula (Ia) or (Ib) has a molecular weight ranging from 8 to 100 kDa, even more preferably ranging from 10 to 80 kDa, even more preferably from 12 to 60, even more preferably from 15 to 40 and most preferably —Z of formula (Ia) or (Ib) has a molecular weight of about 20 kDa. In another equally preferred embodiment —Z of formula (Ia) or (Ib) has a molecular weight of about 40 kDa.

The carrier —Z of formula (Ia) or (Ib) comprises a $C_{8-24}$ alkyl or a polymer. Preferably, —Z of formula (Ia) or (Ib) comprises a polymer, preferably a polymer selected from the group consisting of 2-methacryloyl-oxyethyl phosphoyl cholins, poly(acrylic acids), poly(acrylates), poly(acrylamides), poly(alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly(ethylenes), poly(ethyleneglycols), poly (ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly (lactic-co-glycolic acids), poly(methacrylamides), poly (methacrylates), poly(methyloxazolines), poly (organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

In another preferred embodiment, —Z of formula (Ia) or (Ib) comprises a fatty acid derivate. Preferred fatty acid derivatives are those disclosed in WO 2005/027978 A2 and WO 2014/060512 A1 which are herewith incorporated by reference.

In one embodiment —Z of formula (Ia) or (Ib) comprises a protein. Preferred proteins are selected from the group consisting of carboxyl-terminal peptide of the chorionic gonadotropin as described in US 2012/0035101 A1 which are herewith incorporated by reference; albumin; XTEN sequences as described in WO 2011123813 A2 which are herewith incorporated by reference; proline/alanine random coil sequences as described in WO 2011/144756 A1 which are herewith incorporated by reference; proline/alanine/serine random coil sequences as described in WO 2008/155134 A1 and WO 2013/024049 A1 which are herewith incorporated by reference; and Fc fusion proteins.

In one embodiment —Z of formula (Ia) or (Ib) is a polysarcosine.

In another preferred embodiment —Z of formula (Ia) or (Ib) comprises a poly(N-methylglycine).

In a particularly preferred embodiment —Z of formula (Ia) or (Ib) comprises a random coil protein moiety.

In one preferred embodiment —Z of formula (Ia) or (Ib) comprises one random coil protein moiety.

In another preferred embodiment —Z of formula (Ia) or (Ib) comprises two random coil proteins moieties.

In another preferred embodiment —Z of formula (Ia) or (Ib) comprises three random coil proteins moieties.

In another preferred embodiment —Z of formula (Ia) or (Ib) comprises four random coil proteins moieties.

In another preferred embodiment —Z of formula (Ia) or (Ib) comprises five random coil proteins moieties.

In another preferred embodiment —Z of formula (Ia) or (Ib) comprises six random coil proteins moieties.

In another preferred embodiment —Z of formula (Ia) or (Ib) comprises seven random coil proteins moieties.

In another preferred embodiment —Z of formula (Ia) or (Ib) comprises eight random coil proteins moieties.

Preferably such random coil protein moiety comprises at least 25 amino acid residues and at most 2000 amino acids. Even more preferably such random coil protein moiety comprises at least 30 amino acid residues and at most 1500 amino acid residues. Even more preferably such random coil protein moiety comprises at least 50 amino acid residues and at most 500 amino acid residues.

In a preferred embodiment, —Z of formula (Ia) or (Ib) comprises a random coil protein moiety of which at least 80%, preferably at least 85%, even more preferably at least 90%, even more preferably at least 95%, even more preferably at least 98% and most preferably at least 99% of the total number of amino acids forming said random coil protein moiety are selected from alanine and proline. Even more preferably, at least 10%, but less than 75%, preferably less than 65%, of the total number of amino acid residues of such random coil protein moiety are proline residues. Preferably, such random coil protein moiety is as described in WO 2011/144756 A1 which is hereby incorporated by reference in its entirety. Even more preferably —Z comprises at least one moiety selected from the group consisting of SEQ ID NO:1, SEQ ID NO:2, SEQ ID NO:3, SEQ ID NO:4, SEQ ID NO:5, SEQ ID NO:6, SEQ ID NO: 7, SEQ ID NO:8, SEQ ID NO:9, SEQ ID NO:10, SEQ ID NO:11, SEQ ID NO:12, SEQ ID NO:13, SEQ ID NO:14, SEQ ID NO:15, SEQ ID NO:16, SEQ ID NO:17, SEQ ID NO:51 and SEQ ID NO:61 as disclosed in WO2011/144756 which are hereby incorporated by reference. A moiety comprising such random coil protein comprising alanine and proline will be referred to as "PA" or "PA moiety".

Accordingly, —Z of formula (Ia) or (Ib) comprises a PA moiety.

In an equally preferred embodiment, —Z of formula (Ia) or (Ib) comprises a random coil protein moiety of which at least 80%, preferably at least 85%, even more preferably at least 90%, even more preferably at least 95%, even more preferably at least 98% and most preferably at least 99% of the total number of amino acids forming said random coil protein moiety are selected from alanine, serine and proline. Even more preferably, at least 4%, but less than 40% of the total number of amino acid residues of such random coil protein moiety are proline residues. Preferably, such random coil protein moiety is as described in WO 2008/155134 A1 which is hereby incorporated by reference in its entirety. Even more preferably —Z of formula (Ia) or (Ib) comprises at least one moiety selected from the group consisting of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID NO:30, SEQ ID NO:32, SEQ ID NO:34, SEQ ID NO:36, SEQ ID NO:40, SEQ ID NO:42, SEQ ID NO:44, SEQ ID NO:46, SEQ ID NO:50, SEQ ID NO:52, SEQ ID NO:54 and SEQ ID NO:56 as disclosed in WO 2008/155134 A1, which are hereby incorporated by reference. A moiety comprising such random coil protein moiety comprising alanine, serine and proline will be referred to as "PAS" or "PAS moiety".

Accordingly, —Z of formula (Ia) or (Ib) comprises a PAS moiety.

In an equally preferred embodiment, —Z of formula (Ia) or (Ib) comprises a random coil protein moiety of which at least 80%, preferably at least 85%, even more preferably at least 90%, even more preferably at least 95%, even more preferably at least 98% and most preferably at least 99% of the total number of amino acids forming said random coil protein moiety are selected from alanine, glycine and proline. A moiety comprising such random coil protein moiety comprising alanine, glycine and proline will be referred to as "PAG" or "PAG moiety".

Accordingly, —Z of formula (Ia) or (Ib) comprises a PAG moiety.

In an equally preferred embodiment, —Z of formula (Ia) or (Ib) comprises a random coil protein moiety of which at least 80%, preferably at least 85%, even more preferably at least 90%, even more preferably at least 95%, even more preferably at least 98% and most preferably at least 99% of the total number of amino acids forming said random coil protein moiety are selected from proline and glycine. A moiety comprising such random coil protein moiety comprising proline and glycine will be referred to as "PG" or "PG moiety".

Preferably, such PG moiety comprises a moiety of formula (a-0)

$$[(Gly)_p\text{-Pro-}(Gly)_q]_r \qquad \text{(a-0);}$$

wherein p is selected from the group consisting of 0, 1, 2, 3, 4 and 5;

q is selected from the group consisting of 0, 1, 2, 3, 4 and 5;

r is an integer ranging from and including 10 to 1000;

provided that at least one of p and q is at least 1;

Preferably, p of formula (a-0) is selected from the group consisting of 1, 2 and 3.

Preferably, q of formula (a-0) is selected from 0, 1 and 2.

Even more preferably the PG moiety comprises the sequence of SEQ ID: NO 97:

GGPGGPGPGGPGGPGPGGPG

Even more preferably, the PG moiety comprises the sequence of SEQ ID: NO 97 of formula (a-0-a)

$$(GGPGGPGPGGPGGPGPGGPG)_v \quad \text{(a-0-a)},$$

wherein v is an integer ranging from and including 1 to 50.

Accordingly, —Z of formula (Ia) or (Ib) comprises a PG moiety.

In an equally preferred embodiment, —Z of formula (Ia) or (Ib) comprises a random coil protein moiety of which at least 80%, preferably at least 85%, even more preferably at least 90%, even more preferably at least 95%, even more preferably at least 98% and most preferably at least 99% of the total number of amino acids forming said random coil protein moiety are selected from alanine, glycine, serine, threonine, glutamate and proline. Preferably, such random coil protein moiety is as described in WO 2010/091122 A1 which is hereby incorporated by reference. Even more preferably —Z of formula (Ia) or (Ib) comprises at least one moiety selected from the group consisting of SEQ ID NO:182, SEQ ID NO:183, SEQ ID NO:184; SEQ ID NO:185, SEQ ID NO:186, SEQ ID NO:187, SEQ ID NO:188, SEQ ID NO: 189, SEQ ID NO:190, SEQ ID NO:191, SEQ ID NO:192, SEQ ID NO:193, SEQ ID NO: 194, SEQ ID NO:195, SEQ ID NO:196, SEQ ID NO:197, SEQ ID NO:198, SEQ ID NO: 199, SEQ ID NO:200, SEQ ID NO:201, SEQ ID NO:202, SEQ ID NO:203, SEQ ID NO:204, SEQ ID NO:205, SEQ ID NO:206, SEQ ID NO:207, SEQ ID NO:208, SEQ ID NO:209, SEQ ID NO:210, SEQ ID NO:211, SEQ ID NO:212, SEQ ID NO:213, SEQ ID NO:214, SEQ ID NO:215, SEQ ID NO:216, SEQ ID NO:217, SEQ ID NO:218, SEQ ID NO:219, SEQ ID NO:220, SEQ ID NO:221, SEQ ID NO:759, SEQ ID NO:760, SEQ ID NO:761, SEQ ID NO:762, SEQ ID NO:763, SEQ ID NO:764, SEQ ID NO:765, SEQ ID NO:766, SEQ ID NO:767, SEQ ID NO:768, SEQ ID NO:769, SEQ ID NO:770, SEQ ID NO:771, SEQ ID NO:772, SEQ ID NO:773, SEQ ID NO:774, SEQ ID NO:775, SEQ ID NO:776, SEQ ID NO:777, SEQ ID NO:778, SEQ ID NO:779, SEQ ID NO:1715, SEQ ID NO:1716, SEQ ID NO:1718, SEQ ID NO:1719, SEQ ID NO:1720, SEQ ID NO:1721 and SEQ ID NO:1722 as disclosed in WO2010/091122A1, which are hereby incorporated by reference. A moiety comprising such random coil protein moiety comprising alanine, glycine, serine, threonine, glutamate and proline will be referred to as "XTEN" or "XTEN moiety" in line with its designation in WO 2010/091122 A1.

Accordingly, —Z of formula (Ia) or (Ib) comprises an XTEN moiety.

In another preferred embodiment —Z of formula (Ia) or (Ib) is a hyaluronic acid-based polymer.

In one embodiment —Z of formula (Ia) or (Ib) is a carrier as disclosed in WO 2012/02047 A1 which is herewith incorporated by reference.

In another embodiment —Z of formula (Ia) or (Ib) is a carrier as disclosed in WO 2013/024048 A1 which is herewith incorporated by reference.

In another preferred embodiment —Z of formula (Ia) or (Ib) is a PEG-based polymer. Even more preferably —Z is a branched or multi-arm PEG-based polymer.

In a preferred embodiment —Z of formula (Ia) or (Ib) is a branched polymer. In one embodiment —Z of formula (Ia)

or (Ib) is a branched polymer having one, two, three, four, five or six branching points. Preferably, —Z of formula (Ia) or (Ib) is a branched polymer having one, two or three branching points. In one embodiment —Z of formula (Ia) or (Ib) is a branched polymer having one branching point. In another embodiment —Z of formula (Ia) or (Ib) is a branched polymer having two branching points. In another embodiment —Z of formula (Ia) or (Ib) is a branched polymer having three branching points.

A branching point is preferably selected from the group consisting of —N<, —CH< and >C<. Preferably such branched moiety —Z of formula (Ia) or (Ib) is PEG-based.

In one embodiment such branched moiety —Z of formula (Ia) or (Ib) has a molecular weight ranging from and including 5 kDa to 500 kDa, more preferably ranging from and including 10 kDa to 250 Da, even more preferably ranging from and including 10 kDa to 150 kDa, even more preferably ranging from and including 12 kDa to 100 kDa and most preferably ranging from and including 15 kDa to 80 kDa.

Preferably, such branched moiety —Z of formula (Ia) or (Ib) has a molecular weight ranging from and including 10 kDa to 80 kDa. In one embodiment the molecular weight is about 10 kDa. In another embodiment the molecular weight of such branched moiety —Z of formula (Ia) or (Ib) is about 20 kDa. In another embodiment the molecular weight of such branched moiety —Z of formula (Ia) or (Ib) is about 30 kDa. In another embodiment the molecular weight of such a branched moiety —Z of formula (Ia) or (Ib) is about 40 kDa. In another embodiment the molecular weight of such a branched moiety —Z of formula (Ia) or (Ib) is about 50 kDa. In another embodiment the molecular weight of such a branched moiety —Z of formula (Ia) or (Ib) is about 60 kDa. In another embodiment the molecular weight of such a branched moiety —Z of formula (Ia) or (Ib) is about 70 kDa. In another embodiment the molecular weight of such a branched moiety —Z of formula (Ia) or (Ib) is about 80 kDa. Most preferably, such branched moiety —Z of formula (Ia) or (Ib) has a molecular weight of about 40 kDa.

Applicants found that an N-terminal attachment of a moiety $-L^1-L^2-Z$ is significantly more efficient with regard to NEP-stability than attachment at an internal site and that the least efficient attachment site with regard to NEP-stability is at the ring part of a CNP moiety. However, applicants surprisingly found that this disadvantage of attachment to the ring with regard to NEP-stability can be compensated by using a branched moiety —Z having a molecular weight of at least 10 kDa, such as at least 12 kDa, such as at least 15 kDa, such as at least 18 kDa, such as at least 20 kDa, such as at least 24 kDa, such as at least 25 kDa, such as at least 27 kDa, such as at least 30 kDa. Preferably, such branched moiety —Z has a molecular weight of no more than 500 kDa, preferably of no more than 250 kDa, preferably of no more than 200 Da, preferably of no more than 150 kDa and most preferably no more than 100 kDa. Most preferably such branched moiety —Z has a molecular weight of about 40 kDa. Consequently, the use of such branched moiety —Z at the ring part of the CNP moiety does not only lead to increased NEP-stability, but combines increased NEP-stability with reduced NPR—B binding associated with attachment to the ring.

It was surprisingly found that even though the ring moiety is involved in NPR—C binding, attachment of a 5 kDa carrier to the ring moiety did not have a significant effect on NPR—C affinity. Furthermore, it was surprisingly found that a 4×10 kDa carrier attached to the ring moiety is more efficient in reducing NPR—C affinity than a 2×20 kDa carrier, even though the total molecular weight was the same. It is thus not only the total molecular weight of the carrier attached to the ring moiety, but the particular branching pattern of the carrier that influences NPR—C binding affinity.

This finding is also supported by the NPR—C affinity measured with a 4-arm 40 kDa carrier having a different branching pattern which still exhibited a high NPR—C affinity.

In summary, it was surprisingly found that NPR—C affinity can be efficiently reduced with a multi-branched carrier attached to the ring moiety having a first branching point close to the CNP moiety, such as less than 300 atoms from the CNP moiety, preferably 200 atoms from the CNP moiety, even more preferably 100 atoms from the CNP moiety, even more preferably less than 50 atoms from the CNP moiety, even more preferably less than 25 atoms from the CNP moiety and most preferably less than 10 atoms from the CNP moiety.

Even more preferably, one or more further branching point(s) is/are located within less than 500 atoms from the CNP moiety, even more preferably 300 atoms from the CNP moiety, even more preferably less than 200 atoms from the CNP moiety, even more preferably less than 100 atoms from the CNP moiety, even more preferably less than 75 atoms from the CNP moiety, even more preferably less than 50 atoms from the CNP moiety, even more preferably less than 40 atoms from the CNP moiety and most preferably less than 35 atoms from the CNP moiety.

It was in addition also found that such branching pattern is beneficial for in vivo stability of the CNP moiety, i.e. protection against proteolytic degradation. It was surprisingly found that N-terminal degradation was stronger when using a 2×20 kDa carrier compared to 4×10 kDa carrier. Likewise, using a 4-arm 40 kDa carrier having a different branching pattern exhibited even stronger N-terminal degradation.

Preferably, —Z or —Z' comprises a moiety

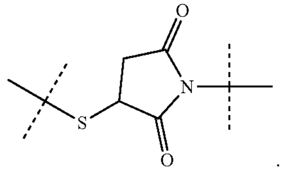

In an equally preferred embodiment —Z or —Z' comprises an amide bond.

In one embodiment —Z of formula (Ia) or (Ib) comprises a moiety of formula (a)

(a)

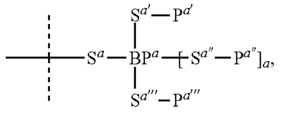

wherein the dashed line indicates attachment to $-L^2-$ or to the remainder of —Z;

$BP^a$ is a branching point selected from the group consisting of —N<, —CR< and >C<;

—R is selected from the group consisting of —H and $C_{1-6}$ alkyl;

a is 0 if $BP^a$ is —N< or —CR< and n is 1 if $BP^a$ is >C<;

$S^a$—, —$S^{a'}$—, —$S^{a''}$— and —$S^{a'''}$— are independently of each other a chemical bond or are selected from the group consisting of $C_{1-50}$ alkyl, $C_{2-50}$ alkenyl, and $C_{2-50}$ alkynyl; wherein $C_{1-50}$ alkyl, $C_{2-50}$ alkenyl, and $C_{2-50}$ alkynyl are optionally substituted with one or more —$R^1$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —C(O)N($R^2$)—, —$S(O)_2N(R^2)$—, —S(O)N($R^2$)—, —$S(O)_2$—, —S(O)—, —$N(R^2)S(O)_2N(R^{2a})$—, —S—, —N($R^2$)—, —OC($OR^2$)($R^{2a}$)—, —N($R^2$)C(O)N($R^{2a}$)—, and —OC(O)N($R^2$)—;

each -T- is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each -T- is independently optionally substituted with one or more —$R^1$, which are the same or different;

each —$R^1$ is independently selected from the group consisting of halogen, —CN, oxo (=O), —$COOR^3$, —$OR^3$, —C(O)$R^3$, —C(O)N($R^3R^{3a}$), —$S(O)_2N(R^3R^{3a})$, —S(O)N($R^3R^{3a}$), —$S(O)_2R^3$, —S(O)$R^3$, —$N(R^3)S(O)_2N(R^{3a}R^{3b})$, —$SR^3$, —N($R^3R^{3a}$), —$NO_2$, —OC(O)$R^3$, —N($R^3$)C(O)$R^{3a}$, —$N(R^3)S(O)_2R^{3a}$, —N($R^3$)S(O)$R^{3a}$, —N($R^3$)C(O)$OR^{3a}$, —N($R^3$)C(O)N($R^{3a}R^{3b}$), —OC(O)N($R^3R^{3a}$), and $C_{1-6}$ alkyl; wherein $C_{1-6}$ alkyl is optionally substituted with one or more halogen, which are the same or different;

each —$R^2$, —$R^{2a}$, —$R^3$, —$R^{3a}$ and —$R^{3b}$ is independently selected from the group consisting of —H, and $C_{1-6}$ alkyl, wherein $C_{1-6}$ alkyl is optionally substituted with one or more halogen, which are the same or different; and —$P^{a'}$, —$P^{a''}$ and —$P^{a'''}$ are independently a polymeric moiety.

Optionally, the moiety of formula (a) is substituted with one or more substituents.

In one embodiment $BP^a$ of formula (a) is —N<.

In another embodiment $BP^a$ of formula (a) is —CR<. Preferably, —R is —H. Accordingly, a of formula (a) is preferably 0.

In another embodiment $BP^a$ of formula (a) is >C<.

In one embodiment —$S^a$— of formula (a) is a chemical bond.

In another embodiment —$S^a$— of formula (a) is selected from the group consisting of $C_{1-10}$ alkyl, $C_{2-10}$ alkenyl and $C_{2-10}$ alkynyl, which $C_{1-10}$ alkyl, $C_{2-10}$ alkenyl and $C_{2-10}$ alkynyl are optionally interrupted by one or more chemical groups selected from the group consisting of —C(O)O—, —O—, —C(O)—, —C(O)N($R^4$)—, —$S(O)_2N(R^4)$—, —S(O)N($R^4$)—, —$S(O)_2$—, —S(O)—, —$N(R^4)S(O)_2N(R^{4a})$—, —S—, —N($R^4$)—, —OC($OR^4$)($R^{4a}$)—, —N($R^4$)C(O)N($R^{4a}$)—, and —OC(O)N($R^4$)—; wherein —$R^4$ and —$R^{4a}$ are independently selected from the group consisting of —H, methyl, ethyl, propyl and butyl. Preferably —$S^a$— of formula (a) is selected from the group consisting of methyl, ethyl, propyl, butyl, which are optionally interrupted by one or more chemical groups selected from the group consisting of —O—, —C(O)— and —C(O)N($R^4$)—.

In one embodiment —$S^{a'}$— of formula (a) is a chemical bond.

In another embodiment —$S^{a'}$— of formula (a) is selected from the group consisting of $C_{1-10}$ alkyl, $C_{2-10}$ alkenyl and $C_{2-10}$ alkynyl, which $C_{1-10}$ alkyl, $C_{2-10}$ alkenyl and $C_{2-10}$ alkynyl are optionally interrupted by one or more chemical groups selected from the group consisting of —C(O)O—, —O—, —C(O)—, —C(O)N($R^4$)—, —$S(O)_2N(R^4)$—, —S(O)N($R^4$)—, —$S(O)_2$—, —S(O)—, —$N(R^4)S(O)_2N(R^{4a})$—, —S—, —N($R^4$)—, —OC($OR^4$)($R^{4a}$)—, —N($R^4$)C(O)N($R^{4a}$)—, and —OC(O)N($R^4$)—; wherein —$R^4$ and —$R^{4a}$ are independently selected from the group consisting of —H, methyl, ethyl, propyl and butyl. Preferably —$S^{a'}$— of formula (a) is selected from the group consisting of methyl, ethyl, propyl, butyl, which are optionally interrupted by one or more chemical groups selected from the group consisting of —O—, —C(O)— and —C(O)N($R^4$)—.

In one embodiment —$S^{a''}$— of formula (a) is a chemical bond.

In another embodiment —$S^{a''}$— of formula (a) is selected from the group consisting of $C_{1-10}$ alkyl, $C_{2-10}$ alkenyl and $C_{2-10}$ alkynyl, which $C_{1-10}$ alkyl, $C_{2-10}$ alkenyl and $C_{2-10}$ alkynyl are optionally interrupted by one or more chemical groups selected from the group consisting of —C(O)O—, —O—, —C(O)—, —C(O)N($R^4$)—, —$S(O)_2N(R^4)$—, —S(O)N($R^4$)—, —$S(O)_2$—, —S(O)—, —$N(R^4)S(O)_2N(R^{4a})$—, —S—, —N($R^4$)—, —OC($OR^4$)($R^{4a}$)—, —N($R^4$)C(O)N($R^{4a}$)—, and —OC(O)N($R^4$)—; wherein —$R^4$ and —$R^{4a}$ are independently selected from the group consisting of —H, methyl, ethyl, propyl and butyl. Preferably —$S^{a''}$— of formula (a) is selected from the group consisting of methyl, ethyl, propyl, butyl, which are optionally interrupted by one or more chemical groups selected from the group consisting of —O—, —C(O)— and —C(O)N($R^4$)—.

In one embodiment —$S^{a'''}$— of formula (a) is a chemical bond.

In another embodiment —$S^{a'''}$— of formula (a) is selected from the group consisting of $C_{1-10}$ alkyl, $C_{2-10}$ alkenyl and $C_{2-10}$ alkynyl, which $C_{1-10}$ alkyl, $C_{2-10}$ alkenyl and $C_{2-10}$ alkynyl are optionally interrupted by one or more chemical groups selected from the group consisting of —C(O)O—, —O—, —C(O)—, —C(O)N($R^4$)—, —$S(O)_2N(R^4)$—, —S(O)N($R^4$)—, —$S(O)_2$—, —S(O)—, —$N(R^4)S(O)_2N(R^{4a})$—, —S—, —N($R^4$)—, —OC($OR^4$)($R^{4a}$)—, —N($R^4$)C(O)N($R^{4a}$)—, and —OC(O)N($R^4$)—; wherein —$R^4$ and —$R^{4a}$ are independently selected from the group consisting of —H, methyl, ethyl, propyl and butyl. Preferably —$S^{a'''}$— of formula (a) is selected from the group consisting of methyl, ethyl, propyl, butyl, which are optionally interrupted by one or more chemical groups selected from the group consisting of —O—, —C(O)— and —C(O)N($R^4$)—.

Preferably, —$P^{a'}$, —$P^{a''}$ and —$P^{a'''}$ of formula (a) independently comprise a polymer selected from the group consisting of 2-methacryloyl-oxyethyl phosphoyl cholins, poly(acrylic acids), poly(acrylates), poly(acrylamides), poly (alkyloxy) polymers, poly(amides), poly(amidoamines), poly(amino acids), poly(anhydrides), poly(aspartamides), poly(butyric acids), poly(glycolic acids), polybutylene terephthalates, poly(caprolactones), poly(carbonates), poly(cyanoacrylates), poly(dimethylacrylamides), poly(esters), poly (ethylenes), poly(ethyleneglycols), poly(ethylene oxides), poly(ethyl phosphates), poly(ethyloxazolines), poly(glycolic acids), poly(hydroxyethyl acrylates), poly(hydroxyethyl-oxazolines), poly(hydroxymethacrylates), poly(hydroxypropylmethacrylamides), poly(hydroxypropyl methacrylates), poly(hydroxypropyloxazolines), poly(iminocarbonates), poly(lactic acids), poly(lactic-co-glycolic acids), poly(methacrylamides), poly(methacrylates), poly (methyloxazolines), poly(organophosphazenes), poly(ortho esters), poly(oxazolines), poly(propylene glycols), poly(siloxanes), poly(urethanes), poly(vinyl alcohols), poly(vinyl amines), poly(vinylmethylethers), poly(vinylpyrrolidones), silicones, celluloses, carbomethyl celluloses, hydroxypropyl methylcelluloses, chitins, chitosans, dextrans, dextrins, gelatins, hyaluronic acids and derivatives, functionalized hyaluronic acids, mannans, pectins, rhamnogalacturonans, starches, hydroxyalkyl starches, hydroxyethyl starches and other carbohydrate-based polymers, xylans, and copolymers thereof.

Preferably, —$P^{a'}$, —$P^{a''}$ and —$P^{a'''}$ of formula (a) independently have a molecular weight ranging from and including 5 kDa to 50 kDa, more preferably have a molecular weight ranging from and including 5 kDa to 40 kDa, even more preferably ranging from and including 7.5 kDa to 35 kDa, even more preferably ranging from and 7.5 to 30 kDa, even more preferably ranging from and including 10 to 30 kDa.

In one embodiment —$P^{a'}$, —$P^{a''}$ and —$P^{a'''}$ of formula (a) have a molecular weight of about 5 kDa.

In another embodiment —$P^{a'}$, —$P^{a''}$ and —$P^{a'''}$ of formula (a) have a molecular weight of about 7.5 kDa.

In another embodiment —$P^{a'}$, —$P^{a''}$ and —$P^{a'''}$ of formula (a) have a molecular weight of about 10 kDa.

In another embodiment —$P^{a'}$, —$P^{a''}$ and —$P^{a'''}$ of formula (a) have a molecular weight of about 12.5 kDa.

In another embodiment —$P^{a'}$, —$P^{a''}$ and —$P^{a'''}$ of formula (a) have a molecular weight of about 15 kDa.

In another embodiment —$P^{a'}$, —$P^{a''}$ and —$P^{a'''}$ of formula (a) have a molecular weight of about 20 kDa.

More preferably, —$P^{a'}$, —$P^{a''}$ and —$P^{a'''}$ of formula (a) independently comprise a PEG-based moiety. Even more preferably, —$P^{a'}$, —$P^{a''}$ and —$P^{a'''}$ of formula (a) independently comprise a PEG-based moiety comprising at least 20% PEG, even more preferably at least 30%, even more preferably at least 40% PEG, even more preferably at least 50% PEG, even more preferably at least 60% PEG, even more preferably at least 70% PEG, even more preferably at least 80% PEG and most preferably at least 90% PEG.

In an equally preferred embodiment —$P^{a'}$, —$P^{a''}$ and —$P^{a'''}$ of formula (a) independently comprise a protein moiety, more preferably a random coil protein moiety and most preferably a random coil protein moiety selected from the group consisting of PA, PAS, PAG, PG and XTEN moieties.

In one embodiment —$P^{a'}$, —$P^{a''}$ and —$P^{a'''}$ of formula (a) are a PA moiety.

In another embodiment —$P^{a'}$, —$P^{a''}$ and —$P^{a'''}$ of formula (a) are a PAS moiety.

In another embodiment —$P^{a'}$, —$P^{a''}$ and —$P^{a'''}$ of formula (a) are a PAG moiety.

In another embodiment —$P^{a'}$, —$P^{a''}$ and —$P^{a'''}$ of formula (a) are a PG moiety.

In another embodiment —$P^{a'}$, —$P^{a''}$ and —$P^{a'''}$ of formula (a) are an XTEN moiety.

In one embodiment —Z comprises one moiety of formula (a).

In another embodiment —Z comprises two moieties of formula (a).

In another embodiment —Z comprises three moieties of formula (a).

In another embodiment —Z comprises four moieties of formula (a).

In another embodiment —Z comprises five moieties of formula (a).

In another embodiment —Z comprises six moieties of formula (a).

In a preferred embodiment —Z comprises two moieties of formula (a).

In a preferred embodiment —Z comprises a moiety of formula (b)

(b)

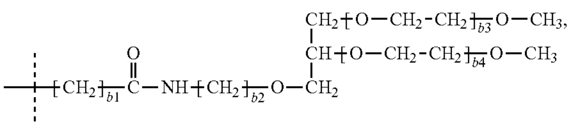

wherein the dashed line indicates attachment to -$L^2$- or to the remainder of —Z;

b1 is selected from the group consisting of 0, 1, 2, 3, 4, 5, 6, 7 and 8;

b2 is selected from the group consisting of 1, 2, 3, 4, 5, 6, 7 and 8;

b3 is an integer ranging from and including 150 to 1000; preferably ranging from and including 150 to 500; and most preferably ranging from and including 200 to 460; and b4 is an integer ranging from and including 150 to 1000; preferably ranging from and including 150 to 500; and most preferably ranging from and including 200 to 460.

Optionally, the moiety of formula (b) is substituted with one or more substituents.

Preferably, b3 and b4 of formula (b) are the same integer.

In one preferred embodiment b3 and b4 both an integer ranging from 200 to 250 and most preferably b3 and b4 of formula (b) are about 225.

In another preferred embodiment b3 and b4 are both an integer ranging from 400 to 500 and most preferably b3 and b4 of formula (b) are about 450.

Preferably, b1 of formula (b) is selected from the group consisting of 0, 1, 2, 3 and 4. More preferably b1 of formula (b) is selected from the group consisting of 1, 2 and 3. Most preferably b1 of formula (b) is 2.

Preferably, b2 of formula (b) is selected from the group consisting of 1, 2, 3, 4 and 5. More preferably b2 of formula (b) is selected from the group consisting of 2, 3 and 4. Most preferably b2 of formula (b) is 3.

In one particularly preferred embodiment b1 of formula (b) is 2, b2 of formula (b) is 3, and b3 and b4 are both about 450.

In another particularly preferred embodiment b1 of formula (b) is 2, b2 of formula (b) is 3, and b3 and b4 are both about 225.

In one embodiment —Z comprises one moiety of formula (b).

In another embodiment —Z comprises two moieties of formula (b).

In another embodiment —Z comprises three moieties of formula (b).

In another embodiment —Z comprises four moieties of formula (b).

In another embodiment —Z comprises five moieties of formula (b).

In another embodiment —Z comprises six moieties of formula (b).

In a preferred embodiment —Z comprises two moieties of formula (b).

In an even more preferred embodiment —Z comprises a moiety of formula (c)

(c)

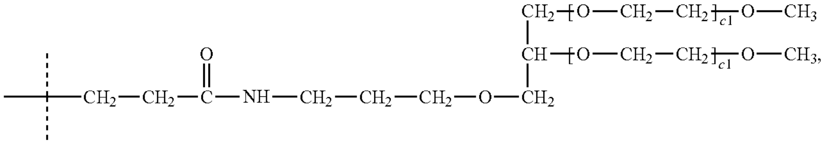

wherein the dashed line indicates attachment to $-L^2-$ or to the remainder of —Z;

c1 and c2 are independently an integer ranging from and including 150 to 500;

preferably ranging from and including 200 to 460.

Optionally, the moiety of formula (c) is substituted with one or more substituents.

Preferably both c1 and c2 of formula (c) are the same integer.

In one preferred embodiment c1 and c2 of formula (c) range from and include 200 to 250 and most preferably are about 225. In another preferred embodiment c1 and c2 of formula (c) range from and include 400 to 500 and most preferably are about 450.

In a preferred embodiment the moiety —Z is a branched PEG-based polymer comprising at least 10% PEG, has one branching point and two PEG-based polymer arms and has a molecular weight of about 40 kDa. Accordingly, each of the two PEG-based polymer arms has a molecular weight of about 20 kDa. Preferably the branching point is —CH<.

In one embodiment —Z comprises one moiety of formula (c).

In another embodiment —Z comprises two moieties of formula (c).

In another embodiment —Z comprises three moieties of formula (c).

In another embodiment —Z comprises four moieties of formula (c).

In another embodiment —Z comprises five moieties of formula (c).

In another embodiment —Z comprises six moieties of formula (c).

In a preferred embodiment —Z comprises two moieties of formula (c).

In one preferred embodiment the moiety —Z is of formula (d)

(d)

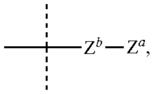

wherein the dashed line indicates attachment to $-L^2-$;

$-Z^b-$ is selected from the group consisting of $C_{1-50}$ alkyl, $C_{2-50}$ alkenyl, and $C_{2-50}$ alkynyl; wherein $C_{1-50}$ alkyl, $C_{2-50}$ alkenyl, and $C_{2-50}$ alkynyl are optionally substituted with one or more $-R^1$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, $-C(O)N(R^2)-$, $-S(O)_2N(R^2)-$, $-S(O)N(R^2)-$, $-S(O)_2-$, —S(O)—, $-N(R^2)S(O)_2N(R^{2a})-$, —S—, $-N(R^2)-$, $-OC(OR^2)(R^{2a})-$, $-N(R^2)C(O)N(R^{2a})-$, and $-OC(O)N(R^2)-$;

each -T- is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each -T- is independently optionally substituted with one or more $-R^1$, which are the same or different;

each $-R^1$ is independently selected from the group consisting of halogen, —CN, oxo (=O), $-COOR^3$, $-OR^3$, $-C(O)R^3$, $-C(O)N(R^3R^{3a})$, $-S(O)_2N(R^3R^{3a})$, $-S(O)N(R^3R^{3a})$, $-S(O)_2R^3$, $-S(O)R^3$, $-N(R^3)S(O)_2N(R^{3a}R^{3b})$, $-SR^3$, $-N(R^3R^{3a})$, $-NO_2$, $-OC(O)R^3$, $-N(R^3)C(O)R^{3a}$, $-N(R^3)S(O)_2R^{3a}$, $-N(R^3)S(O)R^{3a}$, $-N(R^3)C(O)OR^{3a}$, $-N(R^3)C(O)N(R^{3a}R^{3b})$, $-OC(O)N(R^3R^{3a})$, and $C_{1-6}$ alkyl;

wherein $C_{1-6}$ alkyl is optionally substituted with one or more halogen, which are the same or different;

each $-R^2$, $-R^{2a}$, $-R^3$, $-R^{3a}$ and $-R^{3b}$ is independently selected from the group consisting of —H, and $C_{1-6}$ alkyl, wherein $C_{1-6}$ alkyl is optionally substituted with one or more halogen, which are the same or different;

and $-Z^a$ is

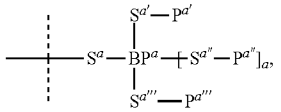

wherein $BP^a$, $-S^a-$, $-S^{a'}-$, $-S^{a''}$, $-S^{a'''}-$, $-P^{a'}$, $-P^{a''}$, $-P^{a'''}$ and a are used as defined for formula (a).

Optionally, the moiety of formula (d) is substituted with one or more substituents.

Preferred embodiments of $BP^a$, $-S^a-$, $-S^{a'}-$, $-S^{a''}-$, $-S^{a'''}$, $-P^{a'}$, $-P^{a''}$, $-P^{a'''}$ of formula (d) are as defined above for formula (a).

In an even more preferred embodiment the moiety —Z of formula (Ia) or (Ib) is of formula (e)

(e)

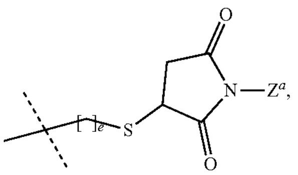

wherein the dashed line indicates attachment to $-L^2-$;

e is selected from the group consisting of 1, 2, 3, 4, 5, 6, 7, 8, 9, 10, 11, 12, 13, 14 and 15; and $-Z^a$ is

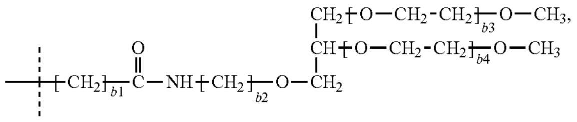

wherein b1, b2, b3 and b4 are used as defined for formula (b).

Optionally, the moiety of formula (e) is substituted with one or more substituents.

Preferred embodiments for b1, b2, b3 and b4 of formula (e) are as defined above for formula (b).

In one embodiment e of formula (e) is 1. In another embodiment e of formula (e) is 2. In another embodiment e of formula (e) is 3. In another embodiment e of formula (e) is 4. In another embodiment e of formula (e) is 5. In another embodiment e of formula (e) is 6. In another embodiment e of formula (e) is 7. In another embodiment e of formula (e) is 8. In another embodiment e of formula (e) is 9. In another embodiment e of formula (e) is 10. In another embodiment e of formula (e) is 11. In another embodiment e of formula (e) is 12. In another embodiment e of formula (e) is 13. In another embodiment e of formula (e) is 14. In another embodiment e of formula (e) is 15.

Preferably e of formula (e) is selected from the group consisting of 2, 3, 4, 5, 6, 7, 8 and 9. Even more preferably, e of formula (e) is selected from 3, 4, 5 and 6. Most preferably e of formula (e) is 5.

Preferably e of formula (e) is 5, b1 of formula (e) is 2, b2 of formula (e) is 3 and b3 and b4 of formula (e) are both about 450.

In an equally preferred embodiment the moiety $-Z$ of formula (Ia) or (Ib) is of formula (e-i) or (e-i'):

(e-i)

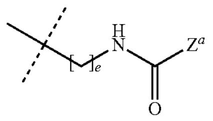

(e-i')

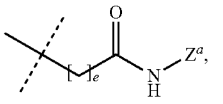

wherein the dashed line indicates attachment to $-L^2-$, e is selected from the group consisting of 1, 2, 3, 4, 5, 6, 7, 8, 9, 10, 11, 12, 13, 14 and 15;

$-Z^a$ is

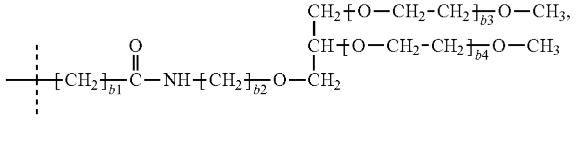

wherein b1, b2, b3 and b4 are used as defined for formula (b).

Preferred embodiments for b1, b2, b3 and b4 of formula (e-i) and (e-i') are as defined above for formula (b).

Preferred embodiments for e of formula (e-i) and (e-i') are as described for formula (e).

Preferably, b1 of formula (e-i) and (e-i') is 2, b2 of formula (e-i) and (e-i') is 3 and b3 and b4 of formula (e-i) and (e-i') are both about 450.

In a preferred embodiment $-Z$ of formula (Ia) or (Ib) is of formula (e-i).

In another preferred embodiment the moiety $-Z$ is a branched PEG-based polymer comprising at least 10% PEG, has three branching points and four PEG-based polymer arms and has a molecular weight of about 40 kDa. Accordingly, each of the four PEG-based polymer arms has a molecular weight of about 10 kDa. Preferably each of the three branching points is $-CH<$.

In a preferred embodiment the moiety $-Z$ is of formula (f)

(f)

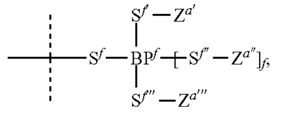

wherein the dashed line indicates attachment to $-L^2-$;

$BP^f$ is a branching point selected from the group consisting of $-N<$, $-CR<$ and $>C<$;

$-R$ is selected from the group consisting of $-H$ and $C_{1-6}$ alkyl;

f is 0 if $BP^f$ is $-N<$ or $-CR<$ and f is 1 if $BP^f$ is $>C<$;

$-S^f-$, $-S^{f'}-$, $-S^{f''}-$ and $-S^{f'''}-$ are independently either a chemical bond or are independently selected from the group consisting of $C_{1-50}$ alkyl, $C_{2-50}$ alkenyl, and $C_{2-50}$ alkynyl; wherein $C_{1-50}$ alkyl, $C_{2-50}$ alkenyl, and $C_{2-50}$ alkynyl are optionally substituted with one or more $-R^1$, which are the same or different and wherein $C_{1-50}$ alkyl, $C_{2-50}$ alkenyl, and $C_{2-50}$ alkynyl are optionally interrupted by one or more groups selected from the group consisting of -T-, $-C(O)O-$, $-O-$, $-C(O)-$, $-C(O)N(R^2)-$, $-S(O)_2N(R^2)-$, $-S(O)N(R^2)-$, $-S(O)_2-$, $-S(O)-$, $-N(R^2)S(O)_2N(R^{2a})-$, $-S-$, $-N(R^2)-$, $-OC(OR^2)(R^{2a})-$, $-N(R^2)C(O)N(R^{2a})-$, and $-OC(O)N(R^2)-$;

each -T- is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each -T- is independently optionally substituted with one or more $-R^1$, which are the same or different;

each $R^1$ is independently selected from the group consisting of halogen, $-CN$, oxo ($=O$), $-COOR^3$, $-OR^3$, $-C(O)R^3$, $-C(O)N(R^3R^{3a})$, $-S(O)_2N(R^3R^{3a})$, $-S(O)N(R^3R^{3a})$, $-S(O)_2R^3$, $-S(O)R^3$, $-N(R^3)S(O)_2N(R^{3a}R^{3b})$, $-SR^3$, $-N(R^3R^{3a})$, $-NO_2$, $-OC(O)R^3$, $-N(R^3)C(O)R^{3a}$, $-N(R^3)S(O)_2R^{3a}$, $-N(R^3)S(O)R^{3a}$, $-N(R^3)C(O)OR^{3a}$, $-N(R^3)C(O)N(R^{3a}R^{3b})$, $-OC(O)N(R^3R^{3a})$, and $C_{1-6}$ alkyl; wherein $C_{1-6}$ alkyl is optionally substituted with one or more halogen, which are the same or different;

each $—R^2$, $—R^{2a}$, $—R^3$, $—R^{3a}$ and $—R^{3b}$ is independently selected from the group consisting of —H, and $C_{1-6}$ alkyl, wherein $C_{1-6}$ alkyl is optionally substituted with one or more halogen, which are the same or different;

and $—Z^{a'}$, $—Z^{a''}$ and $—Z^{a'''}$ are independently

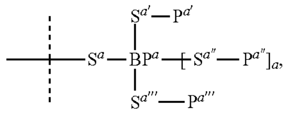

wherein $BP^a$, $—S^a$, $—S^{a'}$, $—S^{a''}—$, $—S^{a'''}$, $—P^{a'}$, $—P^{a''}$, $—P^{a'''}$ and a are used as defined for formula (a).

Optionally, the moiety of formula (f) is substituted with one or more substituents.

Preferred embodiments of $BP^a$, $—S^a—$, $—S^{a'}—$, $—S^{a''}—$, $—S^{a'''}—$, $—P^{a'}$, $—P^{a''}$ and $—P^{a'''}$ of formula (f) are as defined above for formula (a).

Preferably $BP^2$ of formula (f) is —CR< and r is 0. Preferably —R is —H.

Preferably $—S^f—$ of formula (f) is a chemical bond.

Preferably, $—Z^{a'}$, $—Z^{a''}$ and $—Z^{a'''}$ of formula (f) have the same structure. Preferably, $—Z^{a'}$, $—Z^{a''}$ and $—Z^{a'''}$ of formula (f) are of formula (b).

Preferably $—S_f—$ of formula (f) is a chemical bond, $BP^a$ of formula (f) is —CR< with —R being —H. Even more preferably $—S^f—$ of formula (f) is a chemical bond, $BP^a$ of formula (f) is —CR< with —R being —H and $—Z^{a'}$, $—Z^{a''}$ and $—Z^{a'''}$ of formula (f) are of formula (b).

Even more preferably —Z is of formula (g)

(g)

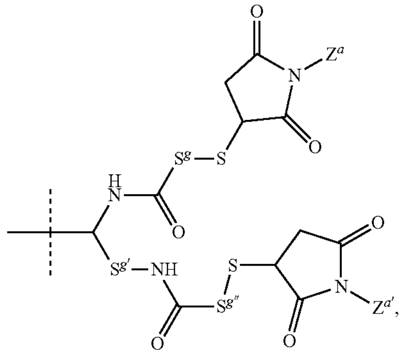

wherein the dashed line indicates attachment to $-L^2-$;

$—S^g—$, $—S^{g'}—$ and $—S^{g''}—$ are independently selected from the group consisting of $C_{1-50}$ alkyl, $C_{2-50}$ alkenyl, and $C_{2-50}$ alkynyl; wherein $C_{1-50}$ alkyl, $C_{2-50}$ alkenyl, and $C_{2-50}$ alkynyl are optionally substituted with one or more $—R^1$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, $—C(O)N(R^2)—$, $—S(O)_2N(R^2)—$, $—S(O)N(R^2)—$, $—S(O)_2—$, —S(O)—, $—N(R^2)S(O)_2N(R^{2a})—$, —S—, $—N(R^2)—$, $—OC(OR^2)(R^{2a})—$, $—N(R^2)C(O)N(R^{2a})—$, and $—OC(O)N(R^2)—$;

each -T- is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each -T- is independently optionally substituted with one or more $—R^1$, which are the same or different;

each $R^1$ is independently selected from the group consisting of halogen, —CN, oxo (=O), $—COOR^3$, $—OR^3$, $—C(O)R^3$, $—C(O)N(R^3R^{3a})$, $—S(O)_2N(R^3R^{3a})$, $—S(O)N(R^3R^{3a})$, $—S(O)_2R^3$, $—S(O)R^3$, $—N(R^3)S(O)_2N(R^{3a}R^{3b})$, $—SR^3$, $—N(R^3R^{3a})$, $—NO_2$, $—OC(O)R^3$, $—N(R^3)C(O)R^{3a}$, $—N(R^3)S(O)_2R^{3a}$, $—N(R^3)S(O)R^{3a}$, $—N(R^3)C(O)OR^{3a}$, $—N(R^3)C(O)N(R^{3a}R^{3b})$, $—OC(O)N(R^3R^{3a})$, and $C_{1-6}$ alkyl;

wherein $C_{1-6}$ alkyl is optionally substituted with one or more halogen, which are the same or different;

each $—R^2$, $—R^{2a}$, $—R^3$, $—R^{3a}$ and $—R^{3b}$ is independently selected from the group consisting of —H, and $C_{1-6}$ alkyl, wherein $C_{1-6}$ alkyl is optionally substituted with one or more halogen, which are the same or different;

and $—Z^a$ and $—Z^{a'}$ are independently

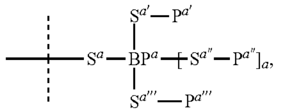

wherein $BP^a$, $—S^a—$, $—S^{a'}—$, $—S^{a''}—$, $—S^{a'''}—$, $—P^{a'}$, $—P^{a''}—$, $—P^{a'''}$ and a are used as defined for formula (a).

Optionally, the moiety of formula (g) is substituted with one or more substituents.

Preferred embodiments of $BP^a$, $—S^a—$, $—S^{a'}—$, $—S^{a''}—$, $—S^{a'''}—$, $—P^{a'}$, $—P^{a''}$ and $—P^{a'''}$ of formula (g) are as defined above for formula (a).

Preferably, $—S^g—$ of formula (g) is selected from the group consisting of $C_{1-6}$ alkyl, $C_{2-6}$ alkenyl and $C_{2-6}$ alkynyl, which are optionally substituted with one or more $—R^1$, which is the same or different, wherein $—R^1$ is selected from the group consisting of halogen, oxo (=O), $—COOR^3$, $—OR^3$, $—C(O)R^3$, $—C(O)N(R^3R^{3a})$, $—S(O)_2N(R^3R^{3a})$, $—S(O)N(R^3R^{3a})$, $—S(O)_2R^3$, $—S(O)R^3$, $—N(R^3)S(O)_2N(R^{3a}R^{3b})$, $—SR^3$, $—N(R^3R^{3a})$, $—NO_2$, $—OC(O)R^3$, $—N(R^3)C(O)R^{3a}$, $—N(R^3)S(O)_2R^{3a}$, $—N(R^3)S(O)R^{3a}$, $—N(R^3)C(O)OR^3a$ $—N(R^3)C(O)N(R^{3a}R^{3b})$, $—OC(O)N(R^3R^{3a})$, and $C_{1-6}$ alkyl; wherein $C_{1-6}$ alkyl is optionally substituted with one or more halogen, which are the same or different; and $—R^3$, $—R^{3a}$ and $—R^{3b}$ are independently selected from —H, methyl, ethyl, propyl and butyl.

Even more preferably $—S^g—$ of formula (g) is selected from $C_{1-6}$ alkyl.

Preferably, $—S^{g'}—$ of formula (g) is selected from the group consisting of $C_{1-6}$ alkyl, $C_{2-6}$ alkenyl and $C_{2-6}$ alkynyl, which are optionally substituted with one or more $—R^1$, which is the same or different, wherein —$R^1$ is selected from the group consisting of halogen, oxo (=O), —$COOR^3$, —$OR^3$, —$C(O)R^3$, —$C(O)N(R^3R^{3a})$, —$S(O)_2N(R^3R^{3a})$, —$S(O)N(R^3R^{3a})$, —$S(O)_2R^3$, —$S(O)R^3$, —$N(R^3)S(O)_2N(R^{3a}R^{3b})$, —$SR^3$, —$N(R^3R^{3a})$, —$NO_2$, —$OC(O)R^3$, —$N(R^3)C(O)R^{3a}$, —$N(R^3)S(O)_2R^{3a}$, —$N(R^3)S(O)R^{3a}$, —$N(R^3)C(O)OR^3$a —$N(R^3)C(O)N(R^{3a}R^{3b})$, —$OC(O)N(R^3R^{3a})$, and $C_{1-6}$ alkyl; wherein $C_{1-6}$ alkyl is optionally substituted with one or more halogen, which are the same or different; and —$R^3$, —$R^{3a}$ and —$R^{3b}$ are independently selected from —H, methyl, ethyl, propyl and butyl.

Even more preferably —$S^{g'}$— of formula (g) is selected from $C_{1-6}$ alkyl.

Preferably, —$S^{g''}$— of formula (g) is selected from the group consisting of $C_{1-6}$ alkyl, $C_{2-6}$ alkenyl and $C_{2-6}$ alkynyl, which are optionally substituted with one or more —$R^1$, which is the same or different, wherein —$R^1$ is selected from the group consisting of halogen, oxo (=O), —$COOR^3$, —$OR^3$, —$C(O)R^3$, —$C(O)N(R^3R^{3a})$, —$S(O)_2N(R^3R^{3a})$, —$S(O)N(R^3R^{3a})$, —$S(O)_2R^3$, —$S(O)R^3$, —$N(R^3)S(O)_2N(R^{3a}R^{3b})$, —$SR^3$, —$N(R^3R^{3a})$, —$NO_2$, —$OC(O)R^3$, —$N(R^3)C(O)R^{3a}$, —$N(R^3)S(O)_2R^{3a}$, —$N(R^3)S(O)R^{3a}$, —$N(R^3)C(O)OR^{3a}$, —$N(R^3)C(O)N(R^{3a}R^{3b})$, —$OC(O)N(R^3R^{3a})$, and $C_{1-6}$ alkyl; wherein $C_{1-6}$ alkyl is optionally substituted with one or more halogen, which are the same or different; and —$R^3$, —$R^{3a}$ and —$R^{3b}$ are independently selected from —H, methyl, ethyl, propyl and butyl.

Even more preferably —$S^{g''}$— of formula (g) is selected from $C_{1-6}$ alkyl.

Preferably, —$Z^a$ and —$Z^{a'}$ of formula (g) have the same structure. Preferably, —$Z^a$ and —$Z^{a'}$ of formula (g) are of formula (b).

In an alternative even more preferred embodiment —Z of formula (Ia) or (Ib) is of formula (g-i)

(g-i)

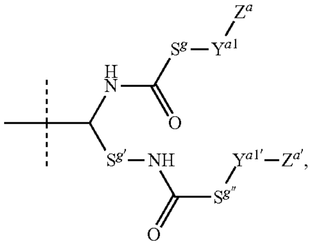

wherein the dashed line indicates attachment to -$L^2$-;

—$S^g$—, —$S^{g'}$— and —$S^{g''}$— are independently selected from the group consisting of $C_{1-50}$ alkyl, $C_{2-50}$ alkenyl, and $C_{2-50}$ alkynyl; wherein $C_{1-50}$ alkyl, $C_{2-50}$ alkenyl, and $C_{2-50}$ alkynyl are optionally substituted with one or more —$R^1$, which are the same or different and wherein $C_{1-50}$ alkyl, $C_{2-50}$ alkenyl, and $C_{2-50}$ alkynyl are optionally interrupted by one or more groups selected from the group consisting of -T-, —C(O)O—, —O—, —C(O)—, —$C(O)N(R^2)$—, —$S(O)_2N(R^2)$—, —$S(O)N(R^2)$—, —$S(O)_2$—, —S(O)—, —$N(R^2)S(O)_2N(R^{2a})$—, —S—, —$N(R^2)$—, —$OC(OR^2)(R^{2a})$—, —$N(R^2)C(O)N(R^{2a})$—, and —$OC(O)N(R^2)$—;

each -T- is independently selected from the group consisting of phenyl, naphthyl, indenyl, indanyl, tetralinyl, $C_{3-10}$ cycloalkyl, 3- to 10-membered heterocyclyl, 8- to 11-membered heterobicyclyl, 8- to 30-membered carbopolycyclyl, and 8- to 30-membered heteropolycyclyl; wherein each -T- is independently optionally substituted with one or more —$R^1$, which are the same or different;

each $R^1$ is independently selected from the group consisting of halogen, —CN, oxo (=O), —$COOR^3$, —$OR^3$, —$C(O)R^3$, —$C(O)N(R^3R^{3a})$, —$S(O)_2N(R^3R^{3a})$, —$S(O)N(R^3R^{3a})$, —$S(O)_2R^3$, —$S(O)R^3$, —$N(R^3)S(O)_2N(R^{3a}R^{3b})$, —$SR^3$, —$N(R^3R^{3a})$, —$NO_2$, —$OC(O)R^3$, —$N(R^3)C(O)R^{3a}$, —$N(R^3)S(O)_2R^{3a}$, —$N(R^3)S(O)R^{3a}$, —$N(R^3)C(O)OR^{3a}$, —$N(R^3)C(O)N(R^{3a}R^{3b})$, —$OC(O)N(R^3R^{3a})$, and $C_{1-6}$ alkyl; wherein $C_{1-6}$ alkyl is optionally substituted with one or more halogen, which are the same or different;

each —$R^2$, —$R^{2a}$, —$R^3$, —$R^{3a}$ and —$R^{3b}$ is independently selected from the group consisting of —H, and $C_{1-6}$ alkyl, wherein $C_{1-6}$ alkyl is optionally substituted with one or more halogen, which are the same or different;

—$Y^{a1}$— and —$Y^{a1'}$— are

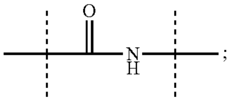

and

—$Z^a$ and —$Z^{a'}$ are independently

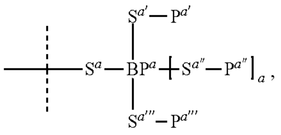

wherein $BP^a$, —$S^a$, —$S^{a'}$—, —$S^{a''}$—, —$S^{a'''}$—, —$P^{a'}$, —$P^{a''}$, —$P^{a'''}$ and a are used as defined for formula (a).

Optionally, the moiety of formula (g-i) is substituted with one or more substituents Preferably, —$Y^{a1}$— and —$Y^{a1'}$— of formula (g-i) are both

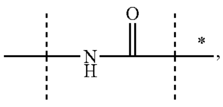

wherein the dashed line marked with the asterisk is attached to —$Z^a$ and —$Z^{a'}$, respectively.

Preferred embodiments of $BP^a$, —$S^a$—, —$S^{a'}$—, —$S^{a''}$, —$S^{a'''}$—, —$P^{a'}$, —$P^{a''}$, and —$P^{a'''}$ of formula (g-i) are as defined above for formula (a).

Preferred embodiments of —$S^g$—, —$S^{g'}$— and —$S^{g''}$— of formula (g-i) are as defined for formula (g).

Preferably, —$Z^a$ and —$Z^{a'}$ of formula (g-i) have the same structure. Preferably, —$Z^a$ and —$Z^{a'}$ of formula (g-i) are of formula (b).

Even more preferably —Z is of formula (h)

(h)

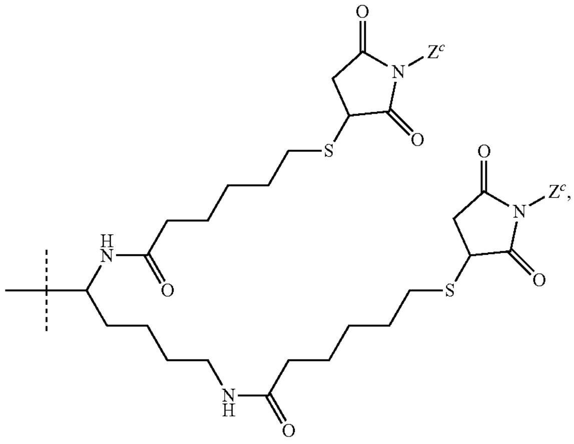

wherein the dashed line indicates attachment to $-L^2-$; and each $—Z^c$ is a moiety

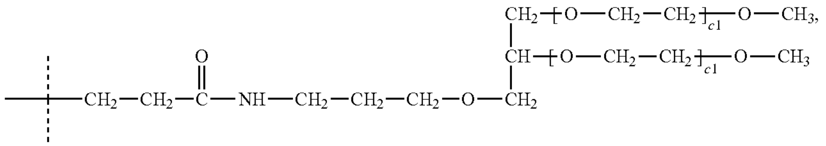

wherein each c1 is an integer independently ranging from about 200 to 250.

Optionally, the moiety of formula (h) is substituted with one or more substituents.

Preferably both c1 of formula (h) are the same.

Preferably both c1 of formula (h) are about 225.

Even more preferably —Z of formula (Ia) or (Ib) is of formula (h-a)

(h-a)

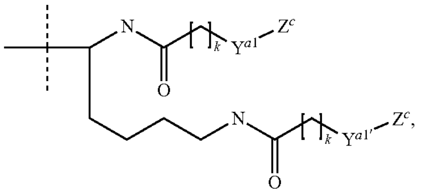

wherein the dashed line indicates attachment to $-L^2-$;

each k is independently of each other selected from the group consisting of 1, 2, 3, 4, 5, 6, 7, 8, 9, 10, 11 and 12;

$—Y^{a1}—$ and $—Y^{a1'}—$ are

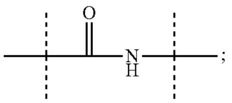

and each $—Z^c$ is a moiety

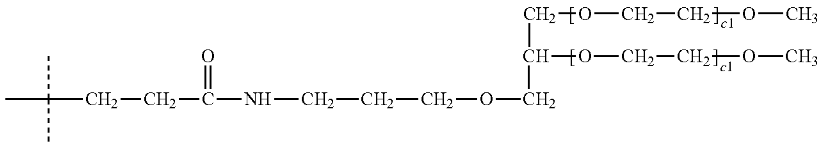

wherein each c1 is an integer independently ranging from about 200 to 250.

Optionally, the moiety of formula (h-a) is substituted with one or more substituents.

Preferably, each k of formula (h-a) is independently selected from the group consisting of 2, 3, 4, 5, 6 and 7. Preferably, both k of formula (h-a) are identical.

Preferably both c1 of formula (h-a) are the same.

Preferably both c1 of formula (h-a) are about 225.

Preferably, $—Y^{a1}—$ and $—Y^{a1'}—$ of formula (h-a) are both

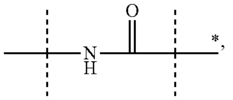

wherein the dashed line marked with the asterisk is attached to $—Z^{a}$ and $—Z^{a'}$, respectively.

In an even more preferred embodiment the moiety —Z is of formula (h-i)

(h-i)

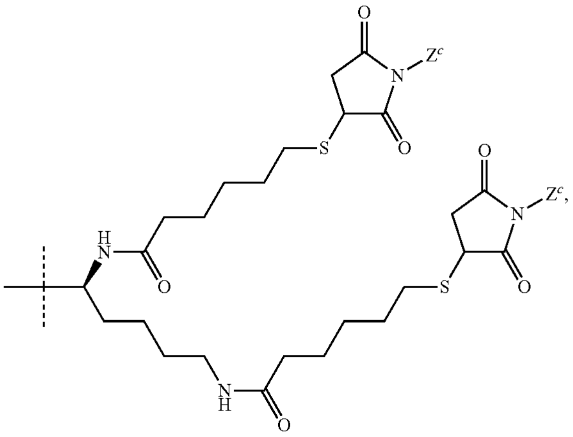

wherein the dashed line indicates attachment to $-L^2-$; and each $—Z^c$ is a moiety

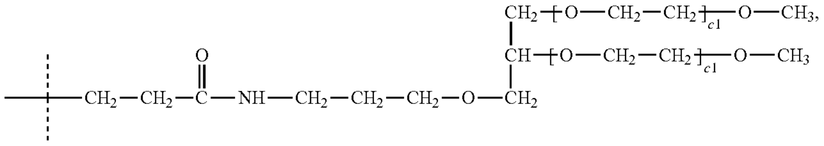

each c1 is an integer independently ranging from 200 to 250.

Optionally, the moiety of formula (h-i) is substituted with one or more substituents.

Preferably both c1 of formula (h-i) are the same.

Preferably both c1 of formula (h-i) are about 225.

In an alternative even more preferred embodiment the moiety —Z of formula (Ia) or (Ib) is of formula (h-ia)

(h-ia)

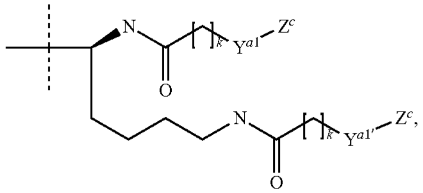

wherein the dashed line indicates attachment to $-L^2-$;

$—Y^{a1}—$ and $—Y^{a1'}—$ are

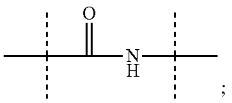

and each —$Z^c$ is a moiety

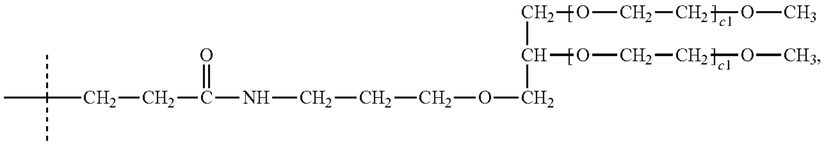

each c1 is an integer independently ranging from 200 to 250.

Preferably, each k of formula (h-ia) is independently selected from the group consisting of 2, 3, 4, 5, 6 and 7. Preferably, both k of formula (h-ia) are identical.

Preferably both c1 of formula (h-ia) are the same.

Preferably both c1 of formula (h-ia) are about 225.

Preferably, —$Y^{a1}$— and —$Y^{a1}$— of formula (h-ia) are both

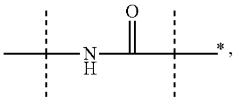

wherein the dashed line marked with the asterisk is attached to —$Z^a$ and —$Z^{a'}$, respectively.

In an equally preferred the embodiment —Z of formula (Ia) or (Ib) comprises a moiety selected from the group consisting of (j-i)

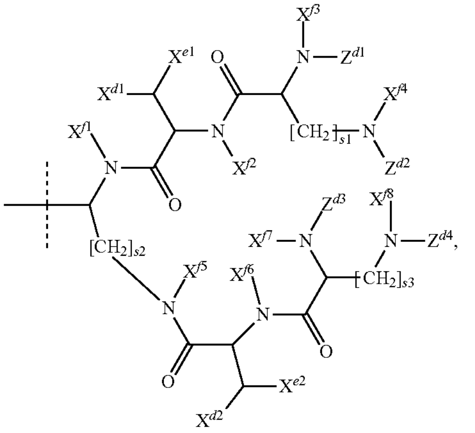

(j-ii)

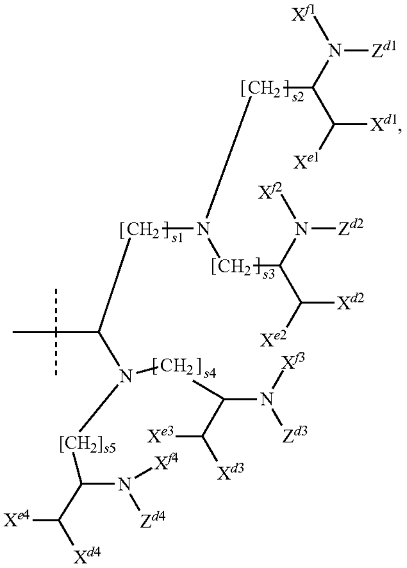

-continued
(j-iii)
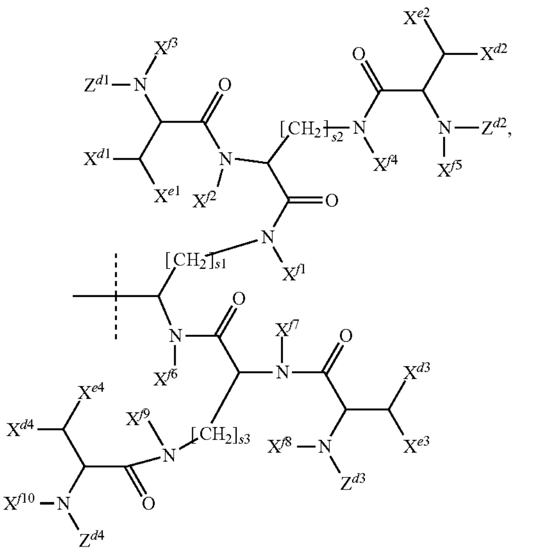
(j-iv)
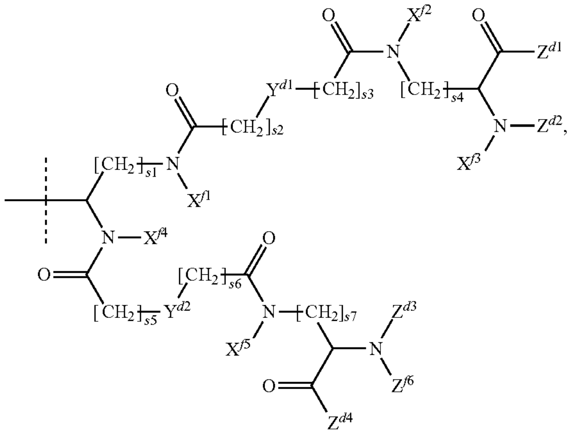
(j-v)
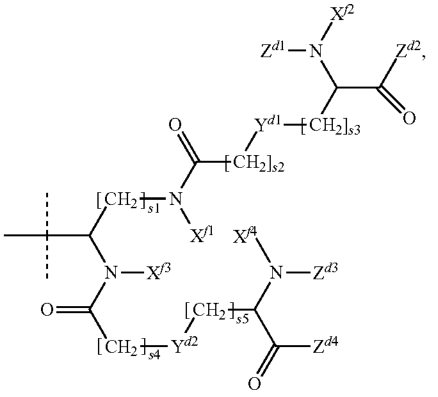
(j-vi)
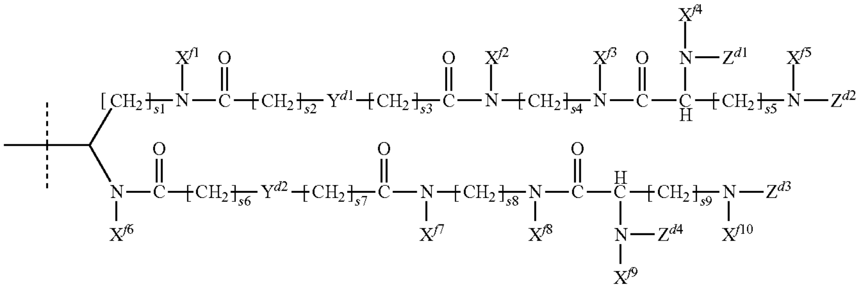
(j-vii)
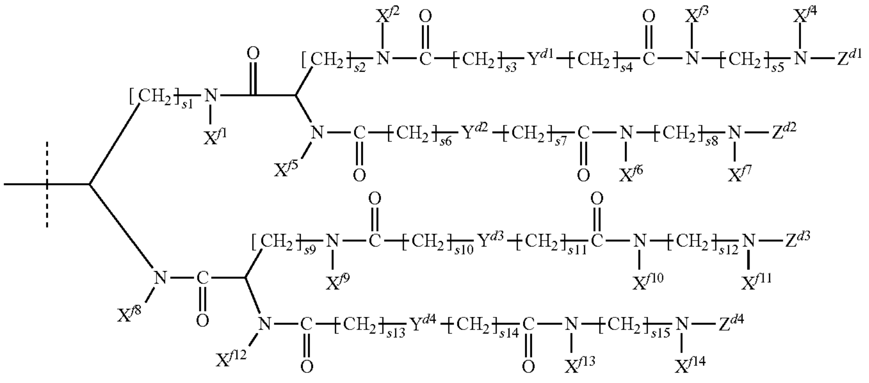

wherein the dashed line indicates attachment to $-L^2-$;

s1, s2, s3, s4, s5, s6, s7, s8, s9, s10, s11, s12, s13, s14 and s15 are independently of each other selected from 1, 2, 3, 4, 5, 6, 7, 8, 9, 10;

$X^{d1}$, $—X^{d2}$, $—X^{d3}$ and $—X^{d4}$ are independently of each other selected from the group consisting of —OH, —SH and $—NR^{g1}R^{g2}$; preferably —OH;

$—X^{e1}$, $—X^{e2}$, $—X^{e3}$ and $—X^{e4}$ are independently of each other selected from the group consisting of —H, $C_{1-6}$ alkyl, $C_{2-6}$ alkenyl and $C_{2-6}$ alkynyl;

$—R^{g1}$ and $—R^{g2}$ are independently of each other selected from the group consisting of —H, $C_{1-6}$ alkyl, $C_{2-6}$ alkenyl and $C_{2-6}$ alkynyl;

$—X^{f1}$, $—X^{f2}$, $—X^{f3}$, $—X^{f4}$, $—X^{f5}$, $—X^{f6}$, $—X^{f7}$, $—X_{f8}$, $—X^{f9}$, $—X^{f10}$, $—X^{f11}$, $—X^{f12}$, $—X^{f13}$ and $—X^{f14}$ are independently of each other selected from the group consisting of —H, $C_{1-6}$ alkyl, $C_{2-6}$ alkenyl and $C_{2-6}$ alkynyl; preferably —H;

$—Y^{d1}$, $—Y^{d2}—$, $—Y^{d3}—$ and $—Y^{d4}—$ are independently of each other selected from the group consisting of

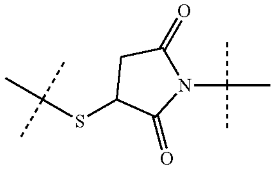 and

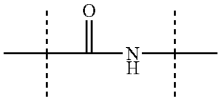;

$—Z^{d1}$, $—Z^{d2}$, $—Z^{d3}$ and $—Z^{d4}$ are independently of each other a protein, more preferably a random coil protein and most preferably a random coil protein selected from the group consisting of PA, PAS, PAG, PG and XTEN.

In one preferred embodiment, $—Y^{d1}—$ and $—Y^{d2}—$ of formula (j-iv), (j-v) and (j-vi) and $—Y^{d1}—$, $—Y^{d2}—$, $—Y^{d3}—$ and $—Y^{d4}—$ of formula (j-vii) are

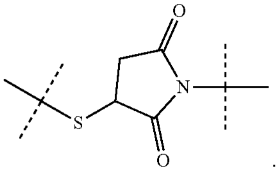.

In another preferred embodiment, $—Y^{d1}—$ and $—Y^{d2}—$ of formula (j-iv), (j-v) and (j-vi) and $—Y^{d1}—$, $—Y^{d2}—$, $—Y^{d3}—$ and $—Y^{d4}—$ of formula (j-vii) are

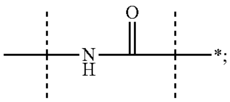*;

wherein the dashed line marked with the asterisk is oriented towards $—Z^{d1}$, $—Z^{d2}$, $—Z^{d3}$ and $—Z^{d4}$, respectively, and the unmarked dashed line is oriented towards $-L^2-$.

Preferably, $—X^{f1}$, $—X^{f2}$, $—X^{f3}$, $—X^{f4}$, $—X^{f5}$, $—X^{f6}$, $—X^{f7}$ and $—X^{f8}$ of formula (j-i) are —H; $—X^{d1}$ and $—X^{d2}$ of formula (j-i) are —OH; $—X^{e1}$ and $—X^{e2}$ of formula (j-i) are selected from the group consisting of —H and methyl; and s1, s2, s3 and s4 of formula (j-i) are selected from the group consisting of 2, 3, 4, 5 and 6. Even more preferably $—X^{f1}$, $—X^{f2}$, $—X^{f3}$, $—X^{f4}$, $—X^{f5}$, $—X^{f6}$, $—X^{f7}$ and $—X^{f8}$ of formula (j-i) are —H; $—X^{d1}$ and $—X^{d2}$ of formula (j-i) are —OH; $—X^{e1}$ and $—X^{e2}$ of formula (j-i) are —H; and s1, s2, s3 and s4 of formula (j-i) are 4.

Preferably, $—X^{f1}$, $—X^{f2}$, $—X^{f3}$ and $—X^{f4}$ of formula (j-ii) are —H; $—X^{d1}$, $—X^{d2}$, $—X^{d3}$ and $—X^{d2}$ of formula (j-ii) are —OH; $—X^{e1}$, $—X^{e2}$, $—X^{e3}$ and $—X^{e4}$ of formula (j-ii) are selected from the group consisting of —H and methyl; s1, s2, s3, s4 and s5 of formula (j-i) are selected from the group consisting of 1, 2, 3, 4, 5 and 6. Even more preferably $—X^{f1}$, $—X^{f2}$, $—X^{f3}$ and $—X^{f4}$ of formula (j-ii) are —H; $—X^{d1}$, $—X^{d2}$, $—X^{d3}$ and $—X^{d2}$ of formula (j-ii) are —OH; $—X^{e1}$, $—X^{e2}$, $—X^{e3}$ and $—X^{e4}$ of formula (j-ii) are —H; s1 is 4 of formula (j-ii) and s2, s3, s4 and s5 of formula (j-ii) are 1.

Preferably, $—X^{f1}$, $—X^{f2}$, $—X_{f3}$, $—X^{f4}$, $—X^{f5}$, $—X^{f6}$, $—X^{f7}$, $—X^{f8}$, $—X^{f9}$ and $—X^{f10}$ of formula (j-iii) are —H; $—X^{d1}$, $—X^{d2}$, $—X^{d3}$ and $—X^{d4}$ of formula (j-iii) are —OH; $—X^{e1}$, $—X^{e2}$, $—X^{e3}$ and $—X^{e4}$ of formula (j-iii) are selected from the group consisting of —H and methyl; and s1, s2 and s3 of formula (j-iii) are selected from the group consisting of 2, 3, 4, 5 and 6. Even more preferably $—X^{f1}$, $—X^{f2}$, $—X^{f3}$, $—X^{f4}$, $—X^{f5}$, $—X^{f6}$, $—X^{f7}$, $—X^{f8}$, $—X^{f9}$ and $—X^{f10}$ of formula (j-iii) are —H; $—X^{d1}$, $—X^{d2}$, $—X^{d3}$ and $—X^{d4}$ of formula (j-iii) are —OH; $—X^{e1}$, $—X^{e2}$, $—X^{e3}$ and $—X^{e4}$ of formula (j-iii) are —H; and s1, s2 and s3 of formula (j-iii) are 4.

Preferably, $—X^{f1}$, $—X^{f2}$, $—X^{f3}$, $—X^{f4}$, $—X^{f5}$ and $—X^{f6}$ of formula (j-iv) are —H; s1, s2, s3, s4, s5, s6 and s7 of formula (j-iv) are selected from the group consisting of 1, 2, 3, 4, 5, 6 and 7; $—Y^{d1}—$ and $—Y^{d2}—$ are selected from the group consisting of

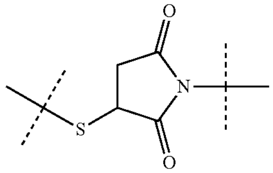 and 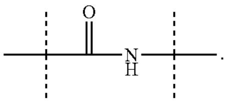.

In an even more preferred embodiment $—X^{f1}$, $—X^{f2}$, $—X^{f3}$, $—X^{f4}$, $—X^{f5}$ and $—X^{f6}$ of formula (j-iv) are —H; s1 of formula (j-iv) is 3, s2 of formula (j-iv) is 5, s3 of formula (j-iv) is 2, s4 of formula (j-iv) is 4, s5 of formula (j-iv) is 5, s6 of formula (j-iv) is 2 and s7 of formula (j-iv) is 4; and $—Y^{d1}—$ and $—Y^{d2}—$ of formula (j-iv) are

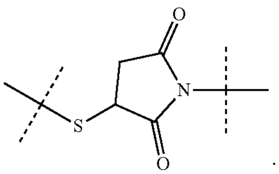.

In an equally preferred embodiment $—X^{f1}$, $—X^{f2}$, $—X^{f3}$, $—X^{f4}$, $—X^{f5}$ and $—X^{f6}$ of formula (j-iv) are —H; s1 of formula (j-iv) is 3, s2 of formula (j-iv) is 5, s3 of formula (j-iv) is 2, s4 of formula (j-iv) is 4, s5 of formula (j-iv) is 5, s6 of formula (j-iv) is 2 and s7 of formula (j-iv) is 4; and —$Y^{d1}$— and —$Y^{d2}$— of formula (j-iv) are

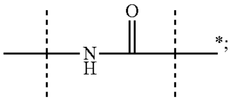

wherein the dashed line marked with the asterisk is oriented towards —$Z^{d1}$, —$Z^{d2}$, —$Z^{d3}$ and —$Z^{d4}$, respectively, and the unmarked dashed line is oriented towards -$L^2$-.

Preferably, —$X^{f1}$, —$X^{f2}$, —$X^{f3}$ and —$X^{f4}$ of formula (j-v) are —H; s1, s2, s3, s4 and s5 of formula (j-v) are selected from the group consisting of 1, 2, 3, 4, 5, 6 and 7; —$Y^{d1}$— and —$Y^{d2}$— of formula (j-v) are selected from the group consisting of

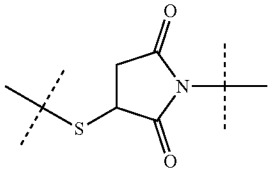
and
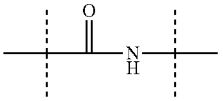
.

In an even more preferred embodiment —$X^{f1}$, —$X^{f2}$, —$X^{f3}$ and —$X^{f4}$ of formula (j-v) are —H; s1 of formula (j-v) is 3, s2 of formula (j-v) is 2, s3 of formula (j-v) is 1, s4 of formula (j-v) is 2 and s5 of formula (j-v) is 1; and —$Y^{d1}$— and —$Y^{d2}$— of formula (j-v) are

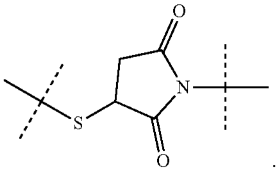
.

In an equally preferred embodiment —$X^{f1}$, —$X^{f2}$, —$X^{f3}$ and —$X^{f4}$ of formula (j-v) are —H; s1 of formula (j-v) is 3, s2 of formula (j-v) is 2, s3 of formula (j-v) is 1, s4 of formula (j-v) is 2 and s5 of formula (j-v) is 1; and —$Y^{d1}$— and —$Y^{d2}$— of formula (j-v) are

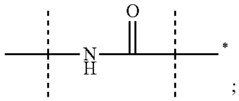
;

wherein the dashed line marked with the asterisk is oriented towards —$Z^{d1}$, —$Z^{d2}$, —$Z^{d3}$ and —$Z^{d4}$, respectively, and the unmarked dashed line is oriented towards -$L^2$-.

Preferably, —$X^{f1}$, —$X^{f2}$, —$X^{f3}$, —$X^{f4}$, —$X^{f5}$, —$X^{f6}$, —$X^{f7}$, —$X^{f8}$, —$X^{f9}$ and —$X^{f10}$ of formula (j-vi) are —H; s1, s2, s3, s4, s5, s6, s7, s8 and s9 of formula (j-vi) are selected from the group consisting of 1, 2, 3, 4, 5, 6 and 7; —$Y^{d1}$— and —$Y^{d2}$— of formula (j-vi) are selected from the group consisting of

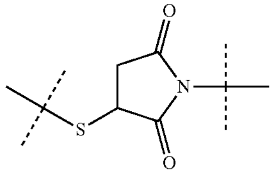
and
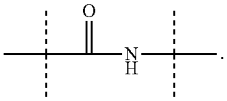
.

In an even more preferred embodiment —$X^{f1}$, —$X^{f2}$, —$X^{f3}$, —$X^{f4}$, —$X^{f5}$, —$X^{f6}$, —$X^{f7}$, —$X^{f8}$, —$X^{f9}$ and —$X^{f10}$ of formula (j-vi) are —H; s1 of formula (j-vi) is 4, s2 of formula (j-vi) is 5, s3 of formula (j-vi) is 2, s4 of formula (j-vi) is 4, s5 of formula (j-vi) is 4, s6 of formula (j-vi) is 5, s7 of formula (j-vi) is 2, s8 of formula (j-vi) is 4 and s9 of formula (j-vi) is 4; and —$Y^{d1}$— and —$Y^{d2}$— of formula (j-v) are

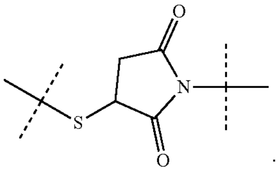
.

In an equally preferred embodiment —$X^{f1}$, —$X^{f2}$, —$X^{f3}$, —$X^{f4}$, —$X^{f5}$, —$X^{f6}$, —$X^{f7}$, —$X^{f8}$, —$X^{f9}$ and —$X^{f10}$ of formula (j-vi) are —H; s1 of formula (j-vi) is 4, s2 of formula (j-vi) is 5, s3 of formula (j-vi) is 2, s4 of formula (j-vi) is 4, s5 of formula (j-vi) is 4, s6 of formula (j-vi) is 5, s7 of formula (j-vi) is 2, s8 of formula (j-vi) is 4 and s9 of formula (j-vi) is 4; and —$Y^{d1}$— and —$Y^{d2}$— of formula (j-v) are

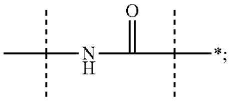

wherein the dashed line marked with the asterisk is oriented towards —$Z^{d1}$, —$Z^{d2}$, —$Z^{d3}$ and —$Z^{d4}$, respectively, and the unmarked dashed line is oriented towards -$L^2$-.

Preferably, —$X^{f1}$, —$X^{f2}$, —$X^{f3}$, —$X^{f4}$, —$X^{f5}$, —$X^{f6}$, —$X^{f7}$, —$X^{f8}$, —$X^{f9}$, —$X^{f10}$, —$X^{f11}$, —$X^{f12}$, —$X^{f13}$ and —$X^{f14}$ of formula (j-vii) are —H; s1, s2, s3, s4, s5, s6, s7, s8, s9, s10, s11, s12, s13, s14 and s15 of formula (j-vii) are selected from the group consisting of 1, 2, 3, 4, 5, 6 and 7; —$Y^{d1}$, —$Y^{d2}$—, —$Y^{d3}$— and —$Y^{d4}$— of formula (j-vii) are selected from the group consisting of

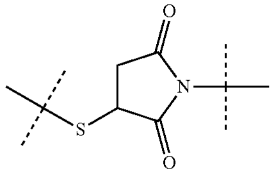
and
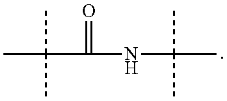
.

In an even more preferred embodiment —$X^{f1}$, —$X^{f2}$, —$X^{f3}$, —$X^{f4}$, —$X^{f5}$, —$X^{f6}$, —$X^{f7}$, —$X^{f8}$, —$X^{f9}$, —$X^{f10}$, —$X^{f11}$, —$X^{f12}$, —$X^{f13}$ and —$X^{f14}$ of formula (j-vii) are —H; are —H; s1 of formula (j-vii) is 4, s2 of formula (j-vii) is 4, s3 of formula (j-vii) is 5, s4 of formula (j-vii) is 2, s5 of formula (j-vii) is 4, s6 of formula (j-vii) is 5, s7 of formula (j-vii) is 2, s8 of formula (j-vii) is 4, s9 of formula (j-vii) is 4, s10 of formula (j-vii) is 5, s11 of formula (j-vii) is 2, s12 of formula (j-vii) is 4, s13 of formula (j-vii) is 5, s14 of formula (j-vii) is 2 and s15 of formula (j-vii) is 4; and $-Y^{d1}-$, $-Y^{d2}-$, $-Y^{d3}-$ and $-Y^{d4}-$ of formula (j-vii) are

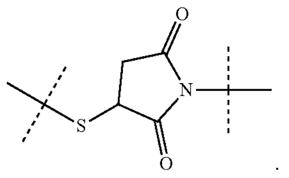

In an equally preferred embodiment $-X^{f1}$, $-X^{f2}$, $-X^{f3}$, $-X^{f4}$, $-X^{f5}$, $-X^{f6}$, $-X^{f7}$, $-X^{f8}$, $-X^{f9}$, $-X^{f10}$, $-X^{f11}$, $-X^{f12}$, $-X^{f13}$ and $-X^{f14}$ of formula (j-vii) are —H; are —H; s1 of formula (j-vii) is 4, s2 of formula (j-vii) is 4, s3 of formula (j-vii) is 5, s4 of formula (j-vii) is 2, s5 of formula (j-vii) is 4, s6 of formula (j-vii) is 5, s7 of formula (j-vii) is 2, s8 of formula (j-vii) is 4, s9 of formula (j-vii) is 4, s10 of formula (j-vii) is 5, s11 of formula (j-vii) is 2, s12 of formula (j-vii) is 4, s13 of formula (j-vii) is 5, s14 of formula (j-vii) is 2 and s15 of formula (j-vii) is 4; and $-Y^{d1}-$, $-Y^{d2}$, $-Y^{d3}-$ and $-Y^{d4}-$ of formula (j-vii) are

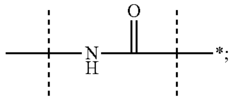

wherein the dashed line marked with the asterisk is oriented towards $-Z^{d1}$, $-Z^{d2}$, $-Z^{d3}$ and $-Z^{d4}$, respectively, and the unmarked dashed line is oriented towards $-L^2-$.

Preferably $-Z^{d1}$, $-Z^{d2}$, $-Z^{d3}$ and $-Z^{d4}$ of formula (j-i), (j-ii), (j-iii), (j-iv), (j-v), (j-vi) and (j-vii) have the same structure.

In one embodiment $-Z^{d1}$, $-Z^{d2}$, $-Z^{d3}$ and $-Z^{d4}$ of formula j-i), (j-ii), (j-iii), (j-iv), (j-v), (j-vi) and (j-vii) are a PA moiety.

In another embodiment $-Z^{d1}$, $-Z^{d2}$, $-Z^{d3}$ and $-Z^{d4}$ of formula (j-i), (j-ii), (j-iii), (j-iv), (j-v), (j-vi) and (j-vii) are a PAS moiety.

In another embodiment $-Z^{d1}$, $-Z^{d2}$, $-Z^{d3}$ and $-Z^{d4}$ of formula (j-i), (j-ii), (j-iii), (j-iv), (j-v), (j-vi) and (j-vii) are a PAG moiety.

In another embodiment $-Z^{d1}$, $-Z^{d2}$, $-Z^{d3}$ and $-Z^{d4}$ of formula (j-i), (j-ii), (j-iii), (j-iv), (j-v), (j-vi) and (j-vii) are a PG moiety.

In another embodiment $-Z^{d1}$, $-Z^{d2}$, $-Z^{d3}$ and $-Z^{d4}$ of formula (j-i), (j-ii), (j-iii), (j-iv), (j-v), (j-vi) and (j-vii) are a XTEN moiety.

In a preferred embodiment the CNP agonist prodrug of the present invention is of formula (IIe)

(IIe)

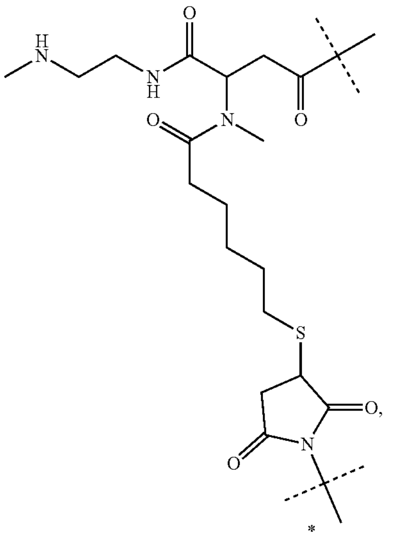

wherein the unmarked dashed line indicates the attachment to a nitrogen of -D which is a CNP agonist moiety by forming an amide bond; and the dashed line marked with the asterisk indicates attachment to a moiety

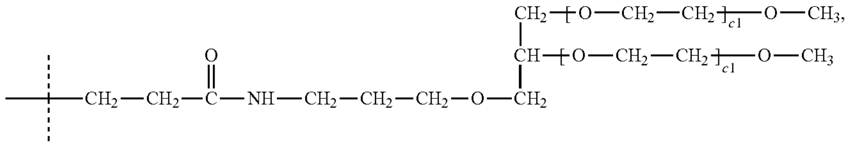

wherein each c1 is an integer independently ranging from 400 to 500.

Preferably, c1 of formula (IIe) is about 450.

In an equally preferred embodiment the CNP agonist prodrug of the present invention is of formula (IIe-i)

(IIe-i)

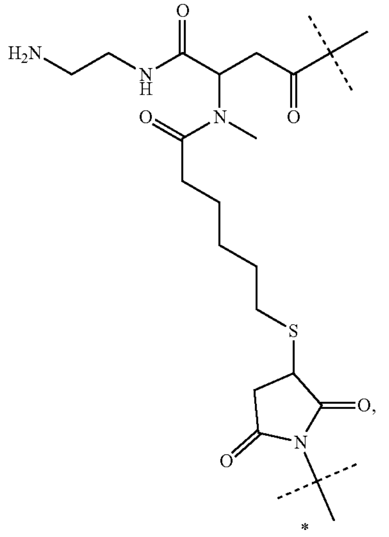

wherein the unmarked dashed line indicates the attachment to a nitrogen of -D which is a CNP agonist moiety by forming an amide bond; and the dashed line marked with the asterisk indicates attachment to a moiety

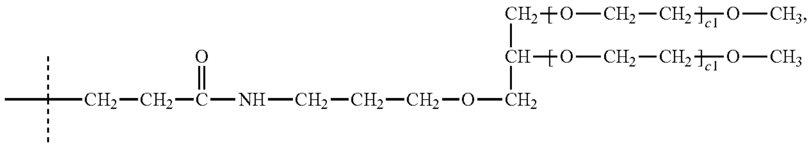

wherein each c1 is an integer independently ranging from 400 to 500.

Preferably, c1 of formula (IIe-i) is about 450.

In another equally preferred embodiment the CNP agonist prodrug of the present invention is of formula (IIe-ii)

(IIe-ii)

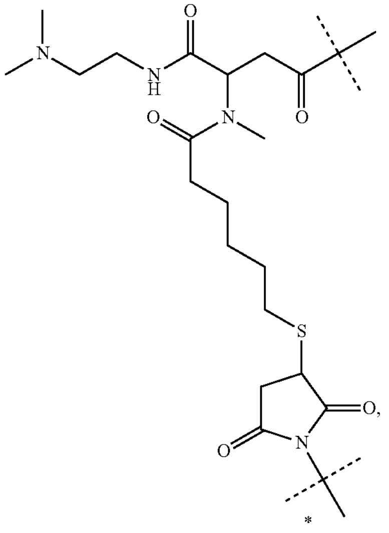

wherein the unmarked dashed line indicates the attachment to a nitrogen of -D which is a CNP agonist moiety by forming an amide bond; and the dashed line marked with the asterisk indicates attachment to a moiety

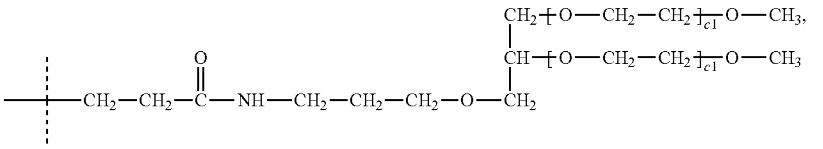

wherein each c1 is an integer independently ranging from 400 to 500.

Preferably, c1 of formula (IIe-ii) is about 450.

Preferably -D of formula (IIe), (IIe-i) and (IIe-ii) is a CNP moiety, i.e. the prodrug of formula (IIe), (IIe-i) and (IIe-ii) is a CNP prodrug. Even more preferably -D of formula (IIe), (IIe-i) and (IIe-ii) is a CNP moiety having the sequence of SEQ ID NO:24, SEQ ID NO:25 or SEQ ID NO:30. Most preferably -D of formula (IIe), (IIe-i) and (IIe-ii) is a CNP moiety CNP having the sequence of SEQ ID NO:24.

In one embodiment -D of formula (IIe), (IIe-i) and (IIe-ii) is a CNP moiety which is attached to $-L^1-$ through the nitrogen of the N-terminal amine functional group of CNP.

In a preferred embodiment -D of formula (IIe), (IIe-i) and (IIe-ii) is a CNP moiety which is attached to $-L^1-$ through a nitrogen provided by the amine functional group of a lysine side chain of the CNP moiety.

In one embodiment said lysine side chain is not part of the ring formed by the disulphide bridge between the cysteine residues at positions 22 and 38, if the CNP moiety is of SEQ ID NO:24.

Accordingly, in one embodiment the CNP moiety is connected to $-L^1-$ in the CNP prodrug of formula (IIe), (IIe-i) and (IIe-ii) through the amine functional group provided by the side chain of the lysine at position 9, if the CNP has the sequence of SEQ ID NO:24.

In another embodiment the CNP moiety is connected to $-L^1-$ in the CNP prodrug of formula (IIe), (IIe-i) and (IIe-ii) through the amine functional group provided by the side chain of the lysine at position 11, if the CNP has the sequence of SEQ ID NO:24.

In another embodiment the CNP moiety is connected to $-L^1-$ in the CNP prodrug of formula (IIe), (IIe-i) and (IIe-ii) through the amine functional group provided by the side chain of the lysine at position 15, if the CNP has the sequence of SEQ ID NO:24.

In another embodiment the CNP moiety is connected to $-L^1-$ in the CNP prodrug of formula (IIe), (IIe-i) and (IIe-ii) through the amine functional group provided by the side chain of the lysine at position 16, if the CNP has the sequence of SEQ ID NO:24.

In another embodiment the CNP moiety is connected to $-L^1-$ in the CNP prodrug of formula (IIe), (IIe-i) and (IIe-ii) through the amine functional group provided by the side chain of the lysine at position 20, if the CNP has the sequence of SEQ ID NO:24.

In a preferred embodiment said lysine side chain is part of the ring formed by the disulphide bridge between the cysteine residues at positions 22 and 38, if the CNP moiety is of SEQ ID NO:24.

Accordingly, in one embodiment the CNP moiety is connected to $-L^1-$ in the CNP prodrug of formula (IIe), (IIe-i) and (IIe-ii) through the amine functional group provided by the side chain of the lysine at position 26, if the CNP has the sequence of SEQ ID NO:24.

It is understood that the positions of the cysteines and lysines mentioned above vary depending on the lengths of the CNP moiety and that the person skilled in the art will have no difficulty identifying the corresponding cysteines and lysines in longer or shorter versions of the CNP moiety and also understands that for example some lysines may not be present in shorter CNP moieties. It is further understood that as a result of for example site-directed mutagenesis there might be more lysine residues in the non-ring forming part and/or ring forming part of the CNP moiety.

In a preferred embodiment the CNP prodrug of the present invention is of formula (IIe), wherein c1 is about 450, -D is a CNP moiety having the sequence of SEQ ID NO:24 and is attached to $-L^1-$ through the amine functional group provided by the side chain of the lysine at position 26.

In another preferred embodiment the CNP prodrug of the present invention is of formula (IIe-i), wherein c1 is about 450, the CNP moiety has the sequence of SEQ ID NO:24 and is attached to $-L^1-$ through the amine functional group provided by the side chain of the lysine at position 26.

In another preferred embodiment the CNP prodrug of the present invention is of formula (IIe-ii), wherein c1 is about 450, the CNP moiety has the sequence of SEQ ID NO:24 and is attached to $-L^1-$ through the amine functional group provided by the side chain of the lysine at position 26.

In another preferred embodiment the CNP agonist prodrug of the present invention is of formula (IIf)

(IIf)

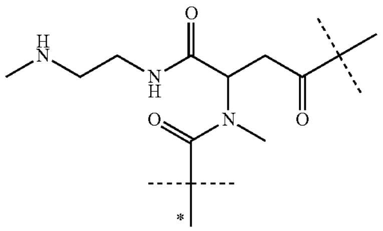

, wherein the unmarked dashed line indicates the attachment to a nitrogen of -D which is a CNP agonist moiety by forming an amide bond; and the dashed line marked with the asterisk indicates attachment to —Z having the structure

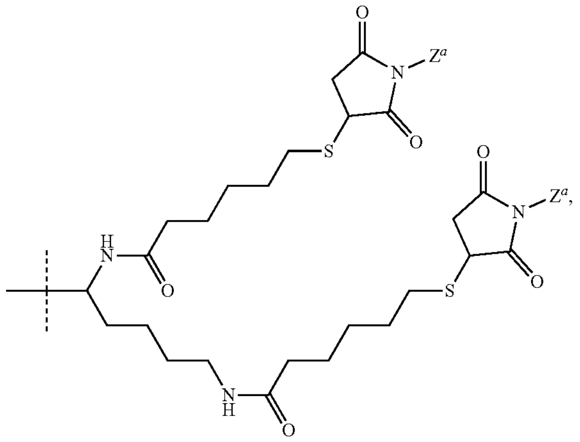

wherein
each —$Z^a$ is

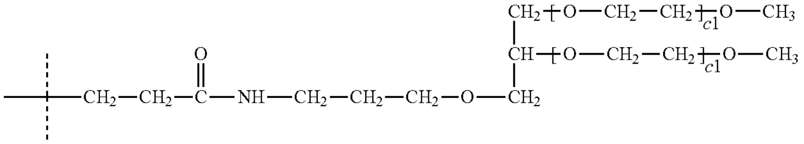

wherein
each c1 is an integer independently ranging from 200 to 250; preferably each n is about 225.

Preferably, each c1 of formula (IIf) is about 225.

In another preferred embodiment the CNP agonist prodrug of the present invention is of formula (IIf-i)

(IIf-i)

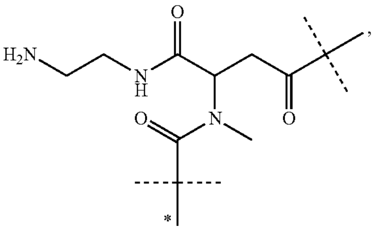

wherein
the unmarked dashed line indicates the attachment to a nitrogen of -D which is a CNP agonist moiety by forming an amide bond; and the dashed line marked with the asterisk indicates attachment to —Z having the structure

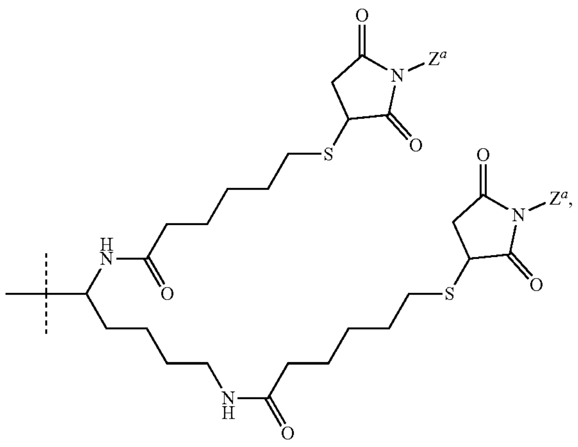

wherein
each —$Z^a$ is

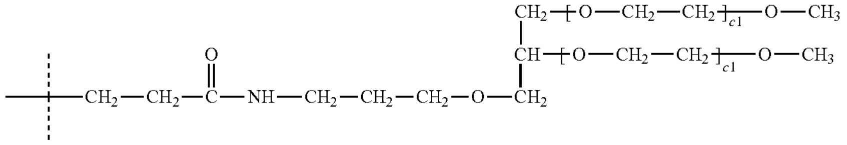

wherein each c1 is an integer independently ranging from 200 to 250; preferably each n is about 225.

Preferably, each c1 of formula (IIf-i) is about 225.

In another preferred embodiment the CNP agonist prodrug of the present invention is of formula (IIf-ii)

(IIf-ii)

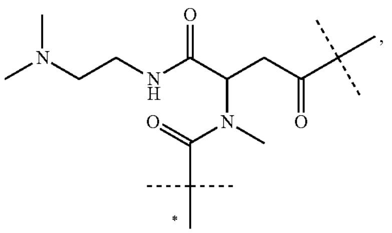

wherein the unmarked dashed line indicates the attachment to a nitrogen of -D which is a CNP agonist moiety by forming an amide bond; and the dashed line marked with the asterisk indicates attachment to —Z having the structure

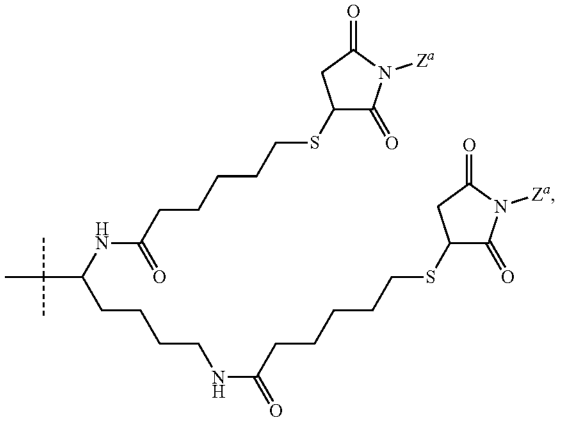

wherein each —$Z^a$ is

In one embodiment -D of formula (IIf), (IIf-i) and (IIf-ii) is a CNP moiety which is attached to -$L^1$- through the nitrogen of the N-terminal amine functional group of CNP.

In a preferred embodiment -D of formula (IIf), (IIf-i) and (IIf-ii) is a CNP moiety which is attached to -$L^1$- through a nitrogen provided by the amine functional group of a lysine side chain of the CNP moiety.

In one embodiment said lysine side chain is not part of the ring formed by the disulphide bridge between the cysteine residues at positions 22 and 38, if the CNP moiety is of SEQ ID NO:24.

Accordingly, in one embodiment the CNP moiety is connected to -$L^1$- in the CNP prodrug of formula (IIf), (IIf-i) and (IIf-ii) through the amine functional group provided by the side chain of the lysine at position 9, if the CNP has the sequence of SEQ ID NO:24.

In another embodiment the CNP moiety is connected to -$L^1$- in the CNP prodrug of formula (IIf), (IIf-i) and (IIf-ii) through the amine functional group provided by the side chain of the lysine at position 11, if the CNP has the sequence of SEQ ID NO:24.

In another embodiment the CNP moiety is connected to -$L^1$- in the CNP prodrug of formula (IIf), (IIf-i) and (IIf-ii) through the amine functional group provided by the side chain of the lysine at position 15, if the CNP has the sequence of SEQ ID NO:24.

In another embodiment the CNP moiety is connected to -$L^1$- in the CNP prodrug of formula (IIf), (IIf-i) and (IIf-ii) through the amine functional group provided by the side chain of the lysine at position 16, if the CNP has the sequence of SEQ ID NO:24.

In another embodiment the CNP moiety is connected to -$L^1$- in the CNP prodrug of formula (IIf), (IIf-i) and (IIf-ii) through the amine functional group provided by the side chain of the lysine at position 20, if the CNP has the sequence of SEQ ID NO:24.

In a preferred embodiment said lysine side chain is part of the ring formed by the disulphide bridge between the cysteine residues at positions 22 and 38, if the CNP moiety is of SEQ ID NO:24.

Accordingly, in one embodiment the CNP moiety is connected to -$L^1$- in the CNP prodrug of formula (IIf) through the amine functional group provided by the side chain of the lysine at position 26, if the CNP has the sequence of SEQ ID NO:24.

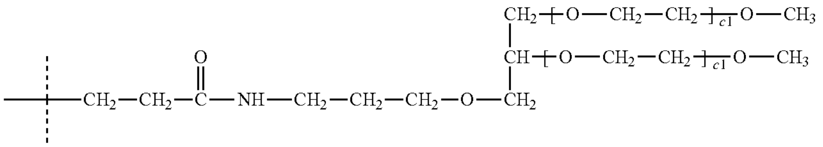

wherein each c1 is an integer independently ranging from 200 to 250; preferably each n is about 225.

Preferably, each c1 of formula (IIf-ii) is about 225.

Preferably -D of formula (IIf), (IIf-i) and (IIf-ii) is a CNP moiety, i.e. the prodrug of formula (IIf), (IIf-i) and (IIf-ii) is a CNP prodrug. Even more preferably -D of formula (IIf), (IIf-i) and (IIf-ii) is a CNP moiety having the sequence of SEQ ID NO:24, SEQ ID NO:25 or SEQ ID NO:30. Most preferably -D of formula (IIf), (IIf-i) and (IIf-ii) is a CNP moiety CNP having the sequence of SEQ ID NO:24.

In another preferred embodiment the CNP prodrug of the present invention is of formula (IIf-i), wherein c1 is about 225, the CNP moiety has the sequence of SEQ ID NO:24 and is attached to -$L^1$- through the amine functional group provided by the side chain of the lysine at position 26.

In another preferred embodiment the CNP prodrug of the present invention is of formula (IIf-ii), wherein c1 is about 225, the CNP moiety has the sequence of SEQ ID NO:24 and is attached to -$L^1$- through the amine functional group provided by the side chain of the lysine at position 26.

It is understood that the positions of the cysteines and lysines mentioned above vary depending on the lengths of the CNP moiety and that the person skilled in the art will have no difficulty identifying the corresponding cysteines and lysines in longer or shorter versions of the CNP moiety and also understands that for example some lysines may not be present in shorter CNP moieties. It is further understood that as a result of for example site-directed mutagenesis there might be more lysine residues in the non-ring forming part and/or ring forming part of the CNP moiety.

In a preferred embodiment the CNP prodrug of the present invention is of formula (IIf), wherein c1 is about 225, -D is a CNP moiety having the sequence of SEQ ID NO:24 and is attached to $-L^1-$ through the amine functional group provided by the side chain of the lysine at position 26.

In another preferred embodiment the CNP prodrug of the present invention is of formula (IIf')

(IIf')

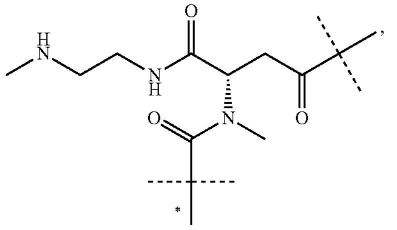

wherein the unmarked dashed line indicates the attachment to a nitrogen provided by the side chain of the lysine at position 26 of the CNP moiety of SEQ ID NO:24 by forming an amide bond; and the dashed line marked with the asterisk indicates attachment to —Z having the structure

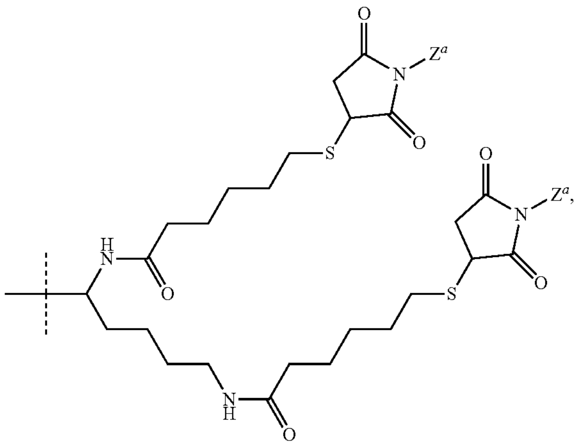

wherein each $Z^a$ is

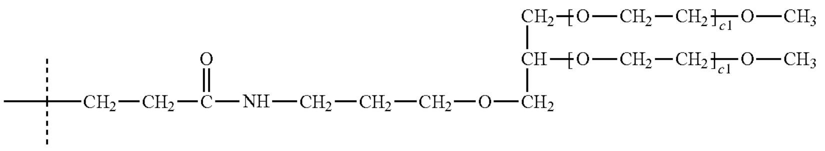

wherein each c1 is an integer independently ranging from 200 to 250.

Preferably, each c1 of formula (IIf') is about 225.

In another preferred embodiment the CNP prodrug of the present invention is of formula (IIf-i')

(IIf-i')

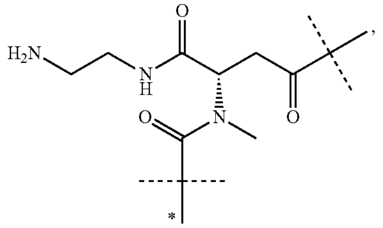

wherein the unmarked dashed line indicates the attachment to a nitrogen provided by the side chain of the lysine at position 26 of the CNP moiety of SEQ ID NO:24 by forming an amide bond; and the dashed line marked with the asterisk indicates attachment to —Z having the structure

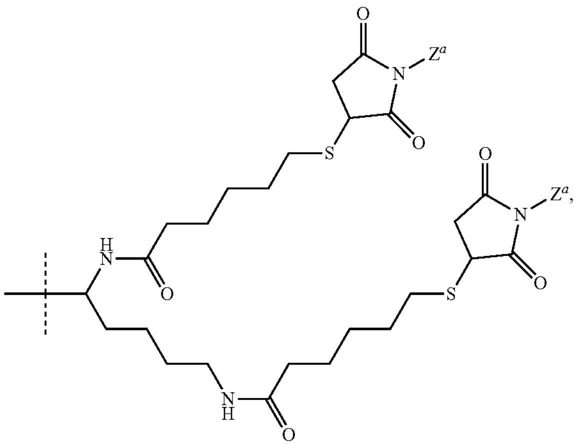

wherein
each $Z^a$ is

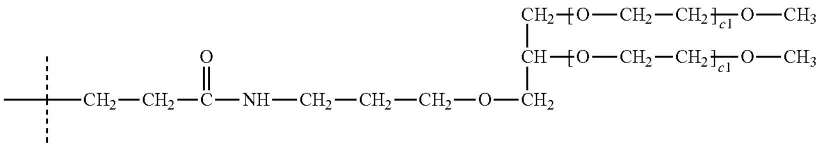

wherein
each c1 is an integer independently ranging from 200 to 250.

Preferably, each c1 of formula (IIf-i') is about 225.

In another preferred embodiment the CNP prodrug of the present invention is of formula (IIf-ii')

(IIf-ii')

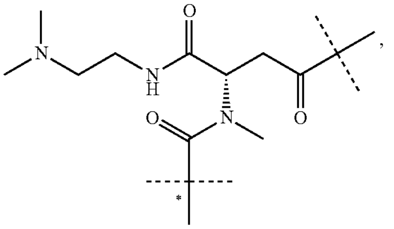

wherein
the unmarked dashed line indicates the attachment to a nitrogen provided by the side chain of the lysine at position 26 of the CNP moiety of SEQ ID NO:24 by forming an amide bond; and
the dashed line marked with the asterisk indicates attachment to —Z having the structure

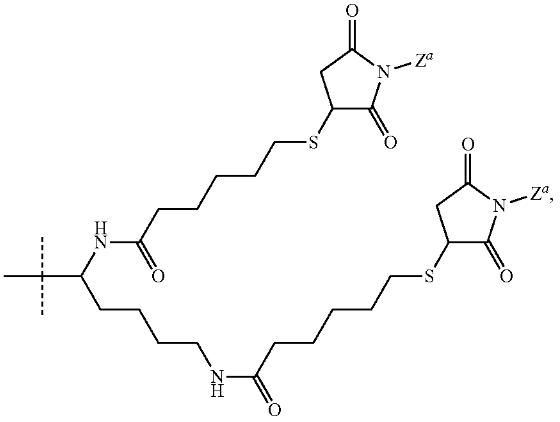

wherein
each $Z^a$ is

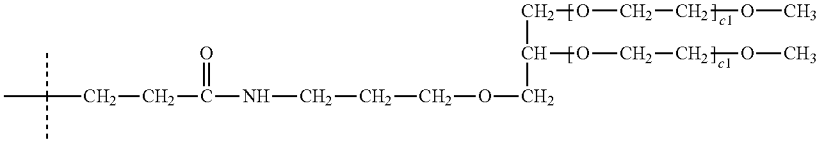

wherein
each c1 is an integer independently ranging from 200 to 250.

Preferably, each c1 of formula (IIf-ii') is about 225.

In an equally preferred embodiment the CNP agonist prodrug of the present invention is of formula (IIea)

(IIea)

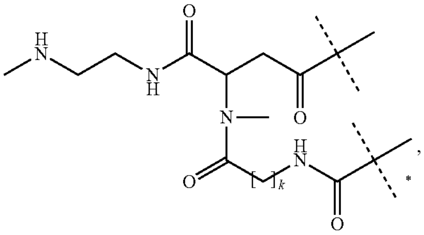

wherein the unmarked dashed line indicates the attachment to a nitrogen of -D which is a CNP agonist moiety by forming an amide bond;

k is selected from the group consisting of 1, 2, 3, 4, 5, 6, 7, 8, 9, 10, 11 and 12; and the dashed line marked with the asterisk indicates attachment to a moiety

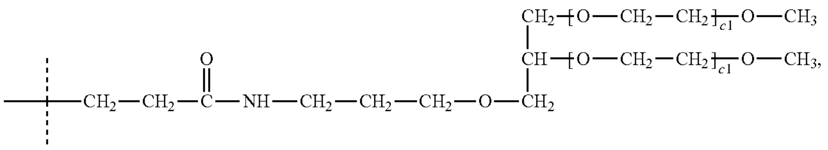

wherein each c1 is an integer independently ranging from 400 to 500.

Preferably, c1 of formula (IIea) is about 450.

Preferably, k of formula (IIea) is selected from the group consisting of 2, 3, 4, 5, 6 and 7.

In an equally preferred embodiment the CNP agonist prodrug of the present invention is of formula (IIea-i)

(IIea-i)

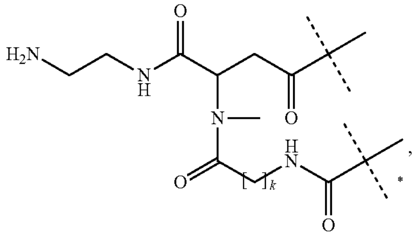

wherein the unmarked dashed line indicates the attachment to a nitrogen of -D which is a CNP agonist moiety by forming an amide bond;

k is selected from the group consisting of 1, 2, 3, 4, 5, 6, 7, 8, 9, 10, 11 and 12; and the dashed line marked with the asterisk indicates attachment to a moiety

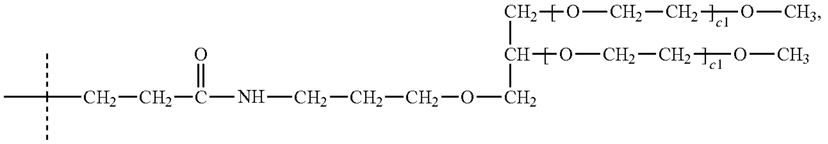

wherein each c1 is an integer independently ranging from 400 to 500.

Preferably, k of formula (IIea-i) is selected from the group consisting of 2, 3, 4, 5, 6 and 7.

Preferably, c1 of formula (IIea-i) is about 450.

In another equally preferred embodiment the CNP agonist prodrug of the present invention is of formula (IIea-ii)

(IIea-ii)

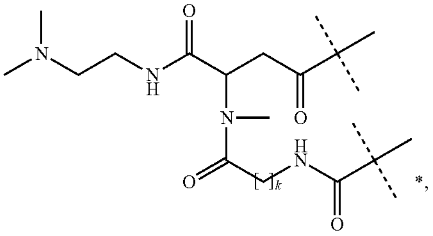

wherein the unmarked dashed line indicates the attachment to a nitrogen of -D which is a CNP agonist moiety by forming an amide bond;

k is selected from the group consisting of 1, 2, 3, 4, 5, 6, 7, 8, 9, 10, 11 and 12; and the dashed line marked with the asterisk indicates attachment to a moiety

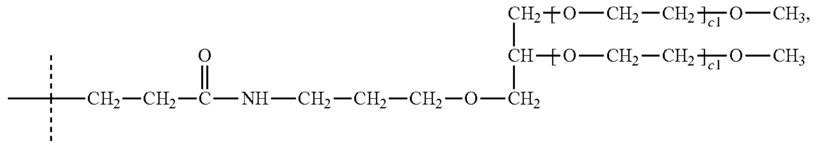

wherein each c1 is an integer independently ranging from 400 to 500.

Preferably, k of formula (IIea-ii) is selected from the group consisting of 2, 3, 4, 5, 6 and 7.

Preferably, c1 of formula (IIea-ii) is about 450.

Preferably -D of formula (IIea), (IIea-i) and (IIea-ii) is a CNP moiety, i.e. the prodrug of formula (IIea), (IIea-i) and (IIea-ii) is a CNP prodrug. Even more preferably -D of formula (IIea), (IIea-i) and (IIea-ii) is a CNP moiety having the sequence of SEQ ID NO:24, SEQ ID NO:25 or SEQ ID NO:30. Most preferably -D of formula (IIea), (IIea-i) and (IIea-ii) is a CNP moiety CNP having the sequence of SEQ ID NO:24.

In one embodiment -D of formula (IIea), (IIea-i) and (IIea-ii) is a CNP moiety which is attached to $-L^1-$ through the nitrogen of the N-terminal amine functional group of CNP.

In a preferred embodiment -D of formula (IIea), (IIea-i) and (IIea-ii) is a CNP moiety which is attached to $-L^1-$ through a nitrogen provided by the amine functional group of a lysine side chain of the CNP moiety.

In one embodiment said lysine side chain is not part of the ring formed by the disulphide bridge between the cysteine residues at positions 22 and 38, if the CNP moiety is of SEQ ID NO:24.

Accordingly, in one embodiment the CNP moiety is connected to $-L^1-$ in the CNP prodrug of formula (IIea), (IIea-i) and (IIea-ii) through the amine functional group provided by the side chain of the lysine at position 9, if the CNP has the sequence of SEQ ID NO:24.

In another embodiment the CNP moiety is connected to $-L^1-$ in the CNP prodrug of formula (IIea), (IIea-i) and (IIea-ii) through the amine functional group provided by the side chain of the lysine at position 11, if the CNP has the sequence of SEQ ID NO:24.

In another embodiment the CNP moiety is connected to $-L^1-$ in the CNP prodrug of formula (IIea), (IIea-i) and (IIea-ii) through the amine functional group provided by the side chain of the lysine at position 15, if the CNP has the sequence of SEQ ID NO:24.

In another embodiment the CNP moiety is connected to $-L^1-$ in the CNP prodrug of formula (IIea), (IIea-i) and (IIea-ii) through the amine functional group provided by the side chain of the lysine at position 16, if the CNP has the sequence of SEQ ID NO:24.

In another embodiment the CNP moiety is connected to $-L^1-$ in the CNP prodrug of formula (IIea), (IIea-i) and (IIea-ii) through the amine functional group provided by the side chain of the lysine at position 20, if the CNP has the sequence of SEQ ID NO:24.

In a preferred embodiment said lysine side chain is part of the ring formed by the disulphide bridge between the cysteine residues at positions 22 and 38, if the CNP moiety is of SEQ ID NO:24.

Accordingly, in one embodiment the CNP moiety is connected to $-L^1-$ in the CNP prodrug of formula (IIea), (IIea-i) and (IIea-ii) through the amine functional group provided by the side chain of the lysine at position 26, if the CNP has the sequence of SEQ ID NO:24.

It is understood that the positions of the cysteines and lysines mentioned above vary depending on the lengths of the CNP moiety and that the person skilled in the art will have no difficulty identifying the corresponding cysteines and lysines in longer or shorter versions of the CNP moiety and also understands that for example some lysines may not be present in shorter CNP moieties. It is further understood that as a result of for example site-directed mutagenesis there might be more lysine residues in the non-ring forming part and/or ring forming part of the CNP moiety.

In a preferred embodiment the CNP prodrug of the present invention is of formula (IIea), wherein c1 is about 450, -D is a CNP moiety having the sequence of SEQ ID NO:24 and is attached to $-L^1-$ through the amine functional group provided by the side chain of the lysine at position 26.

In another preferred embodiment the CNP prodrug of the present invention is of formula (IIea-i), wherein c1 is about 450, the CNP moiety has the sequence of SEQ ID NO:24 and is attached to $-L^1-$ through the amine functional group provided by the side chain of the lysine at position 26.

In another preferred embodiment the CNP prodrug of the present invention is of formula (IIea-ii), wherein c1 is about 450, the CNP moiety has the sequence of SEQ ID NO:24 and is attached to $-L^1-$ through the amine functional group provided by the side chain of the lysine at position 26.

Accordingly, in a preferred embodiment the CNP prodrug of the present invention is of formula (IIea')

(IIea')

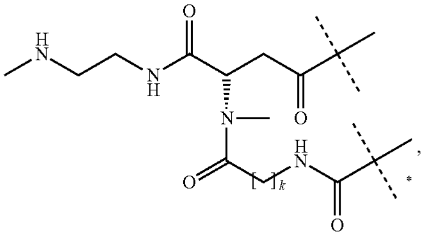

wherein the unmarked dashed line indicates the attachment to the nitrogen provided by the side chain of the lysine at position 26 of the CNP moiety of SEQ ID NO:24 by forming an amide bond;

k is selected from the group consisting of 1, 2, 3, 4, 5, 6, 7, 8, 9, 10, 11 and 12; and the dashed line marked with the asterisk indicates attachment to a moiety

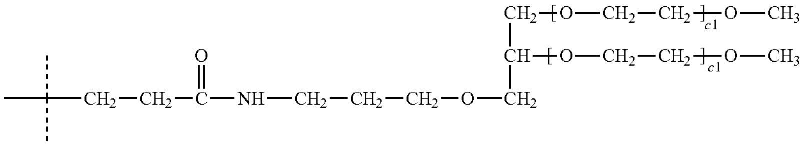

wherein each c1 is an integer independently ranging from 400 to 500.

Preferably, k of formula (IIea') is selected from the group consisting of 2, 3, 4, 5, 6 and 7.

Preferably, each c1 of formula (IIea') is about 450.

In another preferred embodiment the CNP prodrug of the present invention is of formula (IIea-i')

(IIea-i')

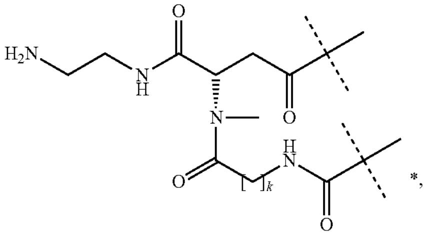

wherein the unmarked dashed line indicates the attachment to a nitrogen provided by the side chain of the lysine at position 26 of the CNP moiety of SEQ ID NO:24 by forming an amide bond;

k is selected from the group consisting of 1, 2, 3, 4, 5, 6, 7, 8, 9, 10, 11 and 12; and the dashed line marked with the asterisk indicates attachment to a moiety

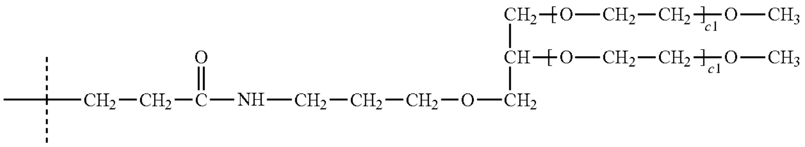

wherein each c1 is an integer independently ranging from 400 to 500.

Preferably, k of formula (IIea-i') is selected from the group consisting of 2, 3, 4, 5, 6 and 7.

Preferably, each c1 of formula (IIea-i') is about 450.

In another preferred embodiment the CNP prodrug of the present invention is of formula (IIea-ii')

(IIea-ii')

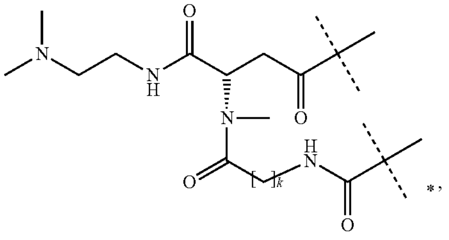

wherein the unmarked dashed line indicates the attachment to a nitrogen provided by the side chain of the lysine at position 26 of the CNP moiety of SEQ ID NO:24 by forming an amide bond;

k is selected from the group consisting of 1, 2, 3, 4, 5, 6, 7, 8, 9, 10, 11 and 12; and the dashed line marked with the asterisk indicates attachment to a moiety

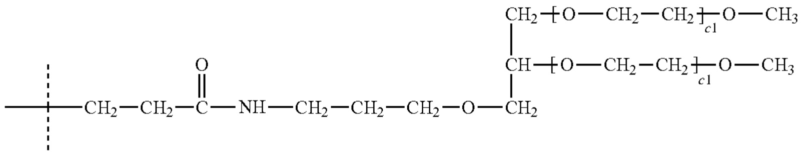

wherein each c1 is an integer independently ranging from 400 to 500.

Preferably, k of formula (IIea-ii') is selected from the group consisting of 2, 3, 4, 5, 6 and 7.

Preferably, each c1 of formula (IIea-ii') is about 450.

In another preferred embodiment the CNP prodrug of the present invention is of formula (IIfa)

(IIfa)

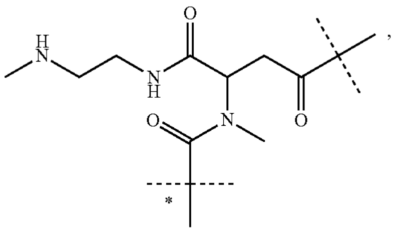

wherein the unmarked dashed line indicates the attachment to a nitrogen of -D which is a CNP moiety by forming an amide bond; and the dashed line marked with the asterisk indicates attachment to —Z having the structure

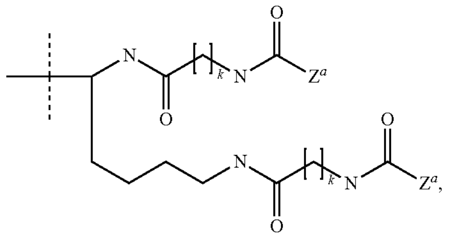

wherein k is selected from the group consisting of 1, 2, 3, 4, 5, 6, 7, 8, 9, 10, 11 and 12;

each —$Z^a$ is

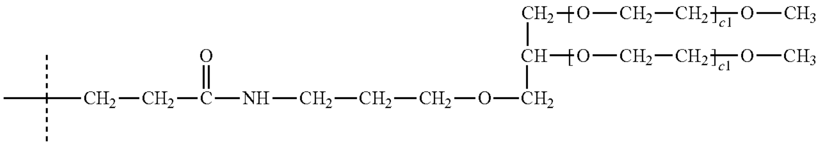

wherein each c1 is an integer independently ranging from 200 to 250; preferably each n is about 225.

Preferably, k of formula (IIfa) is selected from the group consisting of 2, 3, 4, 5, 6 and 7.

Preferably, each c1 of formula (IIfa) is about 225.

In another preferred embodiment the CNP prodrug of the present invention is of formula (IIfa-i)

(IIfa-i)

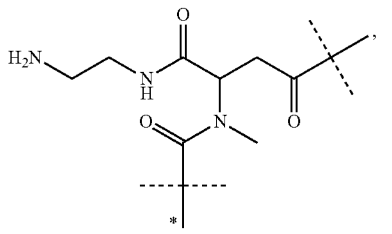

wherein the unmarked dashed line indicates the attachment to a nitrogen of -D which is a CNP moiety by forming an amide bond; and the dashed line marked with the asterisk indicates attachment to —Z having the structure

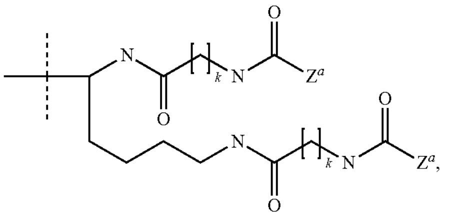

wherein k is selected from the group consisting of 1, 2, 3, 4, 5, 6, 7, 8, 9, 10, 11 and 12;

each —$Z^a$ is

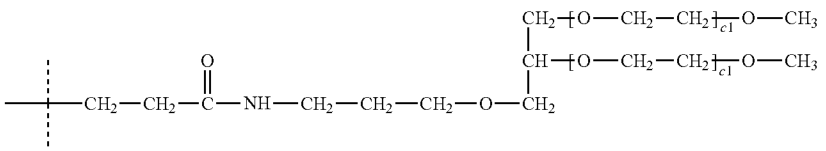

wherein each c1 is an integer independently ranging from 200 to 250; preferably each n is about 225.

Preferably, k of formula (IIfa-i) is selected from the group consisting of 2, 3, 4, 5, 6 and 7.

Preferably, each c1 of formula (IIfa-i) is about 225.

In another preferred embodiment the CNP prodrug of the present invention is of formula (IIfa-ii)

(IIfa-ii)

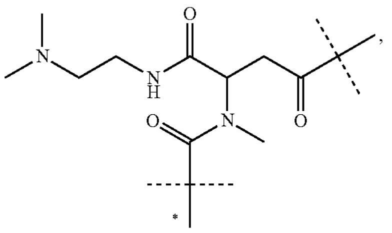

wherein the unmarked dashed line indicates the attachment to a nitrogen of -D which is a CNP moiety by forming an amide bond; and the dashed line marked with the asterisk indicates attachment to —Z having the structure

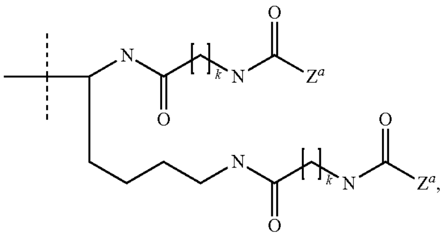

wherein k is selected from the group consisting of 1, 2, 3, 4, 5, 6, 7, 8, 9, 10, 11 and 12;

each —$Z^a$ is

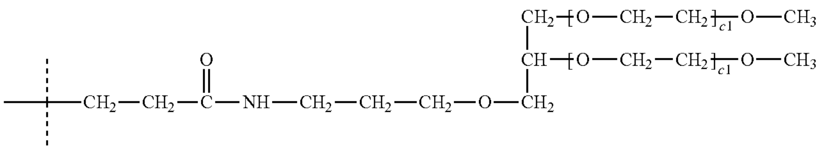

wherein each c1 is an integer independently ranging from 200 to 250; preferably each n is about 225.

Preferably, each c1 of formula (IIfa-ii) is about 225.

In one embodiment the CNP moiety of the CNP prodrug of formula (IIfa), (IIfa-i) and (IIfa-ii) has the sequence of SEQ ID NO:25.

In another embodiment the CNP moiety of the CNP prodrug of formula (IIfa), (IIfa-i) and (IIfa-ii) has the sequence of SEQ ID NO:30.

In a preferred embodiment the CNP moiety of the CNP prodrug of formula (IIfa), (IIfa-i) and (IIfa-ii) has the sequence of SEQ ID NO:24.

In one embodiment the CNP moiety is attached to $-L^1-$ in the CNP prodrug of formula (IIfa), (IIfa-i) and (IIfa-ii) through the nitrogen of the N-terminal amine functional group of CNP.

In another preferred embodiment the CNP prodrug of the present invention is of formula (IIf a')

(IIfa')

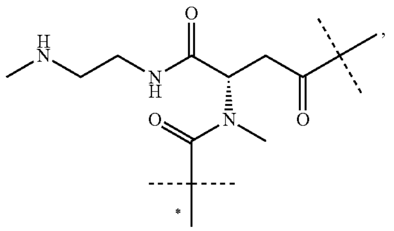

wherein the unmarked dashed line indicates the attachment to the nitrogen provided by the side chain of the lysine at position 26 of the CNP moiety of SEQ ID NO:24 by forming an amide bond; and the dashed line marked with the asterisk indicates attachment to —Z having the structure

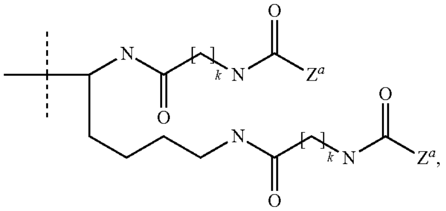

wherein k is selected from the group consisting of 1, 2, 3, 4, 5, 6, 7, 8, 9, 10, 11 and 12;

each $Z^a$ is

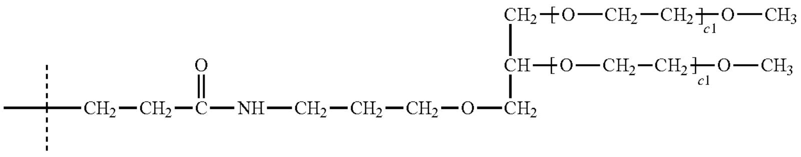

wherein each c1 is an integer independently ranging from 200 to 250.

Preferably, k of formula (IIfa') is selected from the group consisting of 2, 3, 4, 5, 6 and 7.

Preferably, each c1 of formula (IIfa') is about 225.

In another preferred embodiment the CNP prodrug of the present invention is of formula (IIfa-i')

(IIfa-i')

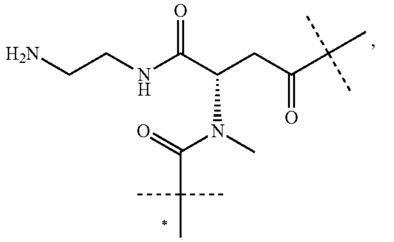

wherein the unmarked dashed line indicates the attachment to a nitrogen provided by the side chain of the lysine at position 26 of the CNP moiety of SEQ ID NO:24 by forming an amide bond; and the dashed line marked with the asterisk indicates attachment to —Z having the structure

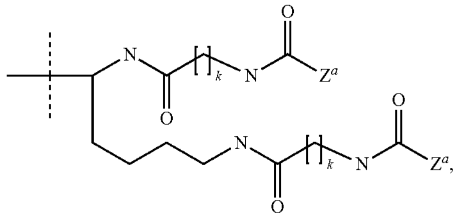

wherein k is selected from the group consisting of 1, 2, 3, 4, 5, 6, 7, 8, 9, 10, 11 and 12;

each $Z^a$ is

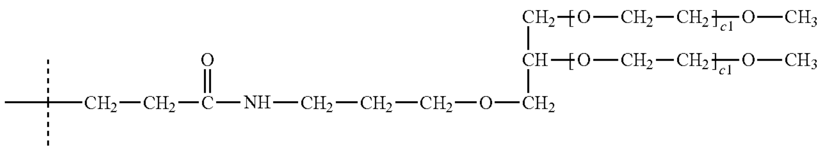

wherein each c1 is an integer independently ranging from 200 to 250.

Preferably, k of formula (IIfa-i') is selected from the group consisting of 2, 3, 4, 5, 6 and 7.

Preferably, each c1 of formula (IIfa-i') is about 225.

In another preferred embodiment the CNP prodrug of the present invention is of formula (IIfa-ii')

(IIfa-ii')

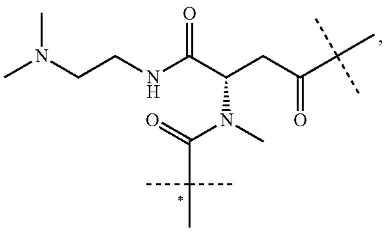

wherein the unmarked dashed line indicates the attachment to a nitrogen provided by the side chain of the lysine at position 26 of the CNP moiety of SEQ ID NO:24 by forming an amide bond; and the dashed line marked with the asterisk indicates attachment to —Z having the structure

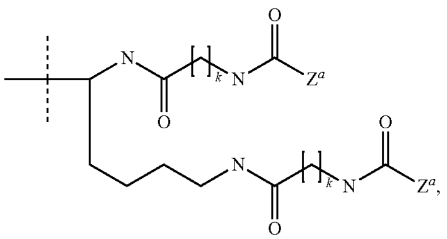

wherein k is selected from the group consisting of 1, 2, 3, 4, 5, 6, 7, 8, 9, 10, 11 and 12;

each $Z^a$ is

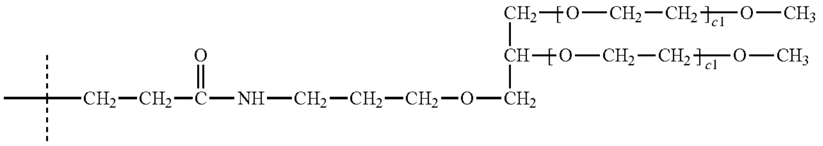

wherein each c1 is an integer independently ranging from 200 to 250.

Preferably, k of formula (IIfa-ii') is selected from the group consisting of 2, 3, 4, 5, 6 and 7.

Preferably, each c1 of formula (IIfa-ii') is about 225.

It is understood that each combination of a controlled-release CNP agonist and the at least one further biologically active moiety or drug has certain preferred ranges of ratios with may vary depending on the disease to be treated.

For example, in one embodiment the at least one further drug is a statin. An efficient dose for rosuvastatin ranges from about 0.01 mg/kg to about 10 mg/kg, more preferred 0.1 mg/kg to 5 mg/kg, even more preferred about 1 mg/kg.

Based on the conversion table (Table 1) below, a person skilled in the art will be able to select the doses of other statins.

Approximate Equivalent Daily Doses of Statins (based on LDL Lowering effect)

| Lovastatin | Simvastatin | Fluvastatin | Pravastatin | Atorvastatin | Rosuvastatin | Pitavastatin |
|---|---|---|---|---|---|---|
| 20 mg | 10 mg | 40 mg | 20 mg | — | — | 1 mg |
| 40 mg | 20 mg | 80 mg | 40 mg | 10 mg | — | 2 mg |
| 80 mg | 40 mg | — | — | 20 mg | — | 4 mg |
| — | 80 mg | — | — | 40 mg | 10 mg | — |
| — | — | — | — | 80 mg | 20 mg | — |

If the controlled-release CNP agonist is for example combined with rosuvastatin, the ratios of controlled-release CNP agonist as measured in mg/kg CNP agonist equivalents to rosuvastatin preferably ranges from 1:1 to 24:1.

Typical and preferred ranges for other drugs are provided above.

The CNP agonist, preferably the controlled-release CNP agonist, and the at least one further biologically active moiety can be formulated for simultaneous, separate or sequential administration.

In one embodiment the CNP agonist, preferably the controlled-release CNP agonist, and the at least one further biologically active moiety are formulated for simultaneous administration.

In another embodiment the CNP agonist, preferably the controlled-release CNP agonist, and the at least one further biologically active moiety are formulated for separate administration.

In another embodiment the CNP agonist, preferably the controlled-release CNP agonist, and the at least one further biologically active moiety are formulated for sequential administration. When the CNP agonist, preferably the controlled-release CNP agonist, and the at least one further biologically active moiety are administered sequentially, the administration of each can be by the same or different methods. The CNP agonist, preferably the controlled-release CNP agonist, may be administered at the same time as the at least one further biologically active moiety, may be administered less often, or may be administered more often. Sequential administration also includes a combination where the CNP agonist, preferably the controlled-release CNP agonist, and the at least one further biologically active moiety may be administered at different times or by different routes or both, but which act in combination to provide a beneficial effect.

In one embodiment the CNP agonist, preferably the controlled-release CNP agonist, is administered every 24 hours, every 48 hours, every 72 hours, every 96 hours, every 120 hours, every 144 hours, every 168 hours, every 192 hours, every 216 hours or every week. In one embodiment the CNP agonist, preferably the controlled-release CNP agonist, is administered every 24 hours. In another embodiment the CNP agonist, preferably controlled-release CNP agonist, is administered every week.

In one embodiment the at least one further biologically active moiety is administered every 24 hours, every 48 hours, every 72 hours, every 96 hours, every 120 hours, every 144 hours, every 168 hours, every 192 hours, every 216 hours or every week. In one embodiment the at least one further biologically active moiety is administered every 24 hours. In another embodiment at least one further biologically active moiety is administered every week.

The CNP agonist, preferably the controlled-release CNP agonist, and the at least one further biologically active moiety may be administered via topical, enteral or parenteral administration and by methods of external application, injection or infusion, including intraarticular, periarticular, intradermal, subcutaneous, intramuscular, intravenous, intraosseous, intraperitoneal, intrathecal, intracapsular, intraorbital, intravitreal, intratympanic, intravesical, intracardiac, transtracheal, subcuticular, subcapsular, subarachnoid, intraspinal, intraventricular, intrasternal injection and infusion, direct delivery to the brain via implanted device allowing delivery of the invention or the like to brain tissue or brain fluids (e.g., Ommaya Reservoir), direct intracerebroventricular injection or infusion, injection or infusion into brain or brain associated regions, injection into the subchoroidal space, retro-orbital injection and ocular instillation, preferably via subcutaneous injection.

A preferred mode of administration is via intravenous or subcutaneous injection and most preferably is via subcutaneous injection.

A preferred combination is a controlled-release CNP agonist, preferably the controlled-release CNP agonist of formula (IIf) and a controlled-release growth hormone, preferably human growth hormone and most preferably the human growth hormone having the sequence of SEQ ID NO:99. Most preferably the controlled-release growth hormone has the structure of formula (A1).

Preferably, the CNP agonist, preferably the controlled-release CNP agonist, and the at least one further biologically active moiety are formulated for simultaneous administration, i.e. both the CNP agonist, preferably the controlled-release CNP agonist, and the at least one further biologically active moiety are formulated in one pharmaceutical composition. Preferably, such pharmaceutical composition is administered once weekly.

Accordingly, another aspect of the present invention is a pharmaceutical composition comprising at least one controlled-release CNP agonist, wherein the pharmaceutical composition comprises at least one further biologically active moiety or drug.

In one embodiment the pharmaceutical composition of the present invention is a liquid or suspension formulation. It is understood that the pharmaceutical composition is a suspension formulation if at least one of the controlled-release CNP agonist or the at least one further biologically active moiety or drug is water-insoluble.

In another embodiment the pharmaceutical composition of the present invention is a dry formulation.

Preferably, the pharmaceutical composition of the present invention comprises one or more excipients.

Excipients used in parenteral formulations may be categorized as, for example, buffering agents, isotonicity modifiers, preservatives, stabilizers, anti-adsorption agents, oxidation protection agents, viscosifiers/viscosity enhancing agents, or other auxiliary agents. However, in some cases, one excipient may have dual or triple functions. Preferably, the at least one excipient comprised in the pharmaceutical composition of the present invention is selected from the group consisting of (i) Buffering agents: physiologically tolerated buffers to maintain pH in a desired range, such as sodium phosphate, bicarbonate, succinate, histidine, citrate and acetate, sulphate, nitrate, chloride, pyruvate; antacids such as $Mg(OH)_2$ or $ZnCO_3$ may be also used;

(ii) Isotonicity modifiers: to minimize pain that can result from cell damage due to osmotic pressure differences at the injection depot; glycerin and sodium chloride are examples; effective concentrations can be determined by osmometry using an assumed osmolality of 285-315 mOsmol/kg for serum;

(iii) Preservatives and/or antimicrobials: multidose parenteral formulations require the addition of preservatives at a sufficient concentration to minimize risk of patients becoming infected upon injection and corresponding regulatory requirements have been established; typical preservatives include m-cresol, phenol, methylparaben, ethylparaben, propylparaben, butylparaben, chlorobutanol, benzyl alcohol, phenylmercuric nitrate, thimerosal, sorbic acid, potassium sorbate, benzoic acid, chlorocresol, and benzalkonium chloride;

(iv) Stabilizers: Stabilisation is achieved by strengthening of the protein-stabilising forces, by destabilisation of the denatured state, or by direct binding of excipients to the protein; stabilizers may be amino acids such as alanine, arginine, aspartic acid, glycine, histidine, lysine, proline, sugars such as glucose, sucrose, trehalose, polyols such as glycerol, mannitol, sorbitol, salts such as potassium phosphate, sodium sulphate, chelating agents such as EDTA, hexaphosphate, ligands such as divalent metal ions (zinc, calcium, etc.), other salts or organic molecules such as phenolic derivatives; in addition, oligomers or polymers such as cyclodextrins, dextran, dendrimers, PEG or PVP or protamine or HSA may be used;

(v) Anti-adsorption agents: Mainly ionic or non-ionic surfactants or other proteins or soluble polymers are used to coat or adsorb competitively to the inner surface of the formulation's container; e.g., poloxamer (Pluronic F-68), PEG dodecyl ether (Brij 35), polysorbate 20 and 80, dextran, polyethylene glycol, PEG-polyhistidine, BSA and HSA and gelatins; chosen concentration and type of excipient depends on the effect to be avoided but typically a monolayer of surfactant is formed at the interface just above the CMC value;

(vi) Oxidation protection agents: antioxidants such as ascorbic acid, ectoine, methionine, glutathione, monothioglycerol, morin, polyethylenimine (PEI), propyl gallate, and vitamin E; chelating agents such as citric acid, EDTA, hexaphosphate, and thioglycolic acid may also be used;

(vii) Viscosifiers or viscosity enhancers: retard settling of the particles in the vial and syringe and are used in order to facilitate mixing and resuspension of the particles and to make the suspension easier to inject (i.e., low force on the syringe plunger); suitable viscosifiers or viscosity enhancers are, for example, carbomer viscosifiers like Carbopol 940, Carbopol Ultrez 10, cellulose derivatives like hydroxypropylmethylcellulose (hypromellose, HPMC) or diethylaminoethyl cellulose (DEAE or DEAE-C), colloidal magnesium silicate (Veegum) or sodium silicate, hydroxyapatite gel, tricalcium phosphate gel, xanthans, carrageenans like Satia gum UTC 30, aliphatic poly(hydroxy acids), such as poly(D,L- or L-lactic acid) (PLA) and poly (glycolic acid) (PGA) and their copolymers (PLGA), terpolymers of D,L-lactide, glycolide and caprolactone, poloxamers, hydrophilic poly(oxyethylene) blocks and hydrophobic poly(oxypropylene) blocks to make up a triblock of poly(oxyethylene)-poly(oxypropylene)-poly(oxyethylene) (e.g. Pluronic®), polyetherester copolymer, such as a polyethylene glycol terephthalate/polybutylene terephthalate copolymer, sucrose acetate isobutyrate (SAIB), dextran or derivatives thereof, combinations of dextrans and PEG, polydimethylsiloxane, collagen, chitosan, polyvinyl alcohol (PVA) and derivatives, polyalkylimides, poly (acrylamide-co-diallyldimethyl ammonium (DADMA)), polyvinylpyrrolidone (PVP), glycosaminoglycans (GAGs) such as dermatan sulfate, chondroitin sulfate, keratan sulfate, heparin, heparan sulfate, hyaluronan, ABA triblock or AB block copolymers composed of hydrophobic A-blocks, such as polylactide (PLA) or poly(lactide-co-glycolide) (PLGA), and hydrophilic B-blocks, such as polyethylene glycol (PEG) or polyvinyl pyrrolidone; such block copolymers as well as the abovementioned poloxamers may exhibit reverse thermal gelation behavior (fluid state at room temperature to facilitate administration and gel state above sol-gel transition temperature at body temperature after injection);

(viii) Spreading or diffusing agent: modifies the permeability of connective tissue through the hydrolysis of components of the extracellular matrix in the interstitial space such as but not limited to hyaluronic acid, a polysaccharide found in the intercellular space of connective tissue; a spreading agent such as but not limited to hyaluronidase temporarily decreases the viscosity of the extracellular matrix and promotes diffusion of injected drugs; and (ix) Other auxiliary agents: such as wetting agents, viscosity modifiers, antibiotics, hyaluronidase; acids and bases such as hydrochloric acid and sodium hydroxide are auxiliary agents necessary for pH adjustment during manufacture.

Another aspect of the present invention is the pharmaceutical composition of the present invention for use as a medicament.

Another aspect of the present invention is the pharmaceutical composition of the present invention for use in the treatment of a patient suffering from a disorder that benefits from stimulating growth.

Preferably, the patient is a mammalian patient, more preferably a human patient.

Preferably, disorders that benefit from stimulating growth are selected from the group comprising achondroplasia, hypochondroplasia, short stature, dwarfism, osteochondrodysplasias, thanatophoric dysplasia, osteogenesis imperfecta, achondrogenesis, chondrodysplasia *punctata*, homozygous achondroplasia, camptomelic dysplasia, congenital lethal hypophosphatasia, perinatal lethal type of osteogenesis imperfecta, short-rib polydactyly syndromes, rhizomelic type of chondrodysplasia *punctata*, Jansen-type metaphyseal dysplasia, spondyloepiphyseal dysplasia congenita, atelosteogenesis, diastrophic dysplasia, congenital short femur, Langer-type mesomelic dysplasia, Nievergelt-type mesomelic dysplasia, Robinow syndrome, Reinhardt syndrome, acrodysostosis, peripheral dysostosis, Kniest dysplasia, fibrochondrogenesis, Roberts syndrome, acromesomelic dysplasia, micromelia, Morquio syndrome, Kniest syndrome, metatrophic dysplasia, and spondyloepimetaphyseal dysplasia. Most preferably, the disorder that benefits from stimulating growth is achondroplasia.

Another aspect of the present invention is a method of treating a patient suffering from a disorder that benefits from stimulating growth by administering the pharmaceutical composition of the present invention.

Preferably, the patient is a mammalian patient, more preferably a human patient.

Preferably, such disorders that benefit from stimulating growth are selected from the group comprising achondroplasia, hypochondroplasia, short stature, dwarfism, osteochondrodysplasias, thanatophoric dysplasia, osteogenesis imperfecta, achondrogenesis, chondrodysplasia *punctata*, homozygous achondroplasia, camptomelic dysplasia, congenital lethal hypophosphatasia, perinatal lethal type of osteogenesis imperfecta, short-rib polydactyly syndromes, rhizomelic type of chondrodysplasia *punctata*, Jansen-type metaphyseal dysplasia, spondyloepiphyseal dysplasia congenita, atelosteogenesis, diastrophic dysplasia, congenital short femur, Langer-type mesomelic dysplasia, Nievergelt-type mesomelic dysplasia, Robinow syndrome, Reinhardt syndrome, acrodysostosis, peripheral dysostosis, Kniest dysplasia, fibrochondrogenesis, Roberts syndrome, acromesomelic dysplasia, micromelia, Morquio syndrome, Kniest syndrome, metatrophic dysplasia, and spondyloepimetaphyseal dysplasia. Most preferably, the disorder that benefits from stimulating growth is achondroplasia.

If the CNP agonist is a polypeptide, such polypeptide may be prepared by standard solid-phase peptide synthesis methods, e.g. by Boc chemistry (R. B. Merrifield, J. Am. Chem. Soc., 85(14): 2149-2154 (1963)). Alternatively, Fmoc (fluorenylmethoxycarbonyl) chemistry may be employed.

Methods known in the art can be employed to improve purity and/or yield, including the use of pseudoproline or other dipeptide building blocks, fragment coupling and others (J. Wade et al., Lett. Pept. Sci., 7(2):107-(2000); Y. Fujiwara et al., Chem. Pharm. Bull., 44(7):1326-1331 (1996); P. Cherkupally et al., Eur. J. Org. Chem., 6372-6378 (2013)).

Alternatively, if the CNP agonist is a polypeptide, such polypeptide may be produced by recombinant synthesis processes.

Methods

Reversible Lys26 CNP-38 PEG4×10 kDa conjugate 1 was synthesized as described in WO2016/110577, example 11 (compound 11i).

EXAMPLES

Example 1

Administration of Reversible Lys26 CNP-38 PEG4×10 kDa Conjugate in Combination with Rosuvastatin is More Effective in Ameliorating the Achondroplasia Phenotype than Either Agent Alone Method: Rosuvastatin and the reversible Lys26 CNP-38 PEG4×10 kDa conjugate are administered by intraperitoneal or subcutaneous injection, respectively, to Fgfr3Y367C/+ mice from day 1 of birth and for a total of 15 days. Animals are sacrificed on day 16 and tissues fixed for histologic or immunohistochemical analysis. Either compound is administered alone or in combination. The dose levels employed for Rosuvastatin are 0.25, 0.5, 1.0 and 2.0 mg/kg. The reversible Lys26 CNP-38 PEG4×10 kDa conjugate is employed at dose levels of 1.5 3.0 and 6.0 mg/kg CNP equivalents. The reversible Lys26 CNP-38 PEG4×10 kDa conjugate/Rosuvastatin ratios are based on doses administered in mg/kg for Rosuvastatin or CNP equivalents for the reversible Lys26 CNP-38 PEG4×10 kDa conjugate/Rosuvastatin. The ratios ranges from 1:1-24:1

Reversion of phenotypical features are assessed using whole body autoradiography. The animals are placed on their right side, with the left hind leg more forward than the right, to allow both hind legs to be visible on the X-ray. Bones obtained at necropsy include femur, tibia, humerus, ulna, lumbar vertebra segment L 4-6 and are measured with a caliper.

Results: The combination of Rosuvastatin and the reversible Lys26 CNP-38 PEG4×10 kDa conjugate are found to increase body length and length of extremities. Amelioration of key relevant achondroplasia clinical features including bowed femur and tibia, anterior crossbite and domed skull are observed in treated animals. The beneficial effect on reversal of the achondroplasic phenotype is observed in both animals treated with a single agent and in combination.

Combination of reversible Lys26 CNP-38 PEG4×10 kDa conjugate and Rosuvastatin are found to be superior in efficacy to an equivalent dose of the reversible Lys26 CNP-38 PEG4×10 kDa conjugate or Rosuvastatin administered alone.

Example 2

Administration of Lys26 CNP-38 PEG4×10 kDa Conjugate (TransCon CNP, ACP-015) in Combination with Somatropin is More Effective in Growth Induction in Hypophysectomized Rats than Either Agent Alone Method: This study was performed in order to test and compare the effect of Lys26 CNP-38 PEG4×10 kDa conjugate, Somatropin and combinations of the two compounds in an animal model relevant for investigating treatment of growth deficiency. The Somatropin (human growth hormone, hGH) was a United States Pharmacopeia (USP) Reference Standard and was prepared according to supplier instructions. Lys26 CNP-38 PEG4×10 kDa conjugate and Somatropin were administered alone or in combination via subcutaneous injection to hypophysectomized (HYPOX) SPF Sprague Dawley rats for a total of 29 days. The animals were dosed daily with Somatropin or vehicle, and weekly with Lys26 CNP-38 PEG4×10 kDa conjugate (at two different sites in animals receiving both test items on days 1, 8, 15, 22, and 29). The dose levels employed for Lys26 CNP-38 PEG4×10 kDa conjugate were 0.3, 1.0, and 2.0 mg/kg. Somatropin was employed at 10 μL/animal with a concentration of 10 μg/mL (~8-10 μg/kg with animal weights between 100-120 g during the study period). The animals were weighed predose and once daily during the dosing period. Body weight gain was calculated from these data. Animals were sacrificed on day 30, and femur and tibia were trimmed and their length measured using a caliper. Hereafter, right tibia was fixed and processed for histologic and histomorphometric analysis.

Results: Significant body weight gains were observed for HYPOX rats treated with Somatropin or Lys26 CNP-38 PEG4×10 kDa conjugate alone compared to vehicle treated group. Administration of Lys26 CNP-38 PEG4×10 kDa conjugate and Somatropin in combination were found to increase body weight in an additive manner (Table 2).

TABLE 2

Body weight gain (BWG) from day 0 (predose) to day 28. Low dose = 0.3 mg/mL, mid dose = 1.0 mg/mL, high dose = 2.0 mg/mL.

| | Average BWG (g) (±SE) |
|---|---|
| Vehicle | −0.78 (±0.64) |
| Somatropin | 4.44 (±0.94) |
| Lys26 CNP-38 PEG4x10 kDa conjugate low dose | 7.89 (±1.53) |
| Lys26 CNP-38 PEG4x10 kDa conjugate mid dose | 8.44 (±0.93) |
| Lys26 CNP-38 PEG4x10 kDa conjugate high dose | 8.89 (±1.24) |
| Somatropin + Lys26 CNP-38 PEG4x10 kDa conjugate low dose | 7.78 (±1.17) |
| Somatropin + Lys26 CNP-38 PEG4x10 kDa conjugate mid dose | 11.89 (±1.23) |
| Somatropin + Lys26 CNP-38 PEG4x10 kDa conjugate high dose | 13.00 (±0.75) |

A dose related increase in mean longitudinal growth of long bones were found in Lys26 CNP-38 PEG4×10 kDa conjugate treated animals (femur: 0.95±0.20, 1.29±0.16, 1.81±0.17 mm, tibia: 1.43±0.28, 1.85±0.18, 2.06±0.18 mm for 0.3, 1.0, and 2.0 mg/kg Lys26 CNP-38 PEG4×10 kDa conjugate, respectively). Only a small increase in bone length was observed on tibia (0.55±0.17 mm) and no increase on femur (−0.04±0.08 mm) in Somatropin treated animals relative to the vehicle group. Hence, it was a surprise to find that Somatropin enhanced the mean effect (30) of 2.0 mg/Lys26 CNP-38 PEG4×10 kDa conjugate on femur length when the two compounds were administered in combination (2.35±0.24 mm).

A histologic evaluation examining the width of the endochondral/ossification zone after treatment with vehicle, Somatropin, Lys26 CNP-38 PEG4×10 kDa conjugate, or Somatropin+Lys26 CNP-38 PEG4×10 kDa conjugate demonstrated superior efficacy (growth potential) in the combination groups compared to groups that received Lys26 CNP-38 PEG4×10 kDa conjugate alone. The endochondral/ossification zone width in Somatropin treated animals did not differ from background (vehicle).

TABLE 3

Histologic evaluation of HE stained right tibia with focus on growth zone morphology.

| | Decrease | | Increase | | | Sum of |
|---|---|---|---|---|---|---|
| | Minimal | Normal | Minimal | Mild | Moderate | grades |
| Vehicle | 2 | 7 | | | | |
| Somatropin | | 9 | | | | |
| Lys26 CNP-38 PEG4x10 kDa conjugate Low dose | | 0 | | 9 | | 18 |
| Lys26 CNP-38 PEG4x10 kDa conjugate Mid dose | | 0 | | 9 | | 18 |
| Lys26 CNP-38 PEG4x10 kDa conjugate High dose | | 0 | | 7 | 2 | 20 |
| Somatropin + Lys26 CNP-38 PEG4x10 kDa conjugate Low dose | | 0 | | 9 | | 18 |

TABLE 3-continued

Histologic evaluation of HE stained right tibia with focus on growth zone morphology.

| | Decrease | | Increase | | | Sum of |
|---|---|---|---|---|---|---|
| | Minimal | Normal | Minimal | Mild | Moderate | grades |
| Somatropin + Lys26 CNP-38 PEG4x10 kDa conjugate Mid dose | | 0 | | 5 | 4 | 22 |
| Somatropin + Lys26 CNP-38 PEG4x10 kDa conjugate High dose | | 0 | | 1 | 8 | 26 |

Width of the endochondral/ossification zone was classified using the following 5-grade system: normal = 0 (within normal range), minimal = 1, mild = 2, moderate = 3, marked = 4, and massive = 5.Number of animals observed in each group are listed within the categories. Sum of grades = (n animals * grade 1) + (n animals * grade 2) + (n animals * grade 3).

Hence, it was a surprise to find the width of the endochondral/ossification zone increased by 30% in animals treated with the combination of Somatropin and 2.0 mg/mL Lys26 CNP-38 PEG4×10 kDa conjugate compared to animals treated with solely 2.0 mg/mL Lys26 CNP-38 PEG4×10 kDa conjugate (ACP-015) (Table 3).

Figure 2:
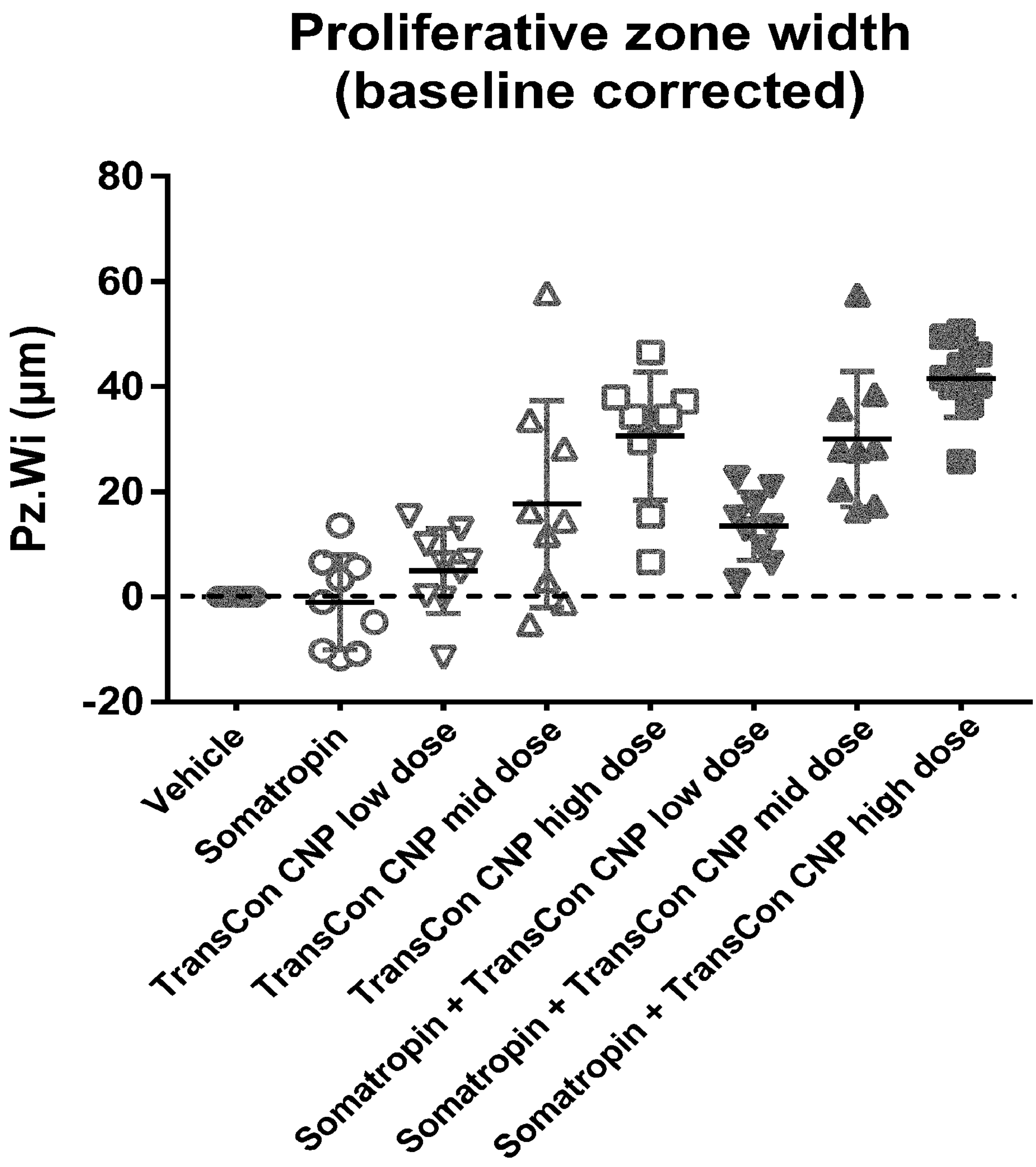
FIG. 2: Proliferative zone width (Pz.Wi; μm) of right tibia measured using histomorphometry.

These observations of surprising benefits from combining treatment of Lys26 CNP-38 PEG4×10 kDa conjugate and Somatropin were supported by histomorphometric measurements of the proliferative zone width in the same tibial growth plates. The width of the proliferative zone in Somatropin treated animals was not different from control (vehicle) animals. A dose-related increase in mean width (±SE) of the proliferative zone was found in Lys26 CNP-38 PEG4×10 kDa conjugate treated animals (4.94±2.69, 17.69±6.57, 30.61±4.06 μm for 0.3, 1.0, and 2.0 mg/kg Lys26 CNP-38 PEG4×10 kDa conjugate, respectively). A similar but further augmented dose related increase in mean width of the proliferative zone was found in animals treated with the combination of Somatropin and Lys26 CNP-38 PEG4×10 kDa conjugate (13.45±2.16, 30.05±4.27, 41.60±2.50 μm for 0.3, 1.0, and 2.0 mg/kg Lys26 CNP-38 PEG4×10 kDa conjugate (ACP-015)+Somatropin, respectively). It was a surprise to find this increase in width in combination-treated animals compared to animals treated with only Lys26 CNP-38 PEG4×10 kDa conjugate since the tested dose of Somatropin on its own failed to stimulate the proliferative zone. Moreover, it was surprising to find that Lys26 CNP-38 PEG4×10 kDa conjugate and Somatropin in combination stimulated a response in all dosed animals compared to animals treated only with Lys26 CNP-38 PEG4×10 kDa conjugate where non- and low-responders were observed within the groups (FIG. 2). This was also reflected in the reduced distribution of individual responses within the combination treated groups compared to groups of animals treated only with Lys26 CNP-38 PEG4×10 kDa conjugate.

Conclusion: Combination of Lys26 CNP-38 PEG4×10 kDa conjugate and Somatropin were found to be superior in efficacy compared to Lys26 CNP-38 PEG4×10 kDa conjugate or Somatropin administered alone. The presented data shows a combinatorial effect from hGH and Lys26 CNP-38 PEG4×10 kDa conjugate treatment with both additive and surprising synergistic effects (above 25% an additive effect). Importantly, the combination of Lys26 CNP-38 PEG4×10 kDa conjugate and Somatropin were found to eliminate the non- and low-responders observed in groups of animals dosed only with Lys26 CNP-38 PEG4×10 kDa conjugate.

The invention claimed is:

1. A method of stimulating bone growth in a patient, the method comprising administering to the patient an effective amount of a controlled-release C-type natriuretic peptide (CNP) agonist, wherein the patient is also administered human growth hormone resulting in a synergistic increase in bone growth from the controlled-release CNP agonist and the human growth hormone acting in combination;

wherein the controlled-release CNP agonist releases a CNP moiety, the amino acid sequence of which consists of SEQ ID NO:24, under physiological conditions with a release half-life of at least 6 hours, wherein the controlled-release CNP agonist is a compound of formula (IIf):

(IIf)

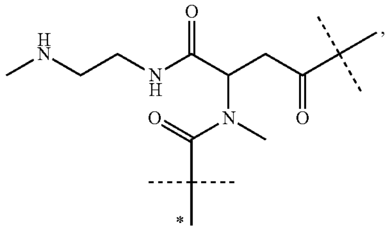

or a pharmaceutically acceptable salt thereof;

wherein the unmarked dashed line indicates the attachment to a nitrogen provided by the side-chain of the lysine at position 26 of the CNP moiety by forming an amide bond; and the dashed line marked with the asterisk indicates attachment to —Z having the structure

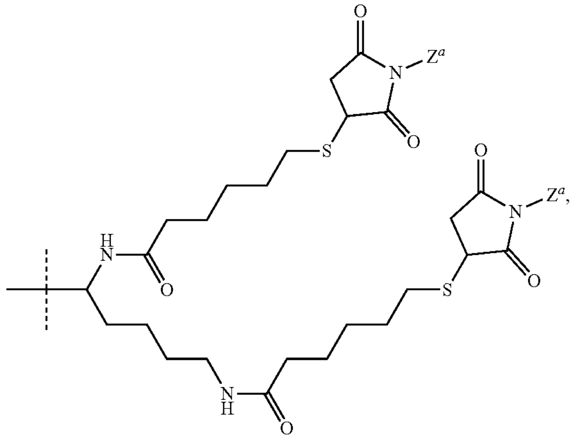

wherein each —$Z^a$ is

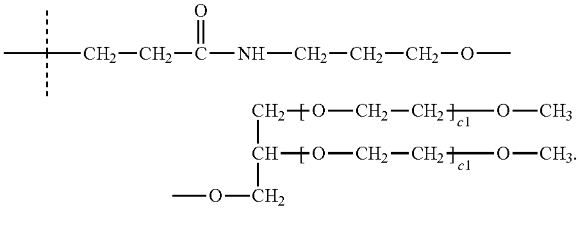

wherein each c1 is an integer independently ranging from 200 to 250.

2. The method of claim 1, wherein the human growth hormone is in its free form.

3. The method of claim 1, wherein the human growth hormone is in the form of a stable conjugate.

4. The method of claim 1, wherein the human growth hormone is a controlled-release compound.

5. The method of claim 1, wherein the controlled-release CNP agonist and the human growth hormone are administered separately.

6. The method of claim 1, wherein the controlled-release CNP agonist and the human growth hormone are formulated in one pharmaceutical composition for simultaneous administration.

7. The method of claim 1, wherein the disorder that benefits from stimulating bone growth is selected from the group consisting of achondroplasia, hypochondroplasia, short stature, dwarfism, osteochondrodysplasias, thanatophoric dysplasia, osteogenesis imperfecta, achondrogenesis, chondrodysplasia *punctata*, homozygous achondroplasia, camptomelic dysplasia, congenital lethal hypophosphatasia, perinatal lethal type of osteogenesis imperfecta, short-rib polydactyly syndromes, rhizomelic type of chondrodysplasia *punctata*, Jansen-type metaphyseal dysplasia, spondyloepiphyseal dysplasia congenita, atelosteogenesis, diastrophic dysplasia, congenital short femur, Langer-type mesomelic dysplasia, Nievergelt-type mesomelic dysplasia, Robinow syndrome, Reinhardt syndrome, acrodysostosis, peripheral dysostosis, Kniest dysplasia, fibrochondrogenesis, Roberts syndrome, acromesomelic dysplasia, micromelia, Morquio syndrome, metatrophic dysplasia, and spondyloepimetaphyseal dysplasia.

8. The method of claim 1, wherein the disorder that benefits from stimulating bone growth is achondroplasia.

9. The method of claim 1, further comprising administering the human growth hormone to the patient.

10. The method of claim 9, wherein the CNP agonist and the human growth hormone are administered separately to the patient.

11. The method of claim 9, wherein the human growth hormone is of formula (A1):

(A1)

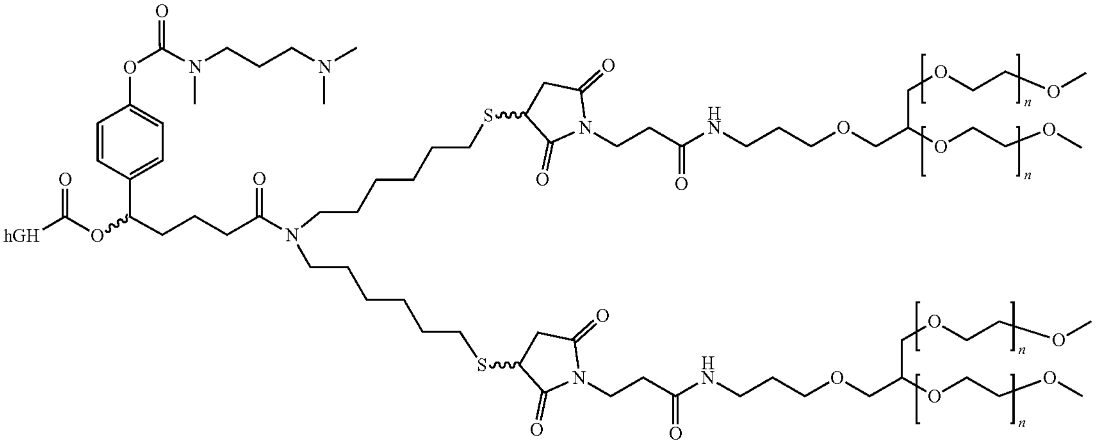

n = 200-250 wherein n=200-250, or a pharmaceutically acceptable salt thereof.

12. The method of claim 1, wherein the controlled-release CNP agonist is a compound of formula (IIf'):

(IIf')

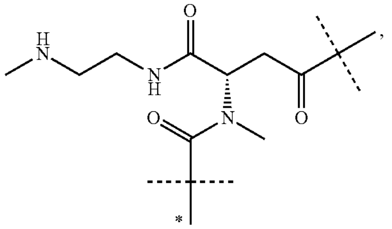

or a pharmaceutically acceptable salt thereof.

13. The method of claim 12, wherein the dashed line marked with the asterisk in formula (IIf'), indicates attachment to —Z having the structure:

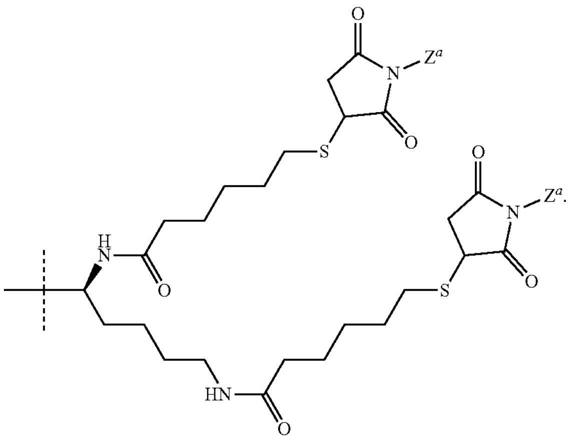

14. The method of claim 1, wherein each c1 is about 225.

15. The method of claim 1, wherein the amino acid sequence of the human growth hormone consists of SEQ ID NO:99.

16. The method of claim 1, wherein the controlled-release CNP agonist and human growth hormone are administered subcutaneously.

17. The method of claim 1, wherein the controlled-release CNP agonist and human growth hormone are administered via subcutaneous injection.

* * * * *